United States Patent
Blank et al.

(10) Patent No.: US 12,365,688 B2
(45) Date of Patent: Jul. 22, 2025

(54) SUBSTITUTED PYRAZOLOPYRAZINES, IMIDAZOPYRAZINES AND [1,2,4]TRIAZOLOPYRAZINES AS ALLOSTERIC SHP2 INHIBITORS

(71) Applicant: Revolution Medicines, Inc., Redwood City, CA (US)

(72) Inventors: Brian R. Blank, Redwood City, CA (US); Jennifer Pitzen, Redwood City, CA (US); Gang Wang, Redwood City, CA (US); Walter S. Won, Redwood City, CA (US); Christos Tzitzilonis, Redwood City, CA (US); Jie Jack Li, Redwood City, CA (US); Elena S. Koltun, Redwood City, CA (US); Naing Aay, Redwood City, CA (US); Andreas Buckl, Redwood City, CA (US); Kevin Mellem, Redwood City, CA (US); Christopher Semko, Redwood City, CA (US); Ash Jogalekar, Redwood City, CA (US); Gert Kiss, Redwood City, CA (US); Adrian Gill, Redwood City, CA (US)

(73) Assignee: Revolution Medicines, Inc., Redwood City, CA (US)

( * ) Notice: Subject to any disclaimer, the term of this patent is extended or adjusted under 35 U.S.C. 154(b) by 0 days.

(21) Appl. No.: 18/220,196

(22) Filed: Jul. 10, 2023

(65) Prior Publication Data

US 2024/0199616 A1    Jun. 20, 2024

Related U.S. Application Data

(60) Division of application No. 16/518,798, filed on Jul. 22, 2019, now Pat. No. 11,739,093, which is a continuation of application No. PCT/US2018/013023, filed on Jan. 9, 2018.

(60) Provisional application No. 62/449,530, filed on Jan. 23, 2017.

(51) Int. Cl.
| | |
|---|---|
| A61K 31/4985 | (2006.01) |
| C07D 471/04 | (2006.01) |
| C07D 487/04 | (2006.01) |
| C07D 513/04 | (2006.01) |
| C07D 519/00 | (2006.01) |

(52) U.S. Cl.
CPC ......... *C07D 487/04* (2013.01); *C07D 471/04* (2013.01); *C07D 513/04* (2013.01); *C07D 519/00* (2013.01)

(58) Field of Classification Search
CPC .......................... A61K 31/4985; C07D 487/04
USPC ................................... 514/249; 544/350
See application file for complete search history.

(56) References Cited

U.S. PATENT DOCUMENTS

| | | |
|---|---|---|
| 2,572,728 A | 10/1951 | Hultquist et al. |
| 2,636,882 A | 4/1953 | Dunlop et al. |
| 3,701,779 A | 10/1972 | Donninger et al. |
| 4,687,848 A | 8/1987 | Brunnmueller et al. |
| 5,262,564 A | 11/1993 | Kun et al. |
| 6,921,762 B2 | 7/2005 | Cai et al. |
| 7,863,288 B2 | 1/2011 | Ibrahim et al. |
| 8,324,200 B2 | 12/2012 | Li et al. |
| 8,703,770 B2 | 4/2014 | Coleman et al. |
| 9,169,261 B2 | 10/2015 | Fan et al. |
| 9,394,368 B2 | 7/2016 | Brogdon et al. |
| 10,590,090 B2 | 3/2020 | Koltun et al. |
| 2004/0213795 A1 | 10/2004 | Collins et al. |
| 2004/0220189 A1 | 11/2004 | Sun et al. |
| 2006/0189664 A1 | 8/2006 | Barth et al. |
| 2008/0176309 A1 | 7/2008 | Wu et al. |
| 2009/0325973 A1 | 12/2009 | Watterson et al. |
| 2010/0190980 A1 | 7/2010 | Umemiya et al. |
| 2011/0257184 A1 | 10/2011 | Qu et al. |
| 2012/0034186 A1 | 2/2012 | Wu et al. |
| 2012/0065205 A1 | 3/2012 | Mercer et al. |
| 2012/0266264 A1 | 10/2012 | Lee |
| 2012/0330012 A1 | 12/2012 | Frank et al. |
| 2013/0005949 A1 | 1/2013 | Fertig et al. |
| 2014/0154179 A1 | 6/2014 | Fan et al. |
| 2016/0031976 A1 | 2/2016 | Seubert et al. |

(Continued)

FOREIGN PATENT DOCUMENTS

| | | |
|---|---|---|
| CN | 102869666 A | 1/2013 |
| CN | 103181918 A | 7/2013 |

(Continued)

OTHER PUBLICATIONS

Hackam, et al. JAMA, 296(14), 2006, 1731-1732.*

(Continued)

*Primary Examiner* — Douglas M Willis
(74) *Attorney, Agent, or Firm* — Armstrong Teasdale LLP

(57) ABSTRACT

The present disclosure is directed to inhibitors of SHP2 having the formula:

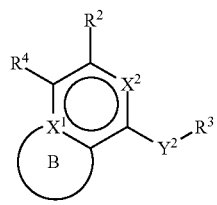

IV and their use in the treatment of disease. Also disclosed are pharmaceutical compositions comprising the same.

36 Claims, No Drawings

(56) References Cited

U.S. PATENT DOCUMENTS

| | | |
|---|---|---|
| 2017/0042881 A1 | 2/2017 | Fagin et al. |
| 2018/0200381 A1 | 7/2018 | Kannan et al. |
| 2019/0210977 A1 | 7/2019 | Jogalekar et al. |
| 2019/0290649 A1 | 9/2019 | Xie et al. |
| 2020/0017511 A1 | 1/2020 | Blank et al. |
| 2020/0017517 A1 | 1/2020 | Gill et al. |
| 2020/0108071 A1 | 4/2020 | Chin et al. |
| 2020/0339552 A1 | 10/2020 | Li et al. |
| 2020/0368238 A1 | 11/2020 | Nichols et al. |
| 2020/0407372 A1 | 12/2020 | Koltun et al. |
| 2021/0053989 A1 | 2/2021 | Zou et al. |
| 2021/0101870 A1 | 4/2021 | Koltun et al. |
| 2021/0154190 A1 | 5/2021 | Wildes et al. |
| 2022/0031695 A1 | 2/2022 | Nichols et al. |
| 2022/0073521 A1 | 3/2022 | Zou et al. |
| 2022/0127271 A1 | 4/2022 | Wan et al. |

FOREIGN PATENT DOCUMENTS

| | | |
|---|---|---|
| CN | 103554038 A | 2/2014 |
| CN | 105175330 A | 12/2015 |
| CN | 105916845 A | 8/2016 |
| CN | 110156786 A | 8/2019 |
| EP | 0088593 A2 | 9/1983 |
| EP | 0579835 A1 | 1/1994 |
| GB | 1459571 | 12/1976 |
| JP | S5762269 A | 4/1982 |
| JP | H0249775 A | 2/1990 |
| JP | H04112877 A | 4/1992 |
| JP | H09510987 A | 11/1997 |
| JP | 2007277097 A | 10/2007 |
| JP | 2007530434 A | 11/2007 |
| JP | 2010520238 A | 6/2010 |
| JP | 2013522222 A | 6/2013 |
| JP | 2013526526 | 6/2013 |
| JP | 2013531025 A | 8/2013 |
| JP | 2017502993 A | 1/2017 |
| JP | 2017502994 A | 1/2017 |
| JP | 2017503000 A | 1/2017 |
| JP | 2017522346 A | 8/2017 |
| WO | 93/09664 A1 | 5/1993 |
| WO | 95/26957 A1 | 10/1995 |
| WO | 97/29109 A1 | 8/1997 |
| WO | 98/56376 A1 | 12/1998 |
| WO | 01/16097 A1 | 3/2001 |
| WO | 01/60806 A2 | 8/2001 |
| WO | 03/029422 A2 | 4/2003 |
| WO | 03/045924 A1 | 6/2003 |
| WO | 03/082191 A2 | 10/2003 |
| WO | 2004024719 A1 | 3/2004 |
| WO | 2004099201 A1 | 11/2004 |
| WO | 2004111034 A1 | 12/2004 |
| WO | 2005000817 A2 | 1/2005 |
| WO | 2005028480 A2 | 3/2005 |
| WO | 2005035532 A1 | 4/2005 |
| WO | 2005040151 A1 | 5/2005 |
| WO | 2005106286 A1 | 11/2005 |
| WO | 2006002284 A1 | 1/2006 |
| WO | 2006071759 A2 | 7/2006 |
| WO | 2006113704 A2 | 10/2006 |
| WO | 2007048067 A2 | 4/2007 |
| WO | 2007106142 A2 | 9/2007 |
| WO | 2007127448 A2 | 11/2007 |
| WO | 2007131991 A1 | 11/2007 |
| WO | 2007138072 A2 | 12/2007 |
| WO | 2007145921 A1 | 12/2007 |
| WO | 2008122615 A1 | 10/2008 |
| WO | 2008138842 A1 | 11/2008 |
| WO | 2008138843 A1 | 11/2008 |
| WO | 2009020642 A1 | 2/2009 |
| WO | 2009025823 A1 | 2/2009 |
| WO | 2010011666 A2 | 1/2010 |
| WO | 2011022440 A2 | 2/2011 |
| WO | 2011112766 A2 | 9/2011 |
| WO | 2011154327 A1 | 12/2011 |
| WO | 2012007539 A1 | 1/2012 |
| WO | 2012055942 A1 | 5/2012 |
| WO | 2012116237 A2 | 8/2012 |
| WO | 2013105063 A1 | 7/2013 |
| WO | 2014023385 A1 | 2/2014 |
| WO | 2014072881 A1 | 5/2014 |
| WO | 2014113584 A1 | 7/2014 |
| WO | 2014121885 A1 | 8/2014 |
| WO | 2015107493 A1 | 7/2015 |
| WO | 2015107494 A1 | 7/2015 |
| WO | 2015107495 A1 | 7/2015 |
| WO | 2016007731 A1 | 1/2016 |
| WO | 2016081290 A1 | 5/2016 |
| WO | 2016100116 A1 | 6/2016 |
| WO | 2016103155 A1 | 6/2016 |
| WO | 2016112295 A1 | 7/2016 |
| WO | 2016125169 A1 | 8/2016 |
| WO | 2016161282 A1 | 10/2016 |
| WO | 2016203404 A1 | 12/2016 |
| WO | 2016203405 A1 | 12/2016 |
| WO | 2016203406 A1 | 12/2016 |
| WO | 2017059207 A1 | 4/2017 |
| WO | 2017111076 A | 6/2017 |
| WO | 2017156397 A1 | 9/2017 |
| WO | 2017162524 A1 | 9/2017 |
| WO | 2017211303 A1 | 12/2017 |
| WO | 2017216706 A1 | 12/2017 |
| WO | 2018013597 A1 | 1/2018 |
| WO | 2018057884 A1 | 3/2018 |
| WO | 2018081091 A1 | 5/2018 |
| WO | 2018130928 A1 | 7/2018 |
| WO | 2018136264 A1 | 7/2018 |
| WO | 2018136265 A1 | 7/2018 |
| WO | 2018172984 A1 | 9/2018 |
| WO | 2018187401 A1 | 10/2018 |
| WO | 2018187423 A1 | 10/2018 |
| WO | 2018218133 A1 | 11/2018 |
| WO | 2019051084 A1 | 3/2019 |
| WO | 2019075265 A1 | 4/2019 |
| WO | 2019118909 A1 | 6/2019 |
| WO | 2019199792 A1 | 10/2019 |
| WO | 2019212990 A1 | 11/2019 |
| WO | 2019212991 A1 | 11/2019 |
| WO | 2020055761 A1 | 3/2020 |
| WO | 2020061101 A1 | 3/2020 |
| WO | 2020094104 A1 | 5/2020 |
| WO | 2020106647 A2 | 5/2020 |
| WO | 2020108590 A1 | 6/2020 |
| WO | 2020132597 A1 | 6/2020 |
| WO | 2021091967 A1 | 5/2021 |

OTHER PUBLICATIONS

Adam et al., "Concise synthesis of 1H-pyrazin-2-ones and 2-aminopyrazines," Synlett 2004, No. 11, pp. 2031-2033, compounds 6a, 6c and 6d.

Akhapkina et al., "Fundamentals of modulatory concept and classification of modulatory drugs," RMZh, N19, 2012, pp. 933-951.

Amato et al., "Modulation of a proteolytic enzyme activity by means of photochromic inhibitor," Journal of Photochemistry and Photobiology B: Biology, 1995, vol. 28(1), pp. 71-75.

Anonymous: RMC-4630, Jul. 20, 2018, Retrieved from the Internet: URL:https://integrity.clarivate.com/integrity/xmlxsl/pk_prod_list.exec_form_pro_pr, pp. 1-1.

ANONYMOUS: 3-Amino-6-phenyl-4-trifluoromethylpyridine, C12H9F3N2, PubChem CID 129781129, retrieved from https://pubchem.ncbi.nlm.nih.gov/compound/129781129 on Oct. 20, 2021, 8 pages.

Banker et al., Modern Pharmaceutics, Third Edition, Revised and Expanded, 1976, pp. 451 and 596.

Belanger et al., "Discovery of imidazo [1,2-a] pyrazine-based Aurora kinase inhibitors," Bioorganic & Medicinal Chemistry Letters, 2010, vol. 20, No. 17, pp. 5170-5174.

Belikov, Pharmaceutical chemistry. Fourth edition, revised and enlarged, Chapter 2.6 "The relationship between the chemical structure, the properties of substances and their effects on the body," Moscow "MEDpress-inform", 2007, pp. 27-29. Translation.

(56) References Cited

OTHER PUBLICATIONS

Belton, "A Novel N -> S Oxygen Migration in 2,1,3-Benzoxadiazole Systems," Proceedings of the Royal Irish Academy, Section B: Biological, Geological, and Chemical Science, Royal Irish Academy, 1974, vol. 74, pp. 185-192.
Bhatia et al., "A Review on Bioisosterism: A Rational Approach for Drug Design and Molecular Modification," Pharmacologyonline, 2011, vol. 1, pp. 272-299.
Boamah et al., "Pyridazines. XXXVII [1,2]. Novel Triazanaphthalene Derivatives via Intramolecular Cyclization Reactions of vic-Disubstituted Pyridazines," Journal of Heterocyclic Chemistry, 1988, vol. 25, No. 3, pp. 879-883.
CAS Registry No. 174531-55-6, Entry date Mar. 26, 1996.
CAS Registry No. 3657-73-6, Entry date Nov. 16, 1984.
CAS Registry No. 1349160-17-3; STN Entry Date Dec. 5, 2011; 5-(2-Chloro-4-methoxyphenyl)-3,6-diethyl-N-(1-ethylbutyl)-2-pyrazinamine, 1 page.
CAS Registry No. 1349131-06-1; STN Entry Date Dec. 5, 2011; 3,6-Diethyl-N-(1-ethylpropyl)-5-[6-(1-methylethyl)-2-[(2-methylpropyl)amino]-3-pyridinyl]-2-pyrazinamine, 1 page.
CAS Registry No. 1350134-68-7; STN Entry Date Dec. 7, 2011; N-[(3S,4S)-4-Butoxytetrahydro-3-furanyl]-5-(2-chloro-4-methoxyphenyl)-3,6-diethyl-2-pyrazinamine, 1 page.
CAS Registry No. 1027540-93-7; STN Entry Date Jun. 12, 2008; 5-(2,4-Dichlorophenyl)-N-(4-ethoxy-1-methyl-3-pyrrolidinyl)-3,6-diethyl-2-pyrazinamine, 1 page.
CAS Registry No. 1026750-06-0; STN Entry Date Jun. 9, 2008; 5-[2-(Cyclohexyloxy)-6-methyl-4-pyrimidinyl]-2,3-dihydro-2-[3-methyl-5-(4-methyl-1-piperazinyl)-2-pyrazinyl]-2-thiazolamine, 1 page.
CAS Registry No. 777880-58-7; Entry date Nov. 10, 2004; 2,1,3-Benzoxadiazole, 4-(1-piperidinyl)-7-(1-piperidinylsulfonyl)-(CA Index Name), 1 page.
CAS Registry No. 777873-58-2; Entry date Nov. 10, 2004; 2,1,3-Benzoxadiazole, 4-(4-methyl-1-piperidinyl)-7-[(4-methyl-1-piperidinyl)sulfonyl]-(CA Index Name), 1 page.
CAS Registry No. 777873-55-9; Entry date Nov. 10, 2004; 2,1,3-Benzoxadiazole, 4-(3-methyl-1-piperidinyl)-7-[(3-methyl-1-piperidinyl)sulfonyl]-(CA Index Name), 1 page.
CAS Registry No. 1918848-03-9, Entry date May 26, 2016; 4-Piperidinamine, 1-[2-(1-methylethyl)pyrazolo[1,5-a] pyrazin-4-yl]-(CA Index Name), 1 page.
CAS Registry No. 1918847-95-6, Entry date May 26, 2016; 4-Piperidinamine, 1-[2-(1,1-dimethylethyl)pyrazolo[1,5-a] pyrazin-4-yl]-(CA Index Name), 1 page.
Chen et al., "Allosteric inhibition of SHP2 phosphatase inhibits cancers driven by receptor tyrosine kinases," Nature, 2016, vol. 535, pp. 148-152.
Chen et al., "Identification of demethylincisterol A3 as a selective inhibitor of protein tyrosine phosphatase Shp2," European Journal of Pharmacology, 2017, vol. 795, pp. 124-133.
Dardaei et al., "SHP2 inhibition restores sensitivity to ALK inhibitors in resistant ALK-rearranged non-small cell lung cancer," Nature Medicine, 2018, vol. 24, No. 4, pp. 512-517.
Dardaei et al., Supplemental Material, "SHP2 inhibition restores sensitivity to ALK inhibitors in resistant ALK-rearranged non-small cell lung cancer," Nature Medicine, Mar. 5, 2018, vol. 24, 58 pages.
Database Registry [Online] Chemical Abstracts Service, Columbus, Ohio, US; Apr. 27, 2011 (Apr. 27, 2011), XP002787392, retrieved from STN Database accession No. 1286273-60-6 compound with CAS registry No. 1286273-60-6, 1 page.
Database Registry [Online] Chemical Abstracts Service, Columbus, Ohio, US; Nov. 9, 2007 (Nov. 9, 2007), XP002787393, retrieved from stn Database accession No. 952723-55-6 compound with CAS registry No. 952723-55-6, 1 page.
Database Registry [Online] Chemical Abstracts Service, Columbus, Ohio, US; Jan. 22, 2015 (Jan. 22, 2015), XP002787394, retrieved from stn Database accession No. 1643677-14-8 compound with CAS registry No. 1643677-14-8, 1 page.
Database Registry [Online] Chemical Abstracts Service, Columbus, Ohio, US; Nov. 16, 1984 (Nov. 16, 1984), XP002787395, retrieved from stn Database accession No. 86663-20-9 compound with CAS registry No. 86663-20-9, 1 page.
Database Registry [Online] Chemical Abstracts Service, Columbus, Ohio, US; Dec. 18, 1984 (Dec. 18, 1984), XP002787396, retrieved from stn Database accession No. 93034-72-1 compound with CAS registry No. 93034-72-1, 1 page.
Database Registry [Online] Chemical Abstracts Service, Columbus, Ohio, US; Nov. 16, 1984 (Nov. 16, 1984), XP002787397, retrieved from stn Database accession No. 68559-45-5 compound with CAS registry No. 68559-45-5, 1 page.
Database Registry [Online] Chemical Abstracts Service, Columbus, Ohio, US; Nov. 23, 2004 (Nov. 23, 2004), XP002787398, retrieved from stn Database accession No. 786652-86-6 compound with CAS registry No. 786652-86-6, 1 page.
Database Registry [Online] Chemical Abstracts Service, Columbus, Ohio, US; Nov. 23, 2004 (Nov. 23, 2004), XP002787399, retrieved from stn Database accession No. 786652-83-3 compound with CAS registry No. 786652-83-3, 1 page.
Database Registry [Online] Chemical Abstracts Service, Columbus, Ohio, US; Apr. 6, 1990 (Apr. 6, 1990), XP002787400, retrieved from stn Database accession No. 126317-60-0 compound with CAS registry No. 126317-60-0, 1 page.
Database Registry [Online] Chemical Abstracts Service, Columbus, Ohio, US; May 31, 2006 (May 31, 2006), XP002787401, retrieved from stn Database accession No. 886208-65-7 compound with CAS registry No. 886208-65-7, 1 page.
Database Registry [Online] Chemical Abstracts Service, Columbus, Ohio, US; Aug. 27, 2010 (Aug. 27, 2010), XP002787406, retrieved from stn Database accession No. 1239320-06-9 compound with CAS registry No. 1239320-06-9, 1 page.
Database Registry, Compound with CAS Registry No. 78246-19-2. 3-Methyl-5-(2-methylpropyl)-2-(phenylthio)pyrazine, Nov. 16, 1984. Citation is not enclosed due to copyright restrictions.
Database Registry, Compound with CAS Registry No. 15033-82-6. 4-[(3,5,6-Trimethyl-2-pyrazinyl)sulfonyl]benzenamine, Nov. 16, 1984. Citation is not enclosed due to copyright restrictions.
Database Registry, Compound with CAS Registry No. 1119718-06-7, 1,4-Dioxa-8-azaspiro[4.5]decane, 8-[5-(6,7-dimethoxy-4-cinnolinyl)-3-methyl-2-pyridinyl], Mar. 12, 2009, 1 page.
Database Registry, Compound with CAS Registry No. 1384576-77-5, 1,4-Dioxa-8-azaspiro[4.5]decane, 8-[6-(3-fluorophenyl)-4-methyl-3-pyridazinyl], Jul. 27, 2012. 1 page.
Database Registry, RN 893294-18-3, entered STN Jul. 17, 2006, 1 page.
Database Registry, RN 893792-24-0, entered STN Jul. 17, 2006, 1 page.
Database Registry, RN 893792-68-2, entered STN Jul. 17, 2006, 1 page.
Database Registry, RN 893794-10-0, entered STN Jul. 17, 2006, 1 page.
Database Registry, RN 893795-14-7, entered STN Jul. 17, 2006, 1 page.
Database Registry, RN 893796-38-8, entered STN Jul. 17, 2006, 1 page.
Database Registry, RN 893796-42-4, entered STN Jul. 17, 2006, 1 page.
Database Registry, RN 893797-57-4, entered STN Jul. 17, 2006, 1 page.
Masuda et al., "Synthesis of Alkoxy-, (Alkylthio)-, Phenoxy-, and (Phenylthio) pyrazines and Their Olfactive Properties," J. Agric. Food Chem., 1986, vol. 34, No. 2, pp. 377-381.
Mehta et al., "Microwave-Assisted Palladium-Catalyzed Phosphonium Coupling of 2(1H)-Pyrazinones," J. Org. Chem., 2010, vol. 75, No. 3, pp. 976-979.
Meurer et al., "Synthesis and SAR of 5,6-diarylpyridines as human CB1 inverse agonists," Bioorganic & Medicinal Chemistry Letters, 2005, vol. 15, pp. 645-651.
Mohi et al., "The role of Shp2 (PTPN11) in cancer," Current Opinion in Genetics & Development, 2007, vol. 17, pp. 23-30.

(56) References Cited

OTHER PUBLICATIONS

Monson et al., "The reactions of some ketones with hexamethylphosphoric triamide a novel synthesis of 3,5-dialkyl-2,6-diphenylpyridines," Tetrahedron, 1975, vol. 31, pp. 1145-1147.
Neel et al., "Differential subcellular localization regulates oncogenic signaling by ROS1 kinase fusion proteins," Cancer Research, 2018, vol. 79, No. 3, pp. 546-556.
Nichols et al., "RAS nucleotide cycling underlies the SHP2 phosphatase dependence of mutant BRAF-, NF1- and RAS-driven cancers," Nat Cell Biol., 2018, vol. 20(9), pp. 1064-1073.
Nichols et al., "Efficacy of SHP2 phosphatase inhibition in cancers with nucleotide-cycling oncogenic RAS, RAS-GTP dependent oncogenic BRAF and NF1 loss," bioRxiv preprint first posted online Sep. 14, 2017, 16 pages.
Ozawa et al., "The importance of CH/π hydrogen bonds in rational drug design: An ab initio fragment molecular orbital study to leukocyte-specific protein tyrosine (LCK) kinase," Bioorganic & Medicinal Chemistry, 2008, vol. 16, p. 10311-10318.
Patani et al., "Bioisosterism: A Rational Approach in Drug Design," Chemical Reviews, 1996, vol. 96, pp. 3147-3176.
Perez et al., "Palladium-Catalyzed C,N-Cross Coupling Reactions of 3-Halo-2-aminopyridines," Organic Letters, 2011, vol. 13, No. 8, pp. 1984-1987, compound 5 of Figure 2; compounds 12 and 13 of Scheme 2.
Pisaneschi et al., "The 3S Enantiomer Drives Enolase Inhibitory Activity in SF2312 and Its Analogues," Molecules, 2019, vol. 24(13), 2510, pp. 1-18.
Ran et al., "Sticking It to Cancer with Molecular Glue for SHP2," Cancer Cell, Aug. 8, 2016, vol. 30, pp. 194-196.
Rauen, "The RASopathies," Annu Rev Genomics Hum Genet., 2013, vol. 14, pp. 355-369.
Registry List of Novel Compounds, STN 2015, 5 pages.
Ruess et al., "Mutant KRAS-driven cancers depend on PTPN11/SHP2 phosphatase," Nature Medicine, 2018, vol. 24, pp. 954-960.
Sansfacon et al., "SHP-2 phosphatase contributes to KRAS-driven intestinal oncogenesis but prevents colitis-associated cancer development," Oncotarget, 2016, vol. 7, No. 40, pp. 65676-65695.
Sayer, "The Synthesis of Imidazo[1,2-a] pyrazines as Inhibitors of the VirB11 ATPase and their Incorporation into Bivalent Compounds," Diss. UCL (University College London), 2013, 396 pages.
Sun et al., "Selective inhibition of leukemia-associated SHP2E69K mutant by the allosteric SHP2 inhibitor SHP099," Leukemia, Jan. 30, 2018, vol. 32, No. 5, pp. 1246-1249.
Tol et al., "Chemotherapy, bevacizumab, and cetuximab in metastatic colorectal cancer," The New England Journal of Medicine, 2009, vol. 360(6), pp. 563-572.
Vernier et al., "Thioether benzenesulfonamide inhibitors of carbonic anhydrases II and IV: Structure-based drug design, synthesis, and biological evaluation," Bioorganic & Medicinal Chemistry, 2010, vol. 18, No. 9, pp. 3307-3319.
Vippagunta et al., "Crystalline solids," Advanced Drug Delivery Reviews, 2001, vol. 48, pp. 3-26.
Voena et al., "The Tyrosine Phosphatase Shp2 Interacts with NPM-ALK and Regulates Anaplastic Lymphoma Cell Growth and Migration," Cancer Research, 2007, vol. 67, No. 9, pp. 4278-4286.
Wang et al., "Palladium-Catalyzed Direct Heck Arylation of Dual π-Deficient/π-Excessive Heteroaromatics. Synthesis of C-5 Arylated Imidazo[1,5-a]pyrazines," Organic Letters, 2008, vol. 10, No. 14, pp. 2923-2926.
Wayback Internet Archive Machine, Oct. 27, 2007, Retrieved from: https://xumuk.ru/encyklopedia/1022.html—Machine Translation.
Wolff, "Burger's Medicinal Chemistry and Drug Discovery," Fifth Edition, vol. I: Principles and Practice, New York: John Wiley & Sons, 1994, pp. 975-977.
Wustrow et al., "Aminopyrazine CB1 receptor inverse agonists," Bioorganic & Medicinal Chemistry Letters, 2008, vol. 18, No. 11, pp. 3376-3381.
Xiao et al., "Myeloid-restricted ablation of Shp2 restrains melanoma growth by amplifying the reciprocal promotion of CXCL9 and IFN-γ production in tumor microenvironment," Oncogene, 2018, vol. 37, No. 37, pp. 5088-5100.
Xie et al., "Allosteric Inhibitors of SHP2 with Therapeutic Potential for Cancer Treatment," Journal of Medicinal Chemistry, 2017, vol. 60, pp. 10205-10219.
Yamanishi et al., "Syntheses of Trimethyl Pyrazine Derivatives and their Antibacterial Properties," Yakugaku Zasshi, 1967, vol. 87, No. 1, pp. 105-107. Translation
Yatsyuk et al., "General principles of xenobiotic metabolism as a basis for the development of methods for the synthesis of prodrugs," State Educational Institution of Higher Vocational Education Kursk State Medical University, Department of Bioorganic Chemistry, Elective course textbook, 2009, pp. 71-84. Translation.
Yu et al., "A phase 1/2 trial of ruxolitinib and erlotinib in patients with EGFR-mutant lung adenocarcinomas with acquired resistance to erlotinib," Journal of Thoracic Oncology, 2017, vol. 12, No. 1, pp. 102-109.
Zefirova et al., "On the Origin and Development of the Concept of Bioisosterism," Vestn Mosk Un-Ta Ser 2 Chemistry, 2002, vol. 43(4), pp. 251-256. Machine Translation.
Zhao et al., "SHP2 inhibition triggers anti-tumor immunity and synergizes with PD-1 blockade," Acta Pharmaceutica Sinica B, 2019, vol. 9, No. 2, pp. 304-315.
Zou et al., "PF-06463922 is a potent and selective next-generation ROS1/ALK inhibitor capable of blocking crizotinib-resistant ROS1 mutations," PNAS, 2015, vol. 112, No. 11, pp. 3493-3498.
9-(4-chlorophenyl)-5-(4-morpholinyl)tetrazolo[1,5-c]-thieno[3,2-e]pyrimidine, entered STN Jul. 17, 2006, 1 page.
9-(4-chlorophenyl)-5-(4-morpholinyl)thieno[3,2-e]-1,2,4-triazolo[4,3-c]pyrimidine, entered STN Jul. 17, 2006, 1 page.
9-phenyl-5-(1-pyrrolidinyl)tetrazolo[1,5-c]thieno[3,2-e]pyrimidine, entered STN Jul. 17, 2006, 1 page.
9-phenyl-5-(1-pyrrolidinyl)thieno[3,2-e]-1,2,4-triazolo[4,3-c]pyrimidine, entered STN Jul. 17, 2006, 1 page.
International Search Report and Written Opinion mailed on Dec. 20, 2017, for International Application No. PCT/US2017/041577, 18 pages.
International Search Report and Written Opinion mailed on Sep. 21, 2018, for International Application No. PCT/US2018/013018, 10 pages.
International Search Report and Written Opinion mailed on Apr. 5, 2018, for International Application No. PCT/US2018/013023, 13 pages.
International Search Report and Written Opinion mailed on Jan. 24, 2019, for International Application No. PCT/US2018/055502, 16 pages.
International Search Report and Written Opinion mailed on Dec. 12, 2018, for International Application No. PCT/US2018/049744, 13 pages.
International Search Report and Written Opinion mailed on Feb. 20, 2019, for International Application No. PCT/US2018/065817, 11 pages.
Chen et al., "Copper-catalyzed C5-selective thio/selenocyanation of 8-aminoquinolines", Org. Chem. Front., 2017, vol. 4, pp. 130-134.
Elderfield et al., "The Reaction of 8-Nitroquinoline with Thiophenol-Thiopehenoxide Ion. An Example of Anionic Substitution", J. Am. Chem. Society, 195, vol. 74, pp. 2953-2959.
Winter et al., "The Preparation of Some 2-Pyridyl and 8-Quinolyl Phenyl Sulfides and Sulfones", J. Am. Chem. Society, 1940, vol. 62, pp. 3508-3510.
Zawistoski, Michael P., "The Synthesis and Chemistry of 5-Carboxy-8-mercaptoquinoline Hydrochloride Monohydrate: An intermediate in the Synthesis of Novel H+, K+-ATPase Inhibitors", J. Heterocyclic Chemistry, 1991, vol. 28, No. 3, pp. 657-665.
Zhu et al., "Copper-Mediated Remote C—H Bond Chaldogenation of Quinolines on the C5 Position", Organic Letters, 2015, vol. 17, No. 22, pp. 5528-5331.
Database Registry, RN 893797-61-0, entered STN Jul. 17, 2006, 1 page.
Database Registry, RN 893799-39-8, entered STN Jul. 17, 2006, 1 page.
Database Registry, RN 893799-43-4, entered STN Jul. 17, 2006, 1 page.

(56) References Cited

OTHER PUBLICATIONS

Database Registry, RN 893799-47-8, entered STN Jul. 17, 2006, 1 page.
Database Registry, RN 893801-34-8, entered STN Jul. 17, 2006, 1 page.
Database Registry, RN 893803-59-3, entered STN Jul. 17, 2006, 1 page.
Database Registry, RN 893806-50-3, entered STN Jul. 17, 2006, 1 page.
Database Registry, RN 893807-90-4, entered STN Jul. 17, 2006, 1 page.
Database Registry, RN 893808-63-4, entered STN Jul. 17, 2006, 1 page.
Database Registry, RN 893810-11-2, entered STN Jul. 17, 2006, 1 page.
Database Registry, RN 1957154-25-4, 1956595-47-3, entered STN Jul. 21, 2016, 1 page.
Database Registry, RN 1949800-28-5, entered STN Jul. 11, 2016, 1 page.
Database Registry, RN 1952095-25-8, entered STN Jul. 14, 2016, 1 page.
Database Registry, RN 1953046-94-0, 1952680-38, entered STN Jul. 15, 2016, 1 page.
Database Registry, RN 1629858-36-1, entered STN Oct. 23, 2014, 1 page.
Database Registry, RN 1028262-30-7, entered STN Jun. 15, 2008, 1 page.
Database Registry, RN 1027952-21-1, entered STN Jun. 13, 2008, 1 page.
Database Registry, RN 1026418-24-5, entered STN Jun. 8, 2008, 1 page.
Database Registry, RN 1026270-53-0, entered STN Jun. 8, 2008, 1 page.
Database Registry, RN 1026250-49-6, entered STN Jun. 8, 2008, 1 page.
Database Registry, RN 1334203-33-6, entered STN Sep. 30, 2011, 1 page.
Database Registry, RN 1334203-32-5, entered STN Sep. 30, 2011, 1 page.
Database Registry, RN 900624-41-1, entered STN Aug. 11, 2006, 1 page.
Database Registry, RN 893813-11-1, entered STN Jul. 17, 2006, 1 page.
Database Registry, RN 893813-68-2, entered STN Jul. 17, 2006, 1 page.
Database Registry, RN 590404-14-1, entered STN Sep. 22, 2003, 1 page.
Database Registry, RN 1860803-32-2, entered STN Feb. 5, 2016, 1 page.
Davare et al., "Foretinib is a potent inhibitor of oncogenic ROS1 fusion proteins," PNAS, 2013, vol. 110, No. 48, pp. 19519-19524.
Dayakar et al., "Synthesis and antimycobacterial activity of 1H-1,2,3-triazolylisonicotinohydrazi," Indian Journal of Chemistry, Section B: Organic Chemistry Including Medicinal Chemistry, 2016, vol. 55B, pp. 882-887, intermediates 9c to 9f.
Ellsworth et al., "Discovery of pyrazine carboxamide CB1 antagonists: The introduction of a hydroxyl group improves the pharmaceutical properties and in vivo efficacy of the series," Bioorganic & Medicinal Chemistry Letters, 2007, vol. 17, No. 14, pp. 3978-3982.
European Patent Office, European Office Action for European Application No. 18701883.3, dated Sep. 15, 2021, 6 pages.
European Patent Office, European Office Action for European Application No. 18701882.5, dated Mar. 23, 2022, 4 pages.
European Patent Office, International Preliminary Report on Patentability for PCT International Application No. PCT/US2019/026543, dated Oct. 13, 2020, 15 pages.
European Patent Office, International Search Report mailed on Sep. 2, 2019, for International Application No. PCT/US2019/026543, 9 pages.
Fedele et al., "SHP2 Inhibition Prevents Adaptive Resistance to MEK inhibitors in Multiple Cancer Models," Cancer Discov., 2018, vol. 8, No. 10, pp. 1237-1249.
Fialkov, "Solvent as a means of controlling a chemical process," Publishing house "Chemistry", 1990, p. 240.
Fortanet et al., "Allosteric Inhibition of SHP2: Identification of a Potent, Selective, and Orally Efficacious Phosphatase Inhibitor," Journal of Medicinal Chemistry, 2016, vol. 59, pp. 7773-7782.
Fundamentals of Medical Prevention. Educational and Methodological Manual for Students and Cadets of Professional Development Cycles of State Professional Educational Institutions. Novosibirsk, 2016, UDC 614.2-084, BBC 51.1(2)2, pp. 13-21, Available online https://rcmpnso.ru/profila/m_mater/docs/osnovi_med_pomoshi.pdf?ysclid=I5wi7xgplo450927514.
Giori et al., "Synthesis of 6,7-Disubstituted Pteridine-2,4-Diones," Heterocycles, 1991, vol. 32, No. 1, 6 pages.
Huang et al, "Discovery of First-in-Class, Potent, and Orally Bioavailable Embryonic Ectoderm Development (EED) Inhibitor with Robust Anticancer Efficacy," Journal of Medicinal Chemistry, 2017, vol. 60, No. 6, pp. 2215-2226.
Hydrates, products of the addition of water (hydration) to molecules, atoms, or ions. M. b. gaseous, liquid, and solid; the last called. crystal hydrates. XUMUK, Wayback internet archive machine, Oct. 27, 2007. (machine translated from Russian) [retrieved Sep. 3, 2021] Retrieved from the Internet: <URL: https://xumuk.ru/encyklopedia/1022.html> 2 pages.
Jiang et al., "Optimal therapeutic positioning of a selective bi-steric inhibitor of MTORC1 in genetically defined cancers," European Journal of Cancer, 2020, vol. 138, pp. S53-S54.
Jordan, "Tamoxifen: A Most Unlikely Pioneering Medicine," Nature Reviews: Drug Discovery, 2003, vol. 2, pp. 205-213.
Krosigk et al., "Expanding the Genetic Alphabet: Pyrazine Nucleosides That Support a Donor-Donor-Acceptor Hydrogen-Bonding Pattern," Helv. Chim. Acta, 2004, vol. 87, pp. 1299-1324.
Larochelle et al., "Identification of an allosteric benzothiazolopyrimidone inhibitor of the oncogenic protein tyrosine phosphatase SHP2," Bioorganic & Medicinal Chemistry, 2017, vol. 25, pp. 6479-6485.
Larochelle et al., "Structural and Functional Consequences of Three Cancer-Associated Mutations of the Oncogenic Phosphatase SHP2," Biochemistry, 2016, vol. 55, No. 15, pp. 2269-2277.
Larochelle et al., "Structural reorganization of SHP2 by oncogenic mutations and implications for oncoprotein resistance to allosteric inhibition," Nature Communications, 2018, vol. 9, No. 1, pp. 1-10.
Leroy et al., "Di-tert-butyl(methyl) phosphonium Tetrafluoroborate," e-EROS Encyclopedia of Reagents for Organic Synthesis, Dec. 31, 2015, pp. 1-7.
Li et al., "Exploring the effect of D61G mutation on SHP2 cause gain of function activity by a molecular dynamics study," Journal of Biomolecular Structure and Dynamics, 2018, vol. 36, No. 14, pp. 3856-3868.
Mainardi et al., "SHP2 is required for growth of KRAS-mutant non-small-cell lung cancer in vivo," Nature Medicine, 2018, vol. 24, pp. 961-967.

* cited by examiner

SUBSTITUTED PYRAZOLOPYRAZINES, IMIDAZOPYRAZINES AND [1,2,4]TRIAZOLOPYRAZINES AS ALLOSTERIC SHP2 INHIBITORS

CROSS REFERENCE TO RELATED APPLICATIONS

This application is a divisional of U.S. patent application Ser. No. 16/518,798, filed Jul. 22, 2019, now U.S. Pat. No. 11,739,093, which is a continuation of International Patent Application No. PCT/US2018/013023, filed Jan. 9, 2018, which claims the benefit of U.S. Provisional Application No. 62/449,530, filed Jan. 23, 2017, the contents of each of which are incorporated herein by reference in their entirety.

FIELD OF THE INVENTION

The present disclosure relates to inhibitors of protein tyrosine phosphatase SHP2 useful in the treatment of diseases or disorders. Specifically, this disclosure is concerned with compounds and compositions inhibiting SHP2, methods of treating diseases associated with SHP2, and methods of synthesizing these compounds.

BACKGROUND OF THE DISCLOSURE

SH2 domain-containing protein tyrosine phosphatase-2 (SHP2) is a non-receptor protein tyrosine phosphatase encoded by the PTPNI1 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors leads to exposure of the catalytic site resulting in enzymatic activation of SHP2.

Mutations in the PTPNI1 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present disclosure fulfill the need for small molecules to that inhibit the activity of SHP2.

SUMMARY OF THE DISCLOSURE

The present disclosure relates to compounds capable of inhibiting the activity of SHP2. The disclosure further provides a process for the preparation of compounds disclosed herein, pharmaceutical preparations comprising such compounds and methods of using such compounds and compositions in the management of diseases or disorders associated with the aberrant activity of SHP2.

One aspect of the disclosure relates to compounds of Formula I':

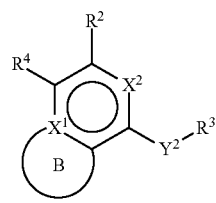

and pharmaceutically acceptable salts, prodrugs, solvates, hydrates, tautomers, or isomers thereof, wherein:

$R^4$ is H or

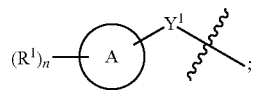

A is a 5- to 12-membered monocyclic or polycyclic cycloalkyl, heterocycloalkyl, aryl, or heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2NH$—, —$C(=CH_2)$—, —CH—, or —$S(O)$—;

$X^1$ is N or C;

$X^2$ is N or CH;

B, including the atoms at the points of attachment, is a monocyclic or polycyclic 5- to 12-membered heterocycle or a monocyclic or polycyclic 5- to 12-membered heteroaryl;

$R^2$ is —H, —$OR^b$, —$NR^5R^6$, —CN, —$C_1$-$C_6$alkyl, —$C_2$-$C_6$alkenyl, —$C_4$-$C_8$cycloalkenyl, —$C_2$-$C_6$alkynyl, —$NH_2$, halogen, —$C(O)OR^b$, —$C_3$-$C_8$cycloalkyl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$Y^2$ is —$NR^a$—, —$(CR^a_2)_m$—, —C(O)—, —$C(R^a)_2NH$—, —$(CR^3_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of Y², as drawn, is bound to the ring and the bond on the right side of the Y² moiety, as drawn, is bound to R³;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^3$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

R³ is —H, —C$_1$-C$_6$alkyl, a 3- to 12-membered monocyclic or polycyclic heterocycle, —C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R³ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R⁵ and R⁶ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR⁷, —SR⁷, halogen, —NR⁷R⁸, —NO$_2$, or —CN;

R⁷ and R⁸ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to compounds of Formula I:

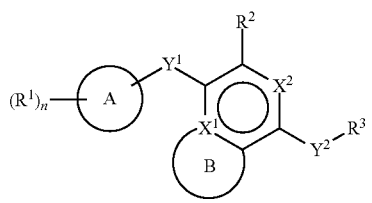

I and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

R¹ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR⁵R⁶, —SR⁵, —S(O)$_2$NR⁵R⁶, —S(O)$_2$R⁵, —NR⁵S(O)$_2$NR⁵R⁶, —NR⁵S(O)$_2$R⁶, —S(O)NR⁵R⁶, —S(O)R⁵, —NR⁵S(O)NR⁵R⁶, —NR⁵S(O)R⁶, —C(O)R⁵, or —CO$_2$R⁵, wherein each alkyl, alkenyl, cycloalkenyl, alkynyl, or cycloalkyl is optionally substituted with one or more —OH, halogen, —NO$_2$, oxo, —CN, —R⁵, —OR⁵, —NR⁵R⁶, —SR⁵, —S(O)$_2$NR⁵R⁶, —S(O)$_2$R⁵, —NR⁵S(O)$_2$NR⁵R⁶, —NR⁵S(O)$_2$R⁶, —S(O)NR⁵R⁶, —S(O)R⁵, —NR⁵S(O)NR⁵R⁶, —NR⁵S(O)R⁶, heterocycle, aryl, or heteroaryl;

Y¹ is —S—, a direct bond, —NH—, —S(O)$_2$—, —S(O)$_2$—NH—, —C(=CH$_2$)—, —CH—, or —S(O)—;

X¹ is N or C;

X² is N or CH;

B, including the atoms at the points of attachment, is a monocyclic or polycyclic 5- to 12-membered heterocycle or a monocyclic or polycyclic 5- to 12-membered heteroaryl;

R² is —H, —OR$^b$, —NR⁵R⁶, —CN, —C$_1$-C$_6$alkyl, —C$_2$-C$_6$alkenyl, —C$_4$-C$_8$cycloalkenyl, —C$_2$-C$_6$alkynyl, —NH$_2$, halogen, —C(O)OR$^b$, —C$_3$-C$_8$cycloalkyl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO$_2$, oxo, —CN, —R⁵, —OR⁵, —NR⁵R⁶, —SR⁵, —S(O)$_2$NR⁵R⁶, —S(O)$_2$R⁵, —NR⁵S(O)$_2$NR⁵R⁶, —NR⁵S(O)$_2$R⁶, —S(O)NR⁵R⁶, —S(O)R⁵, —NR'S(O)NR⁵R⁶, —NR⁵S(O)R⁶, heterocycle, aryl, or heteroaryl; and wherein the heterocyclyl or heteroaryl is not attached via a nitrogen atom;

Y² is —NR$^a$—, —(CR$^a$$_2$)$_m$—, —C(O)—, —C(R$^a$)$_2$NH—, —(CR$^a$$_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y², as drawn, is bound to the ring and the bond on the right side of the Y² moiety, as drawn, is bound to R³;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R⁵, —OR⁵, —NR⁵R⁶, —SR⁵, —S(O)$_2$NR⁵R⁶, —S(O)$_2$R⁵, —NR⁵S(O)$_2$NR⁵R⁶, —NR⁵S(O)$_2$R⁶, —S(O)NR⁵R⁶, —S(O)R⁵, —NR⁵S(O)NR⁵R⁶, —NR⁵S(O)R⁶, heterocycle, aryl, heteroaryl, —(CH$_2$)$_n$OH, —C$_1$-C$_6$alkyl, —CF$_3$, —CHF$_2$, or —CH$_2$F;

R³ is —H, —C$_1$-C$_6$alkyl, a 3- to 12-membered monocyclic or polycyclic heterocycle, —C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to compounds of Formula II:

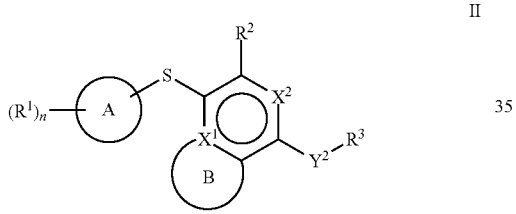

II and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$ NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

X$^1$ is N or C;

X$^2$ is N or CH;

B, including the atoms at the points of attachment, is a monocyclic or polycyclic 5- to 12-membered heterocycle or a monocyclic or polycyclic 5- to 12-membered heteroaryl;

R$^2$ is —H, —OR$^b$, —NR$^5$R$^6$, —CN, —C$_1$-C$_6$alkyl, —C$_2$-C$_6$alkenyl, —C$_4$-C$_8$cycloalkenyl, —C$_2$-C$_6$alkynyl, —NH$_2$, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR'S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

Y$^2$ is —NR$^a$—, —(CR$^a{}_2$)$_m$—, —C(O)—, —C(R$^a$)$_2$NH—, —(CR$^2{}_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the ring and the bond on the right side of the Y$^2$ moiety, as drawn, is bound to R$^3$;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is, at each occurrence, selected from the group consisting of —H, —C$_1$-C$_6$alkyl, a 3- to 12-membered monocyclic or polycyclic heterocycle, C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$), NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to compounds of Formula III:

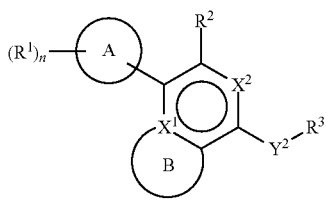

and pharmaceutically acceptable salts, prodrugs, solvates, hydrates, tautomers, or isomers thereof, wherein;

A is a 5- to 12-membered monocyclic or polycyclic cycloalkyl, heterocycloalkyl, aryl, or heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$X^1$ is N or C;

$X^2$ is N or CH;

B, including the atoms at the points of attachment, is a monocyclic or polycyclic 5- to 12-membered heterocycle or a monocyclic or polycyclic 5- to 12-membered heteroaryl;

$R^2$ is —H, —$OR^b$, —$NR^5R^6$, —CN, —$C_1$-$C_6$alkyl, —$C_2$-$C_6$alkenyl, —$C_4$-$C_8$cycloalkenyl, —$C_2$-$C_6$alkynyl, —$NH_2$, halogen, —$C(O)OR^b$, —$C_3$-$C_8$cycloalkyl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —NR'S(O)$NR^5R^6$, —$NR^5S(O)R^6$, heterocycle, aryl, or heteroaryl; and wherein the heterocyclyl or heteroaryl is not attached via a nitrogen atom;

$Y^2$ is —$NR^a$—, —$(CR^a_2)_m$—, —C(O)—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_n$OH, —$C_1$-$C_6$alkyl, —$CF_3$, —$CHF_2$, or —$CH_2F$;

$R^3$ is —H, —$C_1$-$C_6$alkyl, a 3- to 12-membered monocyclic or polycyclic heterocycle, —$C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula IV:

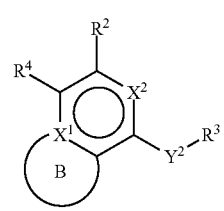

and pharmaceutically acceptable salts, prodrugs, solvates, hydrates, tautomers, or isomers thereof, wherein;

R⁴ is H or

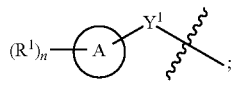

A is a 5- to 12-membered monocyclic or polycyclic cycloalkyl, heterocycloalkyl, aryl, or heteroaryl, provided that the heteroaryl is not

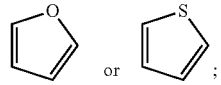 [SMILES: c1ccoc1 ; c1ccsc1]

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^5$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2$—NH—, —$C(=CH_2)$—, —CH—, or —S(O)—;

$X^1$ is N or C;

$X^2$ is N or CH;

B, including the atoms at the points of attachment, is a monocyclic or polycyclic 5- to 12-membered heterocycle or a monocyclic or polycyclic 5- to 12-membered heteroaryl, wherein each heterocycle or heteroaryl is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$;

$R^2$ is —H, —OH, —$NR^5R^6$, —$C_1$-$C_6$alkyl, —$C_2$-$C_6$alkenyl, —$C_4$-$C_8$cycloalkenyl, —$C_2$-$C_6$alkynyl, —$NH_2$, halogen, —$C_3$-$C_8$cycloalkyl, or heterocyclyl containing 1-5 heteroatoms selected from the group consisting of N, S, P, and O; wherein each alkyl, alkenyl, cycloalkenyl, alkynyl, cycloalkyl, or heterocyclyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl is not attached via a nitrogen atom;

$Y^2$ is —$NR^a$—, —$(CR^a_2)_m$—, —C(O)—, —$C(R^a)_2NH$—, —$(CR^2_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR'S(O)_2R^6$, —$S(O)NR^5R^6$, —$S(O)R^5$, —$NR^5S(O)NR^5R^6$, —$NR'S(O)R^6$, heterocycle, aryl, heteroaryl, —$(CH_2)OH$, —$C_1$-$C_6$alkyl, —$CF_3$, —$CHF_2$, or —$CH_2F$;

$R^3$ is —H, —$C_1$-$C_6$alkyl, a 3- to 12-membered monocyclic or polycyclic heterocycle, —$C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$, provided that the heterocycle formed by the combination of $R^3$ and $R^a$ is not an optionally substituted piperazinyl;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula IV that are compounds of Formula IV-Q:

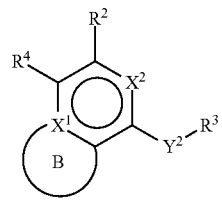

IV-Q and pharmaceutically acceptable salts, prodrugs, solvates, hydrates, tautomers, or isomers thereof, wherein;

$R^4$ is H or

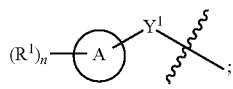

A is a 5- to 12-membered monocyclic or polycyclic aryl or heteroaryl, provided that the heteroaryl is not

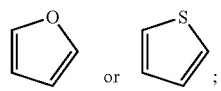 [SMILES: c1ccoc1 ; c1ccsc1]

$R^1$ is independently, at each occurrence, —H, —OR$^5$, halogen, —C$_1$-C$_6$alkyl, —CN, or —NR$^5$R$^6$;
$Y^1$ is —S— or a direct bond;
$X^1$ is N or C;
$X^2$ is N or CH;
B, including the atoms at the points of attachment, is a monocyclic or polycyclic 5- to 12-membered heterocycle or a monocyclic or polycyclic 5- to 12-membered heteroaryl, wherein each heterocycle or heteroaryl is optionally substituted with one or more —C$_1$-C$_6$alkyl, —OH, —NH$_2$, oxo, —(CH$_2$)$_n$NH$_2$, —(CH$_2$)$_n$OH, —CF$_3$, —CHF$_2$, or —CH$_2$F;
$R^2$ is —H, —OH, —NR$^5$R$^6$, —C$_1$-C$_6$alkyl, or —NH$_2$; wherein each alkyl is optionally substituted with one or more —OH, halogen, —OR$^5$, or —NR$^5$R$^6$;
$Y^2$ is —NR$^a$—, wherein the bond on the left side of Y$^2$, as drawn, is bound to the ring and the bond on the right side of the Y$^2$ moiety, as drawn, is bound to R$^3$;
$R^3$ is combined with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, —(CH$_2$)$_n$NH$_2$, —(CH$_2$)$_n$OH, —CF$_3$, —CHF$_2$, or —CH$_2$F, provided that the heterocycle formed by the combination of R$^3$ and R$^a$ is not an optionally substituted piperazinyl;
$R^5$ and $R^6$ are independently, at each occurrence, —H or —C$_1$-C$_6$alkyl;
m is independently, at each occurrence, 1, 2, 3, 4, 5 or 6; and
n is independently, at each occurrence, 0, 1, 2, 3, 4, 5, 6, 7, 8, 9, or 10.

Another aspect of the disclosure relates to methods of treating a disease associated with SHP2 modulation in a subject in need thereof, comprising administering to the subject an effective amount of one or more compounds disclosed herein (e.g., compounds of Formula I', I, II, III, IV, or V, and pharmaceutically acceptable salts, prodrugs, solvates, hydrates, tautomers, or isomers thereof).

Another aspect of the disclosure relates to methods of inhibiting SHP2. The method comprises administering to a patient in need thereof, an effective amount of one or more compounds disclosed herein (e.g., compounds of Formula I', I, II, III, IV, or V, and pharmaceutically acceptable salts, prodrugs, solvates, hydrates, tautomers, or isomers thereof).

Another aspect of the disclosure is directed to pharmaceutical compositions comprising one or more compounds disclosed herein (e.g., compounds of Formula I', I, II, III, IV, or V, and pharmaceutically acceptable salts, prodrugs, solvates, hydrates, tautomers, or isomers thereof) and a pharmaceutically acceptable carrier. The pharmaceutically acceptable carrier can further comprise an excipient, diluent, or surfactant. The pharmaceutical composition can be effective for treating a disease associated with SHP2 modulation in a subject in need thereof.

Another aspect of the disclosure relates to methods of treating a disease associated with SHP2 modulation in a subject in need thereof, comprising administering to the subject an effective amount of a pharmaceutical composition comprising one or more compounds disclosed herein (e.g., compounds of Formula I', I, II, III, IV, or V, and pharmaceutically acceptable salts, prodrugs, solvates, hydrates, tautomers, or isomers thereof).

Another aspect of the disclosure relates to methods of inhibiting SHP2 comprising administering to a patient in need thereof, an effective amount of a pharmaceutical composition comprising one or more compounds disclosed herein (e.g., compounds of Formula I', I, II, III, IV, or V, and pharmaceutically acceptable salts, prodrugs, solvates, hydrates, tautomers, or isomers thereof).

Another aspect of the disclosure relates to one or more compounds disclosed herein (e.g., compounds of Formula I', I, II, III, IV, or V, and pharmaceutically acceptable salts, prodrugs, solvates, hydrates, tautomers, or isomers thereof), for use in treating or preventing a disease associated with SHP2 modulation. One aspect of the disclosure relates to pharmaceutical compositions comprising one or more compounds disclosed herein (e.g., compounds of Formula I', I, II, III, IV, or V, and pharmaceutically acceptable salts, prodrugs, solvates, hydrates, tautomers, or isomers thereof), and a pharmaceutically acceptable carrier, for use in treating of preventing a disease associated with SHP2 modulation.

Another aspect of the disclosure relates to the use of one or more compounds disclosed herein (e.g., compounds of Formula I', I, II, III, IV, or V, and pharmaceutically acceptable salts, prodrugs, solvates, hydrates, tautomers, or isomers thereof), in the manufacture of a medicament for treating or preventing a disease associated with SHP2 modulation. Another aspect of the disclosure relates to the use of pharmaceutical compositions comprising one or more compounds disclosed herein (e.g., compounds of Formula I', I, II, III, IV, or V, and pharmaceutically acceptable salts, prodrugs, solvates, hydrates, tautomers, or isomers thereof), and a pharmaceutically acceptable carrier, in the manufacture of a medicament for treating or preventing a disease associated with SHP2 modulation.

Another aspect of the disclosure relates to one or more compounds disclosed herein (e.g., compounds of Formula I', I, II, III, IV, or V, and pharmaceutically acceptable salts, prodrugs, solvates, hydrates, tautomers, or isomers thereof), for use as a medicament. Another aspect of the disclosure relates to pharmaceutical compositions comprising one or more compounds disclosed herein (e.g., compounds of Formula I', I, II, III, IV, or V, and pharmaceutically acceptable salts, prodrugs, solvates, hydrates, tautomers, or isomers thereof), for use as a medicament. In some embodiments, the medicament is used for treating or preventing a disease associated with SHP2 modulation.

The present disclosure also provides compounds and pharmaceutical compositions that are useful in inhibiting SHP2.

DETAILED DESCRIPTION OF THE DISCLOSURE

In a first aspect, compounds of Formula I' are described:

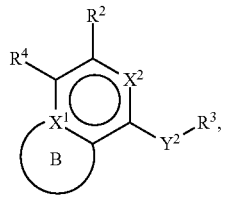

I' and pharmaceutically acceptable salts, prodrugs, solvates, hydrates, tautomers, or isomers thereof, wherein B, $X^1$, $X^2$, $R^2$, $R^3$, $R^4$, and $Y^2$ are described as above.

In another aspect, compounds of the Formula I are described:

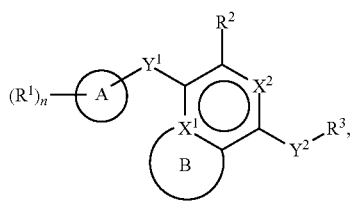

I and pharmaceutically acceptable salts, prodrugs, solvates, hydrates, tautomers, or isomers thereof, wherein A, B, $X^1$, $X^2$, $R^1$, $R^2$, $R^3$, $Y^1$, $Y^2$, and n are described as above.

In another aspect, compounds of the Formula II are described:

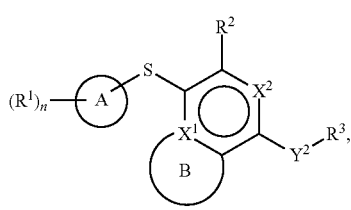

II and pharmaceutically acceptable salts, prodrugs, solvates, hydrates, tautomers, or isomers thereof, wherein A, B, $X^1$, $X^2$, $R^1$, $R^2$, $R^3$, $Y^2$, and n are described as above.

In another aspect, compounds of the Formula III are described:

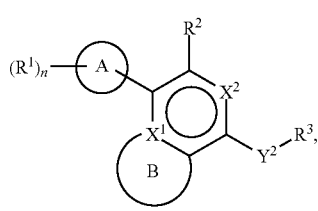

III and pharmaceutically acceptable salts, prodrugs, solvates, hydrates, tautomers, or isomers thereof, wherein A, B, $X^1$, $X^2$, $R^1$, $R^2$, $R^3$, $Y^2$, and n are described as above.

In a first aspect, compounds of Formula IV are described:

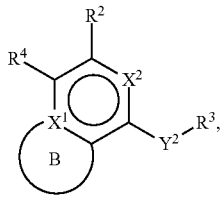

IV and pharmaceutically acceptable salts, prodrugs, solvates, hydrates, tautomers, or isomers thereof, wherein B, $X^1$, $X^2$, $R^2$, $R^3$, $R^4$, and $Y^2$ are described as above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

General Information

The articles "a" and "an" are used in this disclosure and may refer to one or more than one (i.e., to at least one) of the grammatical object of the article. By way of example, "an element" may mean one element or more than one element.

The term "and/or" is used in this disclosure to possibly mean either "and" or "or" unless indicated otherwise.

As used herein, "optional" or "optionally," may mean that the subsequently described event or circumstance may or may not occur, and that the description includes instances where the event or circumstance occurs and instances in which it does not. For example, "optionally substituted aryl" may encompass both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "optionally substituted" is understood to possibly mean that a given chemical moiety (e.g. an alkyl group) can (but is not required to) be bonded other substituents (e.g. heteroatoms). For instance, an alkyl group that is optionally substituted may be a fully saturated alkyl chain (i.e. a pure hydrocarbon). Alternatively, the same optionally substituted alkyl group may have substituents different from hydrogen. For instance, it can, at any point along the chain be bonded to a halogen atom, a hydroxyl group, or any other substituent described herein. Thus the term "optionally substituted" may mean that a given chemical moiety has the potential to contain other functional groups, but does not necessarily have any further functional groups.

The term "aryl" may refer to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —O$C_2$-$C_6$alkenyl, —O$C_2$-$C_6$alkynyl, —$C_2$-$C_6$alkenyl, —$C_2$-$C_6$alkynyl, —OH, —OP(O)(OH)$_2$, —OC(O) $C_1$-$C_6$alkyl, —C(O)$C_1$-$C_6$alkyl. —OC(O)O$C_1$-$C_6$alkyl, —NH$_2$, —NH ($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted.

Unless otherwise specifically defined, "heteroaryl" may mean a monovalent or multivalent monocyclic aromatic radical or a polycyclic aromatic radical of 5 to 24 ring atoms, containing one or more ring heteroatoms selected from N, S, P, and O, the remaining ring atoms being C. Heteroaryl as herein defined also may mean a bicyclic heteroaromatic group wherein the heteroatom is selected from N, S, P, and O. The term may also include multiple condensed ring systems that have at least one such aromatic ring, which multiple condensed ring systems are further described below. The term may also include multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1,2,3,4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen). The heteroaromatic radical may by optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, benzimidazolyl, thieno[3,2-b]thiophene, triazolyl, triavinyl, imidazo[1,2-b]pyrazolyl, furo[2,3-c]pyridinyl, imidazo[1,2-a]pyridinyl, imidazo[1,5-a]pyrazinyl, indazolyl, 1-methyl-1H-indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1.2.4]triazolo[4,3-a]pyridinyl, isoindolyl, isoindolin-1-one, indolin-2-one, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, benzo[d]isoxazolyl, benzo[d]oxazolyl, furo[3,2-c]pyridinyl, furo[2,3-c]pyridinyl, 1H-pyrido[3,4-b][1,4]thiazinyl, 2-methylbenzo[d]oxazolyl, 1,2,3,4-tetrahydropyrrolo[1,2-a]pyrimidyl, 2,3-dihydrobenzofuranyl, benzooxazolyl, benzoisoxazolyl, furo[2,3-b]pyridinyl, benzothiophenyl, 1,5-naphthyridinyl, furo[3,2-b]pyridinyl, [1.2.4]triazolo[1,5-a]pyridinyl, benzo[1,2,3]triazolyl, 1-methyl-1H-benzo[d][1,2,3]triazolyl, imidazo[1,2-a]pyrimidinyl, [1,2,4]triazolo[4,3-b]pyridazinyl, benzo[c][1,2,5]thiadiazolyl, quinoxalinyl, benzo[c][1,2,5]oxadiazolyl, 1,3-dihydro-2H-benzo[d]imidazol-2-one, 3,4-dihydro-2H-pyrazolo[1,5-b][1,2]oxazinyl, 3,4-dihydro-2H-benzo[b][1,4]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, benzo[d][1,3]dioxolyl, pyrazolo[1,5-a]pyridinyl, and derivatives of any of the foregoing.

"Alkyl" may refer to a straight or branched chain saturated hydrocarbon. $C_1$-$C_6$alkyl groups contain 1 to 6 carbon atoms. Examples of a $C_1$-$C_6$alkyl group may include, but are not limited to, methyl, ethyl, propyl, butyl, pentyl, isopropyl, isobutyl, sec-butyl and tert-butyl, isopentyl and neopentyl.

The term "alkenyl" may mean an aliphatic hydrocarbon group containing a carbon-carbon double bond and which may be straight or branched having about 2 to about 6 carbon atoms in the chain. Certain alkenyl groups may have about 2 to about 4 carbon atoms in the chain. Branched may mean that one or more lower alkyl groups such as methyl, ethyl, or propyl are attached to a linear alkenyl chain. Exemplary alkenyl groups may include, but are not limited to, ethenyl, propenyl, n-butenyl, and i-butenyl. A $C_2$-$C_6$ alkenyl group is an alkenyl group containing between 2 and 6 carbon atoms.

The term "alkynyl" may mean an aliphatic hydrocarbon group containing a carbon-carbon triple bond and which may be straight or branched having about 2 to about 6 carbon atoms in the chain. Certain alkynyl groups may have about 2 to about 4 carbon atoms in the chain. Branched may mean that one or more lower alkyl groups such as methyl, ethyl, or propyl are attached to a linear alkynyl chain. Exemplary alkynyl groups may include, but are not limited to, ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" may mean monocyclic or polycyclic saturated carbon rings containing 3-18 carbon atoms. Examples of cycloalkyl groups may include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group may be fused (e.g., decalin) or bridged (e.g., norbornane).

The term "cycloalkenyl" may mean monocyclic, non-aromatic unsaturated carbon rings containing 4-18 carbon atoms. Examples of cycloalkenyl groups may include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

In some embodiments, the terms "heterocyclyl" or "heterocycloalkyl" or "heterocycle" may refer to monocyclic or polycyclic 3 to 24-membered rings containing carbon and heteroatoms selected from oxygen, phosphorus, nitrogen, and sulfur and wherein there are no delocalized π electrons (aromaticity) shared among the ring carbon or heteroatoms. Heterocyclyl rings may include, but are not limited to, oxetanyl, azetidinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring may also be fused or bridged, e.g., can be a bicyclic ring.

In some embodiments "heterocyclyl" or "heterocycloalkyl" or "heterocycle" may be a saturated, partially saturated or unsaturated, mono or bicyclic ring containing 3-24 atoms of which at least one atom is chosen from nitrogen, sulfur or oxygen, which may, unless otherwise specified, be carbon or nitrogen linked, wherein a —$CH_2$— group can optionally be replaced by a —C(O)— or a ring sulfur atom may be optionally oxidised to form the S-oxides. "Heterocyclyl" may be a saturated, partially saturated or unsaturated, mono or bicyclic ring containing 5 or 6 atoms of which at least one atom is chosen from nitrogen, sulfur or oxygen, which may, unless otherwise specified, be carbon or nitrogen linked, wherein a —$CH_2$— group can optionally be replaced by a —C(O)— or a ring sulfur atom may be optionally oxidised to form S-oxide(s). Non-limiting examples and suitable values of the term "heterocyclyl" may include thiazolidinyl, pyrrolidinyl, pyrrolidin-2-one, pyrrolinyl, 2-pyrrolidonyl, 2,5-dioxopyrrolidinyl, 2-benzoxazolinonyl, 1,1-dioxotetrahydro thienyl, 2,4-dioxoimidazolidinyl, 2-oxo-1,3,4-(4-triazolinyl), 2-oxazolidinonyl, 5,6-dihydro uracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

As used herein, the term "halo" or "halogen" may mean a fluoro, chloro, bromo, or iodo group.

The term "carbonyl" may refer to a functional group comprising a carbon atom double-bonded to an oxygen atom. It can be abbreviated herein as "oxo," as C(O), or as C=O.

"Spirocycle" or "spirocyclic" may mean carbogenic bicyclic ring systems with both rings connected through a single atom. The ring can be different in size and nature, or identical in size and nature. Examples may include, but are not limited to, spiropentane, spirohexane, spiroheptane, spirooctane, spirononane, or spirodecane. One or both of the rings in a spirocycle can be fused to another carbocyclic, heterocyclic, aromatic, or heteroaromatic ring. One or more of the carbon atoms in the spirocycle can be substituted with a heteroatom (e.g., O, N, S, or P). A $C_5$-$C_{12}$ spirocycle is a spirocycle containing between 5 and 12 carbon atoms. One or more of the carbon atoms can be substituted with a heteroatom.

The term "spirocyclic heterocycle," "spiroheterocyclyl," or "spiroheterocycle" is understood to possibly mean a spirocycle wherein at least one of the rings is a heterocycle (e.g., at least one of the rings is furanyl, morpholinyl, or piperadinyl). A spirocyclic heterocycle can contain between 5 and 12 atoms, at least one of which is a heteroatom selected from N, O, S and P.

The disclosure also includes pharmaceutical compositions comprising an effective amount of one or more disclosed compounds and a pharmaceutically acceptable carrier. As used herein "pharmaceutically acceptable carrier, diluent or excipient" may include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier that has been approved by the United States Food and Drug Administration as being acceptable for use in humans or domestic animals.

The disclosure may include pharmaceutically acceptable salts of the compounds disclosed herein. Representative "pharmaceutically acceptable salts" may include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, 1,1-methene-bis-2-hydroxy-3-naphthoate, einbonate, pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

"Pharmaceutically acceptable salt" also includes both acid and base addition salts. "Pharmaceutically acceptable acid addition salt" may refer to those salts which retain the biological effectiveness and properties of the free bases, which are not biologically or otherwise undesirable, and which may be formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid. 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" may refer to those salts that retain the biological effectiveness and properties of the free acids, which are not biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. For example, inorganic salts may include, but are not limited to, ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

The term "tautomers" may refer to a set of compounds that have the same number and type of atoms, but differ in bond connectivity and are in equilibrium with one another. A "tautomer" is a single member of this set of compounds. Typically a single tautomer is drawn but it may be understood that this single structure may represent all possible tautomers that might exist. Examples include enol-ketone tautomerism. When a ketone is drawn it may be understood that both the enol and ketone forms are part of the disclosure.

For example, compounds of the Present disclosure can exist in tautomeric form. In some embodiments of Formula I, II, III, or IV, $R^2$ can be —OH and tautomers of the compounds can exist in equilibrium:

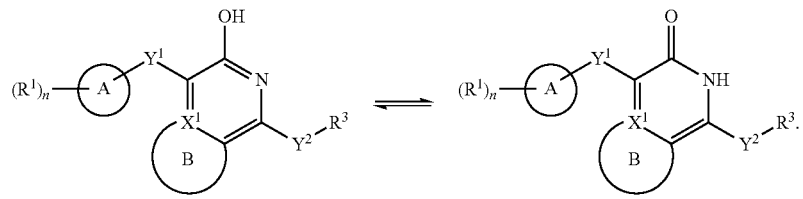

The disclosure may include prodrugs of the compounds described herein. The term "prodrug," as used in this disclosure, may mean a compound which is convertible in vivo by metabolic means (e.g., by hydrolysis) to a disclosed compound. Furthermore, as used herein a prodrug may be a drug which is inactive in the body, but may be transformed in the body typically either during absorption or after absorption from the gastrointestinal tract into the active compound. The conversion of the prodrug into the active compound in the body may be done chemically or biologically (i.e., using an enzyme).

The disclosure may include solvates of the compounds described herein. The term "solvate" may refer to a complex of variable stoichiometry formed by a solute and solvent. Such solvents for the purpose of the disclosure may not interfere with the biological activity of the solute. Examples of suitable solvents may include, but are not limited to, water, MeOH, EtOH, and AcOH. Solvates wherein water is the solvent molecule are typically referred to as hydrates.

Hydrates may include compositions containing stoichiometric amounts of water, as well as compositions containing variable amounts of water.

The disclosure may include isomers of the compounds described herein. The term "isomer" may refer to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of present disclosure may have one or more asymmetric carbon atom and may occur as racemates, racemic mixtures and as individual enantiomers or diastereomers.

The disclosure may include stereoisomers of the compounds described herein. The term "stereoisomers" may refer to the set of compounds which have the same number and type of atoms and share the same bond connectivity between those atoms, but differ in three dimensional structure. The term "stereoisomer" may refer to any member of this set of compounds. For instance, a stereoisomer may be an enantiomer or a diastereomer.

In addition, the present disclosure may embrace all geometric and positional isomers. For example, if a compound of the present disclosure incorporates a double bond or a fused ring, both the cis- and trans-forms, as well as mixtures, are embraced within the scope of the disclosure. If the compound contains a double bond, the substituent may be in the E or Z configuration. If the compound contains a disubstituted cycloalkyl, the cycloalkyl substituent may have a cis or trans configuration.

The term "enantiomers" may refer to a pair of stereoisomers which are non-superimposable mirror images of one another. The term "enantiomer" may refer to a single member of this pair of stereoisomers. The term "racemic" may refer to a 1:1 mixture of a pair of enantiomers. The disclosure may include enantiomers of the compounds described herein. Each compound herein disclosed includes all the enantiomers that conform to the general structure of the compound. The compounds may be in a racemic or enantiomerically pure form, or any other form in terms of stereochemistry. In some embodiments the compounds may be the (S)-enantiomer. In other embodiments the compounds may be the (R)-enantiomer. In yet other embodiments, the compounds may be the (+) or (−) enantiomers.

In some embodiments, compounds and compositions of the disclosure may be enriched to provide predominantly one enantiomer of a compound described herein. An enantiomerically enriched mixture may comprise, for example, at least 60 mol percent of one enantiomer, or more preferably at least 75, 80, 85, 90, 95, 96, 97, 98, 99, 99.5 or even 100 mol percent. In some embodiments, the compound described herein enriched in one enantiomer may be substantially free of the other enantiomer, wherein substantially free may mean that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2 mol percent of the second enantiomer.

The term "diastereomers" may refer to the set of stereoisomers which cannot be made superimposable by rotation around single bonds. For example, cis- and trans-double bonds, endo- and exo-substitution on bicyclic ring systems, and compounds containing multiple stereogenic centers with different relative configurations may be considered to be diastereomers. The term "diastereomer" may refer to any member of this set of compounds. In some examples presented, the synthetic route may produce a single diastereomer or a mixture of diastereomers. The disclosure may include diastereomers of the compounds described herein.

In some embodiments, the compounds and compositions of the disclosure may be enriched to provide predominantly one diastereomer of a compound disclosed herein. A diastereomerically enriched mixture may comprise, for example, at least 60 mol percent of one diastereomer, or more preferably at least 75, 99, 95, 96, 97, 98, 99, or even 100 mol percent.

The compounds described herein further include all pharmaceutically acceptable isotopically labeled compounds. An "isotopically" or "radio-labeled" compound may be a compound where one or more atoms are replaced or substituted by an atom having an atomic mass or mass number different from the atomic mass or mass number typically found in nature (i.e., naturally occurring). For example, in some embodiments, in the compounds described herein hydrogen atoms are replaced or substituted by one or more deuterium or tritium. Certain isotopically labeled compounds of this disclosure, for example, those incorporating a radioactive isotope, may be useful in drug and/or substrate tissue distribution studies. The radioactive isotopes tritium, i.e., $^3$H, and carbon 14, i.e., $^{14}$C, may be particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances. Suitable isotopes that may be incorporated in compounds described herein include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. Substitution with positron emitting isotopes, such as $^{11}$C, $^{18}$F, $^{15}$O, and $^{13}$N, can be useful in Positron Emission Topography (PET) studies.

An "effective amount" when used in connection with a compound may be an amount effective for treating or preventing a disease in a subject as described herein.

The term "carrier," as used in this disclosure, may encompass carriers, excipients, and diluents and may mean a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, may refer to improving at least one symptom of the subject's disorder. Treating may include curing, improving, or at least partially ameliorating the disorder.

The term "prevent" or "preventing" with regard to a subject may refer to keeping a disease or disorder from afflicting the subject. Preventing may include prophylactic treatment. For instance, preventing can include administering to the subject one or more compounds disclosed herein before a subject is afflicted with a disease and the administration will keep the subject from being afflicted with the disease.

The term "disorder" is used in this disclosure and may be used interchangeably with, the terms disease, condition, or illness, unless otherwise indicated.

The term "administer," "administering," or "administration" as used in this disclosure refers to either directly administering one or more disclosed compounds or a pharmaceutically acceptable salt of the one or more disclosed compounds or a composition comprising one or more disclosed compounds to a subject, or administering a prodrug derivative or analog of the one or more disclosed compounds or pharmaceutically acceptable salts of the one or more disclosed compounds or compositions to the subject, which may form an equivalent amount of active compound within the subject's body.

A "patient" or "subject" may be a mammal, e.g., a human, mouse, rat, guinea pig, dog, cat, horse, cow, pig, or non-human primate, such as a monkey, chimpanzee, baboon or rhesus.

Compounds of the Disclosure

Compounds of the disclosure include compounds of Formula I' I, II, III, IV, or V, and pharmaceutically acceptable salts, prodrugs, solvates, hydrates, tautomers, or isomers of any of the foregoing.

In one or more embodiments of the compounds of Formula I, the compound is of the Formula I-A:

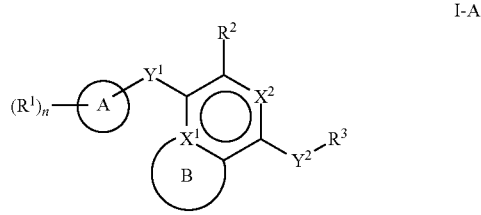

I-A and pharmaceutically acceptable salts, prodrugs, solvates, hydrates, tautomers, or isomers thereof, wherein:

A is aryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2$—NH—, —C(=$CH_2$)—, —CH—, or —S(O)—;

$X^1$ is N or C;

X² is N or CH;

B, including the atoms at the points of attachment, is a monocyclic or polycyclic 5- to 12-membered heterocycle or a monocyclic or polycyclic 5- to 12-membered heteroaryl;

R² is —H, —OR$^b$, —NR⁵R⁶, —CN, —C₁-C₆alkyl, —C₂-C₆alkenyl, —C₄-C₈cycloalkenyl, —C₂-C₆alkynyl, —NH₂, halogen, —C(O)OR$^b$, —C₃-C₈cycloalkyl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR'S(O)NR⁵R⁶, —NR⁵S(O)R⁶, heterocycle, aryl, or heteroaryl; and wherein the heterocyclyl or heteroaryl is not attached via a nitrogen atom;

Y² —NR$^a$—, —(CR$^a$₂)$_m$—, —C(O)—, —C(R$^a$)₂NH—, —(CR$^a$₂)$_m$O—, —C(O)N(R$^a$)—, —N(R$^a$)C(O)—, —S(O)₂N(R$^a$)—, —N(R$^a$)S(O)₂—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y², as drawn, is bound to the ring and the bond on the right side of the Y² moiety, as drawn, is bound to R³.

R$^a$ is independently, at each occurrence, —H, -D, —OH, —C₃-C₈cycloalkyl, or —C₁-C₆alkyl, wherein each alkyl or cycloalkyl is optionally substituted with one or more —NH₂, wherein 2 R$^a$, together with the carbon atom to which they are both attached, can combine to form a 3- to 8-membered cycloalkyl;

R$^b$ is independently, at each occurrence, —H, -D, —C₁-C₆alkyl, —C₃-C₈cycloalkyl, —C₂-C₆alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR³R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, heteroaryl, —(CH₂)$_n$OH, —C₁-C₆alkyl, —CF₃, —CHF₂, or —CH₂F;

R³ is —H, —C₁-C₆alkyl, a 3- to 12-membered monocyclic or polycyclic heterocycle, —C₃-C₈cycloalkyl, or —(CH₂)$_n$—R$^b$, wherein each alkyl, heterocycle, or cycloalkyl is optionally substituted with one or more —C₁-C₆alkyl, —OH, —NH₂, —OR$^b$, —NHR$^b$, —(CH₂)$_n$OH, heterocyclyl, or spiroheterocyclyl; or R³ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, —OH, —NH₂, heteroaryl, heterocyclyl, —(CH₂)$_n$NH₂, —COOR$^b$, —CONHR$^b$, —CONH(CH₂)$_n$COOR$^b$, —NHCOOR$^b$, —CF₃, —CHF₂, or —CH₂F;

R⁵ and R⁶ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, or —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of the compounds of Formula I, the compound is of the Formula I-B:

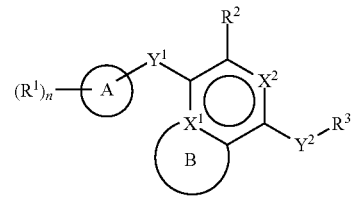

I-B and pharmaceutically acceptable salts, prodrugs, solvates, hydrates, tautomers, or isomers thereof, wherein:

A is heteroaryl;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, or —CO₂R⁵, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

Y¹ is —S—, a direct bond, —NH—, —S(O)₂—, —S(O)₂—NH—, —C(=CH₂)—, —CH—, or —S(O)—;

X¹ is N or C;

X² is N or CH;

B, including the atoms at the points of attachment, is a monocyclic or polycyclic 5- to 12-membered heterocycle or a monocyclic or polycyclic 5- to 12-membered heteroaryl;

R² is —H, —OR$^b$, —NR⁵R⁶, —CN, —C₁-C₆alkyl, —C₂-C₆alkenyl, —C₄-C₈cycloalkenyl, —C₂-C₆alkynyl, —NH₂, halogen, —C(O)OR$^b$, C₃-C₈cycloalkyl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR'S(O)NR⁵R⁶, —NR⁵S(O)R⁶, heterocycle, aryl, or heteroaryl; and wherein the heterocyclyl or heteroaryl is not attached via a nitrogen atom;

Y² is —NR$^a$—, —(CR$^a$₂)$_m$—, —C(O)—, —C(R$^a$)₂NH—, —(CR$^a$₂)$_m$O—, —C(O)N(R$^a$)—, —N(R$^a$)C(O)—, —S(O)₂N(R$^a$)—, —N(R$^a$)S(O)₂—, —N(R$^a$)C(O)N(R$^a$)—, —N(R$^a$)C(S)N(R$^a$)—, —C(O)O—,

—OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the ring and the bond on the right side of the Y$^2$ moiety, as drawn, is bound to R$^3$;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$. —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is —H, —C$_1$-C$_6$alkyl, a 3- to 12-membered monocyclic or polycyclic heterocycle, —C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of the compounds of Formula II, the compound is of the Formula II-A:

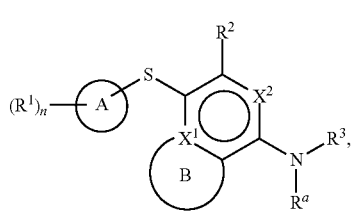

II-A and pharmaceutically acceptable salts, prodrugs, solvates, hydrates, tautomers, or isomers thereof.

In one or more embodiments of the compounds of the Formula II-A, the compound is of the Formula II-A1:

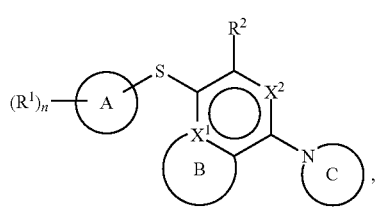

II-A1 and pharmaceutically acceptable salts, prodrugs, solvates, hydrates, tautomers, or isomers thereof, wherein:

C forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —C$_1$-C$_6$alkyl, —OH, or —NH$_2$.

In one or more embodiments of the compounds of Formula II-A, the compound is of the Formula II-A2:

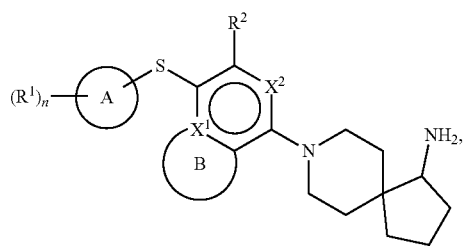

II-A2 and pharmaceutically acceptable salts, prodrugs, solvates, hydrates, tautomers, or isomers thereof.

In one or more embodiments of the compounds of Formula II-A, the compound is of the Formula II-A3:

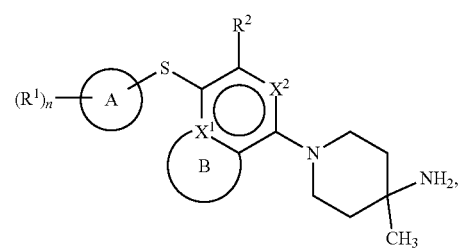

II-A3 and pharmaceutically acceptable salts, prodrugs, solvates, hydrates, tautomers, or isomers thereof.

In one or more embodiments of the compounds of Formula II, the compound is of the Formula II-B:

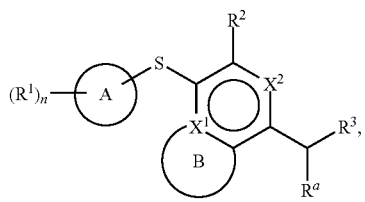

II-B and pharmaceutically acceptable salts, prodrugs, solvates, hydrates, tautomers, or isomers thereof.

In one or more embodiments of the compounds of Formula II-B, the compound is of the Formula II-B1:

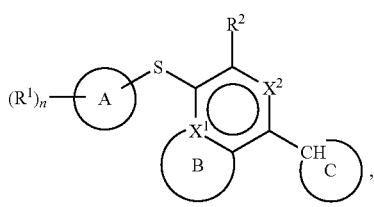

II-B1 and pharmaceutically acceptable salts, prodrugs, solvates, hydrates, tautomers, or isomers thereof, wherein:

C forms a 3- to 12-membered monocyclic or polycyclic heterocycle or a 5- to 12-membered spiroheterocycle along with the carbon atom to which it is attached, wherein the heterocycle or spiroheterocycle is optionally substituted with one or more —$C_1$-$C_6$alkyl, —OH, or —$NH_2$.

In one or more embodiments of the compounds of Formula II-B, the compound is of the Formula II-B2:

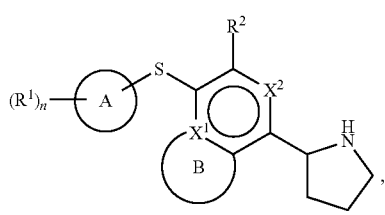

II-B2 and pharmaceutically acceptable salts, prodrugs, solvates, hydrates, tautomers, or isomers thereof.

In one or more embodiments of the compounds of Formula II-B, the compound is of the Formula II-B3:

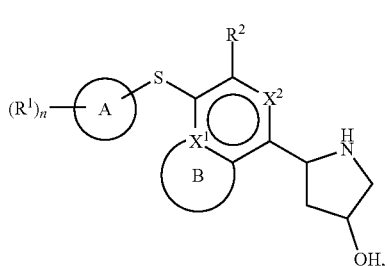

II-B3 and pharmaceutically acceptable salts, prodrugs, solvates, hydrates, tautomers, or isomers thereof.

In one or more embodiments of the compounds of Formula II-B, the compound is of the Formula II-B4:

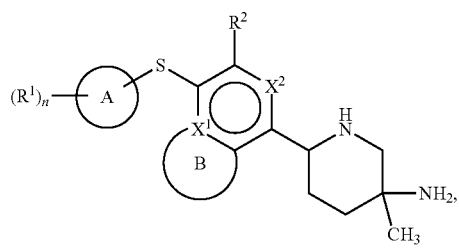

II-B4 and pharmaceutically acceptable salts, prodrugs, solvates, hydrates, tautomers, or isomers thereof.

In one or more embodiments of the compounds of Formula II-B, the compound is of the Formula II-B5:

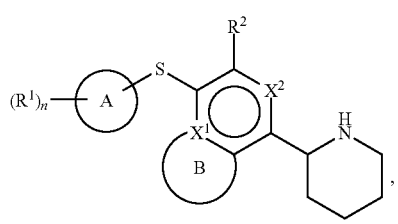

II-B5 and pharmaceutically acceptable salts, prodrugs, solvates, hydrates, tautomers, or isomers thereof.

In one or more embodiments of the compounds of Formula II-B, the compound is of the Formula II-B6:

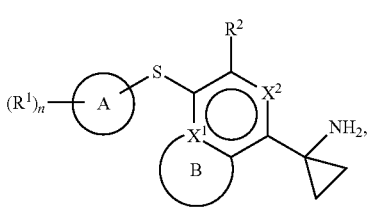

II-B6 and pharmaceutically acceptable salts, prodrugs, solvates, hydrates, tautomers, or isomers thereof.

In one or more embodiments of the compounds of Formula II, the compound is of the Formula II-C:

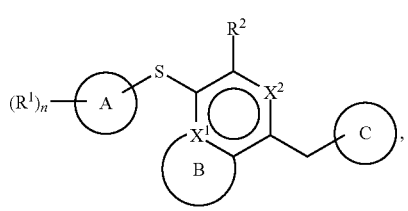

II-C and pharmaceutically acceptable salts, prodrugs, solvates, hydrates, tautomers, or isomers thereof, wherein:

C forms a 3- to 12-membered monocyclic or polycyclic heterocycle, wherein the heterocycle or spiroheterocycle is optionally substituted with one or more —$C_1$-$C_6$alkyl, —OH, or —$NH_2$.

In one or more embodiments of the compounds of Formula II-C, the compound is of the Formula II-C1:

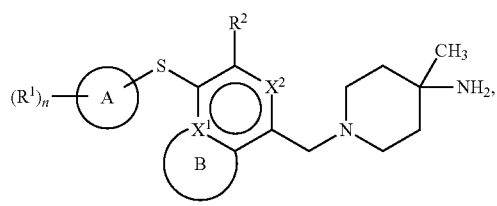

II-C1 and pharmaceutically acceptable salts, prodrugs, solvates, hydrates, tautomers, or isomers thereof.

In one or more embodiments of the compounds of Formula II, the compound is of the Formula II-D:

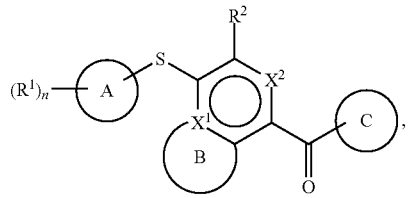

II-D and pharmaceutically acceptable salts, prodrugs, solvates, hydrates, tautomers, or isomers thereof, wherein:

C forms a 3- to 12-membered monocyclic or polycyclic heterocycle, wherein the heterocycle or spiroheterocycle is optionally substituted with one or more —$C_1$-$C_6$alkyl, —OH, or —$NH_2$.

In one or more embodiments of the compounds of Formula II-D, the compound is of the Formula II-D1:

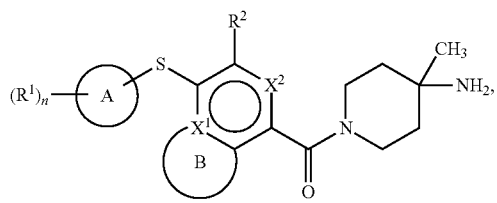

II-D1 and pharmaceutically acceptable salts, prodrugs, solvates, hydrates, tautomers, or isomers thereof.

In one or more embodiments of the compounds of Formula II, the compound is of the Formula II-E:

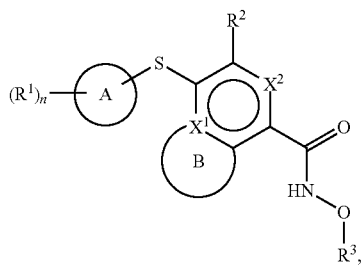

II-E and pharmaceutically acceptable salts, prodrugs, solvates, hydrates, tautomers, or isomers thereof.

In one or more embodiments of the compounds of Formula II, the compound is of the Formula II-F:

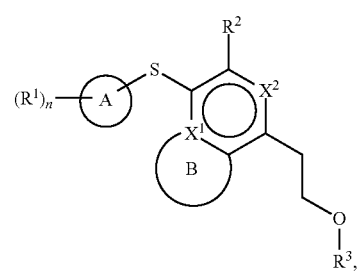

II-F and pharmaceutically acceptable salts, prodrugs, solvates, hydrates, tautomers, or isomers thereof.

In one or more embodiments of the compounds of Formula II, the compound is of the Formula II-G:

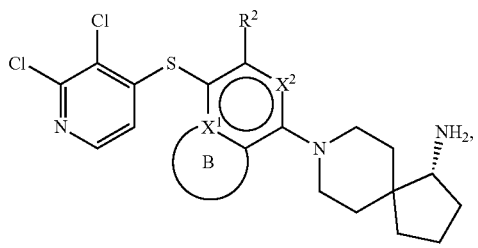

II-G and pharmaceutically acceptable salts, prodrugs, solvates, hydrates, tautomers, or isomers thereof, wherein $R^2$ is an aryl or heteroaryl.

In one or more embodiments of the compounds of Formula III, the compound is of the Formula III-A:

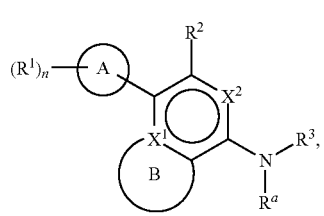

III-A and pharmaceutically acceptable salts, prodrugs, solvates, hydrates, tautomers, or isomers thereof.

In one or more embodiments of the compounds of Formula III-A, the compound is of the Formula III-A1:

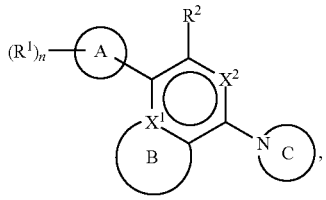

III-A1 and pharmaceutically acceptable salts, prodrugs, solvates, hydrates, tautomers, or isomers thereof, wherein C forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —C$_1$-C$_6$alkyl, —OH, or —NH$_2$.

In one or more embodiments of the compounds of Formula III-A, the compound is of the Formula III-A2:

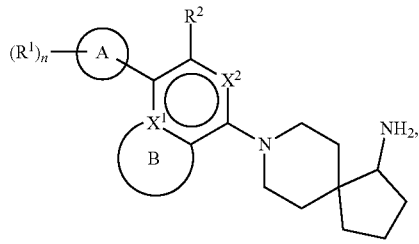

III-A2 and pharmaceutically acceptable salts, prodrugs, solvates, hydrates, tautomers, or isomers thereof.

In one or more embodiments of the compounds of Formula III-A, the compound is of the Formula III-A3:

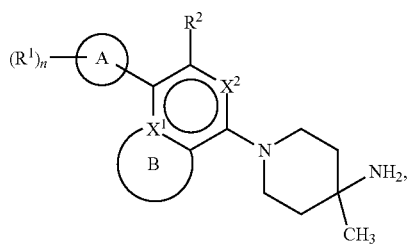

III-A3 and pharmaceutically acceptable salts, prodrugs, solvates, hydrates, tautomers, or isomers thereof.

In some embodiments, the compounds of the disclosure are compounds of Formula IV:

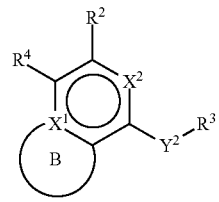

IV and pharmaceutically acceptable salts, prodrugs, solvates, hydrates, tautomers, or isomers thereof, wherein:

R$^4$ is H or

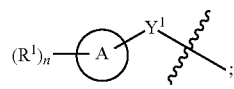

;

A is a 5- to 12-membered monocyclic or polycyclic cycloalkyl, heterocycloalkyl, aryl, or heteroaryl, provided that the heteroaryl is not

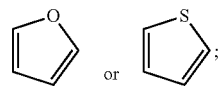 [SMILES: c1ccoc1 ; c1ccsc1]

;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^5$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

Y$^1$ is —S—, a direct bond, —NH—, —S(O)$_2$—, —S(O)$_2$—NH—, —C(=CH$_2$)—, —CH—, or —S(O)—;

X$^1$ is N or C;

X$^2$ is N or CH;

B, including the atoms at the points of attachment, is a monocyclic or polycyclic 5- to 12-membered heterocycle or a monocyclic or polycyclic 5- to 12-membered heteroaryl, wherein each heterocycle or heteroaryl is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F;

R$^2$ is —H, —OH, —NR$^5$R$^6$, —C$_1$-C$_6$alkyl, —C$_2$-C$_6$alkenyl, —C$_4$-C$_8$cycloalkenyl, —C$_2$-C$_6$alkynyl, —NH$_2$, halogen, —C$_3$-C$_8$cycloalkyl, or heterocyclyl containing 1-5 heteroatoms selected from the group consisting of N, S, P, and O; wherein each alkyl, alkenyl, cycloalkenyl, alkynyl, cycloalkyl, or heterocyclyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR'S(O)R$^6$, heterocycle, aryl, or heteroaryl; and wherein the heterocyclyl is not attached via a nitrogen atom;

$Y^2$ is —$NR^a$—, —$(CR^a{}_2)_m$—, —C(O)—, —$C(R^a)_2$NH—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)OH$, —$C_1$-$C_6$alkyl, —$CF_3$, —$CHF_2$, or —$CH_2F$;

$R^3$ is —H, —$C_1$-$C_6$alkyl, a 3- to 12-membered monocyclic or polycyclic heterocycle, —$C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, oxo, heteroaryl, heterocyclyl, —$(CH_2)_nNH_2$, —$(CH_2)OH$, —$CF_3$, —$CHF_2$, or —$CH_2F$, provided that the heterocycle formed by the combination of $R^3$ and $R^a$ is not an optionally substituted piperazinyl;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of Formula IV, $R^4$ is H.

In one or more embodiments of Formula IV, $R^4$ is

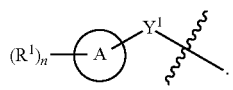

.

In certain such embodiments, $Y^1$ is —S— or a direct bond. In one or more embodiments of Formula IV, $Y^1$ is —S—. In one or more embodiments of Formula IV, $Y^1$ is a direct bond.

In one or more embodiments of the compounds of Formula IV, $Y^2$ is —$(CR^a{}_2)_m$—. In one or more embodiments of the compounds of Formula IV, $Y^2$ is —$NR^a$—.

In one or more embodiments of Formula IV, A is a monocyclic or polycyclic cycloalkyl. In one or more embodiments of Formula IV, A is a monocyclic or polycyclic heterocycloalkyl. In one or more embodiments of Formula IV, A is a monocyclic or polycyclic aryl. In one or more embodiments of Formula IV, A is phenyl. In one or more embodiments of Formula IV, A is a monocyclic or polycyclic heteroaryl. In one or more embodiments of Formula IV, A is pyridinyl. In one or more embodiments of Formula IV, A is indazolyl. In one or more embodiments of Formula IV, A is a 5- to 12-membered monocyclic or polycyclic aryl or heteroaryl.

In one or more embodiments of Formula IV, n is independently, at each occurrence, 0, 1, 2, or 3. In one or more embodiments of Formula IV, n is independently, at each occurrence, 1 or 2.

In one or more embodiments of Formula IV, $R^1$ is independently, at each occurrence, —H, —$OR^5$, halogen, —$C_1$-$C_6$alkyl, —CN, or —$NR^5R^6$. In one or more embodiments of Formula IV, $R^1$ is independently, at each occurrence, —H, —$OR^5$ or halogen. In one or more embodiments of Formula IV, $R^1$ is independently, at each occurrence, —H or —$OR^5$. In one or more embodiments of Formula IV, $R^1$ is independently, at each occurrence, —H or halogen. In one or more embodiments of Formula IV, $R^1$ is independently, at each occurrence, —H or —$NR^5R^6$. In one or more embodiments of Formula IV, $R^1$ is independently, at each occurrence, —H, —$OR^5$ or —$NR^5R^6$. In one or more embodiments of Formula IV, $R^1$ is independently, at each occurrence, —H, halogen or —$NR^5R^6$. In certain such embodiments, $R^5$ and $R^6$ are both —H. In one or more embodiments of Formula IV, $R^1$ is independently, at each occurrence, —H, methyl, fluoro, chloro, or —$NH_2$. In one or more embodiments of Formula IV, $R^1$ is independently, at each occurrence, —H, —CN or halogen.

In one or more embodiments of Formula IV, $R^5$ and $R^6$ are independently, at each occurrence, —H or —$C_1$-$C_6$alkyl. In one or more embodiments of Formula IV, $R^5$ and $R^6$ are independently, at each occurrence, —H. In one or more embodiments of Formula IV, $R^5$ and $R^6$ are independently, at each occurrence, —$C_1$-$C_6$alkyl.

In one or more embodiments of Formula IV, $R^2$ is —H. In one or more embodiments of Formula IV, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV, $R^2$ is —OH. In one or more embodiments of Formula IV, $R^2$ is —$NR^5R^6$. In one or more embodiments of Formula IV, $R^2$ is —$NH_2$.

In one or more embodiments of Formula IV, $R^a$ is —H.

In one or more embodiments of Formula IV, $R^3$ is an optionally substituted —$C_1$-$C_6$alkyl. In one or more embodiments of Formula IV, $R^3$ is an optionally substituted 3- to 12-membered monocyclic or polycyclic heterocycle. In one or more embodiments of Formula IV, $R^3$ is an optionally substituted 3- to 12-membered monocyclic heterocycle. In one or more embodiments of Formula IV, $R^3$ is an optionally substituted 5- to 12-membered polycyclic heterocycle.

In one or more embodiments of Formula IV, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV, $R^3$ and $R^a$ together with the atom to which they are attached combine to form a 3- to 12-membered monocyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV, $R^3$ and $R^a$ together with the atom to which they are attached combine to form a 3- to 12-membered polycyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV, $R^3$ and $R^a$ together with the atoms to which they are attached combine to form a 5- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV. $R^3$ and $R^a$ together with the atoms to which they are attached combine to form a 5- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$(CH_2)_nNH_2$, —$(CH_2)OH$, —$CF_3$, —$CHF_2$, or —$CH_2F$. In one or more embodiments of Formula IV, $R^3$ and $R^a$ together with the atoms to which they are attached combine to form a 10- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV. $R^3$ and $R^a$ together with the atoms to which they are attached combine to form a 10- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV, $X^1$ is N and $X^2$ is N. In one or more embodiments of Formula IV, $X^1$ is C and $X^2$ is CH. In one or more embodiments of Formula IV, $X^1$ is C and $X^2$ is N. In one or more embodiments of Formula IV, $X^1$ is N and $X^2$ is CH.

In one or more embodiments of Formula IV, B, including the atoms at the points of attachment, is an optionally substituted monocyclic or polycyclic 5- to 12-membered heterocycle. In one or more embodiments of Formula IV, B, including the atoms at the points of attachment, is an optionally substituted monocyclic 5 to 6-membered heterocycle. In one or more embodiments of Formula IV, B, including the atoms at the points of attachment, is an optionally substituted monocyclic 7- to 12-membered heterocycle.

In one or more embodiments of Formula IV, B, including the atoms at the points of attachment, is an optionally substituted polycyclic 5- to 12-membered heterocyclyl. In certain embodiments, the heteroycyclyl ring is fused. In one or more embodiments of Formula IV, the heterocyclyl ring is bridged.

In one or more embodiments of Formula IV, B, including the atoms at the points of attachment, is an optionally substituted monocyclic or polycyclic 5- to 12-membered heteroaryl. In one or more embodiments of Formula IV, B, including the atoms at the points of attachment, is an optionally substituted monocyclic 5 to 6-membered heteroaryl. In one or more embodiments of Formula IV, B, including the atoms at the points of attachment, is a monocyclic 7- to 12-membered heteroaryl.

In one or more embodiments of Formula IV, B, including the atoms at the points of attachment, is an optionally substituted polycyclic 5- to 12-membered heteroaryl. In one or more embodiments of Formula IV, the polycyclic heteroaryl is a multiple condensed ring as described above. The rings of the multiple condensed ring system can be connected to each other via fused, spiro and bridged bonds when allowed by valency requirements.

In one or more embodiments of Formula IV, B is substituted with one or more —$(CH_2)_nOH$. In certain such embodiments, n is 1. In one or more embodiments of Formula IV, B is substituted with one or more —$C_1$-$C_6$alkyl, —OH, —$NH_2$, oxo, —$(CH_2)_nNH_2$, —$(CH_2)OH$, —$CF_3$, —$CHF_2$, or —$CH_2F$. In one or more embodiments of Formula IV. B is substituted with one or more oxo. In one or more embodiments of Formula IV, B is substituted with one or more —$C_1$-$C_6$alkyl. In one or more embodiments of Formula IV, B is substituted with one or more —OH. In one or more embodiments of Formula IV, B is substituted with one or more —$NH_2$. In one or more embodiments of Formula IV. B is substituted with one or more —$CF_3$. In one or more embodiments of Formula IV, B is substituted with one or more —$CHF_2$. In one or more embodiments of Formula IV, B is substituted with one or more —$CH_2F$. In one or more embodiments of Formula IV, B is substituted with one or more —$(CH_2)_nNH_2$. In certain such embodiments, n is 1.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is H;
b) $X^1$ is C and $X^2$ is CH;

c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is H;
b) $X^1$ is N and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is H;
b) $X^1$ is C and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is H;
b) $X^1$ is N and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is H;
b) $X^1$ is C and $X^2$ is CH;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is H;
b) $X^1$ is N and $X^2$ is N;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is H;
b) $X^1$ is C and $X^2$ is N;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;

e) $Y^2$ is —$NR^a$—, wherein the bond on the left side of $Y^2$, as drawn, is bound to the ring and the bond on the right side of the $Y^2$ moiety, as drawn, is bound to $R^3$;

f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is H;
b) $X^1$ is N and $X^2$ is CH;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is H;
b) $X^1$ is C and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is H;
b) $X^1$ is N and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is H;
b) $X^1$ is C and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is H;
b) $X^1$ is N and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is H;
b) $X^1$ is C and $X^2$ is CH;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_nNH_2$, —$(CH_2)_nOH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is H;
b) $X^1$ is N and $X^2$ is N;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_nNH_2$, —$(CH_2)OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is H;
b) $X^1$ is C and $X^2$ is N;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_nNH_2$, —$(CH_2)_nOH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is H;
b) $X^1$ is N and $X^2$ is CH;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_nNH_2$, —$(CH_2)OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

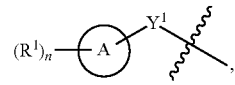

A is a monocyclic or polycyclic aryl or pyridinyl, and $Y^1$ is —S—;
b) $X^1$ is C and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_nNH_2$, —$(CH_2)_nOH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

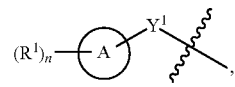

A is a monocyclic or polycyclic aryl or pyridinyl, and $Y^1$ is —S—;
b) $X^1$ is N and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_nNH_2$, —$(CH_2)_nOH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

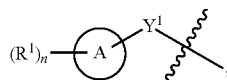

A is a monocyclic or polycyclic aryl or pyridinyl, and $Y^1$ is —S—;
b) $X^1$ is C and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

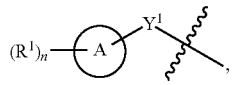

A is a monocyclic or polycyclic aryl or pyridinyl, and $Y^1$ is —S—;
b) $X^1$ is N and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

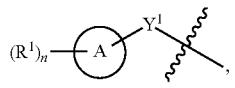

A is a monocyclic or polycyclic aryl or pyridinyl, and $Y^1$ is —S—;
b) $X^1$ is C and $X^2$ is CH;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

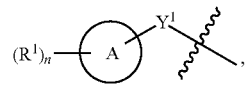

A is a monocyclic or polycyclic aryl or pyridinyl, and $Y^1$ is —S—;
b) $X^1$ is N and $X^2$ is N;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

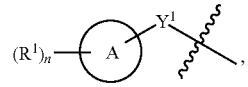

A is a monocyclic or polycyclic aryl or pyridinyl, and $Y^1$ is —S—;
b) $X^1$ is C and $X^2$ is N;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2 F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2 F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

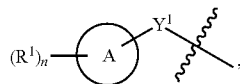

A is a monocyclic or polycyclic aryl or pyridinyl, and $Y^1$ is —S—;
b) $X^1$ is N and $X^2$ is CH;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2 F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2 F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

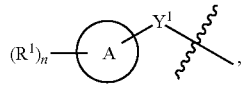

A is a monocyclic or polycyclic aryl or pyridinyl, and $Y^1$ is —S—;
b) $X^1$ is C and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2 F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;

f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2 F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

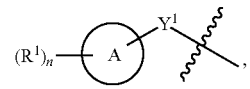

A is a monocyclic or polycyclic aryl or pyridinyl, and $Y^1$ is —S—;
b) $X^1$ is N and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2 F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2 F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

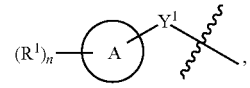

A is a monocyclic or polycyclic aryl or pyridinyl, and $Y^1$ is —S—;
b) $X^1$ is C and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2 F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2 F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

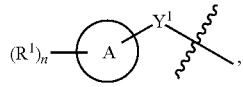

A is a monocyclic or polycyclic aryl or pyridinyl, and $Y^1$ is —S—;
b) $X^1$ is N and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

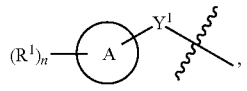

A is a monocyclic or polycyclic aryl or pyridinyl, and $Y^1$ is —S—;
b) $X^1$ is C and $X^2$ is CH;
c) B, including the atoms at the points of attachment, is a monocyclic 5- to 12-membered heteroaryl, wherein the heteroaryl is optionally substituted with one or more
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

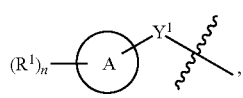

A is a monocyclic or polycyclic aryl or pyridinyl, and $Y^1$ is —S—;
b) $X^1$ is N and $X^2$ is CH;
c) B, including the atoms at the points of attachment, is a monocyclic 5- to 12-membered heteroaryl, wherein the heteroaryl is optionally substituted with one or more A is a monocyclic or polycyclic aryl or pyridinyl, and $Y^1$ is —S—;
b) $X^1$ is N and $X^2$ is N;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

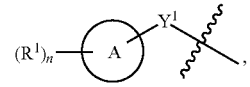

A is a monocyclic or polycyclic aryl or pyridinyl, and $Y^1$ is —S—;
b) $X^1$ is C and $X^2$ is N;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:
a) $R^4$ is

A is a monocyclic or polycyclic aryl or pyridinyl, and $Y^1$ is —S—;
b) $X^1$ is N and $X^2$ is CH;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_nNH_2$, —$(CH_2)_nOH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

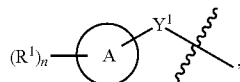

A is a monocyclic or polycyclic aryl or pyridinyl, and $Y^1$ is a direct bond;
b) $X^1$ is C and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_nNH_2$, —$(CH_2)_nOH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

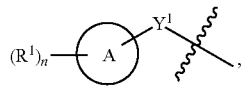

A is a monocyclic or polycyclic aryl or pyridinyl, and $Y^1$ is a direct bond;
b) $X^1$ is N and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;

f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_nNH_2$, —$(CH_2)_nOH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

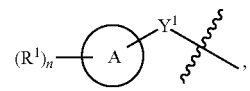

A is a monocyclic or polycyclic aryl or pyridinyl, and $Y^1$ is a direct bond;
b) $X^1$ is C and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n$ $NH_2$, —$(CH_2)_nOH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_nNH_2$, —$(CH_2)_nOH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

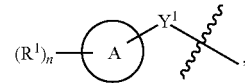

A is a monocyclic or polycyclic aryl or pyridinyl, and $Y^1$ is a direct bond;
b) $X^1$ is N and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n$ $NH_2$, —$(CH_2)_nOH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_nNH_2$, —$(CH_2)_nOH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

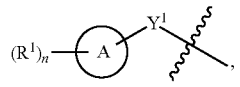

A is a monocyclic or polycyclic aryl or pyridinyl, and $Y^1$ is a direct bond;
b) $X^1$ is C and $X^2$ is CH;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

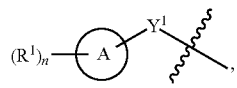

A is a monocyclic or polycyclic aryl or pyridinyl, and $Y^1$ is a direct bond;
b) $X^1$ is N and $X^2$ is N;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

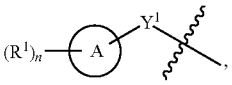

A is a monocyclic or polycyclic aryl or pyridinyl, and $Y^1$ is a direct bond;
b) $X^1$ is C and $X^2$ is N;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

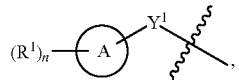

A is a monocyclic or polycyclic aryl or pyridinyl, and $Y^1$ is a direct bond;
b) $X^1$ is N and $X^2$ is CH;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 3- to 12-membered monocyclic heterocycle, wherein the heterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

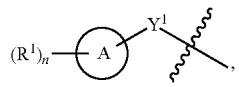

A is a monocyclic or polycyclic aryl or pyridinyl, and $Y^1$ is a direct bond;

b) $X^1$ is C and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n$$NH_2$, —$(CH_2)_n$OH, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n$$NH_2$, —$(CH_2)_n$OH, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

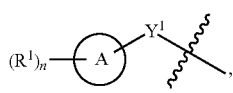

A is a monocyclic or polycyclic aryl or pyridinyl, and $Y^1$ is a direct bond;
b) $X^1$ is N and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n$$NH_2$, —$(CH_2)_n$OH, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n$$NH_2$, —$(CH_2)_n$OH, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

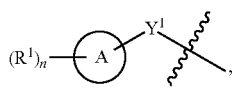

A is a monocyclic or polycyclic aryl or pyridinyl, and $Y^1$ is a direct bond;
b) $X^1$ is C and $X^2$ is N;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n$$NH_2$, —$(CH_2)_n$OH, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n$$NH_2$, —$(CH_2)_n$OH, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

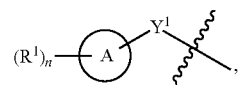

A is a monocyclic or polycyclic aryl or pyridinyl, and $Y^1$ is a direct bond;
b) $X^1$ is N and $X^2$ is CH;
c) B, including the atoms at the points of attachment, is a monocyclic 5- to 12-membered heterocycle, wherein the heterocycle is optionally substituted with one or more —$C_1$-$C_6$alkyl, —OH, —$NH_2$, oxo, —$(CH_2)_n$$NH_2$, —$(CH_2)_n$OH, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n$$NH_2$, —$(CH_2)_n$OH, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

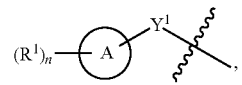

A is a monocyclic or polycyclic aryl or pyridinyl, and $Y^1$ is a direct bond;
b) $X^1$ is C and $X^2$ is CH;
c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n$$NH_2$, —$(CH_2)_n$OH, —$CF_3$, —$CHF_2$, or —$CH_2F$;
d) $R^2$ is —H, —$C_1$-$C_6$alkyl, or —$NH_2$;
e) $Y^2$ is —$NR^a$—, wherein the bond on the left side of $Y^2$, as drawn, is bound to the ring and the bond on the right side of the $Y^2$ moiety, as drawn, is bound to $R^3$;
f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n$$NH_2$, —$(CH_2)_n$OH, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

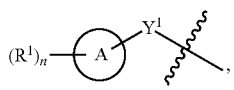

A is a monocyclic or polycyclic aryl or pyridinyl, and $Y^1$ is a direct bond;

b) $X^1$ is N and $X^2$ is N;

c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;

d) $R^2$ is —H, —$C_1$-$C_6$alkyl, or —$NH_2$;

e) $Y^2$ is —$NR^a$—, wherein the bond on the left side of $Y^2$, as drawn, is bound to the ring and the bond on the right side of the $Y^2$ moiety, as drawn, is bound to $R^3$;

f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

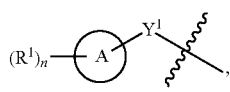

A is a monocyclic or polycyclic aryl or pyridinyl, and $Y^1$ is a direct bond;

b) $X^1$ is C and $X^2$ is N;

c) B, including the atoms at the points of attachment, is a monocyclic 5- to 12-membered heteroaryl, wherein the heteroaryl is optionally substituted with one or d) $R^2$ is —H, —$C_1$-$C_6$alkyl, or —$NH_2$;

e) $Y^2$ is —$NR^a$—, wherein the bond on the left side of $Y^2$, as drawn, is bound to the ring and the bond on the right side of the $Y^2$ moiety, as drawn, is bound to $R^3$;

f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In some embodiments, the compounds of the disclosure compounds of Formula IV, and pharmaceutically acceptable salts, prodrugs, solvates, hydrates, tautomers, or isomers thereof, have one, two, or three or more of the following features:

a) $R^4$ is

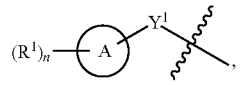

A is a monocyclic or polycyclic aryl or pyridinyl, and $Y^1$ is a direct bond;

b) $X^1$ is N and $X^2$ is CH;

c) B, including the atoms at the points of attachment, is a monocyclic 5- to 12-membered heteroaryl, wherein the heteroaryl is optionally substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$;

d) $R^2$ is —H, —$C_1$-$C_6$alkyl, or —$NH_2$;

e) $Y^2$ is —$NR^a$—, wherein the bond on the left side of $Y^2$, as drawn, is bound to the ring and the bond on the right side of the $Y^2$ moiety, as drawn, is bound to $R^3$;

f) $R^3$ is combined with $R^a$ to form a 5- to 12-membered spiroheterocycle, wherein the spiroheterocycle is optionally substituted with one or more —$C_1$-$C_6$alkyl, —OH, —$NH_2$, —$(CH_2)_n NH_2$, —$(CH_2)_n OH$, —$CF_3$, —$CHF_2$, or —$CH_2F$.

In certain embodiments of Formula IV, the compound is of Formula IV-A:

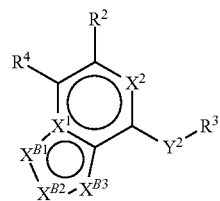

IV-A and pharmaceutically acceptable salts, prodrugs, solvates, hydrates, tautomers, and isomers thereof, wherein $X^{B1}$ is N, $NR^9$, $CR^9$, S, or O; $X^{B2}$ is N, $NR^9$, $CR^9$, S, or O; and $X^{B3}$ is N, $NR^9$, $CR^9$, S, or O, wherein $R^9$ is independently, at each occurrence, —H, —$C_1$-$C_6$alkyl, —OH, —$NH_2$, heteroaryl, heterocyclyl, —$(CH_2)_n NH_2$, —$(CH_2)_n OH$, —$CF_3$, —$CHF_2$, or —$CH_2F$, provided that if $X^1$ is C, at least one of $X^{B1}$, $X^{B2}$, and $X^{B3}$ is not $CR^9$, or provided that if each of $X^{B1}$, $X^{B2}$, and $X^{B3}$ are $CR^9$, $X^1$ must be N.

In certain embodiments of Formula IV-A, $X^{B1}$ is N or $NR^9$. In certain embodiments of Formula IV-A, $X^{B1}$ is $CR^9$. In certain embodiments of Formula IV-A, $X^{B1}$ is S. In certain embodiments of Formula IV-A, $X^{B1}$ is O. In certain embodiments of Formula IV-A, $X^{B2}$ is N or $NR^9$. In certain embodiments of Formula IV-A, $X^{B2}$ is $CR^9$. In certain embodiments of Formula IV-A, $X^{B2}$ is S. In certain embodiments of Formula IV-A, $X^{B2}$ is O. In certain embodiments of Formula IV-A, $X^{B3}$ is N or $NR^9$. In certain embodiments of Formula IV-A, $X^{B3}$ is $CR^9$. In certain embodiments of Formula IV-A, $X^{B3}$ is S. In certain embodiments of Formula IV-A, $X^{B3}$ is O.

In certain embodiments of Formula IV-A, $X^{B1}$ is N, $NR^9$, or $CR^9$; $X^{B2}$ is N, $NR^9$, or $CR^9$; and $X^{B3}$ is N, $NR^9$, or $CR^9$. In certain embodiments of Formula IV-A, $X^{B1}$ is N or $NR^9$. In certain embodiments of Formula IV-A, $X^{B1}$ is $CR^9$. In certain embodiments of Formula IV-A, $X^{B2}$ is N or $NR^9$. In certain embodiments of Formula IV-A, $X^{B2}$ is $CR^9$. In certain embodiments of Formula IV-A, $X^{B3}$ is N or $NR^9$. In certain embodiments of Formula IV-A, $X^{B3}$ is $CR^9$.

In some embodiments of Formula IV-A, $R^9$ is —$(CH_2)_n$OH and n is 1. In some embodiments of Formula IV-A, $R^9$ is H.

In certain embodiments of Formula IV-A,

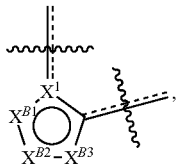

wherein ===== is a single bond or double bond to satisfy valency rules, is

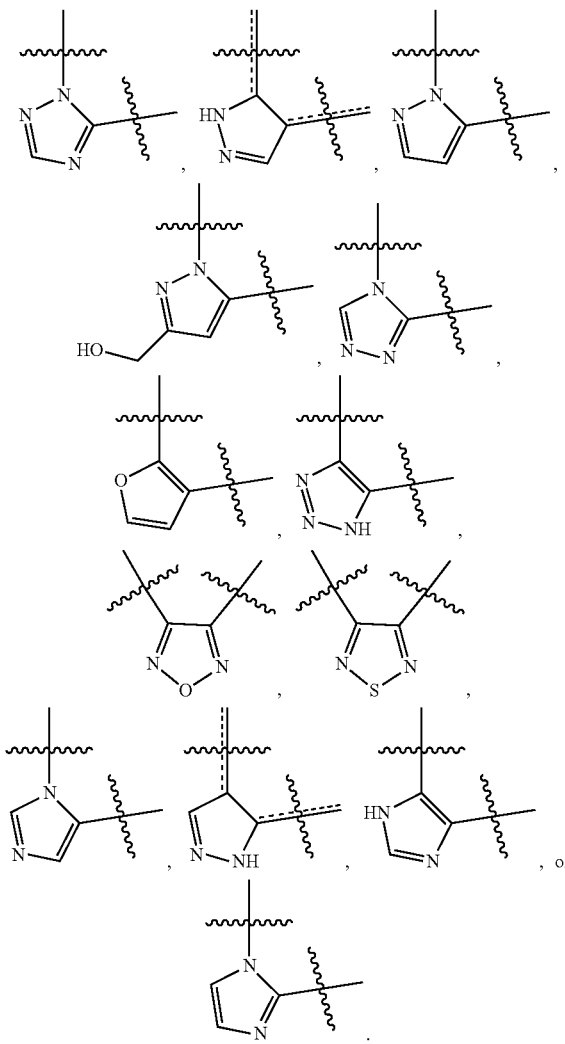

, or

In one or more embodiments of Formula IV-A, $R^4$ is H. In one or more embodiments of Formula IV-A, $R^4$ is

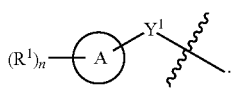

.

In certain such embodiments, $Y^1$ is —S— or a direct bond. In one or more embodiments of Formula IV-A, $Y^1$ is —S—. In one or more embodiments of Formula IV-A, $Y^1$ is a direct bond.

In one or more embodiments of the compounds of Formula IV-A, $Y^2$ is —$(CR^a{}_2)_m$—. In one or more embodiments of the compounds of Formula IV-A, $Y^2$ is —$NR^a$—.

In one or more embodiments of Formula IV-A, A is a monocyclic or polycyclic cycloalkyl. In one or more embodiments of Formula IV-A, A is a monocyclic or polycyclic heterocycloalkyl. In one or more embodiments of Formula IV-A, A is a monocyclic or polycyclic aryl. In one or more embodiments of Formula IV-A, A is phenyl. In one or more embodiments of Formula IV-A, A is a monocyclic or polycyclic heteroaryl. In one or more embodiments of Formula IV-A, A is pyridinyl. In one or more embodiments of Formula IV-A, A is indazolyl. In one or more embodiments of Formula IV-A, A is a 5- to 12-membered monocyclic or polycyclic aryl or heteroaryl.

In one or more embodiments of Formula IV-A, n is independently, at each occurrence, 0, 1, 2, or 3. In one or more embodiments of Formula IV-A, n is independently, at each occurrence, 1 or 2.

In one or more embodiments of Formula IV-A, $R^1$ is independently, at each occurrence, —H, —$OR^5$, halogen, —$C_1$-$C_6$alkyl, —CN, or —$NR^5R^6$. In one or more embodiments of Formula IV-A, $R^1$ is independently, at each occurrence, —H, —$OR^5$ or halogen. In one or more embodiments of Formula IV-A, $R^1$ is independently, at each occurrence, —H or —$OR^5$. In one or more embodiments of Formula IV-A, $R^1$ is independently, at each occurrence, —H or halogen. In one or more embodiments of Formula IV-A, $R^1$ is independently, at each occurrence, —H or —$NR^5R^6$. In one or more embodiments of Formula IV-A, $R^1$ is independently, at each occurrence, —H, —$OR^5$ or —$NR^5R^6$. In one or more embodiments of Formula IV-A, $R^1$ is independently, at each occurrence, —H, halogen or —$NR^5R^6$. In certain such embodiments, $R^5$ and $R^6$ are both-H. In one or more embodiments of Formula IV-A. $R^1$ is independently, at each occurrence, —H, methyl, fluoro, chloro, or —$NH_2$. In one or more embodiments of Formula IV-A, $R^1$ is independently, at each occurrence, —H, —CN or halogen.

In one or more embodiments of Formula IV-A. $R^5$ and $R^6$ are independently, at each occurrence, —H or —$C_1$-$C_6$alkyl. In one or more embodiments of Formula IV-A, $R^5$ and $R^6$ are independently, at each occurrence, —H. In one or more embodiments of Formula IV-A. $R^5$ and $R^6$ are independently, at each occurrence, —$C_1$-$C_6$alkyl.

In one or more embodiments of Formula IV-A, $R^2$ is —H. In one or more embodiments of Formula IV-A, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-A, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV-A, $R^2$ is —OH. In one or more embodiments of Formula IV-A, $R^2$ is —$NR^5R^6$. In one or more embodiments of Formula IV-A, $R^2$ is —$NH_2$.

In one or more embodiments of Formula IV-A, $R^a$ is —H.
In one or more embodiments of Formula IV-A, $R^3$ is an optionally substituted —$C_1$-$C_6$alkyl. In one or more embodiments of Formula IV-A, $R^3$ is an optionally substituted 3- to 12-membered monocyclic or polycyclic heterocycle. In one or more embodiments of Formula IV-A, $R^3$ is an optionally substituted 3- to 12-membered monocyclic heterocycle. In one or more embodiments of Formula IV-A, $R^3$ is an optionally substituted 5- to 12-membered polycyclic heterocycle.

In one or more embodiments of Formula IV-A, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$(CH_2)_n NH_2$, —$(CH_2)_n OH$, —$CF_3$, —$CHF_2$, or —$CH_2F$. In one or more embodiments of Formula IV-A, $R^3$ and $R^a$ together with the atom to which they are attached combine to form a 3- to 12-membered monocyclic heterocycle, which is optionally substituted with one or more —$C_1$-$C_6$alkyl, $(CH_2)_n NH_2$, or —$NH_2$. In certain such embodiments, n is 1. In one or more embodiments of Formula IV-A. $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, oxo, heteroaryl, heterocyclyl, —$(CH_2)_n NH_2$, —$(CH_2)_n OH$, —$CF_3$, —$CHF_2$, or —$CH_2F$.

In one or more embodiments of Formula IV-A, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$(CH_2)_n NH_2$, —$(CH_2)_n OH$, —$CF_3$, —$CHF_2$, or —$CH_2F$. In one or more embodiments of Formula IV-A, $R^3$ and $R^a$ together with the atom to which they are attached combine to form a 3- to 12-membered polycyclic heterocycle, which is optionally substituted with one or more —$C_1$-$C_6$alkyl, —$(CH_2)_n NH_2$, or —$NH_2$. In certain such embodiments, n is 1. In one or more embodiments of Formula IV-A, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, oxo, heteroaryl, heterocyclyl, —$(CH_2)_n NH_2$, —$(CH_2)_n OH$, —$CF_3$, —$CHF_2$, or —$CH_2F$.

In one or more embodiments of Formula IV-A, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$(CH_2)_n NH_2$, —$(CH_2)_n OH$, —$CF_3$, —$CHF_2$, or —$CH_2F$. In one or more embodiments of Formula IV-A. $R^3$ and $R^a$ together with the atoms to which they are attached combine to form a 5- to 12-membered spiroheterocycle, which is optionally substituted with one or more —$C_1$-$C_6$alkyl, —$(CH_2)_n NH_2$, or —$NH_2$. In certain such embodiments, n is 1. In one or more embodiments of Formula IV-A. $R^3$ and $R^a$ together with the atoms to which they are attached combine to form a 5- to 12-membered spiroheterocycle, which is optionally substituted with one or more —$C_1$-$C_6$alkyl, —OH, —$NH_2$, oxo, heteroaryl, heterocyclyl, —$(CH_2)_n NH_2$, —$(CH_2)_n OH$, —$CF_3$, —$CHF_2$, or —$CH_2F$.

In one or more embodiments of Formula IV-A, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$(CH_2)_n NH_2$, —$(CH_2)_n OH$, —$CF_3$, —$CHF_2$, or —$CH_2F$. In one or more embodiments of Formula IV-A, $R^3$ and $R^a$ together with the atoms to which they are attached combine to form a 10- to 12-membered spiroheterocycle, which is optionally substituted with one or more —$C_1$-$C_6$alkyl, —$(CH_2)_n NH_2$, or —$NH_2$. In certain such embodiments, n is 1. In one or more embodiments of Formula IV-A, $R^3$ and $R^a$ together with the atoms to which they are attached combine to form a 10- to 12-membered spiroheterocycle, which is optionally substituted with one or more —$C_1$-$C_6$alkyl, —OH, —$NH_2$, oxo, heteroaryl, heterocyclyl, —$(CH_2)_n NH_2$, —$(CH_2)_n OH$, —$CF_3$, —$CHF_2$, or —$CH_2F$.

In one or more embodiments of Formula IV-A, $X^1$ is N and $X^2$ is N. In one or more embodiments of Formula IV-A, $X^1$ is C and $X^2$ is CH. In one or more embodiments of Formula IV-A, $X^1$ is C and $X^2$ is N. In one or more embodiments of Formula IV-A, $X^1$ is N and $X^2$ is CH.

In certain embodiments of Formula IV, the compound is of Formula IV-B:

IV-B

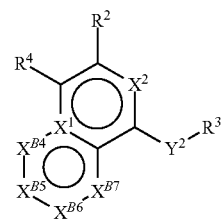

and pharmaceutically acceptable salts, prodrugs, solvates, hydrates, tautomers, and isomers thereof, wherein $X^{B4}$ is N or $CR^9$; $X^{B5}$ is N or $CR^9$; $X^{B6}$ is N or $CR^9$; and $X^{B7}$ is N or $CR^9$, wherein $R^9$ is independently, at each occurrence, —H, —$C_1$-$C_6$alkyl, —OH, —$NH_2$, heteroaryl, heterocyclyl, —$(CH_2)_n NH_2$, —$(CH_2)_n OH$, —$CF_3$, —$CHF_2$, or —$CH_2F$, provided that if $X^1$ is C, at least one of $X^{B4}$, $X^{B5}$, $X^{B6}$, and $X^{B7}$ is not $CR^9$, or provided that if each of $X^{B4}$, $X^{B5}$, $X^{B6}$, and $X^{B7}$ are $CR^9$, $X^1$ must be N.

In certain embodiments of Formula IV-B, $X^{B4}$ is N. In certain embodiments of Formula IV-B, $X^{B4}$ is $CR^9$. In certain embodiments of Formula IV-B, $X^{B5}$ is N. In certain embodiments of Formula IV-B, $X^{B5}$ is $CR^9$. In certain embodiments of Formula IV-B, $X^{B6}$ is N. In certain embodiments of Formula IV-B, $X^{B6}$ is $CR^9$. In certain embodiments of Formula IV-B, $X^{B7}$ is N. In certain embodiments of Formula IV-B, $X^{B7}$ is $CR^9$. In certain embodiments of Formula IV-B, $X^{B4}$ is N, $X^{B5}$ is $CR^9$, $X^{B6}$ is N, and $X^{B7}$ is $CR^9$. In certain such embodiments, $R^9$ is independently, at each occurrence, —H.

In some embodiments of Formula IV-B, $R^9$ is —$(CH_2)_n OH$ and n is 1. In some embodiments of Formula IV-B, $R^9$ is H.

In one or more embodiments of Formula IV-B, $R^4$ is H.

In one or more embodiments of Formula IV-B, $R^4$ is

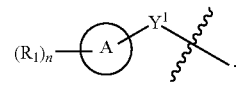

In certain such embodiments, $Y^1$ is —S— or a direct bond. In one or more embodiments of Formula IV-B, $Y^1$ is —S—. In one or more embodiments of Formula IV-B, $Y^1$ is a direct bond.

In one or more embodiments of the compounds of Formula IV-B, $Y^2$ is —$(CR^a{}_2)_m$—. In one or more embodiments of the compounds of Formula IV-B, $Y^2$ is —$NR^a$—.

In one or more embodiments of Formula IV-B, A is a monocyclic or polycyclic cycloalkyl. In one or more embodiments of Formula IV-B, A is a monocyclic or polycyclic heterocycloalkyl. In one or more embodiments of Formula IV-B, A is a monocyclic or polycyclic aryl. In one or more embodiments of Formula IV-B, A is phenyl. In one or more embodiments of Formula IV-B, A is a monocyclic or polycyclic heteroaryl. In one or more embodiments of Formula IV-B, A is pyridinyl. In one or more embodiments of Formula IV-B, A is indazolyl. In one or more embodiments of Formula IV-B, A is a 5- to 12-membered monocyclic or polycyclic aryl or heteroaryl.

In one or more embodiments of Formula IV-B, n is independently, at each occurrence, 0, 1, 2, or 3. In one or more embodiments of Formula IV-B, n is independently, at each occurrence, 1 or 2.

In one or more embodiments of Formula IV-B, $R^1$ is independently, at each occurrence, —H, —$OR^5$, halogen, —$C_1$-$C_6$alkyl, —CN, or —$NR^5R^6$. In one or more embodiments of Formula IV-B, $R^1$ is independently, at each occurrence, —H, —$OR^5$ or halogen. In one or more embodiments of Formula IV-B, $R^1$ is independently, at each occurrence, —H or —$OR^5$. In one or more embodiments of Formula IV-B, $R^1$ is independently, at each occurrence, —H or halogen. In one or more embodiments of Formula IV-B, $R^1$ is independently, at each occurrence, —H or —$NR^5R^6$. In one or more embodiments of Formula IV-B, $R^1$ is independently, at each occurrence, —H, —$OR^5$ or —$NR^5R^6$. In one or more embodiments of Formula IV-B, $R^1$ is independently, at each occurrence, —H, halogen or —$NR^5R^6$. In certain such embodiments, $R^5$ and $R^6$ are both -H. In one or more embodiments of Formula IV-B, $R^1$ is independently, at each occurrence, —H, methyl, fluoro, chloro, or —$NH_2$. In one or more embodiments of Formula IV-B, $R^1$ is independently, at each occurrence, —H, —CN or halogen.

In one or more embodiments of Formula IV-B, $R^5$ and $R^6$ are independently, at each occurrence, —H or —$C_1$-$C_6$alkyl. In one or more embodiments of Formula IV-B, $R^5$ and $R^6$ are independently, at each occurrence, —H. In one or more embodiments of Formula IV-B, $R^5$ and $R^6$ are independently, at each occurrence, —$C_1$-$C_6$alkyl.

In one or more embodiments of Formula IV-B, $R^2$ is —H. In one or more embodiments of Formula IV-B, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-B, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV-B, $R^2$ is —OH. In one or more embodiments of Formula IV-B, $R^2$ is —$NR^5R^6$. In one or more embodiments of Formula IV-B, $R^2$ is —$NH_2$.

In one or more embodiments of Formula IV-B, $R^a$ is —H.

In one or more embodiments of Formula IV-B, $R^3$ is an optionally substituted —$C_1$-$C_6$alkyl. In one or more embodiments of Formula IV-B, $R^3$ is an optionally substituted 3- to 12-membered monocyclic or polycyclic heterocycle. In one or more embodiments of Formula IV-B, $R^3$ is an optionally substituted 3- to 12-membered monocyclic heterocycle. In one or more embodiments of Formula IV-B, $R^3$ is an optionally substituted 5- to 12-membered polycyclic heterocycle.

In one or more embodiments of Formula IV-B, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-B, $R^3$ and $R^a$ together with the atom to which they are attached combine to form a 3- to 12-membered monocyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-B, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-B, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-B, $R^3$ and $R^a$ together with the atom to which they are attached combine to form a 3- to 12-membered polycyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-B, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-B. $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-B. $R^3$ and $R^a$ together with the atoms to which they are attached combine to form a 5- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV-B. $R^3$ and $R^a$ together with the atoms to which they are attached combine to form a 5- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-B, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-B, $R^3$ and $R^a$ together with the atoms to which they are attached combine to form a 10- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV-B, $R^3$ and $R^a$ together with the atoms to which they are attached combine to form a 10- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-B, $X^1$ is N and $X^2$ is N. In one or more embodiments of Formula IV-B, $X^1$ is C and $X^2$ is CH. In one or more embodiments of Formula IV-B, $X^1$ is C and $X^2$ is N. In one or more embodiments of Formula IV-B, $X^1$ is N and $X^2$ is CH.

In certain embodiments of Formula IV, the compound is of Formula IV-C:

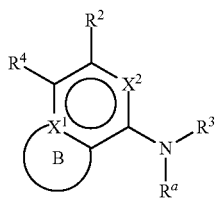

IV-C and pharmaceutically acceptable salts, prodrugs, solvates, hydrates, tautomers, and isomers thereof.

In one or more embodiments of Formula IV-C, $R^4$ is H. In one or more embodiments of Formula IV-C, $R^4$ is

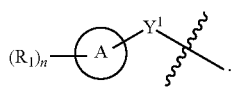

In certain such embodiments, $Y^1$ is —S— or a direct bond. In one or more embodiments of Formula IV-C, $Y^1$ is —S—. In one or more embodiments of Formula IV-C, $Y^1$ is a direct bond.

In one or more embodiments of Formula IV-C, A is a monocyclic or polycyclic cycloalkyl. In one or more embodiments of Formula IV-C, A is a monocyclic or polycyclic heterocycloalkyl. In one or more embodiments of Formula IV-C, A is a monocyclic or polycyclic aryl. In one or more embodiments of Formula IV-C, A is phenyl. In one or more embodiments of Formula IV-C, A is a monocyclic or polycyclic heteroaryl. In one or more embodiments of Formula IV-C, A is pyridinyl. In one or more embodiments of Formula IV-C, A is indazolyl. In one or more embodiments of Formula IV-C, A is a 5- to 12-membered monocyclic or polycyclic aryl or heteroaryl.

In one or more embodiments of Formula IV-C, n is independently, at each occurrence, 0, 1, 2, or 3. In one or more embodiments of Formula IV-C, n is independently, at each occurrence, 1 or 2.

In one or more embodiments of Formula IV-C, $R^1$ is independently, at each occurrence, —H, —OR$^5$, halogen, —C$_1$-C$_6$alkyl, —CN, or —NR$^5$R$^6$. In one or more embodiments of Formula IV-C, $R^1$ is independently, at each occurrence, —H, —OR$^5$ or halogen. In one or more embodiments of Formula IV-C, $R^1$ is independently, at each occurrence, —H or —OR$^5$. In one or more embodiments of Formula IV-C, $R^1$ is independently, at each occurrence, —H or halogen. In one or more embodiments of Formula IV-C, $R^1$ is independently, at each occurrence, —H or —NR$^5$R$^6$. In one or more embodiments of Formula IV-C, $R^1$ is independently, at each occurrence, —H, —OR$^5$ or —NR$^5$R$^6$. In one or more embodiments of Formula IV-C, $R^1$ is independently, at each occurrence, —H, halogen or —NR$^5$R$^6$. In certain such embodiments, $R^5$ and $R^6$ are both-H. In one or more embodiments of Formula IV-C. $R^1$ is independently, at each occurrence, —H, methyl, fluoro, chloro, or —NH$_2$. In one or more embodiments of Formula IV-C, $R^1$ is independently, at each occurrence, —H, —CN or halogen.

In one or more embodiments of Formula IV-C. $R^5$ and $R^6$ are independently, at each occurrence, —H or —C$_1$-C$_6$alkyl. In one or more embodiments of Formula IV-C. $R^5$ and $R^6$ are independently, at each occurrence, —H. In one or more embodiments of Formula IV-C, $R^5$ and $R^6$ are independently, at each occurrence, —C$_1$-C$_6$alkyl.

In one or more embodiments of Formula IV-C, $R^2$ is —H. In one or more embodiments of Formula IV-C, $R^2$ is —C$_1$-C$_6$alkyl, wherein each alkyl is optionally substituted with one or more —OH, halogen, —OR$^5$, or —NR$^5$R$^6$. In certain such embodiments, $R^2$ is methyl. In one or more embodiments of Formula IV-C, $R^2$ is —H, —OH, —NR$^5$R$^6$, —C$_1$-C$_6$alkyl, or —NH$_2$; wherein each alkyl is optionally substituted with one or more —OH, halogen, —OR$^5$, or —NR$^5$R$^6$. In one or more embodiments of Formula IV-C, $R^2$ is —OH. In one or more embodiments of Formula IV-C, $R^2$ is —NR$^5$R$^6$. In one or more embodiments of Formula IV-C, $R^2$ is —NH$_2$.

In one or more embodiments of Formula IV-C, $R^3$ and $R^a$ together with the atom to which they are attached combine to form a 3- to 12-membered monocyclic heterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-C, $R^3$ and $R^a$ together with the atom to which they are attached combine to form a 3- to 12-membered monocyclic heterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-C. $R^3$ and $R^a$ together with the atom to which they are attached combine to form a 3- to 12-membered monocyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-C, $R^3$ and $R^a$ together with the atoms to which they are attached combine to form a 3- to 12-membered polycyclic heterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-C, $R^3$ and $R^a$ together with the atom to which they are attached combine to form a 3- to 12-membered polycyclic heterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-C. $R^3$ and $R^a$ together with the atom to which they are attached combine to form a 3- to 12-membered polycyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-C, $R^3$ and $R^a$ together with the atoms to which they are attached combine to form a 5- to 12-membered spiroheterocycle, which is optionally substituted with one or more —C$_1$-C$_6$alkyl, —NH$_2$, —OH, —(CH$_2$)$_n$NH$_2$, —(CH$_2$)OH, —CF$_3$, —CHF$_2$, or —CH$_2$F. In one or more embodiments of Formula IV-C, $R^3$ and $R^a$ together with the atoms to which they are attached combine to form a 5- to 12-membered spiroheterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-C. $R^3$ and $R^a$ together with the atoms to which they are attached combine to form a 5- to 12-membered spiroheterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-C. $R^3$ and $R^a$ together with the atoms to which they are attached combine to form a 10- to 12-membered spiroheterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-C, R$^3$ and R$^a$ together with the atoms to which they are attached combine to form a 10- to 12-membered spiroheterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-C, R$^3$ and R$^a$ together with the atoms to which they are attached combine to form a 10- to 12-membered spiroheterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-C, X$^1$ is N and X$^2$ is N. In one or more embodiments of Formula IV-C, X$^1$ is C and X$^2$ is CH. In one or more embodiments of Formula IV-C, X$^1$ is C and X$^2$ is N. In one or more embodiments of Formula IV-C, X$^1$ is N and X$^2$ is CH.

In one or more embodiments of Formula IV-C, B, including the atoms at the points of attachment, is an optionally substituted monocyclic or polycyclic 5- to 12-membered heterocycle. In one or more embodiments of Formula IV-C, B, including the atoms at the points of attachment, is an optionally substituted monocyclic 5 to 6-membered heterocycle. In one or more embodiments of Formula IV-C, B, including the atoms at the points of attachment, is an optionally substituted monocyclic 7- to 12-membered heterocycle.

In one or more embodiments of Formula IV-C, B, including the atoms at the points of attachment, is an optionally substituted polycyclic 5- to 12-membered heterocyclyl. In certain embodiments, the heteroycyclyl ring is fused. In one or more embodiments of Formula IV-C, the heterocyclyl ring is bridged.

In one or more embodiments of Formula IV-C, B, including the atoms at the points of attachment, is an optionally substituted monocyclic or polycyclic 5- to 12-membered heteroaryl. In one or more embodiments of Formula IV-C, B, including the atoms at the points of attachment, is an optionally substituted monocyclic 5 to 6-membered heteroaryl. In one or more embodiments of Formula IV-C, B, including the atoms at the points of attachment, is a monocyclic 7- to 12-membered heteroaryl.

In one or more embodiments of Formula IV-C. B, including the atoms at the points of attachment, is an optionally substituted polycyclic 5- to 12-membered heteroaryl. In one or more embodiments of Formula IV-C, the polycyclic heteroaryl is a multiple condensed ring as described above. The rings of the multiple condensed ring system can be connected to each other via fused, spiro and bridged bonds when allowed by valency requirements.

In one or more embodiments of Formula IV-C. B is substituted with one or more —(CH$_2$)$_n$OH. In certain such embodiments, n is 1. In one or more embodiments of Formula IV-C. B is substituted with one or more —C$_1$-C$_6$alkyl, —OH, —NH$_2$, oxo, —(CH$_2$)$_n$NH$_2$, —(CH$_2$)$_n$OH, —CF$_3$, —CHF$_2$, or —CH$_2$F. In one or more embodiments of Formula IV-C, B is substituted with one or more oxo. In one or more embodiments of Formula IV-C. B is substituted with one or more —C$_1$-C$_6$alkyl. In one or more embodiments of Formula IV-C. B is substituted with one or more —OH. In one or more embodiments of Formula IV-C, B is substituted with one or more —NH$_2$. In one or more embodiments of Formula IV-C. B is substituted with one or more —CF$_3$. In one or more embodiments of Formula IV-C. B is substituted with one or more —CHF$_2$. In one or more embodiments of Formula IV-C, B is substituted with one or more —CH$_2$F. In one or more embodiments of Formula IV-C, B is substituted with one or more —(CH$_2$)$_n$NH$_2$. In certain such embodiments, n is 1.

In certain embodiments of Formula IV, the compound is of Formula IV-D:

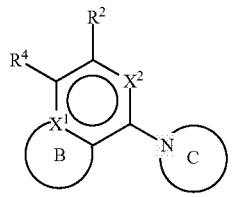

IV-D and pharmaceutically acceptable salts, prodrugs, solvates, hydrates, tautomers, and isomers thereof, wherein:

C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F. In some embodiments of Formula IV-D, the C ring is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In certain such embodiments, n is 1. In some embodiments of Formula IV-D, the C ring is optionally substituted with one or more —C$_1$-C$_6$alkyl, —(CH$_2$)$_n$NH$_2$, or —NH$_2$. In certain such embodiments, n is 1.

In certain embodiments of Formula IV-D, the C ring, along with the nitrogen atom to which it is attached, is an optionally substituted 3- to 12-membered monocyclic heterocycle. In certain embodiments of Formula IV-D, the C ring, along with the nitrogen atom to which it is attached, is an optionally substituted 3- to 12-membered polycyclic heterocycle. In certain embodiments of Formula IV-D, along with the nitrogen atom to which it is attached, is an optionally substituted 5- to 12-membered spiroheterocycle.

In certain embodiments of Formula IV-D, C ring, along with the nitrogen atom to which it is attached, is an optionally substituted

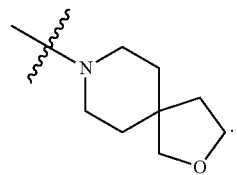 [SMILES: *N1CCC2(CCOC2)CC1]

In certain embodiments of Formula IV-D, C ring, along with the nitrogen atom to which it is attached, is an optionally substituted

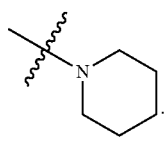

In certain embodiments of Formula IV-D, C ring, along with the nitrogen atom to which it is attached, is an optionally substituted

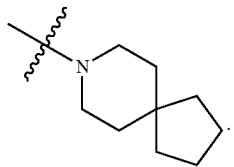 [SMILES: *N1CCC2(CCCC2)CC1]

.

In one or more embodiments of Formula IV-D, $R^4$ is H. In one or more embodiments of Formula IV-D, $R^4$ is

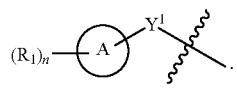

.

In certain such embodiments, $Y^1$ is —S— or a direct bond. In one or more embodiments of Formula IV-D, $Y^1$ is —S—. In one or more embodiments of Formula IV-D, $Y^1$ is a direct bond.

In one or more embodiments of Formula IV-D, A is a monocyclic or polycyclic cycloalkyl. In one or more embodiments of Formula IV-D, A is a monocyclic or polycyclic heterocycloalkyl. In one or more embodiments of Formula IV-D, A is a monocyclic or polycyclic aryl. In one or more embodiments of Formula IV-D, A is phenyl. In one or more embodiments of Formula IV-D, A is a monocyclic or polycyclic heteroaryl. In one or more embodiments of Formula IV-D, A is pyridinyl. In one or more embodiments of Formula IV-D, A is indazolyl. In one or more embodiments of Formula IV-D, A is a 5- to 12-membered monocyclic or polycyclic aryl or heteroaryl.

In one or more embodiments of Formula IV-D, n is independently, at each occurrence, 0, 1, 2, or 3. In one or more embodiments of Formula IV-D, n is independently, at each occurrence, 1 or 2.

In one or more embodiments of Formula IV-D, $R^1$ is independently, at each occurrence, —H, —$OR^5$, halogen, —$C_1$-$C_6$alkyl, —CN, or —$NR^5R^6$. In one or more embodiments of Formula IV-D, $R^1$ is independently, at each occurrence, —H, —$OR^5$ or halogen. In one or more embodiments of Formula IV-D, $R^1$ is independently, at each occurrence, —H or —$OR^5$. In one or more embodiments of Formula IV-D, $R^1$ is independently, at each occurrence, —H or halogen. In one or more embodiments of Formula IV-D, $R^1$ is independently, at each occurrence, —H or —$NR^5R^6$. In one or more embodiments of Formula IV-D, $R^1$ is independently, at each occurrence, —H, —$OR^5$ or —$NR^5R^6$. In one or more embodiments of Formula IV-D, $R^1$ is independently, at each occurrence, —H, halogen or —$NR^5R^6$. In certain such embodiments, $R^5$ and $R^6$ are both-H. In one or more embodiments of Formula IV-D. $R^1$ is independently, at each occurrence, —H, methyl, fluoro, chloro, or —$NH_2$. In one or more embodiments of Formula IV-D, $R^1$ is independently, at each occurrence, —H, —CN or halogen.

In one or more embodiments of Formula IV-D, $R^5$ and $R^6$ are independently, at each occurrence, —H or —$C_1$-$C_6$alkyl. In one or more embodiments of Formula IV-D, $R^5$ and $R^6$ are independently, at each occurrence, —H. In one or more embodiments of Formula IV-D, $R^5$ and $R^6$ are independently, at each occurrence, —$C_1$-$C_6$alkyl.

In one or more embodiments of Formula IV-D, $R^2$ is —H. In one or more embodiments of Formula IV-D, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-D. $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV-D, $R^2$ is —OH. In one or more embodiments of Formula IV-D, $R^2$ is —$NR^5R^6$. In one or more embodiments of Formula IV-D, $R^2$ is —$NH_2$.

In one or more embodiments of Formula IV-D, $X^1$ is N and $X^2$ is N. In one or more embodiments of Formula IV-D, $X^1$ is C and $X^2$ is CH. In one or more embodiments of Formula IV-D, $X^1$ is C and $X^2$ is N. In one or more embodiments of Formula IV-D, $X^1$ is N and $X^2$ is CH.

In one or more embodiments of Formula IV-D, B, including the atoms at the points of attachment, is an optionally substituted monocyclic or polycyclic 5- to 12-membered heterocycle. In one or more embodiments of Formula IV-D, B, including the atoms at the points of attachment, is an optionally substituted monocyclic 5 to 6-membered heterocycle. In one or more embodiments of Formula IV-D, B, including the atoms at the points of attachment, is an optionally substituted monocyclic 7- to 12-membered heterocycle.

In one or more embodiments of Formula IV-D, B, including the atoms at the points of attachment, is an optionally substituted polycyclic 5- to 12-membered heterocyclyl. In certain embodiments, the heteroycyclyl ring is fused. In one or more embodiments of Formula IV-D, the heterocyclyl ring is bridged.

In one or more embodiments of Formula IV-D, B, including the atoms at the points of attachment, is an optionally substituted monocyclic or polycyclic 5- to 12-membered heteroaryl. In one or more embodiments of Formula IV-D, B, including the atoms at the points of attachment, is an optionally substituted monocyclic 5 to 6-membered heteroaryl. In one or more embodiments of Formula IV-D, B, including the atoms at the points of attachment, is a monocyclic 7- to 12-membered heteroaryl.

In one or more embodiments of Formula IV-D, B, including the atoms at the points of attachment, is an optionally substituted polycyclic 5- to 12-membered heteroaryl. In one or more embodiments of Formula IV-D, the polycyclic heteroaryl is a multiple condensed ring as described above. The rings of the multiple condensed ring system can be connected to each other via fused, spiro and bridged bonds when allowed by valency requirements.

In one or more embodiments of Formula IV-D, B is substituted with one or more —$(CH_2)_nOH$. In certain such embodiments, n is 1. In one or more embodiments of Formula IV-D, B is substituted with one or more —$C_1$-$C_6$alkyl, —OH, —$NH_2$, Oxo, —$(CH_2)_nNH_2$, —$(CH_2)_nOH$, —$CF_3$, —$CHF_2$, or —$CH_2F$. In one or more embodiments of Formula IV-D, B is substituted with one or more oxo. In one or more embodiments of Formula IV-D, B is substituted with one or more —$C_1$-$C_6$alkyl. In one or more embodiments of Formula IV-D, B is substituted with one or more —OH. In one or more embodiments of Formula IV-D, B is substituted with one or more —$NH_2$. In one or more embodiments of Formula IV-D, B is substituted with one or more —$CF_3$. In one or more embodiments of Formula IV-D, B is substituted with one or more —$CHF_2$. In one or more embodiments of Formula IV-D, B is substituted with one or more —$CH_2F$. In one or more embodiments of Formula IV-D, B is substituted with one or more —(CH$_2$)$_n$NH$_2$. In certain such embodiments, n is 1.

In certain embodiments of Formula IV, the compound is of Formula IV-E:

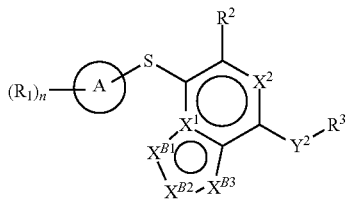

IV-E and pharmaceutically acceptable salts, prodrugs, solvates, hydrates, tautomers, and isomers thereof, wherein X$^{B1}$ is N, NR$^9$, CR$^9$, S, or O; X$^{B2}$ is N, NR$^9$, CR$^9$, S, or O; and X$^{B3}$ is N, NR$^9$, CR$^9$, S, or O, wherein R$^9$ is independently, at each occurrence, —H, —C$_1$-C$_6$alkyl, —OH, —NH$_2$, heteroaryl, heterocyclyl, —(CH$_2$)$_n$NH$_2$, —(CH$_2$)$_n$OH, —CF$_3$, —CHF$_2$, or —CH$_2$F, provided that if X$^1$ is C, at least one of X$^{B1}$, X$^{B2}$, and X$^{B3}$ is not CR$^9$, or provided that if each of X$^{B1}$, X$^{B2}$, and X$^{B3}$ are CR$^9$, X$^1$ must be N.

In certain embodiments of Formula IV-E, X$^{B1}$ is N or NR$^9$. In certain embodiments of Formula IV-E, X$^{B1}$ is CR$^9$. In certain embodiments of Formula IV-E, X$^{B1}$ is S. In certain embodiments of Formula IV-E, X$^{B1}$ is O. In certain embodiments of Formula IV-E, X$^{B2}$ is N or NR$^9$. In certain embodiments of Formula IV-E, X$^{B2}$ is CR$^9$. In certain embodiments of Formula IV-E, X$^{B2}$ is S. In certain embodiments of Formula IV-E, X$^{B2}$ is O. In certain embodiments of Formula IV-E, X$^{B3}$ is N or NR$^9$. In certain embodiments of Formula IV-E, X$^{B3}$ is CR$^9$. In certain embodiments of Formula IV-E, X$^{B3}$ is S. In certain embodiments of Formula IV-E, X$^{B3}$ is O.

In certain embodiments of Formula IV-E, X$^{B1}$ is N, NR$^9$, or CR$^9$; X$^{B2}$ is N, NR$^9$, or CR$^9$; and X$^{B3}$ is N, NR$^9$, or CR$^9$. In certain embodiments of Formula IV-E, X$^{B1}$ is N or NR$^9$. In certain embodiments of Formula IV-E, X$^{B1}$ is CR$^9$. In certain embodiments of Formula IV-E, X$^{B2}$ is N or NR$^9$. In certain embodiments of Formula IV-E, X$^{B2}$ is CR$^9$. In certain embodiments of Formula IV-E, X$^{B3}$ is N or NR$^9$. In certain embodiments of Formula IV-E, X$^{B3}$ is CR$^9$.

In some embodiments of Formula IV-E, R$^9$ is —(CH$_2$)$_n$OH and n is 1. In some embodiments of Formula IV-E, R$^9$ is H.

In certain embodiments of Formula IV-E,

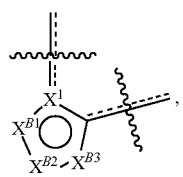

wherein ===== is a single bond or double bond to satisfy valency rules, is

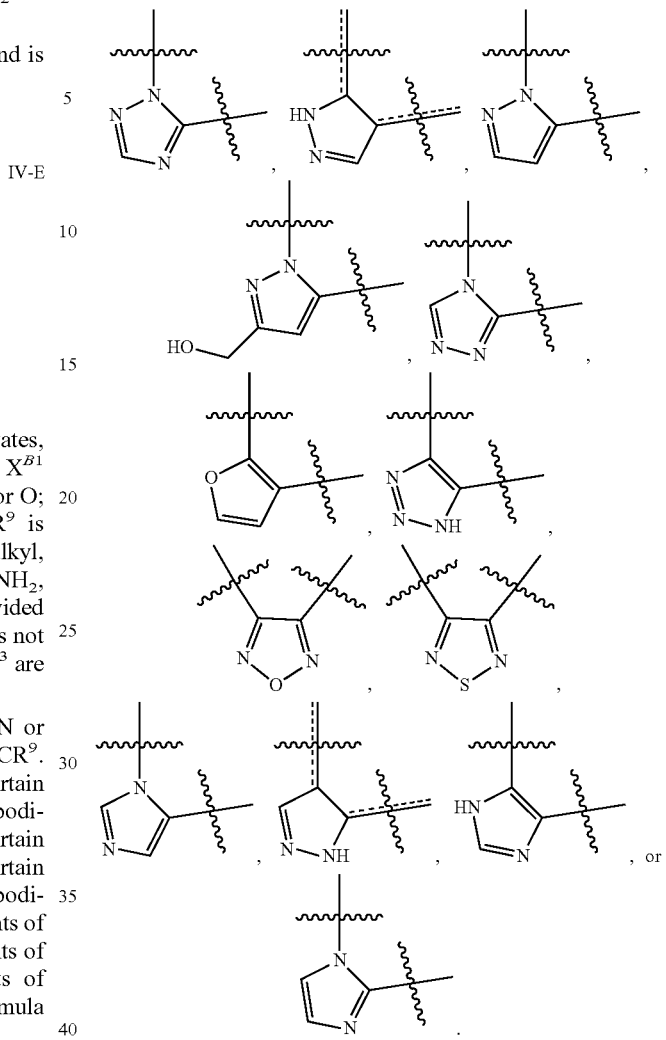

In one or more embodiments of the compounds of Formula IV-E, Y$^2$ is —(CR$^a$$_2$)$_m$—. In one or more embodiments of the compounds of Formula IV-E, Y$^2$ is —NR$^a$—.

In one or more embodiments of Formula IV-E, A is a monocyclic or polycyclic cycloalkyl. In one or more embodiments of Formula IV-E, A is a monocyclic or polycyclic heterocycloalkyl. In one or more embodiments of Formula IV-E, A is a monocyclic or polycyclic aryl. In one or more embodiments of Formula IV-E, A is phenyl. In one or more embodiments of Formula IV-E, A is a monocyclic or polycyclic heteroaryl. In one or more embodiments of Formula IV-E, A is pyridinyl. In one or more embodiments of Formula IV-E, A is indazolyl. In one or more embodiments of Formula IV-E, A is a 5- to 12-membered monocyclic or polycyclic aryl or heteroaryl.

In one or more embodiments of Formula IV-E, n is independently, at each occurrence, 0, 1, 2, or 3. In one or more embodiments of Formula IV-E, n is independently, at each occurrence, 1 or 2.

In one or more embodiments of Formula IV-E, R$^1$ is independently, at each occurrence, —H, —OR$^5$, halogen, —C$_1$-C$_6$alkyl, —CN, or —NR$^5$R$^6$. In one or more embodiments of Formula IV-E, R$^1$ is independently, at each occurrence, —H, —OR$^5$ or halogen. In one or more embodiments of Formula IV-E, R$^1$ is independently, at each occurrence, —H or —OR$^5$. In one or more embodiments of Formula IV-E, R$^1$ is independently, at each occurrence, —H or halogen. In one or more embodiments of Formula IV-E, R$^1$ is independently, at each occurrence, —H or —NR$^5$R$^6$. In one or more embodiments of Formula IV-E, R$^1$ is independently, at each occurrence, —H, —OR$^5$ or —NR$^5$R$^6$. In one or more embodiments of Formula IV-E, R$^1$ is independently, at each occurrence, —H, halogen or —NR$^5$R$^6$. In certain such embodiments, R$^5$ and R$^6$ are both-H. In one or more embodiments of Formula IV-E, R$^1$ is independently, at each occurrence, —H, methyl, fluoro, chloro, or —NH$_2$. In one or more embodiments of Formula IV-E, R$^1$ is independently, at each occurrence, —H, —CN or halogen.

In one or more embodiments of Formula IV-E, R$^5$ and R$^6$ are independently, at each occurrence, —H or —C$_1$-C$_6$alkyl. In one or more embodiments of Formula IV-E, R$^5$ and R$^6$ are independently, at each occurrence, —H. In one or more embodiments of Formula IV-E, R$^5$ and R$^6$ are independently, at each occurrence, —C$_1$-C$_6$alkyl.

In one or more embodiments of Formula IV-E, R$^2$ is —H. In one or more embodiments of Formula IV-E, R$^2$ is —C$_1$-C$_6$alkyl, wherein each alkyl is optionally substituted with one or more —OH, halogen, —OR$^5$, or —NR$^5$R$^6$. In certain such embodiments, R$^2$ is methyl. In one or more embodiments of Formula IV-E, R$^2$ is —H, —OH, —NR$^5$R$^6$, —C$_1$-C$_6$alkyl, or —NH$_2$; wherein each alkyl is optionally substituted with one or more —OH, halogen, —OR$^5$, or —NR$^5$R$^6$. In one or more embodiments of Formula IV-E, R$^2$ is —OH. In one or more embodiments of Formula IV-E, R$^2$ is —NR$^5$R$^6$. In one or more embodiments of Formula IV-E, R$^2$ is —NH$_2$.

In one or more embodiments of Formula IV-E, R$^a$ is —H.

In one or more embodiments of Formula IV-E, R$^3$ is an optionally substituted —C$_1$-C$_6$alkyl. In one or more embodiments of Formula IV-E, R$^3$ is an optionally substituted 3- to 12-membered monocyclic or polycyclic heterocycle. In one or more embodiments of Formula IV-E, R$^3$ is an optionally substituted 3- to 12-membered monocyclic heterocycle. In one or more embodiments of Formula IV-E, R$^3$ is an optionally substituted 5- to 12-membered polycyclic heterocycle.

In one or more embodiments of Formula IV-E, R$^3$ and R$^a$ together with the atom to which they are attached combine to form a 3- to 12-membered monocyclic heterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-E, R$^3$ and R$^a$ together with the atom to which they are attached combine to form a 3- to 12-membered monocyclic heterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-E, R$^3$ and R$^a$ together with the atom to which they are attached combine to form a 3- to 12-membered monocyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-E, R$^3$ and R$^a$ together with the atoms to which they are attached combine to form a 3- to 12-membered polycyclic heterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-E, R$^3$ and R$^a$ together with the atom to which they are attached combine to form a 3- to 12-membered polycyclic heterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-E. R$^3$ and R$^a$ together with the atom to which they are attached combine to form a 3- to 12-membered polycyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-E. R$^3$ and R$^a$ together with the atoms to which they are attached combine to form a 5- to 12-membered spiroheterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-E, R$^3$ and R$^a$ together with the atoms to which they are attached combine to form a 5- to 12-membered spiroheterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-E. R$^3$ and R$^a$ together with the atoms to which they are attached combine to form a 5- to 12-membered spiroheterocycle, which is optionally substituted with one or more —C$_1$-C$_6$alkyl. —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-E. R$^3$ and R$^a$ together with the atoms to which they are attached combine to form a 10- to 12-membered spiroheterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-E, R$^3$ and R$^a$ together with the atoms to which they are attached combine to form a 10- to 12-membered spiroheterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-E. R$^3$ and R$^a$ together with the atoms to which they are attached combine to form a 10- to 12-membered spiroheterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-E, X$^1$ is N and X$^2$ is N. In one or more embodiments of Formula IV-E, X$^1$ is C and X$^2$ is CH. In one or more embodiments of Formula IV-E, X$^1$ is C and X$^2$ is N. In one or more embodiments of Formula IV-E, X$^1$ is N and X$^2$ is CH.

In certain embodiments of Formula IV, the compound is of Formula IV-F:

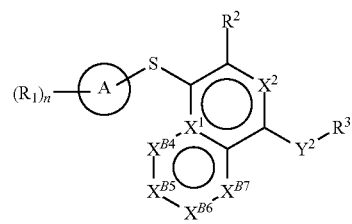

IV-F and pharmaceutically acceptable salts, prodrugs, solvates, hydrates, tautomers, and isomers thereof, wherein X$^{B4}$ is N or CR$^9$; X$^{B5}$ is N or CR$^9$; X$^{B6}$ is N or CR$^9$; and X$^{B7}$ is N or CR$^9$, wherein R$^9$ is independently, at each occurrence, —H, —C$_1$-C$_6$alkyl, —OH, —NH$_2$, heteroaryl, heterocyclyl, —(CH$_2$)$_n$NH$_2$, —(CH$_2$)$_n$OH, —CF$_3$, —CHF$_2$, or —CH$_2$F, provided that if X$^1$ is C, at least one of X$^{B4}$, X$^{B5}$, X$^{B6}$, and X$^{B7}$ is not CR$^9$, or provided that if each of X$^{B4}$, X$^{B5}$ X$^{B6}$, and X$^{B7}$ are CR$^9$, X$^1$ must be N.

In certain embodiments of Formula IV-F, X$^{B4}$ is N. In certain embodiments of Formula IV-F, X$^{B4}$ is CR$^9$. In certain embodiments of Formula IV-F, X$^{B5}$ is N. In certain embodiments of Formula IV-F, X$^{B5}$ is CR$^9$. In certain embodiments of Formula IV-F, X$^{B6}$ is N. In certain embodiments of Formula IV-F, X$^{B6}$ is CR$^9$. In certain embodiments of Formula IV-F, X$^{B7}$ is N. In certain embodiments of Formula IV-F, X$^{B7}$ is CR$^9$. In certain embodiments of Formula IV-F, X$^{B4}$ is N, X$^{B5}$ is CR$^9$, X$^{B6}$ is N, and X$^{B7}$ is CR$^9$. In certain such embodiments, R$^9$ is independently, at each occurrence, —H.

In some embodiments of Formula IV-F, R$^9$ is —(CH$_2$)$_n$OH and n is 1. In some embodiments of Formula IV-F, R$^9$ is H.

In one or more embodiments of the compounds of Formula IV-F, Y$^2$ is —(CR$^a$$_2$)$_m$—. In one or more embodiments of the compounds of Formula IV-F, Y$^2$ is —NR$^a$—.

In one or more embodiments of Formula IV-F, A is a monocyclic or polycyclic cycloalkyl. In one or more embodiments of Formula IV-F, A is a monocyclic or polycyclic heterocycloalkyl. In one or more embodiments of Formula IV-F, A is a monocyclic or polycyclic aryl. In one or more embodiments of Formula IV-F, A is phenyl. In one or more embodiments of Formula IV-F, A is a monocyclic or polycyclic heteroaryl. In one or more embodiments of Formula IV-F, A is pyridinyl. In one or more embodiments of Formula IV-F, A is indazolyl. In one or more embodiments of Formula IV-F, A is a 5- to 12-membered monocyclic or polycyclic aryl or heteroaryl.

In one or more embodiments of Formula IV-F, n is independently, at each occurrence, 0, 1, 2, or 3. In one or more embodiments of Formula IV-F, n is independently, at each occurrence, 1 or 2.

In one or more embodiments of Formula IV-F, R$^1$ is independently, at each occurrence, —H, —OR$^5$, halogen, —C$_1$-C$_6$alkyl, —CN, or —NR$^5$R$^6$. In one or more embodiments of Formula IV-F, R$^1$ is independently, at each occurrence, —H, —OR$^5$ or halogen. In one or more embodiments of Formula IV-F, R$^1$ is independently, at each occurrence, —H or —OR$^5$. In one or more embodiments of Formula IV-F, R$^1$ is independently, at each occurrence, —H or halogen. In one or more embodiments of Formula IV-F, R$^1$ is independently, at each occurrence, —H or —NR$^5$R$^6$. In one or more embodiments of Formula IV-F, R$^1$ is independently, at each occurrence, —H, —OR$^5$ or —NR$^5$R$^6$. In one or more embodiments of Formula IV-F, R$^1$ is independently, at each occurrence, —H, halogen or —NR$^5$R$^6$. In certain such embodiments, R$^5$ and R$^6$ are both-H. In one or more embodiments of Formula IV-F, R$^1$ is independently, at each occurrence, —H, methyl, fluoro, chloro, or —NH$_2$. In one or more embodiments of Formula IV-F, R$^1$ is independently, at each occurrence, —H, —CN or halogen.

In one or more embodiments of Formula IV-F, R$^5$ and R$^6$ are independently, at each occurrence, —H or —C$_1$-C$_6$alkyl. In one or more embodiments of Formula IV-F, R$^5$ and R$^6$ are independently, at each occurrence, —H. In one or more embodiments of Formula IV-F, R$^5$ and R$^6$ are independently, at each occurrence, —C$_1$-C$_6$alkyl.

In one or more embodiments of Formula IV-F, R$^2$ is —H. In one or more embodiments of Formula IV-F, R$^2$ is —C$_1$-C$_6$alkyl, wherein each alkyl is optionally substituted with one or more —OH, halogen, —OR$^5$, or —NR$^5$R$^6$. In certain such embodiments, R$^2$ is methyl. In one or more embodiments of Formula IV-F, R$^2$ is —H, —OH, —NR$^5$R$^6$, —C$_1$-C$_6$alkyl, or —NH$_2$; wherein each alkyl is optionally substituted with one or more —OH, halogen, —OR$^5$, or —NR$^5$R$^6$. In one or more embodiments of Formula IV-F. R$^2$ is —OH. In one or more embodiments of Formula IV-F, R$^2$ is —NR$^5$R$^6$. In one or more embodiments of Formula IV-F. R$^2$ is —NH$_2$.

In one or more embodiments of Formula IV-F, R$^a$ is —H.

In one or more embodiments of Formula IV-F, R$^3$ is an optionally substituted —C$_1$-C$_6$alkyl. In one or more embodiments of Formula IV-F, R$^3$ is an optionally substituted 3- to 12-membered monocyclic or polycyclic heterocycle. In one or more embodiments of Formula IV-F. R$^3$ is an optionally substituted 3- to 12-membered monocyclic heterocycle. In one or more embodiments of Formula IV-F. R$^3$ is an optionally substituted 5- to 12-membered polycyclic heterocycle.

In one or more embodiments of Formula IV-F. R$^3$ and R$^a$ together with the atom to which they are attached combine to form a 3- to 12-membered monocyclic heterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-F. R$^3$ and R$^a$ together with the atom to which they are attached combine to form a 3- to 12-membered monocyclic heterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-F. R$^3$ and R$^a$ together with the atom to which they are attached combine to form a 3- to 12-membered monocyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-F. R$^3$ and R$^a$ together with the atoms to which they are attached combine to form a 3- to 12-membered polycyclic heterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-F. R$^3$ and R$^a$ together with the atom to which they are attached combine to form a 3- to 12-membered polycyclic heterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-F. R$^3$ and R$^a$ together with the atom to which they are attached combine to form a 3- to 12-membered polycyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-F. R$^3$ and R$^a$ together with the atoms to which they are attached combine to form a 5- to 12-membered spiroheterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-F. R$^3$ and R$^a$ together with the atoms to which they are attached combine to form a 5- to 12-membered spiroheterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-F. R$^3$ and R$^a$ together with the atoms to which they are attached combine to form a 5- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-F, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-F, $R^3$ and $R^a$ together with the atoms to which they are attached combine to form a 10- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV-F, $R^3$ and $R^a$ together with the atoms to which they are attached combine to form a 10- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-F, $X^1$ is N and $X^2$ is N. In one or more embodiments of Formula IV-F, $X^1$ is C and $X^2$ is CH. In one or more embodiments of Formula IV-F, $X^1$ is C and $X^2$ is N. In one or more embodiments of Formula IV-F, $X^1$ is N and $X^2$ is CH.

In certain embodiments of Formula IV, the compound is of Formula IV-G:

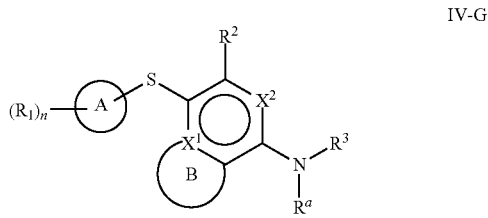

IV-G and pharmaceutically acceptable salts, prodrugs, solvates, hydrates, tautomers, and isomers thereof.

In one or more embodiments of Formula IV-G, A is a monocyclic or polycyclic cycloalkyl. In one or more embodiments of Formula IV-G, A is a monocyclic or polycyclic heterocycloalkyl. In one or more embodiments of Formula IV-G, A is a monocyclic or polycyclic aryl. In one or more embodiments of Formula IV-G, A is phenyl. In one or more embodiments of Formula IV-G, A is a monocyclic or polycyclic heteroaryl. In one or more embodiments of Formula IV-G, A is pyridinyl. In one or more embodiments of Formula IV-G, A is indazolyl. In one or more embodiments of Formula IV-G, A is a 5- to 12-membered monocyclic or polycyclic aryl or heteroaryl.

In one or more embodiments of Formula IV-G, n is independently, at each occurrence, 0, 1, 2, or 3. In one or more embodiments of Formula IV-G, n is independently, at each occurrence, 1 or 2.

In one or more embodiments of Formula IV-G, $R^1$ is independently, at each occurrence, —H, —$OR^5$, halogen, —$C_1$-$C_6$alkyl, —CN, or —$NR^5R^6$. In one or more embodiments of Formula IV-G, $R^1$ is independently, at each occurrence, —H, —$OR^5$ or halogen. In one or more embodiments of Formula IV-G, $R^1$ is independently, at each occurrence, —H or —$OR^5$. In one or more embodiments of Formula IV-G, $R^1$ is independently, at each occurrence, —H or halogen. In one or more embodiments of Formula IV-G, $R^1$ is independently, at each occurrence, —H or —$NR^5R^6$. In one or more embodiments of Formula IV-G, $R^1$ is independently, at each occurrence, —H, —$OR^5$ or —$NR^5R^6$. In one or more embodiments of Formula IV-G, $R^1$ is independently, at each occurrence, —H, halogen or —$NR^5R^6$. In certain such embodiments, $R^5$ and $R^6$ are both-H. In one or more embodiments of Formula IV-G. $R^1$ is independently, at each occurrence, —H, methyl, fluoro, chloro, or —$NH_2$. In one or more embodiments of Formula IV-G, $R^1$ is independently, at each occurrence, —H, —CN or halogen.

In one or more embodiments of Formula IV-G, $R^5$ and $R^6$ are independently, at each occurrence, —H or —$C_1$-$C_6$alkyl. In one or more embodiments of Formula IV-G, $R^5$ and $R^6$ are independently, at each occurrence, —H. In one or more embodiments of Formula IV-G, $R^5$ and $R^6$ are independently, at each occurrence, —$C_1$-$C_6$alkyl.

In one or more embodiments of Formula IV-G, $R^2$ is —H. In one or more embodiments of Formula IV-G, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-G, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV-G, $R^2$ is —OH. In one or more embodiments of Formula IV-G, $R^2$ is —$NR^5R^6$. In one or more embodiments of Formula IV-G, $R^2$ is —$NH_2$.

In one or more embodiments of Formula IV-G, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-G, $R^3$ and $R^a$ together with the atom to which they are attached combine to form a 3- to 12-membered monocyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-G, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-G, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-G, $R^3$ and $R^a$ together with the atom to which they are attached combine to form a 3- to 12-membered polycyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-G, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-G, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-G, $R^3$ and $R^a$ together with the atoms to which they are attached combine to form a 5- to 12-membered spiroheterocycle, which is optionally substituted with one or more $-C_1-C_6$alkyl, $-(CH_2)_nNH_2$, or $-NH_2$. In certain such embodiments, n is 1. In one or more embodiments of Formula IV-G, $R^3$ and $R^a$ together with the atoms to which they are attached combine to form a 5- to 12-membered spiroheterocycle, which is optionally substituted with one or more $-C_1-C_6$alkyl, $-OH$, $-NH_2$, oxo, heteroaryl, heterocyclyl, $-(CH_2)_nNH_2$, $-(CH_2)_nOH$, $-CF_3$, $-CHF_2$, or $-CH_2F$.

In one or more embodiments of Formula IV-G, $R^3$ and $R^a$ together with the atoms to which they are attached combine to form a 10- to 12-membered spiroheterocycle, which is optionally substituted with one or more $-C_1-C_6$alkyl, $-NH_2$, $-OH$, $-(CH_2)_nNH_2$, $-(CH_2)_nOH$, $-CF_3$, $-CHF_2$, or $-CH_2F$. In one or more embodiments of Formula IV-G, $R^3$ and $R^a$ together with the atoms to which they are attached combine to form a 10- to 12-membered spiroheterocycle, which is optionally substituted with one or more $-C_1-C_6$alkyl, $-(CH_2)_nNH_2$, or $-NH_2$. In certain such embodiments, n is 1. In one or more embodiments of Formula IV-G, $R^3$ and $R^a$ together with the atoms to which they are attached combine to form a 10- to 12-membered spiroheterocycle, which is optionally substituted with one or more $-C_1-C_6$alkyl, $-OH$, $-NH_2$, oxo, heteroaryl, heterocyclyl, $-(CH_2)_nNH_2$, $-(CH_2)_nOH$, $-CF_3$, $-CHF_2$, or $-CH_2F$.

In one or more embodiments of Formula IV-G, $X^1$ is N and $X^2$ is N. In one or more embodiments of Formula IV-G, $X^1$ is C and $X^2$ is CH. In one or more embodiments of Formula IV-G, $X^1$ is C and $X^2$ is N. In one or more embodiments of Formula IV-G, $X^1$ is N and $X^2$ is CH.

In one or more embodiments of Formula IV-G, B, including the atoms at the points of attachment, is an optionally substituted monocyclic or polycyclic 5- to 12-membered heterocycle. In one or more embodiments of Formula IV-G, B, including the atoms at the points of attachment, is an optionally substituted monocyclic 5 to 6-membered heterocycle. In one or more embodiments of Formula IV-G, B, including the atoms at the points of attachment, is an optionally substituted monocyclic 7- to 12-membered heterocycle.

In one or more embodiments of Formula IV-G, B, including the atoms at the points of attachment, is an optionally substituted polycyclic 5- to 12-membered heterocyclyl. In certain embodiments, the heteroycyclyl ring is fused. In one or more embodiments of Formula IV-G, the heterocyclyl ring is bridged.

In one or more embodiments of Formula IV-G, B, including the atoms at the points of attachment, is an optionally substituted monocyclic or polycyclic 5- to 12-membered heteroaryl. In one or more embodiments of Formula IV-G, B, including the atoms at the points of attachment, is an optionally substituted monocyclic 5 to 6-membered heteroaryl. In one or more embodiments of Formula IV-G, B, including the atoms at the points of attachment, is a monocyclic 7- to 12-membered heteroaryl.

In one or more embodiments of Formula IV-G, B, including the atoms at the points of attachment, is an optionally substituted polycyclic 5- to 12-membered heteroaryl. In one or more embodiments of Formula IV-G, the polycyclic heteroaryl is a multiple condensed ring as described above. The rings of the multiple condensed ring system can be connected to each other via fused, spiro and bridged bonds when allowed by valency requirements.

In one or more embodiments of Formula IV-G, B is substituted with one or more $-(CH_2)_nOH$. In certain such embodiments, n is 1. In one or more embodiments of Formula IV-G, B is substituted with one or more $-C_1-C_6$alkyl, $-OH$, $-NH_2$, oxo, $-(CH_2)_nNH_2$, $-(CH_2)_nOH$, $-CF_3$, $-CHF_2$, or $-CH_2F$. In one or more embodiments of Formula IV-G, B is substituted with one or more oxo. In one or more embodiments of Formula IV-G, B is substituted with one or more $-C_1-C_6$alkyl. In one or more embodiments of Formula IV-G, B is substituted with one or more $-OH$. In one or more embodiments of Formula IV-G, B is substituted with one or more $-NH_2$. In one or more embodiments of Formula IV-G, B is substituted with one or more $-CF_3$. In one or more embodiments of Formula IV-G, B is substituted with one or more $-CHF_2$. In one or more embodiments of Formula IV-G, B is substituted with one or more $-CH_2F$. In one or more embodiments of Formula IV-G, B is substituted with one or more $-(CH_2)_nNH_2$. In certain such embodiments, n is 1.

In certain embodiments of Formula IV, the compound is of Formula IV-H:

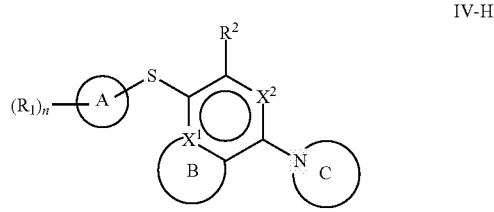

IV-H and pharmaceutically acceptable salts, prodrugs, solvates, hydrates, tautomers, and isomers thereof, wherein:

C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is optionally substituted with one or more $-C_1-C_6$alkyl, $-OH$, $-NH_2$, oxo, heteroaryl, heterocyclyl, $-(CH_2)_nNH_2$, $-(CH_2)_nOH$, $-CF_3$, $-CHF_2$, or $-CH_2F$. In some embodiments of Formula IV-H, the C ring is optionally substituted with one or more $-C_1-C_6$alkyl, $-NH_2$, $-OH$, $-(CH_2)_nNH_2$, $-(CH_2)_nOH$, $-CF_3$, $-CHF_2$, or $-CH_2F$. In certain such embodiments, n is 1. In some embodiments of Formula IV-H, the C ring is optionally substituted with one or more $-C_1-C_6$alkyl, $-(CH_2)_nNH_2$, or $-NH_2$. In certain such embodiments, n is 1.

In certain embodiments of Formula IV-H, the C ring, along with the nitrogen atom to which it is attached, is an optionally substituted 3- to 12-membered monocyclic heterocycle. In certain embodiments of Formula IV-H, the C ring, along with the nitrogen atom to which it is attached, is an optionally substituted 3- to 12-membered polycyclic heterocycle. In certain embodiments of Formula IV-H, along with the nitrogen atom to which it is attached, is an optionally substituted 5- to 12-membered spiroheterocycle.

In certain embodiments of Formula IV-H, C ring, along with the nitrogen atom to which it is attached, is an optionally substituted

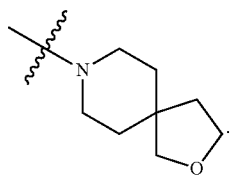 [SMILES: *N1CCC2(CCOC2)CC1]

In certain embodiments of Formula IV-H, C ring, along with the nitrogen atom to which it is attached, is an optionally substituted

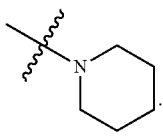 [SMILES: *N1CCCCC1]

In certain embodiments of Formula IV-H, C ring, along with the nitrogen atom to which it is attached, is an optionally substituted

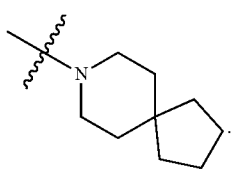 [SMILES: *N1CCC2(CCCC2)CC1]

In one or more embodiments of Formula IV-H, A is a monocyclic or polycyclic cycloalkyl. In one or more embodiments of Formula IV-H, A is a monocyclic or polycyclic heterocycloalkyl. In one or more embodiments of Formula IV-H, A is a monocyclic or polycyclic aryl. In one or more embodiments of Formula IV-H, A is phenyl. In one or more embodiments of Formula IV-H, A is a monocyclic or polycyclic heteroaryl. In one or more embodiments of Formula IV-H, A is pyridinyl. In one or more embodiments of Formula IV-H, A is indazolyl. In one or more embodiments of Formula IV-H, A is a 5- to 12-membered monocyclic or polycyclic aryl or heteroaryl.

In one or more embodiments of Formula IV-H, n is independently, at each occurrence, 0, 1, 2, or 3. In one or more embodiments of Formula IV-H, n is independently, at each occurrence, 1 or 2.

In one or more embodiments of Formula IV-H, $R^1$ is independently, at each occurrence, —H, —$OR^5$, halogen, —$C_1$-$C_6$alkyl, —CN, or —$NR^5R^6$. In one or more embodiments of Formula IV-H, $R^1$ is independently, at each occurrence, —H, —$OR^5$ or halogen. In one or more embodiments of Formula IV-H, $R^1$ is independently, at each occurrence, —H or —$OR^5$. In one or more embodiments of Formula IV-H, $R^1$ is independently, at each occurrence, —H or halogen. In one or more embodiments of Formula IV-H, $R^1$ is independently, at each occurrence, —H or —$NR^5R^6$. In one or more embodiments of Formula IV-H, $R^1$ is independently, at each occurrence, —H, —$OR^5$ or —$NR^5R^6$. In one or more embodiments of Formula IV-H, $R^1$ is independently, at each occurrence, —H, halogen or —$NR^5R^6$. In certain such embodiments, $R^5$ and $R^6$ are both -H. In one or more embodiments of Formula IV-H, $R^1$ is independently, at each occurrence, —H, methyl, fluoro, chloro, or —$NH_2$. In one or more embodiments of Formula IV-H, $R^1$ is independently, at each occurrence, —H, —CN or halogen.

In one or more embodiments of Formula IV-H, $R^5$ and $R^6$ are independently, at each occurrence, —H or —$C_1$-$C_6$alkyl. In one or more embodiments of Formula IV-H, $R^5$ and $R^6$ are independently, at each occurrence, —H. In one or more embodiments of Formula IV-H, $R^5$ and $R^6$ are independently, at each occurrence, —$C_1$-$C_6$alkyl.

In one or more embodiments of Formula IV-H, $R^2$ is —H. In one or more embodiments of Formula IV-H, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-H, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV-H, $R^2$ is —OH. In one or more embodiments of Formula IV-H, $R^2$ is —$NR^5R^6$. In one or more embodiments of Formula IV-H, $R^2$ is —$NH_2$.

In one or more embodiments of Formula IV-H, $X^1$ is N and $X^2$ is N. In one or more embodiments of Formula IV-H, $X^1$ is C and $X^2$ is CH. In one or more embodiments of Formula IV-H, $X^1$ is C and $X^2$ is N. In one or more embodiments of Formula IV-H, $X^1$ is N and $X^2$ is CH.

In one or more embodiments of Formula IV-H, B, including the atoms at the points of attachment, is an optionally substituted monocyclic or polycyclic 5- to 12-membered heterocycle. In one or more embodiments of Formula IV-H, B, including the atoms at the points of attachment, is an optionally substituted monocyclic 5 to 6-membered heterocycle. In one or more embodiments of Formula IV-H, B, including the atoms at the points of attachment, is an optionally substituted monocyclic 7- to 12-membered heterocycle.

In one or more embodiments of Formula IV-H, B, including the atoms at the points of attachment, is an optionally substituted polycyclic 5- to 12-membered heterocyclyl. In certain embodiments, the heteroycyclyl ring is fused. In one or more embodiments of Formula IV-H, the heterocyclyl ring is bridged.

In one or more embodiments of Formula IV-H, B, including the atoms at the points of attachment, is an optionally substituted monocyclic or polycyclic 5- to 12-membered heteroaryl. In one or more embodiments of Formula IV-H, B, including the atoms at the points of attachment, is an optionally substituted monocyclic 5 to 6-membered heteroaryl. In one or more embodiments of Formula IV-H, B, including the atoms at the points of attachment, is a monocyclic 7- to 12-membered heteroaryl.

In one or more embodiments of Formula IV-H, B, including the atoms at the points of attachment, is an optionally substituted polycyclic 5- to 12-membered heteroaryl. In one or more embodiments of Formula IV-H, the polycyclic heteroaryl is a multiple condensed ring as described above. The rings of the multiple condensed ring system can be connected to each other via fused, spiro and bridged bonds when allowed by valency requirements.

In one or more embodiments of Formula IV-H, B is substituted with one or more —$(CH_2)_n$OH. In certain such embodiments, n is 1. In one or more embodiments of Formula IV-H, B is substituted with one or more —$C_1$-$C_6$alkyl, —OH, —$NH_2$, oxo, —$(CH_2)_n NH_2$, —$(CH_2)_n OH$, —$CF_3$, —$CHF_2$, or —$CH_2F$. In one or more embodiments of Formula IV-H, B is substituted with one or more oxo. In one or more embodiments of Formula IV-H, B is substituted with one or more —$C_1$-$C_6$alkyl. In one or more embodiments of Formula IV-H, B is substituted with one or more —OH. In one or more embodiments of Formula IV-H, B is substituted with one or more —NH$_2$. In one or more embodiments of Formula IV-H, B is substituted with one or more —CF$_3$. In one or more embodiments of Formula IV-H, B is substituted with one or more —CHF$_2$. In one or more embodiments of Formula IV-H, B is substituted with one or more —CH$_2$F. In one or more embodiments of Formula IV-H, B is substituted with one or more —(CH$_2$)$_n$NH$_2$. In certain such embodiments, n is 1.

In certain embodiments of Formula IV, the compound is of Formula IV-I:

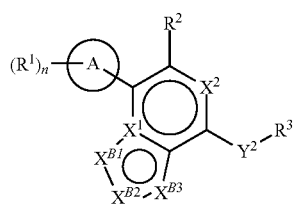

IV-I and pharmaceutically acceptable salts, prodrugs, solvates, hydrates, tautomers, and isomers thereof, wherein $X^{B1}$ is N, NR$^9$, CR$^9$, S, or O; $X^{B2}$ is N, NR$^9$, CR$^9$, S, or O; and $X^{B3}$ is N, NR$^9$, CR$^9$, S, or O, wherein R$^9$ is independently, at each occurrence, —H, —C$_1$-C$_6$alkyl, —OH, —NH$_2$, heteroaryl, heterocyclyl, —(CH$_2$)$_n$NH$_2$, —(CH$_2$)$_n$OH, —CF$_3$, —CHF$_2$, or —CH$_2$F, provided that if X$^1$ is C, at least one of $X^{B1}$, $X^{B2}$, and $X^{B3}$ is not CR$^9$, or provided that if each of $X^{B1}$, $X^{B2}$, and $X^{B3}$ are CR$^9$, X$^1$ must be N.

In certain embodiments of Formula IV-I, $X^{B1}$ is N or NR$^9$. In certain embodiments of Formula IV-I, $X^{B1}$ is CR$^9$. In certain embodiments of Formula IV-I, $X^{B1}$ is S. In certain embodiments of Formula IV-I, $X^{B1}$ is O. In certain embodiments of Formula IV-I, $X^{B2}$ is N or NR$^9$. In certain embodiments of Formula IV-I, $X^{B2}$ is CR$^9$. In certain embodiments of Formula IV-I, $X^{B2}$ is S. In certain embodiments of Formula IV-I, $X^{B2}$ is O. In certain embodiments of Formula IV-I, $X^{B3}$ is N or NR$^9$. In certain embodiments of Formula IV-I, $X^{B3}$ is CR$^9$. In certain embodiments of Formula IV-I, $X^{B3}$ is S. In certain embodiments of Formula IV-I, $X^{B3}$ is O.

In certain embodiments of Formula IV-I, $X^{B1}$ is N, NR$^9$, or CR$^9$; $X^{B2}$ is N, NR$^9$, or CR$^9$; and $X^{B3}$ is N, NR$^9$, or CR$^9$. In certain embodiments of Formula IV-I, $X^{B1}$ is N or NR$^9$. In certain embodiments of Formula IV-I, $X^{B1}$ is CR$^9$. In certain embodiments of Formula IV-I, $X^{B2}$ is N or NR$^9$. In certain embodiments of Formula IV-I, $X^{B2}$ is CR$^9$. In certain embodiments of Formula IV-I, $X^{B3}$ is N or NR$^9$. In certain embodiments of Formula IV-I, $X^{B3}$ is CR$^9$.

In some embodiments of Formula IV-I, R$^9$ is —(CH$_2$)$_n$OH and n is 1. In some embodiments of Formula IV-I, R$^9$ is H.

In certain embodiments of Formula IV-I,

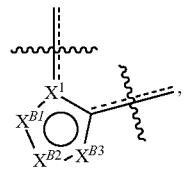

wherein ===== is a single bond or double bond to satisfy valency rules, is

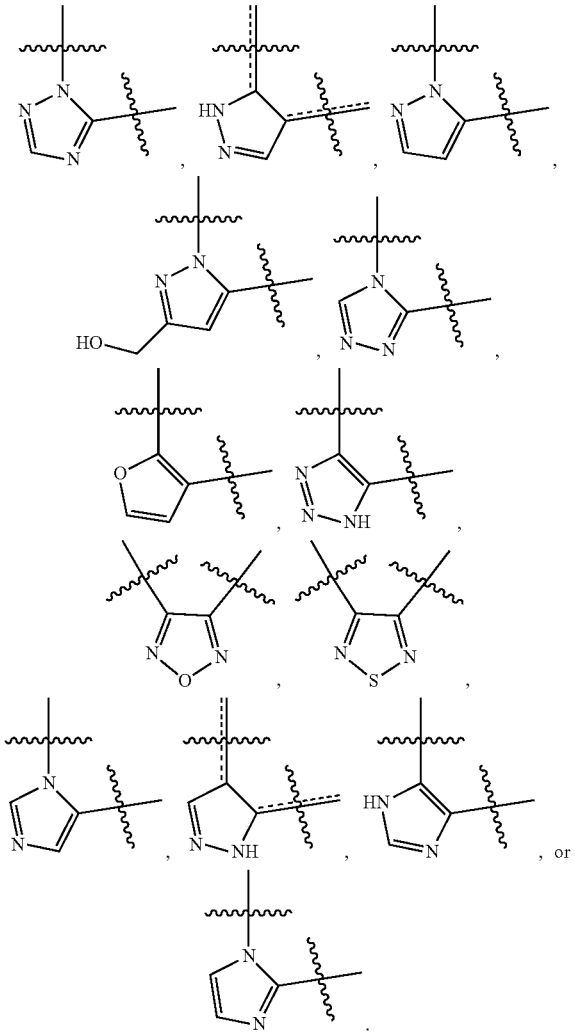

In one or more embodiments of the compounds of Formula IV-I, Y$^2$ is —(CR$^a{}_2$)$_m$—. In one or more embodiments of the compounds of Formula IV-I, Y$^2$ is —NR$^a$—.

In one or more embodiments of Formula IV-I, A is a monocyclic or polycyclic cycloalkyl. In one or more embodiments of Formula IV-I, A is a monocyclic or polycyclic heterocycloalkyl. In one or more embodiments of Formula IV-I, A is a monocyclic or polycyclic aryl. In one or more embodiments of Formula IV-I, A is phenyl. In one or more embodiments of Formula IV-I, A is a monocyclic or polycyclic heteroaryl. In one or more embodiments of Formula IV-I, A is pyridinyl. In one or more embodiments of Formula IV-I, A is indazolyl. In one or more embodiments of Formula IV-I, A is a 5- to 12-membered monocyclic or polycyclic aryl or heteroaryl.

In one or more embodiments of Formula IV-I, n is independently, at each occurrence, 0, 1, 2, or 3. In one or more embodiments of Formula IV-I, n is independently, at each occurrence, 1 or 2.

In one or more embodiments of Formula IV-I, R$^1$ is independently, at each occurrence, —H, —OR$^5$, halogen, —C$_1$-C$_6$alkyl, —CN, or —NR$^5$R$^6$. In one or more embodiments of Formula IV-I, $R^1$ is independently, at each occurrence, —H, —$OR^5$ or halogen. In one or more embodiments of Formula IV-I, $R^1$ is independently, at each occurrence, —H or —$OR^5$. In one or more embodiments of Formula IV-I, $R^1$ is independently, at each occurrence, —H or halogen. In one or more embodiments of Formula IV-I, $R^1$ is independently, at each occurrence, —H or —$NR^5R^6$. In one or more embodiments of Formula IV-I, $R^1$ is independently, at each occurrence, —H, —$OR^5$ or —$NR^5R^6$. In one or more embodiments of Formula IV-I, $R^1$ is independently, at each occurrence, —H, halogen or —$NR^5R^6$. In certain such embodiments, $R^5$ and $R^6$ are both-H. In one or more embodiments of Formula IV-I, $R^1$ is independently, at each occurrence, —H, methyl, fluoro, chloro, or —$NH_2$. In one or more embodiments of Formula IV-I, $R^1$ is independently, at each occurrence, —H, —CN or halogen.

In one or more embodiments of Formula IV-I, $R^5$ and $R^6$ are independently, at each occurrence, —H or —$C_1$-$C_6$alkyl. In one or more embodiments of Formula IV-I, $R^5$ and $R^6$ are independently, at each occurrence, —H. In one or more embodiments of Formula IV-I, $R^5$ and $R^6$ are independently, at each occurrence, —$C_1$-$C_6$alkyl.

In one or more embodiments of Formula IV-I, $R^2$ is —H. In one or more embodiments of Formula IV-I, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-I, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV-I, $R^2$ is —OH. In one or more embodiments of Formula IV-I, $R^2$ is —$NR^5R^6$. In one or more embodiments of Formula IV-I, $R^2$ is —$NH_2$.

In one or more embodiments of Formula IV-I, $R^a$ is —H.

In one or more embodiments of Formula IV-I, $R^3$ is an optionally substituted —$C_1$-$C_6$alkyl. In one or more embodiments of Formula IV-I, $R^3$ is an optionally substituted 3- to 12-membered monocyclic or polycyclic heterocycle. In one or more embodiments of Formula IV-I, $R^3$ is an optionally substituted 3- to 12-membered monocyclic heterocycle. In one or more embodiments of Formula IV-I, $R^3$ is an optionally substituted 5- to 12-membered polycyclic heterocycle.

In one or more embodiments of Formula IV-I, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-I, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-I, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-I, $R^3$ and $R^a$ together with the atom to which they are attached combine to form a 3- to 12-membered polycyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-I, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-I, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-I, $R^3$ and $R^a$ together with the atoms to which they are attached combine to form a 5- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV-I, $R^3$ and $R^a$ together with the atoms to which they are attached combine to form a 5- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-I, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-I, $R^3$ and $R^a$ together with the atoms to which they are attached combine to form a 10- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV-I, $R^3$ and $R^a$ together with the atoms to which they are attached combine to form a 10- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-I, $X^1$ is N and $X^2$ is N. In one or more embodiments of Formula IV-I, $X^1$ is C and $X^2$ is CH. In one or more embodiments of Formula IV-I, $X^1$ is C and $X^2$ is N. In one or more embodiments of Formula IV-I, $X^1$ is N and $X^2$ is CH.

In certain embodiments of Formula IV, the compound is of Formula IV-J:

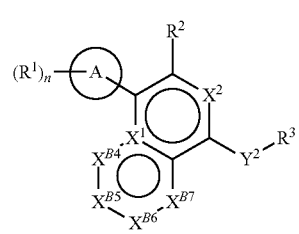

IV-J and pharmaceutically acceptable salts, prodrugs, solvates, hydrates, tautomers, and isomers thereof, wherein $X^{B4}$ is N or $CR^9$; $X^{B5}$ is N or $CR^9$; $X^{B6}$ is N or $CR^9$; and $X^{B7}$ is N or CR$^9$, wherein R$^9$ is independently, at each occurrence, —H, —C$_1$-C$_6$alkyl, —OH, —NH$_2$, heteroaryl, heterocyclyl, —(CH$_2$)$_n$NH$_2$, —(CH$_2$)$_n$OH, —CF$_3$, —CHF$_2$, or —CH$_2$F, provided that if X$^1$ is C, at least one of X$^{B4}$, X$^{B5}$, X$^{B6}$, and X$^{B7}$ is not CR$^9$, or provided that if each of X$^{B4}$, X$^{B5}$ X$^{B6}$, and X$^{B7}$ are CR$^9$, X$^1$ must be N.

In certain embodiments of Formula IV-J, X$^{B4}$ is N. In certain embodiments of Formula IV-J, X$^{B4}$ is CR$^9$. In certain embodiments of Formula IV-J, X$^{B5}$ is N. In certain embodiments of Formula IV-J, X$^{B5}$ is CR$^9$. In certain embodiments of Formula IV-J, X$^{B6}$ is N. In certain embodiments of Formula IV-J, X$^{B6}$ is CR$^9$. In certain embodiments of Formula IV-J, X$^{B7}$ is N. In certain embodiments of Formula IV-J, X$^{B7}$ is CR$^9$. In certain embodiments of Formula IV-J, X$^{B4}$ is N, X$^{B5}$ is CR$^9$, X$^{B6}$ is N, and X$^{B7}$ is CR$^9$. In certain such embodiments, R$^9$ is independently, at each occurrence, —H.

In some embodiments of Formula IV-J, R$^9$ is —(CH$_2$)$_n$OH and n is 1. In some embodiments of Formula IV-J, R$^9$ is H.

In one or more embodiments of the compounds of Formula IV-J, Y$^2$ is —(CR$^a_2$)$_m$—. In one or more embodiments of the compounds of Formula IV-J, Y$^2$ is —NR$^a$—.

In one or more embodiments of Formula IV-J, A is a monocyclic or polycyclic cycloalkyl. In one or more embodiments of Formula IV-J, A is a monocyclic or polycyclic heterocycloalkyl. In one or more embodiments of Formula IV-J, A is a monocyclic or polycyclic aryl. In one or more embodiments of Formula IV-J, A is phenyl. In one or more embodiments of Formula IV-J, A is a monocyclic or polycyclic heteroaryl. In one or more embodiments of Formula IV-J, A is pyridinyl. In one or more embodiments of Formula IV-J, A is indazolyl. In one or more embodiments of Formula IV-J, A is a 5- to 12-membered monocyclic or polycyclic aryl or heteroaryl.

In one or more embodiments of Formula IV-J, n is independently, at each occurrence, 0, 1, 2, or 3. In one or more embodiments of Formula IV-J, n is independently, at each occurrence, 1 or 2.

In one or more embodiments of Formula IV-J, R$^1$ is independently, at each occurrence, —H, —OR$^5$, halogen, —C$_1$-C$_6$alkyl, —CN, or —NR$^5$R$^6$. In one or more embodiments of Formula IV-J. R$^1$ is independently, at each occurrence, —H, —OR$^5$ or halogen. In one or more embodiments of Formula IV-J, R$^1$ is independently, at each occurrence, —H or —OR$^5$. In one or more embodiments of Formula IV-J, R$^1$ is independently, at each occurrence, —H or halogen. In one or more embodiments of Formula IV-J, R$^1$ is independently, at each occurrence, —H or —NR$^5$R$^6$. In one or more embodiments of Formula IV-J. R$^1$ is independently, at each occurrence, —H, —OR$^5$ or —NR$^5$R$^6$. In one or more embodiments of Formula IV-J, R$^1$ is independently, at each occurrence, —H, halogen or —NR$^5$R$^6$. In certain such embodiments, R$^5$ and R$^6$ are both-H. In one or more embodiments of Formula IV-J, R$^1$ is independently, at each occurrence, —H, methyl, fluoro, chloro, or —NH$_2$. In one or more embodiments of Formula IV-J, R$^1$ is independently, at each occurrence, —H, —CN or halogen.

In one or more embodiments of Formula IV-J. R$^5$ and R$^6$ are independently, at each occurrence, —H or —C$_1$-C$_6$alkyl. In one or more embodiments of Formula IV-J. R$^5$ and R$^6$ are independently, at each occurrence, —H. In one or more embodiments of Formula IV-J. R$^5$ and R$^6$ are independently, at each occurrence, —C$_1$-C$_6$alkyl.

In one or more embodiments of Formula IV-J, R$^2$ is —H. In one or more embodiments of Formula IV-J, R$^2$ is —C$_1$-C$_6$alkyl, wherein each alkyl is optionally substituted with one or more —OH, halogen, —OR$^5$, or —NR$^5$R$^6$. In certain such embodiments, R$^2$ is methyl. In one or more embodiments of Formula IV-J, R$^2$ is —H, —OH, —NR$^5$R$^6$, —C$_1$-C$_6$alkyl, or —NH$_2$; wherein each alkyl is optionally substituted with one or more —OH, halogen, —OR$^5$, or —NR$^5$R$^6$. In one or more embodiments of Formula IV-J, R$^2$ is —OH. In one or more embodiments of Formula IV-J. R$^2$ is —NR$^5$R$^6$. In one or more embodiments of Formula IV-J, R$^2$ is —NH$_2$.

In one or more embodiments of Formula IV-J, R$^a$ is —H.

In one or more embodiments of Formula IV-J, R$^3$ is an optionally substituted —C$_1$-C$_6$alkyl. In one or more embodiments of Formula IV-J, R$^3$ is an optionally substituted 3- to 12-membered monocyclic or polycyclic heterocycle. In one or more embodiments of Formula IV-J, R$^3$ is an optionally substituted 3- to 12-membered monocyclic heterocycle. In one or more embodiments of Formula IV-J, R$^3$ is an optionally substituted 5- to 12-membered polycyclic heterocycle.

In one or more embodiments of Formula IV-J, R$^3$ and R$^a$ together with the atom to which they are attached combine to form a 3- to 12-membered monocyclic heterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-J, R$^3$ and R$^a$ together with the atom to which they are attached combine to form a 3- to 12-membered monocyclic heterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-J, R$^3$ and R$^a$ together with the atom to which they are attached combine to form a 3- to 12-membered monocyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-J, R$^3$ and R$^a$ together with the atoms to which they are attached combine to form a 3- to 12-membered polycyclic heterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-J, R$^3$ and R$^a$ together with the atom to which they are attached combine to form a 3- to 12-membered polycyclic heterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-J, R$^3$ and R$^a$ together with the atom to which they are attached combine to form a 3- to 12-membered polycyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-J, R$^3$ and R$^a$ together with the atoms to which they are attached combine to form a 5- to 12-membered spiroheterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-J, R$^3$ and R$^a$ together with the atoms to which they are attached combine to form a 5- to 12-membered spiroheterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-J, R$^3$ and R$^a$ together with the atoms to which they are attached combine to form a 5- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-J, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-J, $R^3$ and $R^a$ together with the atoms to which they are attached combine to form a 10- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV-J, $R^3$ and $R^a$ together with the atoms to which they are attached combine to form a 10- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-J, $X^1$ is N and $X^2$ is N. In one or more embodiments of Formula IV-J, $X^1$ is C and $X^2$ is CH. In one or more embodiments of Formula IV-J, $X^1$ is C and $X^2$ is N. In one or more embodiments of Formula IV-J, $X^1$ is N and $X^2$ is CH.

In certain embodiments of Formula IV, the compound is of Formula IV-K:

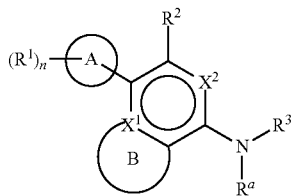

IV-K and pharmaceutically acceptable salts, prodrugs, solvates, hydrates, tautomers, and isomers thereof.

In one or more embodiments of Formula IV-K, A is a monocyclic or polycyclic cycloalkyl. In one or more embodiments of Formula IV-K, A is a monocyclic or polycyclic heterocycloalkyl. In one or more embodiments of Formula IV-K, A is a monocyclic or polycyclic aryl. In one or more embodiments of Formula IV-K, A is phenyl. In one or more embodiments of Formula IV-K, A is a monocyclic or polycyclic heteroaryl. In one or more embodiments of Formula IV-K, A is pyridinyl. In one or more embodiments of Formula IV-K, A is indazolyl. In one or more embodiments of Formula IV-K, A is a 5- to 12-membered monocyclic or polycyclic aryl or heteroaryl.

In one or more embodiments of Formula IV-K, n is independently, at each occurrence, 0, 1, 2, or 3. In one or more embodiments of Formula IV-K, n is independently, at each occurrence, 1 or 2.

In one or more embodiments of Formula IV-K, $R^1$ is independently, at each occurrence, —H, —$OR^5$, halogen, —$C_1$-$C_6$alkyl, —CN, or —$NR^5R^6$. In one or more embodiments of Formula IV-K, $R^1$ is independently, at each occurrence, —H, —$OR^5$ or halogen. In one or more embodiments of Formula IV-K, $R^1$ is independently, at each occurrence, —H or —$OR^5$. In one or more embodiments of Formula IV-K, $R^1$ is independently, at each occurrence, —H or halogen. In one or more embodiments of Formula IV-K, $R^1$ is independently, at each occurrence, —H or —$NR^5R^6$. In one or more embodiments of Formula IV-K, $R^1$ is independently, at each occurrence, —H, —$OR^5$ or —$NR^5R^6$. In one or more embodiments of Formula IV-K, $R^1$ is independently, at each occurrence, —H, halogen or —$NR^5R^6$. In certain such embodiments, $R^5$ and $R^6$ are both -H. In one or more embodiments of Formula IV-K, $R^1$ is independently, at each occurrence, —H, methyl, fluoro, chloro, or —$NH_2$. In one or more embodiments of Formula IV-K, $R^1$ is independently, at each occurrence, —H, —CN or halogen.

In one or more embodiments of Formula IV-K, $R^5$ and $R^6$ are independently, at each occurrence, —H or —$C_1$-$C_6$alkyl. In one or more embodiments of Formula IV-K, $R^5$ and $R^6$ are independently, at each occurrence, —H. In one or more embodiments of Formula IV-K, $R^5$ and $R^6$ are independently, at each occurrence, —$C_1$-$C_6$alkyl.

In one or more embodiments of Formula IV-K, $R^2$ is —H. In one or more embodiments of Formula IV-K, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-K, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV-K, $R^2$ is —OH. In one or more embodiments of Formula IV-K, $R^2$ is —$NR^5R^6$. In one or more embodiments of Formula IV-K, $R^2$ is —$NH_2$.

In one or more embodiments of Formula IV-K, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-K, $R^3$ and $R^a$ together with the atom to which they are attached combine to form a 3- to 12-membered monocyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-K, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-K, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-K, $R^3$ and $R^a$ together with the atom to which they are attached combine to form a 3- to 12-membered polycyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-K, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-K, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-K, $R^3$ and $R^a$ together with the atoms to which they are attached combine to form a 5- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV-K, $R^3$ and $R^a$ together with the atoms to which they are attached combine to form a 5- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-K, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-K, $R^3$ and $R^a$ together with the atoms to which they are attached combine to form a 10- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV-K, $R^3$ and $R^a$ together with the atoms to which they are attached combine to form a 10- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-K, $X^1$ is N and $X^2$ is N. In one or more embodiments of Formula IV-K, $X^1$ is C and $X^2$ is CH. In one or more embodiments of Formula IV-K, $X^1$ is C and $X^2$ is N. In one or more embodiments of Formula IV-K, $X^1$ is N and $X^2$ is CH.

In one or more embodiments of Formula IV-K, B, including the atoms at the points of attachment, is an optionally substituted monocyclic or polycyclic 5- to 12-membered heterocycle. In one or more embodiments of Formula IV-K, B, including the atoms at the points of attachment, is an optionally substituted monocyclic 5 to 6-membered heterocycle. In one or more embodiments of Formula IV-K, B, including the atoms at the points of attachment, is an optionally substituted monocyclic 7- to 12-membered heterocycle.

In one or more embodiments of Formula IV-K, B, including the atoms at the points of attachment, is an optionally substituted polycyclic 5- to 12-membered heterocyclyl. In certain embodiments, the heteroycyclyl ring is fused. In one or more embodiments of Formula IV-K, the heterocyclyl ring is bridged.

In one or more embodiments of Formula IV-K, B, including the atoms at the points of attachment, is an optionally substituted monocyclic or polycyclic 5- to 12-membered heteroaryl. In one or more embodiments of Formula IV-K, B, including the atoms at the points of attachment, is an optionally substituted monocyclic 5 to 6-membered heteroaryl. In one or more embodiments of Formula IV-K, B, including the atoms at the points of attachment, is a monocyclic 7- to 12-membered heteroaryl.

In one or more embodiments of Formula IV-K, B, including the atoms at the points of attachment, is an optionally substituted polycyclic 5- to 12-membered heteroaryl. In one or more embodiments of Formula IV-K, the polycyclic heteroaryl is a multiple condensed ring as described above. The rings of the multiple condensed ring system can be connected to each other via fused, spiro and bridged bonds when allowed by valency requirements.

In one or more embodiments of Formula IV-K, B is substituted with one or more —$(CH_2)_nOH$. In certain such embodiments, n is 1. In one or more embodiments of Formula IV-K, B is substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$. In one or more embodiments of Formula IV-K, B is substituted with one or more oxo. In one or more embodiments of Formula IV-K, B is substituted with one or more —$C_1$-$C_6$alkyl. In one or more embodiments of Formula IV-K, B is substituted with one or more —OH. In one or more embodiments of Formula IV-K, B is substituted with one or more —$NH_2$. In one or more embodiments of Formula IV-K, B is substituted with one or more —$CF_3$. In one or more embodiments of Formula IV-K, B is substituted with one or more —$CHF_2$. In one or more embodiments of Formula IV-K, B is substituted with one or more —$CH_2F$. In one or more embodiments of Formula IV-K, B is substituted with one or more —$(CH_2)_nNH_2$. In certain such embodiments, n is 1.

In certain embodiments of Formula IV, the compound is of Formula IV-L:

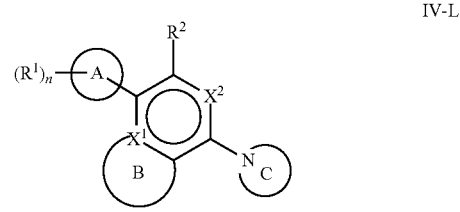

IV-L and pharmaceutically acceptable salts, prodrugs, solvates, hydrates, tautomers, and isomers thereof, wherein:

C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$. In some embodiments of Formula IV-L, the C ring is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In certain such embodiments, n is 1. In some embodiments of Formula IV-L, the C ring is optionally substituted with one or more —$C_1$-$C_6$alkyl, —$(CH_2)_nNH_2$, or —$NH_2$. In certain such embodiments, n is 1.

In certain embodiments of Formula IV-L, the C ring, along with the nitrogen atom to which it is attached, is an optionally substituted 3- to 12-membered monocyclic heterocycle. In certain embodiments of Formula IV-L, the C ring, along with the nitrogen atom to which it is attached, is an optionally substituted 3- to 12-membered polycyclic heterocycle. In certain embodiments of Formula IV-L, along with the nitrogen atom to which it is attached, is an optionally substituted 5- to 12-membered spiroheterocycle.

In certain embodiments of Formula IV-L, C ring, along with the nitrogen atom to which it is attached, is an optionally substituted

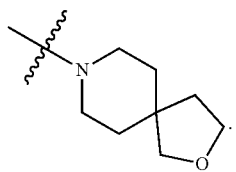 [SMILES: *N1CCC2(CCOC2)CC1]

In certain embodiments of Formula IV-L, C ring, along with the nitrogen atom to which it is attached, is an optionally substituted

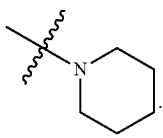 [SMILES: *N1CCCCC1]

In certain embodiments of Formula IV-L, C ring, along with the nitrogen atom to which it is attached, is an optionally substituted

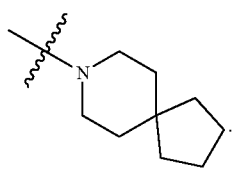 [SMILES: *N1CCC2(CCCC2)CC1]

In one or more embodiments of Formula IV-L, A is a monocyclic or polycyclic cycloalkyl. In one or more embodiments of Formula IV-L, A is a monocyclic or polycyclic heterocycloalkyl. In one or more embodiments of Formula IV-L, A is a monocyclic or polycyclic aryl. In one or more embodiments of Formula IV-L, A is phenyl. In one or more embodiments of Formula IV-L, A is a monocyclic or polycyclic heteroaryl. In one or more embodiments of Formula IV-L, A is pyridinyl. In one or more embodiments of Formula IV-L, A is indazolyl. In one or more embodiments of Formula IV-L, A is a 5- to 12-membered monocyclic or polycyclic aryl or heteroaryl.

In one or more embodiments of Formula IV-L, n is independently, at each occurrence, 0, 1, 2, or 3. In one or more embodiments of Formula IV-L, n is independently, at each occurrence, 1 or 2.

In one or more embodiments of Formula IV-L, $R^1$ is independently, at each occurrence, —H, —$OR^5$, halogen, —$C_1$-$C_6$alkyl, —CN, or —$NR^5R^6$. In one or more embodiments of Formula IV-L, $R^1$ is independently, at each occurrence, —H, —$OR^5$ or halogen. In one or more embodiments of Formula IV-L, $R^1$ is independently, at each occurrence, —H or —$OR^5$. In one or more embodiments of Formula IV-L, $R^1$ is independently, at each occurrence, —H or halogen. In one or more embodiments of Formula IV-L, $R^1$ is independently, at each occurrence, —H or —$NR^5R^6$. In one or more embodiments of Formula IV-L, $R^1$ is independently, at each occurrence, —H, —$OR^5$ or —$NR^5R^6$. In one or more embodiments of Formula IV-L, $R^1$ is independently, at each occurrence, —H, halogen or —$NR^5R^6$. In certain such embodiments, $R^5$ and $R^6$ are both -H. In one or more embodiments of Formula IV-L, $R^1$ is independently, at each occurrence, —H, methyl, fluoro, chloro, or —$NH_2$. In one or more embodiments of Formula IV-L, $R^1$ is independently, at each occurrence, —H, —CN or halogen.

In one or more embodiments of Formula IV-L, $R^5$ and $R^6$ are independently, at each occurrence, —H or —$C_1$-$C_6$alkyl. In one or more embodiments of Formula IV-L, $R^5$ and $R^6$ are independently, at each occurrence, —H. In one or more embodiments of Formula IV-L, $R^5$ and $R^6$ are independently, at each occurrence, —$C_1$-$C_6$alkyl.

In one or more embodiments of Formula IV-L, $R^2$ is —H. In one or more embodiments of Formula IV-L, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-K, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV-L, $R^2$ is —OH. In one or more embodiments of Formula IV-L, $R^2$ is —$NR^5R^6$. In one or more embodiments of Formula IV-L, $R^2$ is —$NH_2$.

In one or more embodiments of Formula IV-L, $X^1$ is N and $X^2$ is N. In one or more embodiments of Formula IV-L, $X^1$ is C and $X^2$ is CH. In one or more embodiments of Formula IV-L, $X^1$ is C and $X^2$ is N. In one or more embodiments of Formula IV-L, $X^1$ is N and $X^2$ is CH.

In one or more embodiments of Formula IV-L, B, including the atoms at the points of attachment, is an optionally substituted monocyclic or polycyclic 5- to 12-membered heterocycle. In one or more embodiments of Formula IV-L, B, including the atoms at the points of attachment, is an optionally substituted monocyclic 5 to 6-membered heterocycle. In one or more embodiments of Formula IV-L, B, including the atoms at the points of attachment, is an optionally substituted monocyclic 7- to 12-membered heterocycle.

In one or more embodiments of Formula IV-L, B, including the atoms at the points of attachment, is an optionally substituted polycyclic 5- to 12-membered heterocyclyl. In certain embodiments, the heteroycyclyl ring is fused. In one or more embodiments of Formula IV-L, the heterocyclyl ring is bridged.

In one or more embodiments of Formula IV-L. B, including the atoms at the points of attachment, is an optionally substituted monocyclic or polycyclic 5- to 12-membered heteroaryl. In one or more embodiments of Formula IV-L, B, including the atoms at the points of attachment, is an optionally substituted monocyclic 5 to 6-membered heteroaryl. In one or more embodiments of Formula IV-L, B, including the atoms at the points of attachment, is a monocyclic 7- to 12-membered heteroaryl.

In one or more embodiments of Formula IV-L, B, including the atoms at the points of attachment, is an optionally substituted polycyclic 5- to 12-membered heteroaryl. In one or more embodiments of Formula IV-L, the polycyclic heteroaryl is a multiple condensed ring as described above. The rings of the multiple condensed ring system can be connected to each other via fused, spiro and bridged bonds when allowed by valency requirements.

In one or more embodiments of Formula IV-L, B is substituted with one or more —$(CH_2)_n$OH. In certain such embodiments, n is 1. In one or more embodiments of Formula IV-L, B is substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$. In one or more embodiments of Formula IV-L, B is substituted with one or more oxo. In one or more embodiments of Formula IV-L, B is substituted with one or more —$C_1$-$C_6$alkyl. In one or more embodiments of Formula IV-L, B is substituted with one or more —OH. In one or more embodiments of Formula IV-L, B is substituted with one or more —NH$_2$. In one or more embodiments of Formula IV-L, B is substituted with one or more —CF$_3$. In one or more embodiments of Formula IV-L, B is substituted with one or more —CHF$_2$. In one or more embodiments of Formula IV-L, B is substituted with one or more —CH$_2$F. In one or more embodiments of Formula IV-L, B is substituted with one or more —(CH$_2$)$_n$NH$_2$. In certain such embodiments, n is 1.

In certain embodiments of Formula IV, the compound is of Formula IV-M:

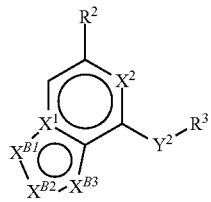

IV-M and pharmaceutically acceptable salts, prodrugs, solvates, hydrates, tautomers, and isomers thereof, wherein $X^{B1}$ is N, NR$^9$, CR$^9$, S, or O; $X^{B2}$ is N, NR$^9$, CR$^9$, S, or O; and $X^{B3}$ is N, NR$^9$, CR$^9$, S, or O, wherein R$^9$ is independently, at each occurrence, —H, —C$_1$-C$_6$alkyl, —OH, —NH$_2$, heteroaryl, heterocyclyl, —(CH$_2$)$_n$NH$_2$, —(CH$_2$)$_n$OH, —CF$_3$, —CHF$_2$, or —CH$_2$F, provided that if X$^1$ is C, at least one of $X^{B1}$, $X^{B2}$, and $X^{B3}$ is not CR$^9$, or provided that if each of $X^{B1}$, $X^{B2}$, and $X^{B3}$ are CR$^9$, X$^1$ must be N.

In certain embodiments of Formula IV-M, $X^{B1}$ is N or NR$^9$. In certain embodiments of Formula IV-M, $X^{B1}$ is CR$^9$. In certain embodiments of Formula IV-M, $X^{B1}$ is S. In certain embodiments of Formula IV-M, $X^{B1}$ is O. In certain embodiments of Formula IV-M, $X^{B2}$ is N or NR$^9$. In certain embodiments of Formula IV-M, $X^{B2}$ is CR$^9$. In certain embodiments of Formula IV-M, $X^{B2}$ is S. In certain embodiments of Formula IV-M, $X^{B2}$ is O. In certain embodiments of Formula IV-M, $X^{B3}$ is N or NR$^9$. In certain embodiments of Formula IV-M, $X^{B3}$ is CR$^9$. In certain embodiments of Formula IV-M, $X^{B3}$ is S. In certain embodiments of Formula IV-M, $X^{B3}$ is O.

In certain embodiments of Formula IV-M, $X^{B1}$ is N, NR$^9$, or CR$^9$; $X^{B2}$ is N, NR$^9$, or CR$^9$; and $X^{B3}$ is N, NR$^9$, or CR$^9$. In certain embodiments of Formula IV-M, $X^{B1}$ is N or NR$^9$. In certain embodiments of Formula IV-M, $X^{B1}$ is CR$^9$. In certain embodiments of Formula IV-M, $X^{B2}$ is N or NR$^9$. In certain embodiments of Formula IV-M, $X^{B2}$ is CR$^9$. In certain embodiments of Formula IV-M, $X^{B3}$ is N or NR$^9$. In certain embodiments of Formula IV-M, $X^{B3}$ is CR$^9$.

In some embodiments of Formula IV-M, R$^9$ is —(CH$_2$)$_n$OH and n is 1. In some embodiments of Formula IV-M, R$^9$ is H.

In certain embodiments of Formula IV-M,

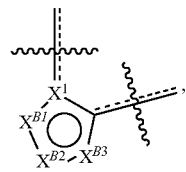

wherein ===== is a single bond or double bond to satisfy valency rules, is

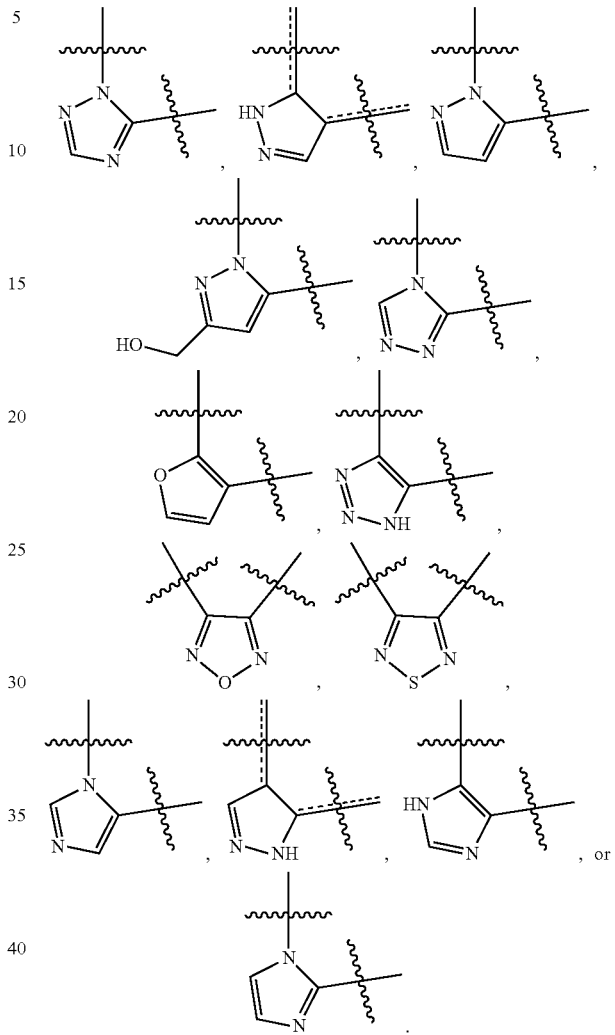

In one or more embodiments of the compounds of Formula IV-M, Y$^2$ is —(CR$^a$$_2$)$_m$—. In one or more embodiments of the compounds of Formula IV-M, Y$^2$ is —NR$^a$—.

In one or more embodiments of Formula IV-M, R$^2$ is —H. In one or more embodiments of Formula IV-M, R$^2$ is —C$_1$-C$_6$alkyl, wherein each alkyl is optionally substituted with one or more —OH, halogen, —OR$^5$, or —NR$^5$R$^6$. In certain such embodiments, R$^2$ is methyl. In one or more embodiments of Formula IV-M, R$^2$ is —H, —OH, —NR$^5$R$^6$, —C$_1$-C$_6$alkyl, or —NH$_2$; wherein each alkyl is optionally substituted with one or more —OH, halogen, —OR$^5$, or —NR$^5$R$^6$. In one or more embodiments of Formula IV-M, R$^2$ is —OH. In one or more embodiments of Formula IV-M, R$^2$ is —NR$^5$R$^6$. In one or more embodiments of Formula IV-M, R$^2$ is —NH$_2$.

In one or more embodiments of Formula IV-M, R$^a$ is —H.

In one or more embodiments of Formula IV-M, R$^3$ is an optionally substituted —C$_1$-C$_6$alkyl. In one or more embodiments of Formula IV-M, R$^3$ is an optionally substituted 3- to 12-membered monocyclic or polycyclic heterocycle. In one or more embodiments of Formula IV-M, R$^3$ is an optionally substituted 3- to 12-membered monocyclic heterocycle. In one or more embodiments of Formula IV-M, $R^3$ is an optionally substituted 5- to 12-membered polycyclic heterocycle.

In one or more embodiments of Formula IV-M, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$(CH_2)_n NH_2$, —$(CH_2)_n OH$, —$CF_3$, —$CHF_2$, or —$CH_2F$. In one or more embodiments of Formula IV-M, $R^3$ and $R^a$ together with the atom to which they are attached combine to form a 3- to 12-membered monocyclic heterocycle, which is optionally substituted with one or more —$C_1$-$C_6$alkyl, —$(CH_2)_n NH_2$, or —$NH_2$. In certain such embodiments, n is 1. In one or more embodiments of Formula IV-M, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, oxo, heteroaryl, heterocyclyl, —$(CH_2)_n NH_2$, —$(CH_2)_n OH$, —$CF_3$, —$CHF_2$, or —$CH_2F$.

In one or more embodiments of Formula IV-M, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$(CH_2)_n NH_2$, —$(CH_2)_n OH$, —$CF_3$, —$CHF_2$, or —$CH_2F$. In one or more embodiments of Formula IV-M, $R^3$ and $R^a$ together with the atom to which they are attached combine to form a 3- to 12-membered polycyclic heterocycle, which is optionally substituted with one or more —$C_1$-$C_6$alkyl, —$(CH_2)_n NH_2$, or —$NH_2$. In certain such embodiments, n is 1. In one or more embodiments of Formula IV-M, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, oxo, heteroaryl, heterocyclyl, —$(CH_2)_n NH_2$, —$(CH_2)_n OH$, —$CF_3$, —$CHF_2$, or —$CH_2F$.

In one or more embodiments of Formula IV-M, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$(CH_2)_n NH_2$, —$(CH_2)_n OH$, —$CF_3$, —$CHF_2$, or —$CH_2F$. In one or more embodiments of Formula IV-M, $R^3$ and $R^a$ together with the atoms to which they are attached combine to form a 5- to 12-membered spiroheterocycle, which is optionally substituted with one or more —$C_1$-$C_6$alkyl, —$(CH_2)_n NH_2$, or —$NH_2$. In certain such embodiments, n is 1. In one or more embodiments of Formula IV-M, $R^3$ and $R^a$ together with the atoms to which they are attached combine to form a 5- to 12-membered spiroheterocycle, which is optionally substituted with one or more —$C_1$-$C_6$alkyl, —OH, —$NH_2$, oxo, heteroaryl, heterocyclyl, —$(CH_2)_n NH_2$, —$(CH_2)_n OH$, —$CF_3$, —$CHF_2$, or —$CH_2F$.

In one or more embodiments of Formula IV-M, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$(CH_2)_n NH_2$, —$(CH_2)_n OH$, —$CF_3$, —$CHF_2$, or —$CH_2F$. In one or more embodiments of Formula IV-M, $R^3$ and $R^a$ together with the atoms to which they are attached combine to form a 10- to 12-membered spiroheterocycle, which is optionally substituted with one or more —$C_1$-$C_6$alkyl, —$(CH_2)_n NH_2$, or —$NH_2$. In certain such embodiments, n is 1. In one or more embodiments of Formula IV-M, $R^3$ and $R^a$ together with the atoms to which they are attached combine to form a 10- to 12-membered spiroheterocycle, which is optionally substituted with one or more —$C_1$-$C_6$alkyl, —OH, —$NH_2$, oxo, heteroaryl, heterocyclyl, —$(CH_2)_n NH_2$, —$(CH_2)_n OH$, —$CF_3$, —$CHF_2$, or —$CH_2F$.

In one or more embodiments of Formula IV-M, $X^1$ is N and $X^2$ is N. In one or more embodiments of Formula IV-M, $X^1$ is C and $X^2$ is CH. In one or more embodiments of Formula IV-M, $X^1$ is C and $X^2$ is N. In one or more embodiments of Formula IV-M, $X^1$ is N and $X^2$ is CH.

In certain embodiments of Formula IV, the compound is of Formula IV-N:

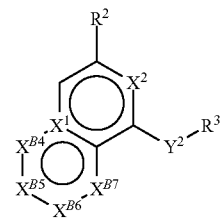

IV-N and pharmaceutically acceptable salts, prodrugs, solvates, hydrates, tautomers, and isomers thereof, wherein $X^{B4}$ is N or $CR^9$; $X^{B5}$ is N or $CR^9$; $X^{B6}$ is N or $CR^9$; and $X^{B7}$ is N or $CR^9$, wherein $R^9$ is independently, at each occurrence, —H, —$C_1$-$C_6$alkyl, —OH, —$NH_2$, heteroaryl, heterocyclyl, —$(CH_2)_n NH_2$, —$(CH_2)_n OH$, —$CF_3$, —$CHF_2$, or —$CH_2F$, provided that if $X^1$ is C, at least one of $X^{B4}$, $X^{B5}$, $X^{B6}$, and $X^{B7}$ is not $CR^9$, or provided that if each of $X^{B4}$, $X^{B5}$ $X^{B6}$, and $X^{B7}$ are $CR^9$, $X^1$ must be N.

In certain embodiments of Formula IV-N, $X^{B4}$ is N. In certain embodiments of Formula IV-N, $X^{B4}$ is $CR^9$. In certain embodiments of Formula IV-N, $X^{B5}$ is N. In certain embodiments of Formula IV-N, $X^{B5}$ is $CR^9$. In certain embodiments of Formula IV-N, $X^{B6}$ is N. In certain embodiments of Formula IV-N, $X^{B6}$ is $CR^9$. In certain embodiments of Formula IV-N, $X^{B7}$ is N. In certain embodiments of Formula IV-N, $X^{B7}$ is $CR^9$. In certain embodiments of Formula IV-N, $X^{B4}$ is N, $X^{B5}$ is $CR^9$, $X^{B6}$ is N, and $X^{B7}$ is $CR^9$. In certain such embodiments, $R^9$ is independently, at each occurrence, —H.

In some embodiments of Formula IV-N, $R^9$ is —$(CH_2)_n$OH and n is 1. In some embodiments of Formula IV-N, $R^9$ is H.

In one or more embodiments of the compounds of Formula IV-N, $Y^2$ is $(CR^a_2)_m$—. In one or more embodiments of the compounds of Formula IV-N, $Y^2$ is —$NR^a$—.

In one or more embodiments of Formula IV-N, $R^2$ is —H. In one or more embodiments of Formula IV-N, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-N, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV-N, $R^2$ is —OH. In one or more embodiments of Formula IV-N, $R^2$ is —$NR^5R^6$. In one or more embodiments of Formula IV-N, $R^2$ is —$NH_2$.

In one or more embodiments of Formula IV-N, $R^a$ is —H.

In one or more embodiments of Formula IV-N, $R^3$ is an optionally substituted —$C_1$-$C_6$alkyl. In one or more embodiments of Formula IV-N, $R^3$ is an optionally substituted 3- to 12-membered monocyclic or polycyclic heterocycle. In one or more embodiments of Formula IV-N, $R^3$ is an optionally substituted 3- to 12-membered monocyclic heterocycle. In one or more embodiments of Formula IV-N, $R^3$ is an optionally substituted 5- to 12-membered polycyclic heterocycle.

In one or more embodiments of Formula IV-N, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-N, $R^3$ and $R^a$ together with the atom to which they are attached combine to form a 3- to 12-membered monocyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-N, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-N, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-N, $R^3$ and $R^a$ together with the atom to which they are attached combine to form a 3- to 12-membered polycyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-N, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-N, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-N, $R^3$ and $R^a$ together with the atoms to which they are attached combine to form a 5- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV-N, $R^3$ and $R^a$ together with the atoms to which they are attached combine to form a 5- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-N, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-N, $R^3$ and $R^a$ together with the atoms to which they are attached combine to form a 10- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula IV-N, $R^3$ and $R^a$ together with the atoms to which they are attached combine to form a 10- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-N, $X^1$ is N and $X^2$ is N. In one or more embodiments of Formula IV-N, $X^1$ is C and $X^2$ is CH. In one or more embodiments of Formula IV-N, $X^1$ is C and $X^2$ is N. In one or more embodiments of Formula IV-N, $X^1$ is N and $X^2$ is CH.

In certain embodiments of Formula IV, the compound is of Formula IV-O:

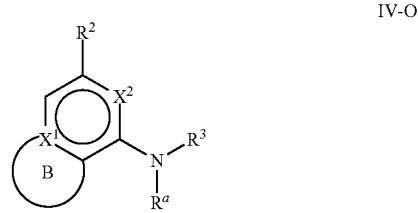

IV-O and pharmaceutically acceptable salts, prodrugs, solvates, hydrates, tautomers, and isomers thereof.

In one or more embodiments of Formula IV-O. $R^2$ is —H. In one or more embodiments of Formula IV-O, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-O, $R^2$ is —H, —OH, —$NR^5R^6$. —$C_1$-$C_6$alkyl, or —$NH_2$; wherein each alkyl is optionally substituted with one or more —OH, halogen, —$OR^5$, or —$NR^5R^6$. In one or more embodiments of Formula IV-O, $R^2$ is —OH. In one or more embodiments of Formula IV-O, $R^2$ is —$NR^5R^6$. In one or more embodiments of Formula IV-O, $R^2$ is —$NH_2$.

In one or more embodiments of Formula IV-O, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-O, $R^3$ and $R^a$ together with the atom to which they are attached combine to form a 3- to 12-membered monocyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-O. $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula IV-O, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula IV-O, $R^3$ and $R^a$ together with the atom to which they are attached combine to form a 3- to 12-membered polycyclic heterocycle, which is optionally substituted with one or more —$C_1$-$C_6$alkyl, —$(CH_2)_nNH_2$, or —$NH_2$. In certain such embodiments, n is 1. In one or more embodiments of Formula IV-O. R³ and Rᵃ together with the atom to which they are attached combine to form a 3- to 12-membered polycyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-O, R³ and Rᵃ together with the atoms to which they are attached combine to form a 5- to 12-membered spiroheterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-O, R³ and Rᵃ together with the atoms to which they are attached combine to form a 5- to 12-membered spiroheterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-O. R³ and Rᵃ together with the atoms to which they are attached combine to form a 5- to 12-membered spiroheterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-O, R³ and Rᵃ together with the atoms to which they are attached combine to form a 10- to 12-membered spiroheterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula IV-O, R³ and Rᵃ together with the atoms to which they are attached combine to form a 10- to 12-membered spiroheterocycle, which is optionally substituted with one or more —C$_1$-C$_6$alkyl, —(CH$_2$)$_n$NH$_2$, or —NH$_2$. In certain such embodiments, n is 1. In one or more embodiments of Formula IV-O, R³ and Rᵃ together with the atoms to which they are attached combine to form a 10- to 12-membered spiroheterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula IV-O, X¹ is N and X² is N. In one or more embodiments of Formula IV-O, X¹ is C and X² is CH. In one or more embodiments of Formula IV-O, X¹ is C and X² is N. In one or more embodiments of Formula IV-O, X¹ is N and X² is CH.

In one or more embodiments of Formula IV-O, B, including the atoms at the points of attachment, is an optionally substituted monocyclic or polycyclic 5- to 12-membered heterocycle. In one or more embodiments of Formula IV-O, B, including the atoms at the points of attachment, is an optionally substituted monocyclic 5 to 6-membered heterocycle. In one or more embodiments of Formula IV-O, B, including the atoms at the points of attachment, is an optionally substituted monocyclic 7- to 12-membered heterocycle.

In one or more embodiments of Formula IV-O, B, including the atoms at the points of attachment, is an optionally substituted polycyclic 5- to 12-membered heterocyclyl. In certain embodiments, the heteroycyclyl ring is fused. In one or more embodiments of Formula IV-O, the heterocyclyl ring is bridged.

In one or more embodiments of Formula IV-O, B, including the atoms at the points of attachment, is an optionally substituted monocyclic or polycyclic 5- to 12-membered heteroaryl. In one or more embodiments of Formula IV-O, B, including the atoms at the points of attachment, is an optionally substituted monocyclic 5 to 6-membered heteroaryl. In one or more embodiments of Formula IV-O, B, including the atoms at the points of attachment, is a monocyclic 7- to 12-membered heteroaryl.

In one or more embodiments of Formula IV-O, B, including the atoms at the points of attachment, is an optionally substituted polycyclic 5- to 12-membered heteroaryl. In one or more embodiments of Formula IV-O, the polycyclic heteroaryl is a multiple condensed ring as described above. The rings of the multiple condensed ring system can be connected to each other via fused, spiro and bridged bonds when allowed by valency requirements.

In one or more embodiments of Formula IV-O, B is substituted with one or more —(CH$_2$)$_n$OH. In certain such embodiments, n is 1. In one or more embodiments of Formula IV-O, B is substituted with one or more —C$_1$-C$_6$alkyl, —OH, —NH$_2$, Oxo, —(CH$_2$)$_n$NH$_2$, —(CH$_2$)$_n$OH, —CF$_3$, —CHF$_2$, or —CH$_2$F. In one or more embodiments of Formula IV-O, B is substituted with one or more oxo. In one or more embodiments of Formula IV-O, B is substituted with one or more —C$_1$-C$_6$alkyl. In one or more embodiments of Formula IV-O, B is substituted with one or more —OH. In one or more embodiments of Formula IV-O, B is substituted with one or more —NH$_2$. In one or more embodiments of Formula IV-O, B is substituted with one or more —CF$_3$. In one or more embodiments of Formula IV-O, B is substituted with one or more —CHF$_2$. In one or more embodiments of Formula IV-O, B is substituted with one or more —CH$_2$F. In one or more embodiments of Formula IV-O, B is substituted with one or more —(CH$_2$)$_n$NH$_2$. In certain such embodiments, n is 1.

In certain embodiments of Formula IV, the compound is of Formula IV-P:

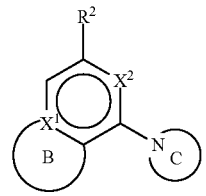

IV-P and pharmaceutically acceptable salts, prodrugs, solvates, hydrates, tautomers, and isomers thereof, wherein:

C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F. In some embodiments of Formula IV-P, the C ring is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In certain such embodiments, n is 1. In some embodiments of Formula IV-P, the C ring is optionally substituted with one or more —C$_1$-C$_6$alkyl, —(CH$_2$)$_n$NH$_2$, or —NH$_2$. In certain such embodiments, n is 1.

In certain embodiments of Formula IV-P, the C ring, along with the nitrogen atom to which it is attached, is an optionally substituted 3- to 12-membered monocyclic heterocycle. In certain embodiments of Formula IV-P, the C ring, along with the nitrogen atom to which it is attached, is an optionally substituted 3- to 12-membered polycyclic heterocycle. In certain embodiments of Formula IV-P, along with the nitrogen atom to which it is attached, is an optionally substituted 5- to 12-membered spiroheterocycle.

In certain embodiments of Formula IV-P, C ring, along with the nitrogen atom to which it is attached, is an optionally substituted

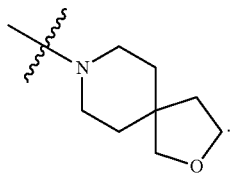

In certain embodiments of Formula IV-P. C ring, along with the nitrogen atom to which it is attached, is an optionally substituted

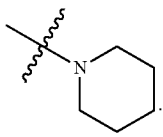 [SMILES: *N1CCCCC1]

In certain embodiments of Formula IV-P, C ring, along with the nitrogen atom to which it is attached, is an optionally substituted

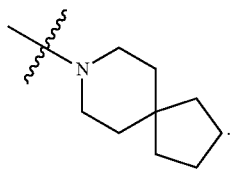 [SMILES: *N1CCC2(CCCC2)CC1]

In one or more embodiments of Formula IV-P, $R^2$ is —H. In one or more embodiments of Formula IV-P, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula IV-P, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula IV-P. $R^2$ is —OH. In one or more embodiments of Formula IV-P, $R^2$ is —$NR^5R^6$. In one or more embodiments of Formula IV-P, $R^2$ is —$NH_2$.

In one or more embodiments of Formula IV-P, $X^1$ is N and $X^2$ is N. In one or more embodiments of Formula IV-P, $X^1$ is C and $X^2$ is CH. In one or more embodiments of Formula IV-P, $X^1$ is C and $X^2$ is N. In one or more embodiments of Formula IV-P, $X^1$ is N and $X^2$ is CH.

In one or more embodiments of Formula IV-P, B, including the atoms at the points of attachment, is an optionally substituted monocyclic or polycyclic 5- to 12-membered heterocycle. In one or more embodiments of Formula IV-P, B, including the atoms at the points of attachment, is an optionally substituted monocyclic 5 to 6-membered heterocycle. In one or more embodiments of Formula IV-P, B, including the atoms at the points of attachment, is an optionally substituted monocyclic 7- to 12-membered heterocycle.

In one or more embodiments of Formula IV-P, B, including the atoms at the points of attachment, is an optionally substituted polycyclic 5- to 12-membered heterocyclyl. In certain embodiments, the heteroycyclyl ring is fused. In one or more embodiments of Formula IV-P, the heterocyclyl ring is bridged.

In one or more embodiments of Formula IV-P, B, including the atoms at the points of attachment, is an optionally substituted monocyclic or polycyclic 5- to 12-membered heteroaryl. In one or more embodiments of Formula IV-P, B, including the atoms at the points of attachment, is an optionally substituted monocyclic 5 to 6-membered heteroaryl. In one or more embodiments of Formula IV-P, B, including the atoms at the points of attachment, is a monocyclic 7- to 12-membered heteroaryl.

In one or more embodiments of Formula IV-P, B, including the atoms at the points of attachment, is an optionally substituted polycyclic 5- to 12-membered heteroaryl. In one or more embodiments of Formula IV-P, the polycyclic heteroaryl is a multiple condensed ring as described above. The rings of the multiple condensed ring system can be connected to each other via fused, spiro and bridged bonds when allowed by valency requirements.

In one or more embodiments of Formula IV-P, B is substituted with one or more —$(CH_2)_n$OH. In certain such embodiments, n is 1. In one or more embodiments of Formula IV-P. B is substituted with one or more —$C_1$-$C_6$alkyl, —OH, —$NH_2$, Oxo, —$(CH_2)_n NH_2$, —$(CH_2)_n OH$, —$CF_3$, —$CHF_2$, or —$CH_2F$. In one or more embodiments of Formula IV-P, B is substituted with one or more oxo. In one or more embodiments of Formula IV-P, B is substituted with one or more —$C_1$-$C_6$alkyl. In one or more embodiments of Formula IV-P, B is substituted with one or more —OH. In one or more embodiments of Formula IV-P, B is substituted with one or more —$NH_2$. In one or more embodiments of Formula IV-P, B is substituted with one or more —$CF_3$. In one or more embodiments of Formula IV-P, B is substituted with one or more —$CHF_2$. In one or more embodiments of Formula IV-P, B is substituted with one or more —$CH_2F$. In one or more embodiments of Formula IV-P, B is substituted with one or more —$(CH_2)_n NH_2$. In certain such embodiments, n is 1.

In certain embodiments of Formula IV, the compound is of Formula IV-Q:

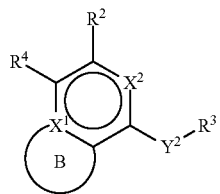

IV-Q and pharmaceutically acceptable salts, prodrugs, solvates, hydrates, tautomers, or isomers thereof, wherein:
$R^4$ is H or

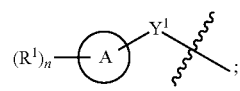

;

A is a 5- to 12-membered monocyclic or polycyclic aryl or heteroaryl, provided that the heteroaryl is not

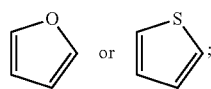

R¹ is independently, at each occurrence, —H, —OR⁵, halogen, —C₁-C₆alkyl, —CN, or —NR⁵R⁶;

Y¹ is —S— or a direct bond;

X¹ is N or C;

X² is N or CH;

B, including the atoms at the points of attachment, is a monocyclic or polycyclic 5- to 12-membered heterocycle or a monocyclic or polycyclic 5- to 12-membered heteroaryl, wherein each heterocycle or heteroaryl is optionally substituted with one or more —C₁-C₆alkyl, —OH, —NH₂, oxo, —(CH₂)$_n$NH₂, —(CH₂)$_n$OH, —CF₃, —CHF₂, or —CH₂F;

R² is —H, —OH, —NR⁵R⁶, —C₁-C₆alkyl, or —NH₂; wherein each alkyl is optionally substituted with one or more —OH, halogen, —OR⁵, or —NR⁵R⁶;

Y² is —NR$^a$—, wherein the bond on the left side of Y², as drawn, is bound to the ring and the bond on the right side of the Y² moiety, as drawn, is bound to R³;

R³ is combined with R$^a$ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, —OH, —NH₂, —(CH₂)$_n$NH₂, —(CH₂)$_n$OH, —CF₃, —CHF₂, or —CH₂F, provided that the heterocycle formed by the combination of R³ and R$^a$ is not an optionally substituted piperazinyl;

R⁵ and R⁶ are independently, at each occurrence, —H or —C₁-C₆alkyl;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of Formula IV-Q, Y¹ is —S—. In one or more embodiments of Formula IV-Q, Y¹ is a direct bond.

In one or more embodiments of Formula IV-Q, A is a monocyclic or polycyclic aryl. In one or more embodiments of Formula IV-Q, A is phenyl. In one or more embodiments of Formula IV-Q, A is a monocyclic or polycyclic heteroaryl. In one or more embodiments of Formula IV-Q, A is pyridinyl. In one or more embodiments of Formula IV-Q, A is indazolyl.

In one or more embodiments of Formula IV-Q, n is independently, at each occurrence, 0, 1, 2, or 3. In one or more embodiments of Formula IV-Q, n is independently, at each occurrence, 1 or 2.

In one or more embodiments of Formula IV-Q, R¹ is independently, at each occurrence, —H, —OR⁵ or halogen. In one or more embodiments of Formula IV-Q, R¹ is independently, at each occurrence, —H or —OR⁵. In one or more embodiments of Formula IV-Q, R¹ is independently, at each occurrence, —H or halogen. In one or more embodiments of Formula IV-Q, R¹ is independently, at each occurrence, —H or —NR⁵R⁶. In one or more embodiments of Formula IV-Q, R¹ is independently, at each occurrence, —H, —OR⁵ or —NR⁵R⁶. In one or more embodiments of Formula IV-Q, R¹ is independently, at each occurrence, —H, halogen or —NR⁵R⁶. In certain such embodiments, R⁵ and R⁶ are both -H. In one or more embodiments of Formula IV-Q, R¹ is independently, at each occurrence, —H, methyl, fluoro, chloro, or —NH₂. In one or more embodiments of Formula IV-Q, R¹ is independently, at each occurrence, —H, —CN or halogen.

In one or more embodiments of Formula IV-Q, R⁵ and R⁶ are independently, at each occurrence, —H. In one or more embodiments of Formula IV-Q, R⁵ and R⁶ are independently, at each occurrence, —C₁-C₆alkyl.

In one or more embodiments of Formula IV-Q, R² is —H. In one or more embodiments of Formula IV-Q, R² is —C₁-C₆alkyl, wherein each alkyl is optionally substituted with one or more —OH, halogen, —OR⁵, or —NR⁵R⁶. In certain such embodiments, R² is methyl. In one or more embodiments of Formula IV-Q, R² is —OH. In one or more embodiments of Formula IV-Q, R² is —NR⁵R⁶. In one or more embodiments of Formula IV-Q, R² is —NH₂.

In one or more embodiments of Formula IV-Q, R³ and R$^a$ together with the atom to which they are attached combine to form a 3- to 12-membered monocyclic heterocycle, which is optionally substituted with one or more —C₁-C₆alkyl, —NH₂, —OH, —(CH₂)$_n$NH₂, —(CH₂)$_n$OH, —CF₃, —CHF₂, or —CH₂F. In one or more embodiments of Formula IV-Q, R³ and R$^a$ together with the atom to which they are attached combine to form a 3- to 12-membered monocyclic heterocycle, which is optionally substituted with one or more —C₁-C₆alkyl, —(CH₂)$_n$NH₂, or —NH₂. In certain such embodiments, n is 1.

In one or more embodiments of Formula IV-Q, R³ and R$^a$ together with the atoms to which they are attached combine to form a 3- to 12-membered polycyclic heterocycle, which is optionally substituted with one or more —C₁-C₆alkyl, —NH₂, —OH, —(CH₂)$_n$NH₂, —(CH₂)$_n$OH, —CF₃, —CHF₂, or —CH₂F. In one or more embodiments of Formula IV-Q, R³ and R$^a$ together with the atom to which they are attached combine to form a 3- to 12-membered polycyclic heterocycle, which is optionally substituted with one or more —C₁-C₆alkyl, —(CH₂)$_n$NH₂, or —NH₂. In certain such embodiments, n is 1.

In one or more embodiments of Formula IV-Q, R³ and R$^a$ together with the atoms to which they are attached combine to form a 5- to 12-membered spiroheterocycle, which is optionally substituted with one or more —C₁-C₆alkyl, —NH₂, —OH, —(CH₂)$_n$NH₂, —(CH₂)$_n$OH, —CF₃, —CHF₂, or —CH₂F. In one or more embodiments of Formula IV-Q, R³ and R$^a$ together with the atoms to which they are attached combine to form a 5- to 12-membered spiroheterocycle, which is optionally substituted with one or more —C₁-C₆alkyl, —(CH₂)$_n$NH₂, or —NH₂. In certain such embodiments, n is 1.

In one or more embodiments of Formula IV-Q, R³ and R$^a$ together with the atoms to which they are attached combine to form a 10- to 12-membered spiroheterocycle, which is optionally substituted with one or more —C₁-C₆alkyl, —NH₂, —OH, —(CH₂)$_n$NH₂, —(CH₂)$_n$OH, —CF₃, —CHF₂, or —CH₂F. In one or more embodiments of Formula IV-Q, R³ and R$^a$ together with the atoms to which they are attached combine to form a 10- to 12-membered spiroheterocycle, which is optionally substituted with one or more —C₁-C₆alkyl, —(CH₂)$_n$NH₂, or —NH₂. In certain such embodiments, n is 1.

In one or more embodiments of Formula IV-Q, X¹ is N and X² is N. In one or more embodiments of Formula IV-Q, X¹ is C and X² is CH. In one or more embodiments of Formula IV-Q, X¹ is C and X² is N. In one or more embodiments of Formula IV-Q, X¹ is N and X² is CH.

In one or more embodiments of Formula IV-Q, B, including the atoms at the points of attachment, is an optionally substituted monocyclic or polycyclic 5- to 12-membered heterocycle. In one or more embodiments of Formula IV-Q, B, including the atoms at the points of attachment, is an optionally substituted monocyclic 5 to 6-membered heterocycle. In one or more embodiments of Formula IV-Q. B, including the atoms at the points of attachment, is an optionally substituted monocyclic 7- to 12-membered heterocycle.

In one or more embodiments of Formula IV-Q, B, including the atoms at the points of attachment, is an optionally substituted polycyclic 5- to 12-membered heterocyclyl. In certain embodiments, the heteroycyclyl ring is fused. In one or more embodiments of Formula IV-Q, the heterocyclyl ring is bridged.

In one or more embodiments of Formula IV-Q, B, including the atoms at the points of attachment, is an optionally substituted monocyclic or polycyclic 5- to 12-membered heteroaryl. In one or more embodiments of Formula IV-Q, B, including the atoms at the points of attachment, is an optionally substituted monocyclic 5 to 6-membered heteroaryl. In one or more embodiments of Formula IV-Q. B, including the atoms at the points of attachment, is a monocyclic 7- to 12-membered heteroaryl.

In one or more embodiments of Formula IV-Q, B, including the atoms at the points of attachment, is an optionally substituted polycyclic 5- to 12-membered heteroaryl. In one or more embodiments of Formula IV-Q, the polycyclic heteroaryl is a multiple condensed ring as described above. The rings of the multiple condensed ring system can be connected to each other via fused, spiro and bridged bonds when allowed by valency requirements.

In one or more embodiments of Formula IV-Q, B is substituted with one or more —(CH$_2$)$_n$OH. In certain such embodiments, n is 1. In one or more embodiments of Formula IV-Q, B is substituted with one or more oxo. In one or more embodiments of Formula IV-Q, B is substituted with one or more —C$_1$-C$_6$alkyl. In one or more embodiments of Formula IV-Q, B is substituted with one or more —OH. In one or more embodiments of Formula IV-Q, B is substituted with one or more —NH$_2$. In one or more embodiments of Formula IV-Q, B is substituted with one or more —CF$_3$. In one or more embodiments of Formula IV-Q, B is substituted with one or more —CHF$_2$. In one or more embodiments of Formula IV-Q, B is substituted with one or more —CH$_2$F. In one or more embodiments of Formula IV-Q, B is substituted with one or more —(CH$_2$)$_n$NH$_2$. In certain such embodiments, n is 1.

In one or more embodiments, a compound of the present disclosure (e.g., a compound of Formula I', I, II, III, or IV) can be selected from:

1

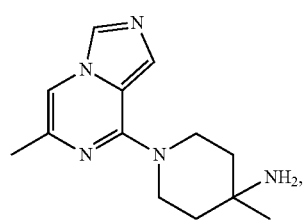

2

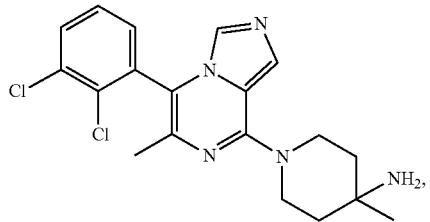

3

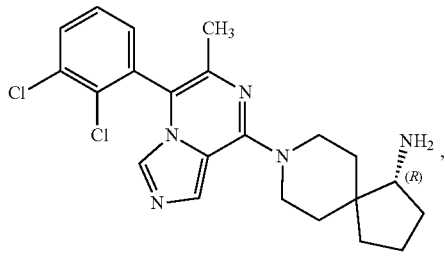

4

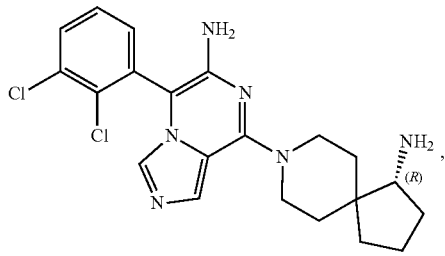

5

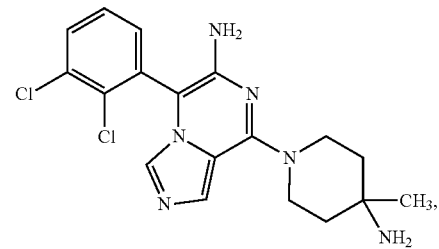

6

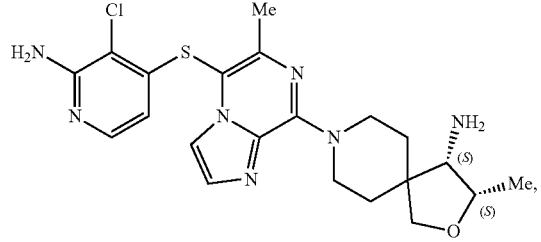

7

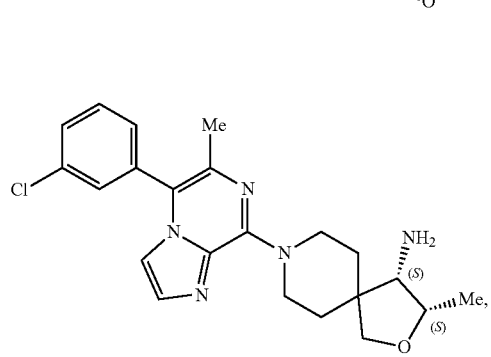

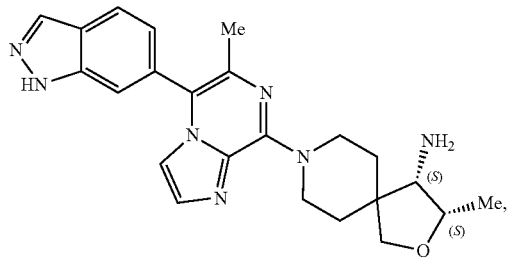
8
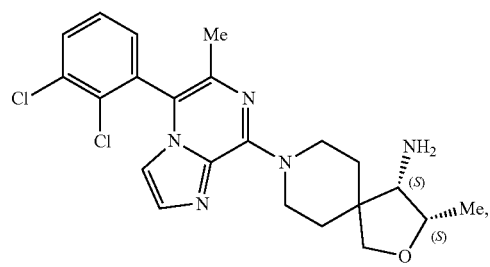
9
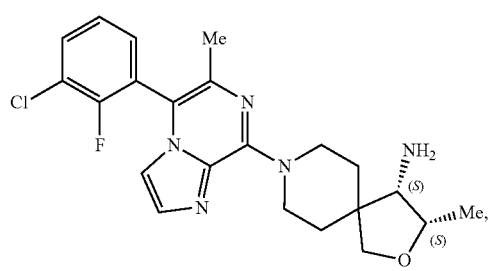
10
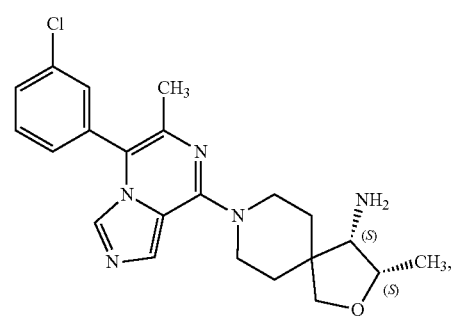
11
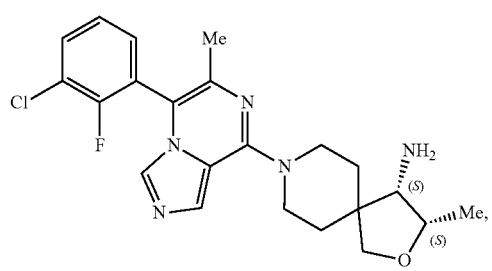
12
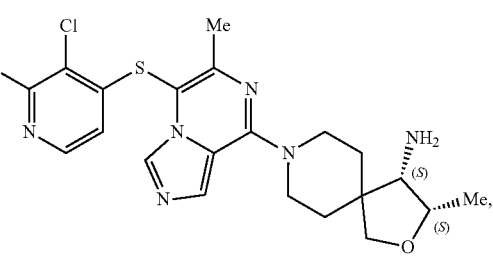
13
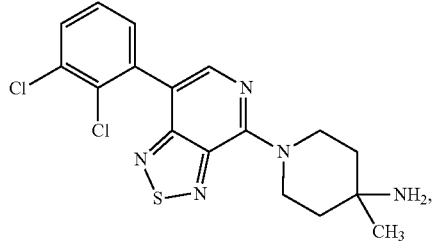
14
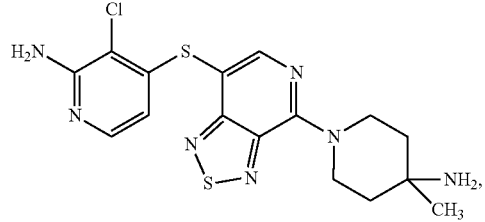
15
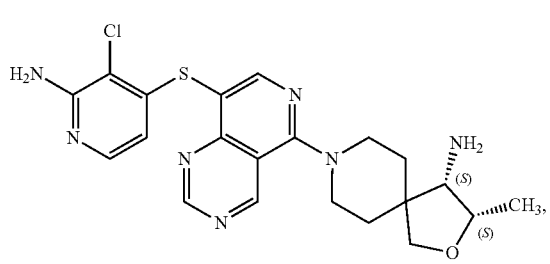
16
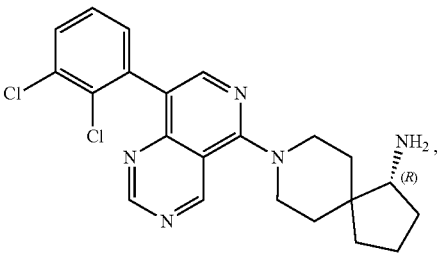
17
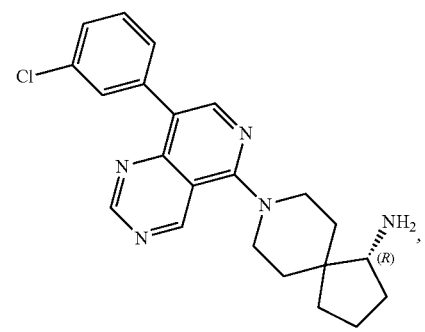
18

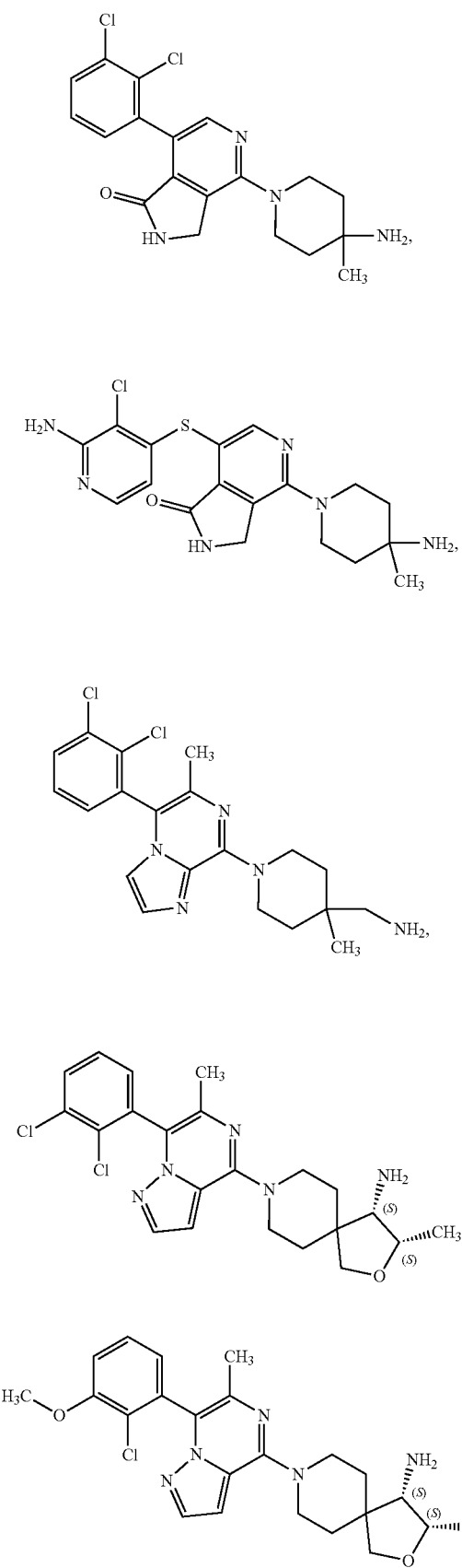

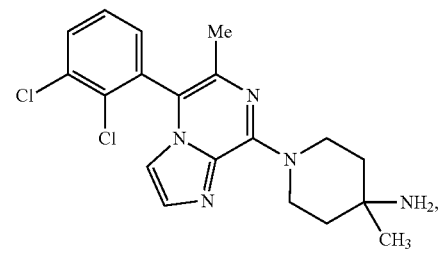
42
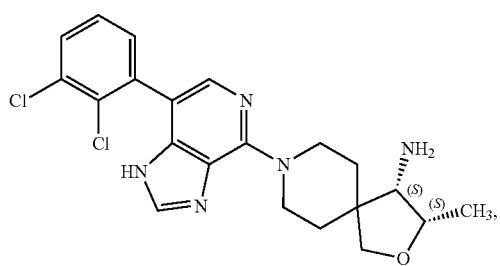
43
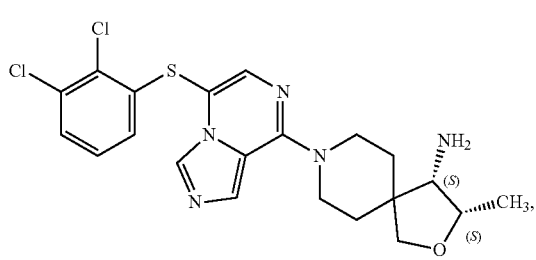
44
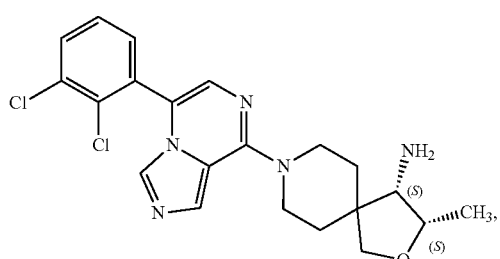
45
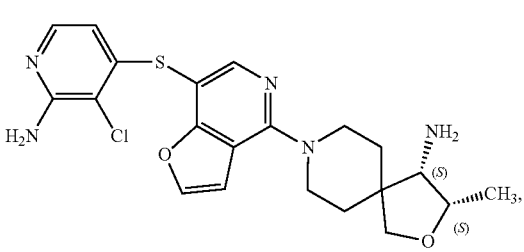
46
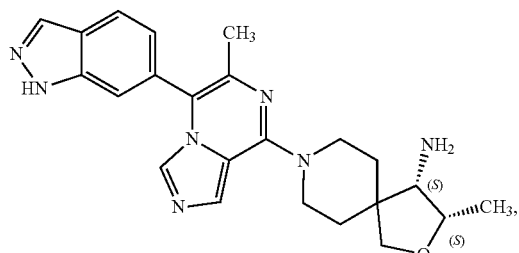
47
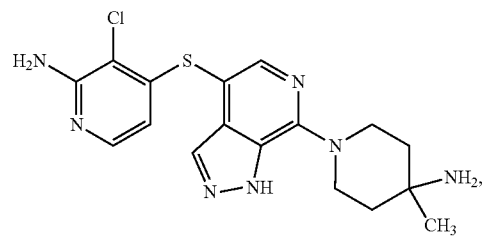
48
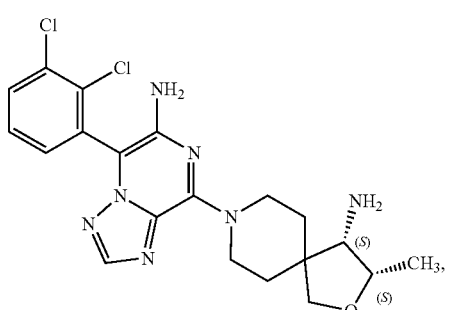
49
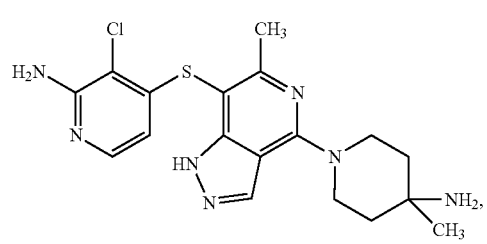
50
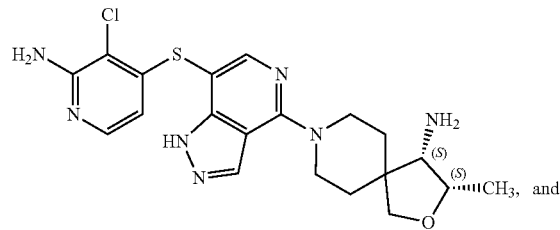
51
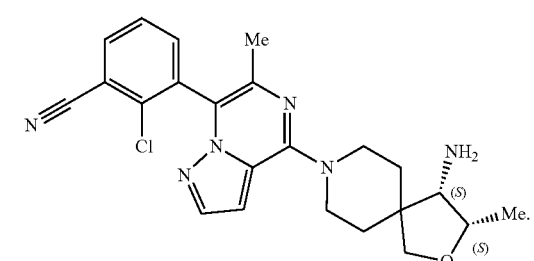
52
and pharmaceutically acceptable salts, prodrugs, solvates, hydrates, tautomers, or isomers of any of the foregoing.
In some embodiments, the compounds of the disclosure are compounds of Formula V:

V and pharmaceutically acceptable salts, prodrugs, solvates, hydrates, tautomers, or isomers thereof, wherein:

$R^4$ is H or

A is a 5- to 12-membered monocyclic or polycyclic cycloalkyl, heterocycloalkyl, aryl, or heteroaryl, provided that the heteroaryl is not $R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^5$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR'S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2$—NH—, —$C(=CH_2)$—, —CH—, or —S(O)—;

B, including the atoms at the points of attachment, is a monocyclic or polycyclic 5- to 12-membered heterocycle or a monocyclic or polycyclic 5- to 12-membered heteroaryl, wherein each heterocycle or heteroaryl is optionally substituted with one or more —$C_1$-$C_6$alkyl, —OH, —$NH_2$, oxo, heteroaryl, heterocyclyl, —$(CH_2)_n$$NH_2$, —$(CH_2)_n$OH, —$CF_3$, —$CHF_2$, or —$CH_2F$;

$R^2$ is —H, —OH, —$NR^5R^6$, —$C_1$-$C_6$alkyl, —$C_2$-$C_6$alkenyl, —$C_4$-$C_8$cycloalkenyl, —$C_2$-$C_6$alkynyl, —$NH_2$, halogen, —$C_3$-$C_8$cycloalkyl, or heterocyclyl containing 1-5 heteroatoms selected from the group consisting of N, S, P, and O; wherein each alkyl, alkenyl, cycloalkenyl, alkynyl, cycloalkyl, or heterocyclyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2$$NR^5R^6$, —$NR^5S(O)_2R^6$, —$S(O)NR^5R^6$, —$S(O)R^5$, —$NR^5S(O)NR^5R^6$, —$NR'S(O)R^6$, heterocycle, aryl, or heteroaryl; and wherein the heterocyclyl is not attached via a nitrogen atom;

$Y^2$ is —$NR^a$—, —$(CR^a_2)_m$—, —C(O)—, —$C(R^a)_2$NH—, —$(CR^a_2)_m$O—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^3)C(S)N(R^3)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^3)$—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_n$OH, —$C_1$-$C_6$alkyl, —$CF_3$, —$CHF_2$, or —$CH_2F$;

$R^3$ is —H, —$C_1$-$C_6$alkyl, a 3- to 12-membered monocyclic or polycyclic heterocycle, —$C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, oxo, heteroaryl, heterocyclyl, —$(CH_2)_n$$NH_2$, —$(CH_2)_n$OH, —$CF_3$, —$CHF_2$, or —$CH_2F$, provided that the heterocycle formed by the combination of $R^3$ and $R^a$ is not an optionally substituted piperazinyl;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN; $R^{10}$ is —H or —$C_1$-$C_6$alkyl;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of Formula V, $R^4$ is H.

In one or more embodiments of Formula V, $R^4$ is

In certain such embodiments, $Y^1$ is —S— or a direct bond. In one or more embodiments of Formula V, $Y^1$ is —S—. In one or more embodiments of Formula V, $Y^1$ is a direct bond.

In one or more embodiments of the compounds of Formula V, $Y^2$ is —$(CR^a{}_2)_m$—. In one or more embodiments of the compounds of Formula V, $Y^2$ is —$NR^a$—.

In one or more embodiments of the compounds of Formula V, $R^{10}$ is —H. In one or more embodiments of the compounds of Formula V, $R^{10}$ is —$C_1$-$C_6$alkyl.

In one or more embodiments of Formula V, A is a monocyclic or polycyclic cycloalkyl. In one or more embodiments of Formula V, A is a monocyclic or polycyclic heterocycloalkyl. In one or more embodiments of Formula V, A is a monocyclic or polycyclic aryl. In one or more embodiments of Formula V, A is phenyl. In one or more embodiments of Formula V, A is a monocyclic or polycyclic heteroaryl. In one or more embodiments of Formula V, A is pyridinyl. In one or more embodiments of Formula V, A is indazolyl. In one or more embodiments of Formula V, A is a 5- to 12-membered monocyclic or polycyclic aryl or heteroaryl.

In one or more embodiments of Formula V, n is independently, at each occurrence, 0, 1, 2, or 3. In one or more embodiments of Formula V, n is independently, at each occurrence, 1 or 2.

In one or more embodiments of Formula V, $R^1$ is independently, at each occurrence, —H, —$OR^5$, halogen, —$C_1$-$C_6$alkyl, —CN, or —$NR^5R^6$. In one or more embodiments of Formula V, $R^1$ is independently, at each occurrence, —$OR^5$ or halogen. In one or more embodiments of Formula V, $R^1$ is independently, at each occurrence, —H or —$OR^5$. In one or more embodiments of Formula V, $R^1$ is independently, at each occurrence, —H or halogen. In one or more embodiments of Formula V, $R^1$ is independently, at each occurrence, —H or —$NR^5R^6$. In one or more embodiments of Formula V, $R^1$ is independently, at each occurrence, —H, —$OR^5$ or —$NR^5R^6$. In one or more embodiments of Formula V, $R^1$ is independently, at each occurrence, —H, halogen or —$NR^5R^6$. In certain such embodiments, $R^5$ and $R^6$ are both -H. In one or more embodiments of Formula V, $R^1$ is independently, at each occurrence, —H, methyl, fluoro, chloro, or —$NH_2$. In one or more embodiments of Formula V. $R^1$ is independently, at each occurrence, —H, —CN or halogen.

In one or more embodiments of Formula V, $R^5$ and $R^6$ are independently, at each occurrence, —H or —$C_1$-$C_6$alkyl. In one or more embodiments of Formula V, $R^5$ and $R^6$ are independently, at each occurrence, —H. In one or more embodiments of Formula V, $R^5$ and $R^6$ are independently, at each occurrence, —$C_1$-$C_6$alkyl.

In one or more embodiments of Formula V, $R^2$ is —H. In one or more embodiments of Formula V, $R^2$ is —$C_1$-$C_6$alkyl, wherein each alkyl is optionally substituted with one or more —OH, halogen, —$OR^5$, or —$NR^5R^6$. In certain such embodiments, $R^2$ is methyl. In one or more embodiments of Formula V, $R^2$ is —H, —OH, —$NR^5R^6$, —$C_1$-$C_6$alkyl, or —$NH_2$; wherein each alkyl is optionally substituted with one or more —OH, halogen, —$OR^5$, or —$NR^5R^6$. In one or more embodiments of Formula V, $R^2$ is —OH. In one or more embodiments of Formula V, $R^2$ is —$NR^5R^6$. In one or more embodiments of Formula V, $R^2$ is —$NH_2$.

In one or more embodiments of Formula V, $R^a$ is —H.

In one or more embodiments of Formula V, $R^3$ is an optionally substituted —$C_1$-$C_6$alkyl. In one or more embodiments of Formula V, $R^3$ is an optionally substituted 3- to 12-membered monocyclic or polycyclic heterocycle. In one or more embodiments of Formula V, $R^3$ is an optionally substituted 3- to 12-membered monocyclic heterocycle. In one or more embodiments of Formula V, $R^3$ is an optionally substituted 5- to 12-membered polycyclic heterocycle.

In one or more embodiments of Formula V, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula V, $R^3$ and $R^a$ together with the atom to which they are attached combine to form a 3- to 12-membered monocyclic heterocycle, which is optionally substituted with one or more —$C_1$-$C_6$alkyl, —$(CH_2)_nNH_2$, or —$NH_2$. In certain such embodiments, n is 1. In one or more embodiments of Formula V, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula V, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula V, $R^3$ and $R^a$ together with the atom to which they are attached combine to form a 3- to 12-membered polycyclic heterocycle, which is optionally substituted with one or more —$C_1$-$C_6$alkyl, —$(CH_2)_nNH_2$, or —$NH_2$. In certain such embodiments, n is 1. In one or more embodiments of Formula V, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula V, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula V, $R^3$ and $R^a$ together with the atoms to which they are attached combine to form a 5- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula V, $R^3$ and $R^a$ together with the atoms to which they are attached combine to form a 5- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula V, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$(CH_2)_nNH_2$, —$(CH_2)_nOH$, —$CF_3$, —$CHF_2$, or —$CH_2F$. In one or more embodiments of Formula V, $R^3$ and $R^a$ together with the atoms to which they are attached combine to form a 10- to 12-membered spiroheterocycle, which is optionally substituted with one or more —$C_1$-$C_6$alkyl, —$(CH_2)_nNH_2$, or —$NH_2$. In certain such embodiments, n is 1. In one or more embodiments of Formula V, $R^3$ and $R^a$ together with the atoms to which they are attached combine to form a 10- to 12-membered spiroheterocycle, which is optionally substituted with one or more —$C_1$-$C_6$alkyl, —OH, —$NH_2$, oxo, heteroaryl, heterocyclyl, —$(CH_2)_nNH_2$, —$(CH_2)_nOH$, —$CF_3$, —$CHF_2$, or —$CH_2F$.

In one or more embodiments of Formula V. B, including the atoms at the points of attachment, is an optionally substituted monocyclic or polycyclic 5- to 12-membered heterocycle. In one or more embodiments of Formula V. B, including the atoms at the points of attachment, is an optionally substituted monocyclic 5 to 6-membered heterocycle. In one or more embodiments of Formula V. B, including the atoms at the points of attachment, is an optionally substituted monocyclic 7- to 12-membered heterocycle.

In one or more embodiments of Formula V, B, including the atoms at the points of attachment, is an optionally substituted polycyclic 5- to 12-membered heterocyclyl. In certain embodiments, the heteroycyclyl ring is fused. In one or more embodiments of Formula V, the heterocyclyl ring is bridged.

In one or more embodiments of Formula V, B, including the atoms at the points of attachment, is an optionally substituted monocyclic or polycyclic 5- to 12-membered heteroaryl. In one or more embodiments of Formula V, B, including the atoms at the points of attachment, is an optionally substituted monocyclic 5 to 6-membered heteroaryl. In one or more embodiments of Formula V, B, including the atoms at the points of attachment, is a monocyclic 7- to 12-membered heteroaryl.

In one or more embodiments of Formula V, B, including the atoms at the points of attachment, is an optionally substituted polycyclic 5- to 12-membered heteroaryl. In one or more embodiments of Formula V, the polycyclic heteroaryl is a multiple condensed ring as described above. The rings of the multiple condensed ring system can be connected to each other via fused, spiro and bridged bonds when allowed by valency requirements.

In one or more embodiments of Formula V, B is substituted with one or more —$(CH_2)_nOH$. In certain such embodiments, n is 1. In one or more embodiments of Formula V, B is substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$. In one or more embodiments of Formula V, B is substituted with one or more oxo. In one or more embodiments of Formula V, B is substituted with one or more —$C_1$-$C_6$alkyl. In one or more embodiments of Formula V, B is substituted with one or more —OH. In one or more embodiments of Formula V, B is substituted with one or more —$NH_2$. In one or more embodiments of Formula V, B is substituted with one or more —$CF_3$. In one or more embodiments of Formula V, B is substituted with one or more —$CHF_2$. In one or more embodiments of Formula V, B is substituted with one or more —$CH_2F$. In one or more embodiments of Formula V, B is substituted with one or more —$(CH_2)_nNH_2$. In certain such embodiments, n is 1.

In certain embodiments of Formula V, the compound is of Formula V-A:

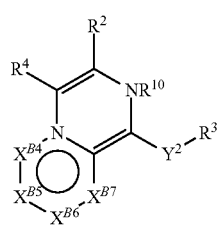

V-A and pharmaceutically acceptable salts, prodrugs, solvates, hydrates, tautomers, and isomers thereof, wherein $X^{B4}$ is N or $CR^9$; $X^{B5}$ is N or $CR^9$; $X^{B6}$ is N or $CR^9$; and $X^{B7}$ is N or $CR^9$, wherein $R^9$ is independently, at each occurrence, —H, —$C_1$-$C_6$alkyl, —OH, —$NH_2$, heteroaryl, heterocyclyl, —$(CH_2)_nNH_2$, —$(CH_2)_nOH$, —$CF_3$, —$CHF_2$, or —$CH_2F$.

In certain embodiments of Formula V-A, $X^{B4}$ is N. In certain embodiments of Formula V-A, $X^{B4}$ is $CR^9$. In certain embodiments of Formula V-A, $X^{B5}$ is N. In certain embodiments of Formula V-A, $X^{B5}$ is $CR^9$. In certain embodiments of Formula V-A, $X^{B6}$ is N. In certain embodiments of Formula V-A, $X^{B6}$ is $CR^9$. In certain embodiments of Formula V-A, $X^{B7}$ is N. In certain embodiments of Formula V-A, $X^{B7}$ is $CR^9$.

In some embodiments of Formula V-A, $R^9$ is —$(CH_2)_n$OH and n is 1. In some embodiments of Formula V-A, $R^9$ is H.

In one or more embodiments of the compounds of Formula V-A, $R^{10}$ is —H. In one or more embodiments of the compounds of Formula V-A, $R^{10}$ is —$C_1$-$C_6$alkyl.

In one or more embodiments of Formula V-A, $R^4$ is H.

In one or more embodiments of Formula V-A, $R^4$ is

In certain such embodiments, $Y^1$ is —S— or a direct bond. In one or more embodiments of Formula V-A, $Y^1$ is —S—. In one or more embodiments of Formula V-A, $Y^1$ is a direct bond.

In one or more embodiments of the compounds of Formula V-A, $Y^2$ is —$(CR^a_2)_m$—. In one or more embodiments of the compounds of Formula V-A, $Y^2$ is —$NR^a$—.

In one or more embodiments of Formula V-A, A is a monocyclic or polycyclic cycloalkyl. In one or more embodiments of Formula V-A, A is a monocyclic or polycyclic heterocycloalkyl. In one or more embodiments of Formula V-A, A is a monocyclic or polycyclic aryl. In one or more embodiments of Formula V-A, A is phenyl. In one or more embodiments of Formula V-A, A is a monocyclic or polycyclic heteroaryl. In one or more embodiments of Formula V-A, A is pyridinyl. In one or more embodiments of Formula V-A, A is indazolyl. In one or more embodiments of Formula V-A, A is a 5- to 12-membered monocyclic or polycyclic aryl or heteroaryl.

In one or more embodiments of Formula V-A, n is independently, at each occurrence, 0, 1, 2, or 3. In one or more embodiments of Formula V-A, n is independently, at each occurrence, 1 or 2.

In one or more embodiments of Formula V-A, $R^1$ is independently, at each occurrence, —H, —$OR^5$, halogen, —$C_1$-$C_6$alkyl, —CN, or —$NR^5R^6$. In one or more embodiments of Formula V-A, $R^1$ is independently, at each occurrence, —H, —$OR^5$ or halogen. In one or more embodiments of Formula V-A, $R^1$ is independently, at each occurrence, —H or —$OR^5$. In one or more embodiments of Formula V-A, $R^1$ is independently, at each occurrence, —H or halogen. In one or more embodiments of Formula V-A, $R^1$ is independently, at each occurrence, —H or —$NR^5R^6$. In one or more embodiments of Formula V-A, $R^1$ is independently, at each occurrence, —H, —$OR^5$ or —$NR^5R^6$. In one or more embodiments of Formula V-A, $R^1$ is independently, at each occurrence, —H, halogen or —$NR^5R^6$. In certain such embodiments, $R^5$ and $R^6$ are both —H. In one or more embodiments of Formula V-A, $R^1$ is independently, at each occurrence, —H, methyl, fluoro, chloro, or —NH$_2$. In one or more embodiments of Formula V-A, $R^1$ is independently, at each occurrence, —H, —CN or halogen.

In one or more embodiments of Formula V-A, $R^5$ and $R^6$ are independently, at each occurrence, —H or —C$_1$-C$_6$alkyl. In one or more embodiments of Formula V-A, $R^5$ and $R^6$ are independently, at each occurrence, —H. In one or more embodiments of Formula V-A, $R^5$ and $R^6$ are independently, at each occurrence, —C$_1$-C$_6$alkyl.

In one or more embodiments of Formula V-A, $R^2$ is —H. In one or more embodiments of Formula V-A, $R^2$ is —C$_1$-C$_6$alkyl, wherein each alkyl is optionally substituted with one or more —OH, halogen, —OR$^5$, or —NR$^5$R$^6$. In certain such embodiments, $R^2$ is methyl. In one or more embodiments of Formula V-A, $R^2$ is —H, —OH, —NR$^5$R$^6$, —C$_1$-C$_6$alkyl, or —NH$_2$; wherein each alkyl is optionally substituted with one or more —OH, halogen, —OR$^5$, or —NR$^5$R$^6$. In one or more embodiments of Formula V-A, $R^2$ is —OH. In one or more embodiments of Formula V-A, $R^2$ is —NR$^5$R$^6$. In one or more embodiments of Formula V-A, $R^2$ is —NH$_2$.

In one or more embodiments of Formula V-A, $R^a$ is —H.

In one or more embodiments of Formula V-A, $R^3$ is an optionally substituted —C$_1$-C$_6$alkyl. In one or more embodiments of Formula V-A, $R^3$ is an optionally substituted 3- to 12-membered monocyclic or polycyclic heterocycle. In one or more embodiments of Formula V-A, $R^3$ is an optionally substituted 3- to 12-membered monocyclic heterocycle. In one or more embodiments of Formula V-A, $R^3$ is an optionally substituted 5- to 12-membered polycyclic heterocycle.

In one or more embodiments of Formula V-A, $R^3$ and $R^a$ together with the atom to which they are attached combine to form a 3- to 12-membered monocyclic heterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula V-A, $R^3$ and $R^a$ together with the atom to which they are attached combine to form a 3- to 12-membered monocyclic heterocycle, which is optionally substituted with one or more —C$_1$-C$_6$alkyl, —(CH$_2$)$_n$NH$_2$, or —NH$_2$. In certain such embodiments, n is 1. In one or more embodiments of Formula V-A, $R^3$ and $R^a$ together with the atom to which they are attached combine to form a 3- to 12-membered monocyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula V-A, $R^3$ and $R^a$ together with the atoms to which they are attached combine to form a 3- to 12-membered polycyclic heterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula V-A, $R^3$ and $R^a$ together with the atom to which they are attached combine to form a 3- to 12-membered polycyclic heterocycle, which is optionally substituted with one or more —C$_1$-C$_6$alkyl, —(CH$_2$)$_n$NH$_2$, or —NH$_2$. In certain such embodiments, n is 1. In one or more embodiments of Formula V-A, $R^3$ and $R^a$ together with the atom to which they are attached combine to form a 3- to 12-membered polycyclic heterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula V-A, $R^3$ and $R^a$ together with the atoms to which they are attached combine to form a 5- to 12-membered spiroheterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula V-A, $R^3$ and $R^a$ together with the atoms to which they are attached combine to form a 5- to 12-membered spiroheterocycle, which is optionally substituted with one or more —C$_1$-C$_6$alkyl, —(CH$_2$)$_n$NH$_2$, or —NH$_2$. In certain such embodiments, n is 1. In one or more embodiments of Formula V-A, $R^3$ and $R^a$ together with the atoms to which they are attached combine to form a 5- to 12-membered spiroheterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula V-A, $R^3$ and $R^a$ together with the atoms to which they are attached combine to form a 10- to 12-membered spiroheterocycle, which is optionally substituted with one or more —C$_1$-C$_6$alkyl, —NH$_2$, —OH, —(CH$_2$)$_n$NH$_2$, —(CH$_2$)$_n$OH, —CF$_3$, —CHF$_2$, or —CH$_2$F. In one or more embodiments of Formula V-A, $R^3$ and $R^a$ together with the atoms to which they are attached combine to form a 10- to 12-membered spiroheterocycle, which is optionally substituted with one or more —C$_1$-C$_6$alkyl, —(CH$_2$)$_n$NH$_2$, or —NH$_2$. In certain such embodiments, n is 1. In one or more embodiments of Formula V-A, $R^3$ and $R^a$ together with the atoms to which they are attached combine to form a 10- to 12-membered spiroheterocycle, which is optionally substituted with one or more —C$_1$-C$_6$alkyl, —OH, —NH$_2$, oxo, heteroaryl, heterocyclyl, —(CH$_2$)$_n$NH$_2$, —(CH$_2$)$_n$OH, —CF$_3$, —CHF$_2$, or —CH$_2$F.

In one or more embodiments of Formula I', IV, or V, $R^4$ is H. In one or more embodiments of Formula I', I, IV, or V, $R^4$ is

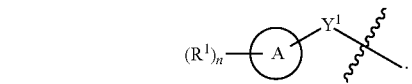

In one or more embodiments of Formula I', I, II, III, IV, or V, A is a 5- to 12-membered monocyclic or polycyclic cycloalkyl. In one or more embodiments of Formula I', I, II, III, IV, or V, A is a monocyclic or polycyclic heterocycloalkyl. In one or more embodiments of Formula I', I, II, III, IV, or V, A is a monocyclic or polycyclic aryl. In one or more embodiments of Formula I', I, II, III, IV, or V, A is a monocyclic or polycyclic heteroaryl.

In one or more embodiments of Formula I', I, IV, or V, $Y^1$ is —S—. In one or more embodiments of Formula I', I, IV, or V, $Y^1$ is a direct bond.

In one or more embodiments of Formula I', I, II, III, IV, or V, $Y^2$ is —NR$^a$—. In one or more embodiments of Formula I', I, II, III, IV, or V, $Y^2$ is —(CR$^a_2$)$_m$—. In one or more embodiments of Formula I', I, II, III, IV, or V, $Y^2$ is —C(O)—. In one or more embodiments of Formula I', I, II, III, IV, or V, $Y^2$ is —C(R$^a$)$_2$NH— or —(CR$^a_2$)$_m$O—. In one or more embodiments of Formula I', I, II, III, IV, or V, $Y^2$ is —C(O)N(R$^a$)—, —N(R$^a$)C(O)—, —S(O)$_2$N(R$^a$)—, —N(R$^a$)S(O)$_2$—, —N(R$^a$)C(S)—, or —C(S)N(R$^a$)—. In one or more embodiments of Formula I', I, II, III, IV, or V, $Y^2$ is —N(R$^a$)C(O)N(R$^a$)—, —N(R$^a$)C(S)N(R$^a$)—, —OC(O)N(R$^a$)—, —N(R$^a$)C(O)O—, or —C(O)N(R$^a$)O—. In one or more embodiments of Formula I', I, II, III, IV, or V, $Y^2$ is —C(O)O—, —OC(O)—, or —OC(O)O—.

In one or more embodiments of Formula I', I, II, III, IV, or V, $R^2$ is —OH. In one or more embodiments of Formula I', I, II, III, IV, or V, $R^2$ is —$C_1$-$C_6$alkyl, wherein each alkyl is optionally substituted with one or more —OH, halogen, —$OR^5$, or —$NR^5R^6$. In one or more embodiments of Formula I', I, II, III, IV, or V, $R^2$ is an optionally substituted-$C_2$-$C_6$alkenyl. In one or more embodiments of Formula I', I, II, III, IV, or V, $R^2$ is an optionally substituted —$C_4$-$C_8$cycloalkenyl. In one or more embodiments of Formula I', I, II, III, IV, or V, $R^2$ is an optionally substituted-$C_2$-$C_6$alkynyl. In one or more embodiments of Formula I', I, II, III, IV, or V, $R^2$ is an optionally substituted-$C_3$-$C_8$cycloalkyl. In one or more embodiments of Formula I', I, II, III, IV, or V, $R^2$ is an optionally substituted monocyclic or polycyclic heterocyclyl containing 1-5 heteroatoms selected from the group consisting of N, S, P, and O.

In one or more embodiments of Formula I', I, II, III, IV, or V, $R^a$ is —H. In one or more embodiments of Formula I', I, II, III, IV, or V, $R^a$ is —OH. In one or more embodiments of Formula I', I, II, III, IV, or V, $R^a$ is an optionally substituted-$C_3$-$C_8$cycloalkyl. In one or more embodiments of Formula I', I, II, III, IV, or V, $R^a$ is an optionally substituted —$C_1$-$C_6$alkyl.

In one or more embodiments of Formula I', I, II, III, IV, or V, $R^b$ is H. In one or more embodiments of Formula I', I, II, III, IV, or V, $R^b$ is an optionally substituted —$C_1$-$C_6$alkyl. In one or more embodiments of Formula I', I, II, III, IV, or V, $R^b$ is an optionally substituted-$C_3$-$C_8$cycloalkyl. In one or more embodiments of Formula I', I, II, III, IV, or V, $R^b$ is an optionally substituted-$C_2$-$C_6$alkenyl. In one or more embodiments of Formula I', I, II, III, IV, or V, $R^b$ is an optionally substituted monocyclic or polycyclic heterocyclyl containing 1-5 heteroatoms selected from the group consisting of N, S, P, and O.

In one or more embodiments of Formula I', I, II, III, IV, or V, $R^3$ is an optionally substituted-$C_1$-$C_6$alkyl. In one or more embodiments of Formula I', I, II, III, IV, or V, $R^3$ is an optionally substituted 3- to 12-membered monocyclic or polycyclic heterocycle. In one or more embodiments of Formula I', I, II, III, IV, or V, $R^3$ is an optionally substituted 3- to 12-membered monocyclic heterocycle. In one or more embodiments of Formula I', I, II, III, IV, or V, $R^3$ is an optionally substituted 5- to 12-membered polycyclic heterocycle.

In one or more embodiments of Formula I', I, II, III, IV, or V, $R^3$ and $R^a$ together with the atom to which they are attached combine to form an optionally substituted 3- to 12-membered monocyclic heterocycle. In one or more embodiments of Formula I', I, II, III, IV, or V, $R^3$ and $R^a$ together with the atoms to which they are attached combine to form an optionally substituted 3- to 12-membered polycyclic heterocycle. In one or more embodiments of Formula I', I, II, III, IV, or V, $R^3$ and $R^a$ together with the atoms to which they are attached combine to form an optionally substituted 5- to 12-membered spiroheterocycle.

In one or more embodiments of Formula I', I, II, III, or IV, $X^1$ is N. In one or more embodiments of Formula I', I, II, III, or IV, $X^1$ is C.

In one or more embodiments of Formula I', I, II, III, or IV, $X^2$ is N. In one or more embodiments of Formula I', I, II, III, or IV, $X^2$ is CH.

In one or more embodiments of Formula I', I, II, III, or IV, $X^1$ is N and $X^2$ is N. In one or more embodiments of Formula I', I, II, III, or IV, $X^1$ is N and $X^2$ is CH. In one or more embodiments of Formula I', I, II, III, or IV, $X^1$ is C and $X^2$ is N. In one or more embodiments of Formula I', I, II, III, or IV, $X^1$ is C and $X^2$ is CH.

In one or more embodiments of Formula I', I, II, III, IV, or V, B, including the atoms at the points of attachment, is a monocyclic or polycyclic 5- to 12-membered heterocycle. In one or more embodiments of Formula I', I, II, III, IV, or V, B, including the atoms at the points of attachment, is a monocyclic 5 to 6-membered heterocycle. In one or more embodiments of Formula I', I, II, III, IV, or V, B, including the atoms at the points of attachment, is a monocyclic 7- to 12-membered heterocycle.

In one or more embodiments of Formula I', I, II, III, IV, or V, B, including the atoms at the points of attachment, is a polycyclic 5- to 12-membered heterocyclyl. In certain embodiments, the heteroycyclyl ring is fused. In one or more embodiments of Formula I', I, II, III, IV, or V, the heterocyclyl ring is bridged.

In one or more embodiments of Formula I', I, II, III, IV, or V, B, including the atoms at the points of attachment, is a monocyclic or polycyclic 5- to 12-membered heteroaryl. In one or more embodiments of Formula I', I, II, III, IV, or V, B, including the atoms at the points of attachment, is a monocyclic 5 to 6-membered heteroaryl. In one or more embodiments of Formula I', I, II, III, IV, or V, B, including the atoms at the points of attachment, is a monocyclic 7- to 12-membered heteroaryl.

In one or more embodiments of Formula I', I, II, III, IV, or V, B, including the atoms at the points of attachment, is a polycyclic 5- to 12-membered heteroaryl. In one or more embodiments of Formula I', I, II, III, IV, or V, the polycyclic heteroaryl is a multiple condensed ring as described above. The rings of the multiple condensed ring system can be connected to each other via fused, spiro and bridged bonds when allowed by valency requirements.

In one or more embodiments of Formula I', I, II, III, or IV, B, including the atoms at the points of attachment, is

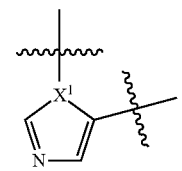

and $X^1$ is N, thereby forming

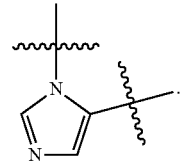 [SMILES: *c1cncn1*]

In one or more embodiments of Formula I', I, II, III, or IV, B, including the atoms at the points of attachment, is

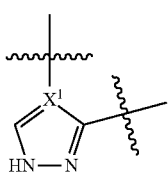

and $X^1$ is C, thereby forming

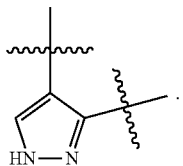 [SMILES: *c1c[nH]nc1*]

In one or more embodiments of Formula I', I, II, III, or IV, B, including the atoms at the points of attachment, is

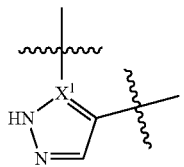

and $X^1$ is C, thereby forming

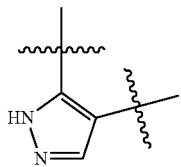

In one variation of Formula I, II, III, IV, or V, $R^2$ is an optionally substituted —$C_1$-$C_6$alkyl and B, including the atoms at the points of attachment, is an optionally substituted monocyclic 5 to 6-membered heteroaryl. In certain instances of Formula I, II, III, IV, or V, $R^2$ is an optionally substituted-$C_1$-$C_6$alkyl and B, including the atoms at the points of attachment, is an optionally substituted monocyclic 5-membered heteroaryl. In certain instances of Formula I, II, III, IV, or V, $R^2$ is an optionally substituted-$C_1$-$C_6$alkyl and B, including the atoms at the points of attachment, is an optionally substituted monocyclic 6-membered heteroaryl.

In one variation of Formula I, II, III, IV, or V, $R^2$ is —OH and B, including the atoms at the points of attachment, is an optionally substituted monocyclic 5 to 6-membered heteroaryl. In certain instances of Formula I, II, III, IV, or V, $R^2$ is —OH and B, including the atoms at the points of attachment, is an optionally substituted monocyclic 5-membered heteroaryl. In certain instances of Formula I, II, III, IV, or V, $R^2$ is —OH and B, including the atoms at the points of attachment, is an optionally substituted monocyclic 6-membered heteroaryl.

In one variation of Formula I, II, III, IV, or V, $Y^1$ is —S— and A is an optionally substituted 5- to 12-membered monocyclic or polycyclic cycloalkyl. In certain instances of Formula I, II, III, IV, or V, $Y^1$ is —S— and A is an optionally substituted monocyclic or polycyclic heterocycloalkyl. In certain instances of Formula I, II, III, IV, or V, $Y^1$ is —S— and A is an optionally substituted monocyclic or polycyclic aryl. In certain instances of Formula I, II, III, IV, or V, $Y^1$ is S and A is an optionally substituted monocyclic or polycyclic heteroaryl.

In one variation of Formula I, II, III, IV, or V, $Y^1$ is a direct bond and A is an optionally substituted 5- to 12-membered monocyclic or polycyclic cycloalkyl. In certain instances of Formula I, II, III, IV, or V, $Y^1$ is a direct bond and A is an optionally substituted monocyclic or polycyclic heterocycloalkyl. In certain instances of Formula I, II, III, IV, or V, $Y^1$ is a direct bond and A is an optionally substituted monocyclic or polycyclic aryl. In certain instances of Formula I, II, III, IV, or V, $Y^1$ is a direct bond and A is an optionally substituted monocyclic or polycyclic heteroaryl.

Methods of Synthesizing the Disclosed Compounds

The compounds of the present disclosure may be made by a variety of methods, including standard chemistry. Suitable synthetic routes are depicted in the schemes given below:

The compounds of any of the formulae described herein may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of the present disclosure.

Those skilled in the art will recognize if a stereocenter exists in any of the compounds of the present disclosure. Accordingly, the present disclosure may include both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Preparation of Compounds

The compounds described herein may be made from commercially available starting materials or synthesized using known organic, inorganic, and/or enzymatic processes.

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. These methods include but are not limited to those methods described below.

Scheme 1. General synthesis of 1-(5-Aryl (or heteroaryl)-6-methylimidazo[1,5-a]pyrazin-8-yl)-4-amines.

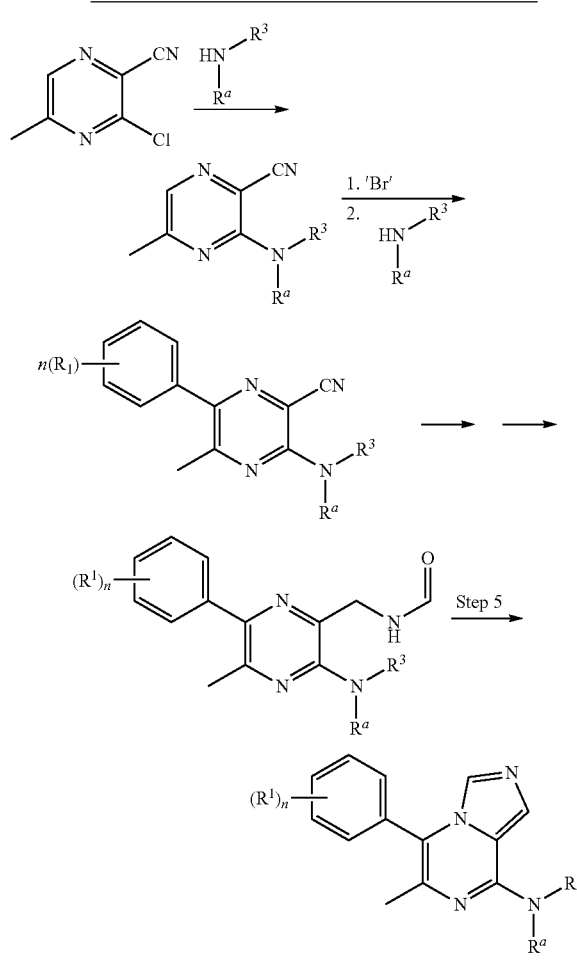

A general synthesis of 1-(5-Aryl (or heteroaryl)-6-methylimidazo[1,5-a]pyrazin-8-yl)-4-amines is in Scheme 1. 2-Chloro-3-cyano-5-methylpyrazine can be coupled to an appropriately substituted amine, brominated and subsequently coupled to an appropriately substituted aryl- or heteroaryl boronic acid in the presence of palladium based catalyst. The resulting bi-aryl compound can then be formylated and cyclized to form an appropriately substituted imidazole-pyrazine. Additional deprotection and/or functionalization steps can be required to produce the final compound.

Scheme 2. General synthesis of amino imidazo[1,5-a]pyrazines (or an alternative bi-cyclic structure).

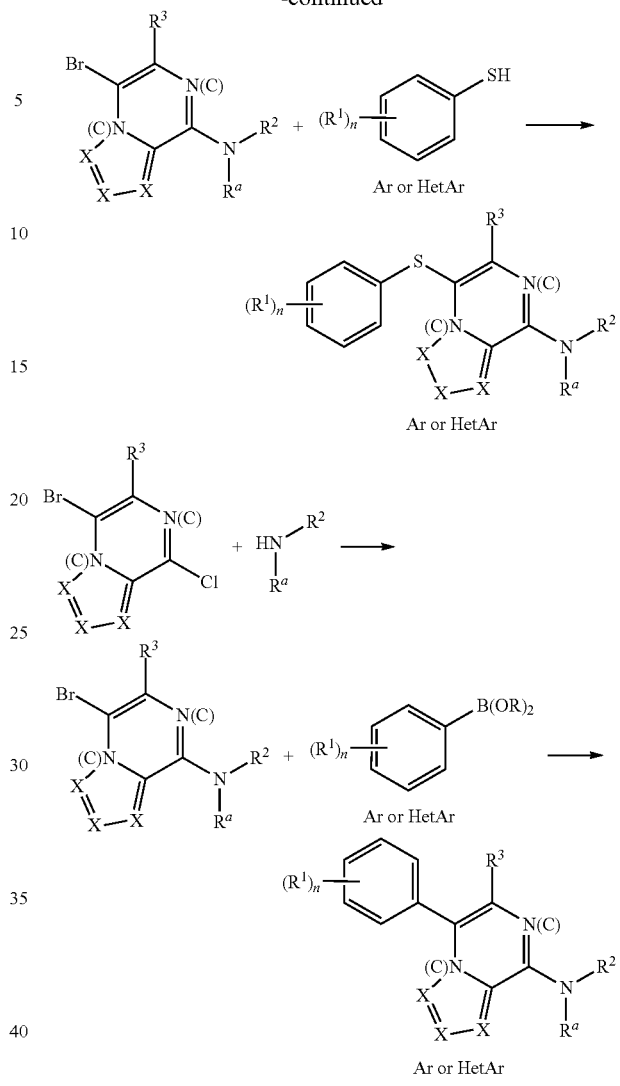

X = C, N, S, CO, O

A general synthesis of amino imidazo[1,5-a]pyrazines (or an alternative bi-cyclic structure) is outlined in Scheme 2. 5-Bromo-8-chloroimidazo[1,5-a]pyrazine (or an alternative bi-cyclic structure) can be coupled to a substituted primary or secondary amine to give 5-bromo-imidazo[1,5-a]pyrazin-8-amine. The resulting intermediate can be coupled to a substituted aryl- or heteroaryl-thiol in the presence of a copper catalyst (e.g., CuI) or under SNAr conditions, alternatively, the resulting intermediate can be coupled to an appropriately substituted aryl or heteroaryl boronic acid in the presence of Pd catalyst. Additional deprotection and/or functionalization steps can be required to produce the final compound.

Methods of Using the Disclosed Compounds and Compositions

Methods and Uses of the Disclosure

Another aspect of the disclosure relates to methods of treating a disease associated with SHP2 modulation in a subject in need thereof. The methods may involve administering to a patient in need of treatment for diseases or disorders associated with SHP2 modulation an effective amount of one or more compounds of the present disclosure (e.g., compounds of Formula I' I, II, III, IV, or V, and pharmaceutically acceptable salts, prodrugs, solvates, hydrates, tautomers, or isomers thereof), or of one or more pharmaceutical compositions of the present disclosure. In some embodiments, the disease can be, but is not limited to Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knockdown of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In addition. SHP2 plays a role in transducing signals originating from immune checkpoint molecules, including but not limited to programmed cell death protein 1 (PD-1) and cytotoxic T-lymphocyte-associated protein 4 (CTLA-4). In this context, modulation of SHP2 function can lead to immune activation, specifically anti-cancer immune responses.

Another aspect of the disclosure is directed to a method of inhibiting SHP2. The method involves administering to a patient in need thereof an effective amount of one or more compounds of the present disclosure (e.g., compounds of Formula I' I, II, III, IV, or V, and pharmaceutically acceptable salts, prodrugs, solvates, hydrates, tautomers, or isomers thereof), or of one or more pharmaceutical compositions of the present disclosure.

The present disclosure relates to compounds or compositions disclosed herein that are capable of modulating the activity of (e.g., inhibiting) SHP2. The present disclosure also relates to the therapeutic use of such compounds and compositions.

One or more disclosed compounds or compositions can be administered in effective amounts to treat or prevent a disorder and/or prevent the development thereof in subjects. In some embodiments, SHP2 is inhibited after treatment with less than 1000 nM of a compound of the disclosure. In some embodiments, SHP2 is inhibited after treatment with about 1 nM to about 10 nM of a compound of the disclosure. In some embodiments, SHP2 is inhibited after treatment with less than about 1 nM of a compound of the disclosure. In some embodiments, SHP2 is inhibited after treatment with about 10 nM to about 100 nM of a compound of the disclosure. In some embodiments, SHP2 is inhibited after treatment with about 100 nM to about 10 μM of a compound of the disclosure.

Another aspect of the present disclosure relates to a one or more compounds of the present disclosure (e.g., compounds of Formula I' I, II, III, IV, or V, and pharmaceutically acceptable salts, prodrugs, solvates, hydrates, tautomers, or isomers thereof), or one or more compositions of the present disclosure, for use in treating or preventing a disease associated with SHP2 modulation. In some embodiments, the disease is Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knockdown of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In another aspect, the present disclosure relates to the use of one or more compounds of the present disclosure (e.g., compounds of Formula I', I, II, III, IV, or V, and pharmaceutically acceptable salts, prodrugs, solvates, hydrates, tautomers, or isomers thereof), in the manufacture of a medicament for treating or preventing a disease. In some embodiments, the disease is associated with SHP2 modulation.

In another aspect, the present disclosure relates to one or more compounds of the present disclosure (e.g., compounds of Formula I', I, II, III, IV, or V, and pharmaceutically acceptable salts, prodrugs, solvates, hydrates, tautomers, or isomers thereof), for use as a medicament. In some embodiments, the medicament is used for treating or preventing a disease associated with SHP2 modulation.

In one aspect, the present disclosure relates to one or more compositions comprising one or more compounds of the present disclosure (e.g., compounds of Formula I', I, II, III, IV, or V, and pharmaceutically acceptable salts, prodrugs, solvates, hydrates, tautomers, or isomers thereof), for use as a medicament. In some embodiments, the medicament is used for treating or preventing a disease associated with SHP2 modulation.

Pharmaceutical Compositions and Modes of Administration of the Disclosure

Another aspect of the present disclosure relates to pharmaceutical compositions comprising one or more compounds of the present disclosure and a pharmaceutically acceptable carrier. The pharmaceutically acceptable carrier can further include an excipient, diluent, or surfactant.

Compositions of the disclosure can be prepared according to conventional mixing, granulating or coating methods, respectively, and the present pharmaceutical compositions can contain from about 0.1% to about 99%, from about 5% to about 90%, or from about 1% to about 20% of one or more of the disclosed compounds by weight or volume.

Administration of the disclosed compounds and compositions may be accomplished via any mode of administration for therapeutic agents. These modes may include systemic or local administration such as oral, nasal, parenteral, intravenous, transdermal, subcutaneous, vaginal, buccal, rectal or topical administration modes.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions may include tablets and gelatin capsules comprising one or more compounds of the present disclosure and a pharmaceutically acceptable carrier, such as, but not limited to, a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, one or more of the disclosed compounds are dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

One or more of the disclosed compounds or compositions can be also formulated as a suppository that can be prepared from fatty emulsions or suspensions; using polyalkylene glycols such as propylene glycol, as the carrier.

One or more disclosed compounds or compositions can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

One or more disclosed compounds or compositions can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the one or more disclosed compounds can be coupled to a class of biodegradable polymers useful in achieving controlled release of a drug, for example, polylactic acid, polyepsilon caprolactone, polyhydroxy butyric acid, polyorthoesters, polyacetals, poly dihydropyrans, polycyanoacrylates and cross-linked or amphipathic block copolymers of hydrogels. In some embodiments, one or more disclosed compounds are not covalently bound to a polymer, e.g., a polycarboxylic acid polymer, or a polyacrylate.

One or more disclosed compounds or compositions can be delivered by parental administration. Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Dosage Regimens of the Disclosure

The dosage regimen utilizing one or more of the disclosed compounds or compositions may be selected in accordance with a variety of factors including type, species, age, weight, sex and medical condition of the patient: the severity of the condition to be treated: the route of administration: the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, may range from about 0.5 mg to about 5000 mg of the disclosed compounds as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compounds, or, in a range of from one amount to another amount in the list of doses. In some embodiments, the compositions are in the form of a tablet that can be scored.

If desired, the effective daily dose of one or more compounds or compositions of this disclosure may be administered as one, two, three, four, five, six, or more sub-doses administered separately at appropriate intervals throughout the day, optionally, in unit dosage forms. In some embodiments of this disclosure, the one or more compounds or compositions of this disclosure, or mixtures thereof, may be administered two or three times daily. In some embodiments, the one or more compounds or compositions of this disclosure will be administered once daily.

In some embodiments, one or more compounds or compositions described herein may be used alone or together or conjointly administered, or used in combination, with another type of therapeutic agent. Conjoint administration or used in combination may refer to any form of administration of two or more different therapeutic compounds or compositions such that the second compound or composition is administered while the previously administered therapeutic compound or composition is still effective in the body. For example, the different therapeutic compounds or compositions can be administered either in the same formulation or in a separate formulation, either simultaneously, sequentially, or by separate dosing of the individual components of the treatment. In some embodiments, the different therapeutic compounds or compositions can be administered within one hour, 12 hours, 24 hours, 36 hours, 48 hours, 72 hours, or a week of one another. Thus, an individual who receives such treatment can benefit from a combined effect of different therapeutic compounds or compositions.

Kits

In some embodiments, this disclosure also provides a pharmaceutical package or kit comprising one or more containers filled with at least one compound or composition of this disclosure. Optionally associated with such a container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both. In some embodiments, the kit comprises at least two containers, at least one of which contains at least one compound or composition of this disclosure. In some embodiments, the kit contains at least two containers, and each of the at least two containers contains at least one compound or composition of this disclosure.

In some embodiments, the kit includes additional materials to facilitate delivery of the subject compounds and compositions. For example, the kit may include one or more of a catheter, tubing, infusion bag, syringe, and the like. In some embodiments, the compounds and compositions may be packaged in a lyophilized form, and the kit includes at least two containers: a container comprising the lyophilized compounds or compositions and a container comprising a suitable amount of water, buffer, or other liquid suitable for reconstituting the lyophilized material.

The foregoing applies to any of the compounds, compositions, methods, and uses described herein. This disclosure specifically contemplates any combination of the features of such compounds, compositions, methods, and uses (alone or in combination) with the features described for the various kits described in this section.

EXEMPLARY EMBODIMENTS

Some embodiments of this disclosure are Embodiment I, as follows:

Embodiment I-1. A compound of the Formula I':

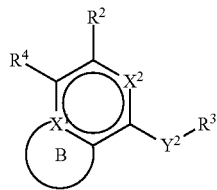

or a pharmaceutically acceptable salt, prodrug, solvate, hydrate, tautomer, or isomer thereof, wherein:

$R^4$ is H or

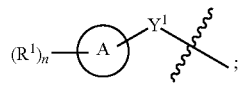

A is a 5- to 12-membered monocyclic or polycyclic cycloalkyl, heterocycloalkyl, aryl, or heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2$ $NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2$—NH—, —$C(=CH_2)$—, —CH—, or —$S(O)$—;

$X^1$ is N or C;

$X^2$ is N or CH;

B, including the atoms at the points of attachment, is a monocyclic or polycyclic 5- to 12-membered heterocycle or a monocyclic or polycyclic 5- to 12-membered heteroaryl;

$R^2$ is —H, —$OR^b$, —$NR^5R^6$, —CN, —$C_1$-$C_6$alkyl, —$C_2$-$C_6$alkenyl, —$C_4$-$C_8$cycloalkenyl, —$C_2$-$C_6$alkynyl, —$NH_2$, halogen, —$C(O)OR^b$, —$C_3$-$C_8$cycloalkyl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR'S(O)R^6$, heterocycle, aryl, or heteroaryl; and wherein the heterocyclyl or heteroaryl is not attached via a nitrogen atom;

$Y^2$ is —$NR^a$—, —$(CR^a_2)_m$—, —$C(O)$—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —$C(O)O$—, —$OC(O)$—, —$OC(O)N(R^a)$—, —$N(R^a)C(O)O$—, —$C(O)N(R^a)O$—, —$N(R^a)C(S)$—, —$C(S)N(R^a)$—, or —$OC(O)O$—; wherein the bond on the left side of $Y^2$, as drawn, is bound to the ring and the bond on the right side of the $Y^2$ moiety, as drawn, is bound to $R^3$;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2$ $NR^5R^6$, —$S(O)_2R^5$, —$NR^5S(O)_2NR^5R^6$, —$NR'S(O)_2$ $R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_n$OH, —$C_1$-$C_6$alkyl, —$CF_3$, —$CHF_2$, or —$CH_2F$;

$R^3$ is, at each occurrence, selected from the group consisting of –H, —$C_1$-$C_6$alkyl, a 3- to 12-membered monocyclic or polycyclic heterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-2. The compound of Embodiment I-1, wherein R$^4$ is —H.

Embodiment I-3. The compound of Embodiment I-1, wherein R$^4$ is

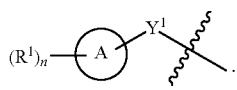

Embodiment I-4. The compound of Embodiment I-1 or I-3, wherein A is a 5- to 12-membered monocyclic or polycyclic cycloalkyl.

Embodiment I-5. The compound of Embodiment I-1 or I-3, wherein A is monocyclic or polycyclic heterocycloalkyl.

Embodiment I-6. The compound of Embodiment I-1 or I-3, wherein A is monocyclic or polycyclic aryl.

Embodiment I-7. The compound of Embodiment I-1 or I-3, wherein A is monocyclic or polycyclic heteroaryl.

Embodiment I-8. The compound of any one of Embodiments I-1 or I-3 to I-7, wherein Y$^1$ is —S—.

Embodiment I-9. The compound of any one of Embodiments I-1 or I-3 to I-7, wherein Y$^1$ is a direct bond.

Embodiment I-10. The compound of any one of Embodiments I-1 to I-9, wherein Y$^2$ is —NR$^a$—.

Embodiment I-11. The compound of any one of Embodiments I-1 to I-9, wherein Y$^2$ is —(CR$^a$$_2$)$_m$—.

Embodiment I-12. The compound of any one of Embodiments I-1 to I-9, wherein Y$^2$ is —C(O)—.

Embodiment I-13. The compound of any one of Embodiments I-1 to I-9, wherein Y$^2$ is —C(R$^a$)$_2$NH— or —(CR$^a$$_2$)$_m$O—.

Embodiment I-14. The compound of any one of Embodiments I-1 to I-9, wherein Y$^2$ is —C(O)N(R$^a$)—, —N(R$^a$)C(O)—, —S(O)$_2$N(R$^a$)—, —N(R$^a$)S(O)$_2$—, —N(R$^a$)C(S)—, or —C(S)N(R$^a$)—.

Embodiment I-15. The compound of any one of Embodiments I-1 to I-9, wherein Y$^2$ is —N(R$^a$)C(O)N(R$^a$)—, —N(R$^a$)C(S)N(R$^a$)—, —OC(O)N(R$^a$)—, —N(R$^a$)C(O)O—, or —C(O)N(R$^3$)O—.

Embodiment I-16. The compound of any one of Embodiments I-1 to I-9, wherein Y$^2$ is —C(O)O—, —OC(O)—, or —OC(O)O—.

Embodiment I-17. The compound of any one of Embodiments I-1 to I-16, wherein R$^2$ is —OR$^b$.

Embodiment I-18. The compound of any one of Embodiments I-1 to I-16, wherein R$^2$ is an optionally substituted-C$_1$-C$_6$alkyl.

Embodiment I-19. The compound of any one of Embodiments I-1 to I-16, wherein R$^2$ is —CN.

Embodiment I-20. The compound of any one of Embodiments I-1 to I-16, wherein R$^2$ is an optionally substituted-C$_2$-C$_6$alkenyl.

Embodiment I-21. The compound of any one of Embodiments I-1 to I-16, wherein R$^2$ is an optionally substituted-C$_4$-C$_8$cycloalkenyl.

Embodiment I-22. The compound of any one of Embodiments I-1 to I-16, wherein R$^2$ is an optionally substituted-C$_2$-C$_6$alkynyl.

Embodiment I-23. The compound of any one of Embodiments I-1 to I-16, wherein R$^2$ is an optionally substituted-C$_3$-C$_8$cycloalkyl.

Embodiment I-24. The compound of any one of Embodiments I-1 to I-16, wherein R$^2$ is an optionally substituted heterocyclyl containing 1-5 heteroatoms selected from the group consisting of N, S, P, and O.

Embodiment I-25. The compound of any one of Embodiments I-1 to I-16, wherein R$^2$ is an optionally substituted heteroaryl containing 1-5 heteroatoms selected from the group consisting of N, S, P, and O.

Embodiment I-26. The compound of any one of Embodiments I-1 to I-25, wherein R$^a$ is —H.

Embodiment I-27. The compound of any one of Embodiments I-1 to I-25, wherein R$^a$ is —OH.

Embodiment I-28. The compound of any one of Embodiments I-1 to I-25, wherein R$^a$ is an optionally substituted-C$_3$-C$_8$cycloalkyl.

Embodiment I-29. The compound of any one of Embodiments I-1 to I-25, wherein R$^a$ is an optionally substituted-C$_1$-C$_6$alkyl.

Embodiment I-30. The compound of any one of Embodiments I-1 to I-29, wherein R$^b$ is —H.

Embodiment I-31. The compound of any one of Embodiments I-1 to I-29, wherein R$^b$ is an optionally substituted-C$_1$-C$_6$alkyl.

Embodiment I-32. The compound of any one of Embodiments I-1 to I-29, wherein R$^b$ is an optionally substituted —C$_3$-C$_8$cycloalkyl.

Embodiment I-33. The compound of any one of Embodiments I-1 to I-29, wherein R$^b$ is an optionally substituted-C$_2$-C$_6$alkenyl.

Embodiment I-34. The compound of any one of Embodiments I-1 to I-29, wherein R$^b$ is an optionally substituted heterocyclyl containing 1-5 heteroatoms selected from the group consisting of N, S, P, and O.

Embodiment I-35. The compound of any one of Embodiments I-1 to I-34, wherein R$^3$ is an optionally substituted-C$_1$-C$_6$alkyl.

Embodiment I-36. The compound of any one of Embodiments I-1 to I-34, wherein R$^3$ is an optionally substituted 3- to 12-membered monocyclic or polycyclic heterocycle.

Embodiment I-37. The compound of any one of Embodiments I-1 to I-34, wherein R$^3$ is an optionally substituted 3- to 12-membered monocyclic heterocycle.

Embodiment I-38. The compound of any one of Embodiments I-1 to I-34, wherein R$^3$ is an optionally substituted 5- to 12-membered polycyclic heterocycle.

Embodiment I-39. The compound of any one of Embodiments I-1 to I-25 or I-30 to I-34, wherein R$^3$ and R$^a$ together with the atom to which they are attached combine to form an optionally substituted 3- to 12-membered monocyclic heterocycle.

Embodiment I-40. The compound of any one of Embodiments I-1 to I-25 or I-30 to I-34, wherein $R^3$ and $R^a$ together with the atoms to which they are attached combine to form an optionally substituted 3- to 12-membered polycyclic heterocycle.

Embodiment I-41. The compound of any one of Embodiments I-1 to I-25 or I-30 to I-34, wherein $R^3$ and $R^a$ together with the atoms to which they are attached combine to form an optionally substituted 5- to 12-membered spiroheterocycle.

Embodiment I-42. The compound of any one of Embodiments I-1 to I-41, wherein $X^1$ is N and $X^2$ is N.

Embodiment I-43. The compound of any one of Embodiments I-1 to I-41, wherein $X^1$ is N and $X^2$ is CH.

Embodiment I-44. The compound of any one of Embodiments I-1 to I-41, wherein $X^1$ is C and $X^2$ is N.

Embodiment I-45. The compound of any one of Embodiments I-1 to I-41, wherein $X^1$ is C and $X^2$ is CH.

Embodiment I-46. The compound of any one of the preceding Embodiments, wherein B, including the atoms at the points of attachment, is a monocyclic 3- to 12-membered heteroaryl.

Embodiment I-47. The compound of any one of Embodiments I-1 to I-41, wherein B, including the atoms at the points of attachment, is

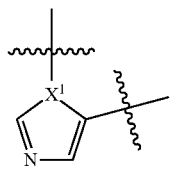

and $X^1$ is N, thereby forming

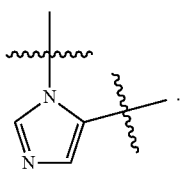 [SMILES: *c1cncn1*]

Embodiment I-48. The compound of any one of Embodiments I-1 to I-41, wherein B, including the atoms at the points of attachment, is

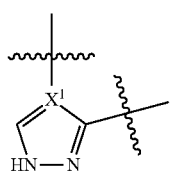

and $X^1$ is C, thereby forming

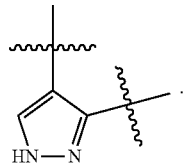

Embodiment I-49. The compound of any one of Embodiments I-1 to I-41, wherein B, including the atoms at the points of attachment, is

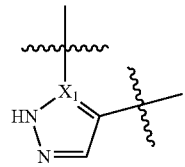

and $X^1$ is C, thereby forming

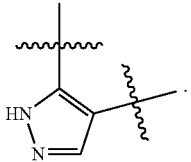

Embodiment I-50. A compound that is

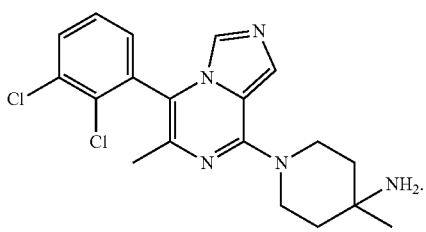 [SMILES: Cc1nc(N2CCC(C)(N)CC2)c2cncn2c1-c1cccc(Cl)c1Cl]

Embodiment I-51. A compound that is

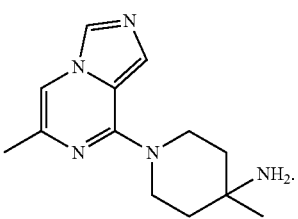 [SMILES: Cc1cn2cncc2c(N2CCC(C)(N)CC2)n1]

Embodiment I-52. A pharmaceutical composition comprising a compound of any one of Embodiments I-1 to I-51 and a pharmaceutically acceptable carrier.

Embodiment I-53. A method of treating a disease associated with SHP2 modulation in a subject in need thereof, comprising administering to the subject an effective amount of a compound of any one of Embodiments I-1 to I-51.

Embodiment I-54. The method of Embodiment I-53, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment I-55. A compound of any one of Embodiments I-1 to I-51 for use in treating or preventing a disease associated with SHP2 modulation.

Embodiment I-56. Use of a compound of any one of Embodiments I-1 to I-51 in the manufacture of a medicament for treating or preventing a disease associated with SHP2 modulation.

Some embodiments of this disclosure are Embodiment II, as follows:

Embodiment II-1. A compound of the Formula IV:

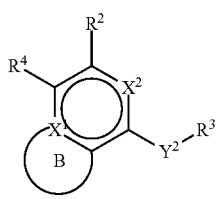

IV or a pharmaceutically acceptable salt, prodrug, solvate, hydrate, tautomer, or isomer thereof, wherein:

$R^4$ is H or

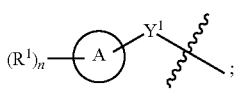

A is a 5- to 12-membered monocyclic or polycyclic cycloalkyl, heterocycloalkyl, aryl, or heteroaryl, provided that the heteroaryl is not

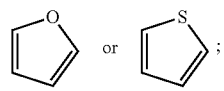 [SMILES: c1ccoc1 ; c1ccsc1]

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^5$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2$NH—, —C(=$CH_2$)—, —CH—, or —S(O)—;

$X^1$ is N or C;

$X^2$ is N or CH;

B, including the atoms at the points of attachment, is a monocyclic or polycyclic 5- to 12-membered heterocycle or a monocyclic or polycyclic 5- to 12-membered heteroaryl, wherein each heterocycle or heteroaryl is optionally substituted with one or more —$C_1$-$C_6$alkyl, —OH, —$NH_2$, oxo, heteroaryl, heterocyclyl, —$(CH_2)_n$$NH_2$, —$(CH_2)_n$OH, —$CF_3$, —$CHF_2$, or —$CH_2F$;

$R^2$ is —H, —OH, —$NR^5R^6$, —$C_1$-$C_6$alkyl, —$C_2$-$C_6$alkenyl, —$C_4$-$C_8$cycloalkenyl, —$C_2$-$C_6$alkynyl, —$NH_2$, halogen, —$C_3$-$C_8$cycloalkyl, or heterocyclyl containing 1-5 heteroatoms selected from the group consisting of N, S, P, and O; wherein each alkyl, alkenyl, cycloalkenyl, alkynyl, cycloalkyl, or heterocyclyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR'S(O)R^6$, heterocycle, aryl, or heteroaryl; and wherein the heterocyclyl is not attached via a nitrogen atom;

$Y^2$ is —$NR^a$—, —$(CR^a_2)_m$—, —C(O)—, —$C(R^a)_2$NH—, —$(CR^a_2)_m$O—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^3)O$—, —$N(R^a)C(S)$—, —$C(S)N(R^a)$—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_n$OH, —$C_1$-$C_6$alkyl, —$CF_3$, —$CHF_2$, or —$CH_2F$;

$R^3$ is —H, —$C_1$-$C_6$alkyl, a 3- to 12-membered monocyclic or polycyclic heterocycle, —$C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, oxo, heteroaryl, heterocyclyl, —$(CH_2)_n$$NH_2$, —$(CH_2)_n$OH, —$CF_3$, —$CHF_2$, or —$CH_2F$, provided that the heterocycle formed by the combination of $R^3$ and $R^a$ is not an optionally substituted piperazinyl;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment II-2. The compound of Embodiment II-1, wherein Y$^2$ is —NR$^a$—.

Embodiment II-3. The compound of Embodiment II-1, wherein Y$^2$ is —(CR$^a$$_2$)$_m$—.

Embodiment II-4. The compound of Embodiment II-1, wherein Y$^2$ is —C(O)—.

Embodiment II-5. The compound of Embodiment II-1, wherein Y$^2$ is —C(R$^a$)$_2$NH— or —(CR$^a$$_2$)$_m$O—.

Embodiment II-6. The compound of Embodiment II-1, wherein Y$^2$ is —C(O)N(R$^a$)—, —N(R$^a$)C(O)—, —S(O)$_2$N(R$^a$)—, —N(R$^a$)S(O)$_2$—, —N(R$^a$)C(S)—, or —C(S)N(R$^a$)—.

Embodiment II-7. The compound of Embodiment II-1, wherein Y$^2$ is —N(R$^a$)C(O)N(R$^a$)—, —N(R$^a$)C(S)N(R$^a$)—, —OC(O)N(R$^a$)—, —N(R$^a$)C(O)O—, or —C(O)N(R$^a$)O—.

Embodiment II-8. The compound of Embodiment II-1, wherein Y$^2$ is —C(O)O—, —OC(O)—, or —OC(O)O—.

Embodiment II-9. The compound of any one of Embodiments II-1 to II-8, wherein R$^a$ is —H.

Embodiment II-10. The compound of any one of Embodiments II-1 to II-8, wherein R$^a$ is —OH.

Embodiment II-11. The compound of any one of Embodiments II-1 to II-8, wherein R$^a$ is an optionally substituted-C$_3$-C$_8$cycloalkyl.

Embodiment II-12. The compound of any one of Embodiments II-1 to II-8, wherein R$^a$ is an optionally substituted-C$_1$-C$_6$alkyl.

Embodiment II-13. The compound of any one of Embodiments II-1 to II-12, wherein R$^b$ is —H.

Embodiment II-14. The compound of any one of Embodiments II-1 to II-12, wherein R$^b$ is an optionally substituted-C$_1$-C$_6$alkyl.

Embodiment II-15. The compound of any one of Embodiments II-1 to II-12, wherein R$^b$ is an optionally substituted-C$_3$-C$_8$cycloalkyl.

Embodiment II-16. The compound of any one of Embodiments II-1 to II-12, wherein R$^b$ is an optionally substituted-C$_2$-C$_6$alkenyl.

Embodiment II-17. The compound of any one of Embodiments II-1 to II-12, wherein R$^b$ is an optionally substituted heterocyclyl containing 1-5 heteroatoms selected from the group consisting of N, S, P, and O.

Embodiment II-18. The compound of any one of Embodiments II-1 to II-17, wherein R$^3$ is an optionally substituted-C$_1$-C$_6$alkyl.

Embodiment II-19. The compound of any one of Embodiments II-1 to II-17, wherein R$^3$ is an optionally substituted 3- to 12-membered monocyclic or polycyclic heterocycle.

Embodiment II-20. The compound of any one of Embodiments II-1 to II-17, wherein R$^3$ is an optionally substituted 3- to 12-membered monocyclic heterocycle.

Embodiment II-21. The compound of any one of Embodiments II-1 to II-17, wherein R$^3$ is an optionally substituted 5- to 12-membered polycyclic heterocycle.

Embodiment II-22. The compound of any one of Embodiments II-1 to II-8, wherein R$^3$ and R$^a$ together with the atom to which they are attached combine to form a 3- to 12-membered monocyclic heterocycle, wherein the heterocycle is optionally substituted with one or more —C$_1$-C$_6$alkyl, —OH, —NH$_2$, —(CH$_2$)$_n$NH$_2$, —(CH$_2$)$_n$OH, —CF$_3$, —CHF$_2$, or —CH$_2$F.

Embodiment II-23. The compound of any one of Embodiments II-1 to II-8, wherein R$^3$ and R$^a$ together with the atoms to which they are attached combine to form a 3- to 12-membered polycyclic heterocycle, wherein the heterocycle is optionally substituted with one or more —C$_1$-C$_6$alkyl, —OH, —NH$_2$, —(CH$_2$)$_n$NH$_2$, —(CH$_2$)$_n$OH, —CF$_3$, —CHF$_2$, or —CH$_2$F.

Embodiment II-24. The compound of any one of Embodiments II-1 to II-8, wherein R$^3$ and R$^a$ together with the atoms to which they are attached combine to form a 5- to 12-membered spiroheterocycle, wherein the spiroheterocycle is optionally substituted with one or more —C$_1$-C$_6$alkyl, —OH, —NH$_2$, —(CH$_2$)$_n$NH$_2$, —(CH$_2$)$_n$OH, —CF$_3$, —CHF$_2$, or —CH$_2$F.

Embodiment II-25. The compound of Embodiment II-22 or II-23, wherein the heterocycle is optionally substituted with one or more —C$_1$-C$_6$alkyl.

Embodiment II-26. The compound of any one of Embodiments II-22, II-23, or II-25, wherein the heterocycle is optionally substituted with one or more —(CH$_2$)$_n$NH$_2$, wherein n is 1.

Embodiment II-27. The compound of any one of Embodiments II-22, II-23, II-25, or II-26, wherein the heterocycle is optionally substituted with one or more —NH$_2$.

Embodiment II-28. The compound of Embodiment II-24, wherein the spiroheterocycle is optionally substituted with one or more —C$_1$-C$_6$alkyl.

Embodiment II-29. The compound of Embodiment II-24 or II-28, wherein the spiroheterocycle is optionally substituted with one or more —(CH$_2$)$_n$NH$_2$, wherein n is 1.

Embodiment II-30. The compound of any one of Embodiments II-24, II-28, or II-29, wherein the spiroheterocycle is optionally substituted with one or more —NH$_2$.

Embodiment II-31. The compound of Embodiment II-1, wherein the compound of Formula IV is a compound of Formula IV-Q:

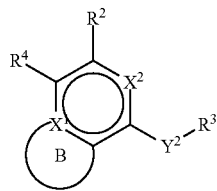

IV-Q or a pharmaceutically acceptable salt, prodrug, solvate, hydrate, tautomer, or isomer thereof, wherein:

R$^4$ is H or

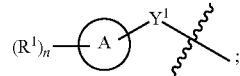

;

A is a 5- to 12-membered monocyclic or polycyclic aryl or heteroaryl, provided that the heteroaryl is not

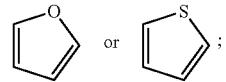 [SMILES: c1ccoc1 ; c1ccsc1]

;

R¹ is independently, at each occurrence, —H, —OR⁵, halogen, —C₁-C₆alkyl, —CN, or —NR⁵R⁶;

Y¹ is —S— or a direct bond;

X¹ is N or C;

X² is N or CH;

B, including the atoms at the points of attachment, is a monocyclic or polycyclic 5- to 12-membered heterocycle or a monocyclic or polycyclic 5- to 12-membered heteroaryl, wherein each heterocycle or heteroaryl is optionally substituted with one or more —C₁-C₆alkyl, —OH, —NH₂, oxo, —(CH₂)ₙNH₂, —(CH₂)ₙOH, —CF₃, —CHF₂, or —CH₂F;

R² is —H, —OH, —NR⁵R⁶, —C₁-C₆alkyl, or —NH₂; wherein each alkyl is optionally substituted with one or more —OH, halogen, —OR⁵, or —NR⁵R⁶;

Y² is —NRᵃ—, wherein the bond on the left side of Y², as drawn, is bound to the ring and the bond on the right side of the Y² moiety, as drawn, is bound to R³;

R³ is combined with Rᵃ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, —OH, —NH₂, —(CH₂)ₙNH₂, —(CH₂)ₙOH, —CF₃, —CHF₂, or —CH₂F, provided that the heterocycle formed by the combination of R³ and Rᵃ is not an optionally substituted piperazinyl;

R⁵ and R⁶ are independently, at each occurrence, —H or —C₁-C₆alkyl;

m is independently, at each occurrence, 1, 2, 3, 4, 5 or 6; and n is independently, at each occurrence, 0, 1, 2, 3, 4, 5, 6, 7, 8, 9, or 10.

Embodiment II-32. The compound of Embodiment II-31, wherein R³ and Rᵃ together with the atom to which they are attached combine to form a 3- to 12-membered monocyclic heterocycle, wherein the heterocycle is optionally substituted with one or more —C₁-C₆alkyl, —OH, —NH₂, —(CH₂)ₙNH₂, —(CH₂)ₙOH, —CF₃, —CHF₂, or —CH₂.

Embodiment II-33. The compound of Embodiment II-31, wherein R³ and Rᵃ together with the atoms to which they are attached combine to form a 3- to 12-membered polycyclic heterocycle, wherein the heterocycle is optionally substituted with one or more —C₁-C₆alkyl, —OH, —NH₂, —(CH₂)ₙNH₂, —(CH₂)ₙOH, —CF₃, —CHF₂, or —CH₂F.

Embodiment II-34. The compound of Embodiment II-31, wherein R³ and Rᵃ together with the atoms to which they are attached combine to form a 5- to 12-membered spiroheterocycle, wherein the spiroheterocycle is optionally substituted with one or more —C₁-C₆alkyl, —OH, —NH₂, —(CH₂)ₙNH₂, —(CH₂)ₙOH, —CF₃, —CHF₂, or —CH₂F.

Embodiment II-35. The compound of Embodiment II-32 or II-33, wherein the heterocycle is optionally substituted with one or more —C₁-C₆alkyl.

Embodiment II-36. The compound of any one of Embodiments II-32, II-33, or II-35, wherein the heterocycle is optionally substituted with one or more —(CH₂)ₙNH₂, wherein n is 1.

Embodiment II-37. The compound of any one of Embodiments II-32, II-33, II-35, or II-36, wherein the heterocycle is optionally substituted with one or more —NH₂.

Embodiment II-38. The compound of Embodiment II-34, wherein the spiroheterocycle is optionally substituted with one or more —C₁-C₆alkyl.

Embodiment II-39. The compound of Embodiment II-34 or II-38, wherein the spiroheterocycle is optionally substituted with one or more —(CH₂)ₙNH₂, wherein n is 1.

Embodiment II-40. The compound of any one of Embodiments II-34, II-38, or II-39, wherein the spiroheterocycle is optionally substituted with one or more —NH₂.

Embodiment II-41. The compound any one of Embodiments II-1 to II-40, wherein R⁴ is

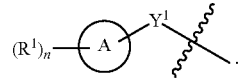

Embodiment II-42. The compound of any one of Embodiments II-1 to II-41, wherein A is monocyclic or polycyclic aryl.

Embodiment II-43. The compound of Embodiment II-42, wherein A is phenyl.

Embodiment II-44. The compound of any one of Embodiments II-1 to II-41, wherein A is monocyclic or polycyclic heteroaryl.

Embodiment II-45. The compound of Embodiment II-44, wherein A is pyridinyl.

Embodiment II-46. The compound of any one of Embodiments II-1 to II-45, wherein Y¹ is —S—.

Embodiment II-47. The compound of any one of Embodiments II-1 to II-45, wherein Y¹ is a direct bond.

Embodiment II-48. The compound of any one of Embodiments II-1 to II-47, wherein R¹ is independently, at each occurrence, —H, —OR⁵ or halogen.

Embodiment II-49. The compound of any one of Embodiments II-1 to II-47, wherein R¹ is independently, at each occurrence, —H, —OR⁵ or —NR⁵R⁶.

Embodiment II-50. The compound of any one of Embodiments II-1 to II-47, wherein R¹ is independently, at each occurrence, —H, halogen or —NR⁵R⁶.

Embodiment II-51. The compound of any one of Embodiments II-1 to II-47, wherein R¹ is independently, at each occurrence, —H or —OR⁵.

Embodiment II-52. The compound of Embodiment II-48 or II-51, wherein R⁵ is —H or —C₁-C₆alkyl.

Embodiment II-53. The compound of any one of Embodiments II-1 to II-47, wherein R¹ is independently, at each occurrence, —H or halogen.

Embodiment II-54. The compound of any one of Embodiments II-1 to II-47, wherein R¹ is independently, at each occurrence, —H or —NR⁵R⁶.

Embodiment II-55. The compound of any one of Embodiments II-1 to II-47, wherein R¹ is independently, at each occurrence, —H, methyl, fluoro, chloro, or —NH₂.

Embodiment II-56. The compound of any one of Embodiments II-49, II-50, or II-54, wherein R⁵ and R⁶ are independently, at each occurrence, —H or —C₁-C₆alkyl.

Embodiment II-57. The compound of Embodiment II-56, wherein R⁵ and R⁶ are independently, at each occurrence, —H.

Embodiment II-58. The compound of Embodiment II-56, wherein R⁵ and R⁶ are independently, at each occurrence, —C₁-C₆alkyl.

Embodiment II-59. The compound any one of Embodiments II-1 to II-40, wherein R⁴ is —H.

Embodiment II-60. The compound of any one of Embodiments II-1 to II-59, wherein R² is —OH.

Embodiment II-61. The compound of any one of Embodiments II-1 to II-59, wherein R² is —C₁-C₆alkyl, wherein the alkyl is optionally substituted with one or more-OH, halogen, —OR⁵, or —NR⁵R⁶.

Embodiment II-62. The compound of any one of Embodiments II-1 to II-59, wherein $R^2$ is methyl.

Embodiment II-63. The compound of any one of Embodiments II-1 to II-59, wherein $R^2$ is —$NR^5R^6$.

Embodiment II-64. The compound of Embodiment II-63, wherein $R^5$ and $R^6$ are independently, at each occurrence, —H.

Embodiment II-65. The compound of Embodiment II-63, wherein $R^5$ and $R^6$ are independently, at each occurrence, —$C_1$-$C_6$alkyl.

Embodiment II-66. The compound of any one of Embodiments II-1 to II-59, wherein $R^2$ is —H.

Embodiment II-67. The compound of any one of Embodiments II-1 to II-59, wherein $R^2$ is —$NH_2$.

Embodiment II-68. The compound of any one of Embodiments II-1 to II-67, wherein $X^1$ is N and $X^2$ is N.

Embodiment II-69. The compound of any one of Embodiments II-1 to II-67, wherein $X^1$ is N and $X^2$ is CH.

Embodiment II-70. The compound of any one of Embodiments II-1 to II-67, wherein $X^1$ is C and $X^2$ is N.

Embodiment II-71. The compound of any one of Embodiments II-1 to II-67, wherein $X^1$ is C and $X^2$ is CH.

Embodiment II-72. The compound of any one of Embodiments II-1 to II-71, wherein B, including the atoms at the points of attachment, is a monocyclic 5- to 12-membered heterocycle, wherein each heterocycle is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$.

Embodiment II-73. The compound of any one of Embodiments II-1 to II-71, wherein B, including the atoms at the points of attachment, is a polycyclic 5- to 12-membered heterocycle, wherein each heterocycle is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$.

Embodiment II-74. The compound of Embodiment II-72 or II-73, wherein the B heterocycle is substituted with one or more oxo.

Embodiment II-75. The compound of any one of Embodiments II-1 to II-71, wherein B, including the atoms at the points of attachment, is a monocyclic 5- to 12-membered heteroaryl, wherein each heteroaryl is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$.

Embodiment II-76. The compound of any one of Embodiments II-1 to II-71, wherein B, including the atoms at the points of attachment, is a polycyclic 5- to 12-membered heteroaryl, wherein each heteroaryl is optionally substituted with one or more —$C_1$-$C_6$alkyl, —OH, —$NH_2$, oxo, —$(CH_2)_nNH_2$, —$(CH_2)_nOH$, —$CF_3$, —$CHF_2$, or —$CH_2F$.

Embodiment II-77. The compound of Embodiment II-75 or II-76, wherein the B heteroaryl is substituted with one or more —$C_1$-$C_6$alkyl.

Embodiment II-78. The compound of any one of Embodiments II-75 to II-77, wherein the B heteroaryl is substituted with one or more —OH.

Embodiment II-79. The compound of any one of Embodiments II-75 to II-78, wherein the B heteroaryl is substituted with one or more —$NH_2$.

Embodiment II-80. The compound of any one of Embodiments II-75 to II-79, wherein the B heteroaryl is substituted with one or more —$(CH_2)_nNH_2$.

Embodiment II-81. The compound of any one of Embodiments II-75 to II-80, wherein the B heteroaryl is substituted with one or more —$(CH_2)_nOH$.

Embodiment II-82. The compound of Embodiment II-80 or II-81, wherein n is 1.

Embodiment II-83. The compound of any one of Embodiments II-75 to II-82, wherein the B heteroaryl is substituted with one or more —$CF_3$.

Embodiment II-84. The compound of any one of Embodiments II-75 to II-83, wherein the B heteroaryl is substituted with one or more —$CHF_2$.

Embodiment II-85. The compound of any one of Embodiments II-75 to II-84, wherein the B heteroaryl is substituted with one or more —$CH_2F$.

Embodiment II-86. A compound selected from the group consisting of:

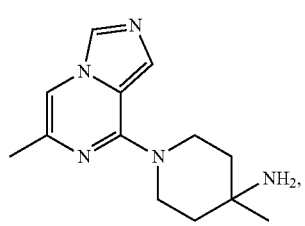

1

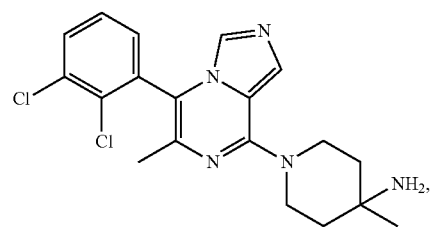

2

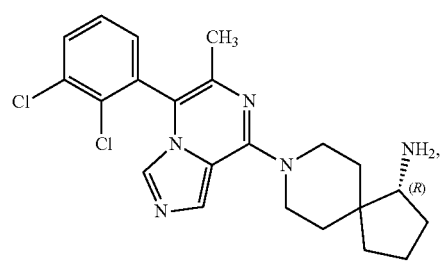

3

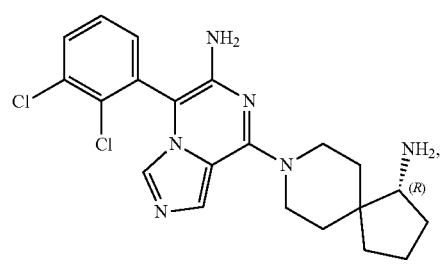

4

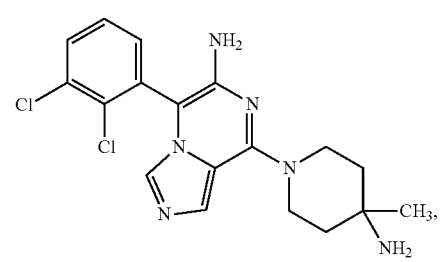

5

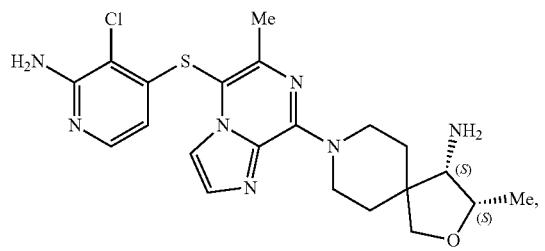
6
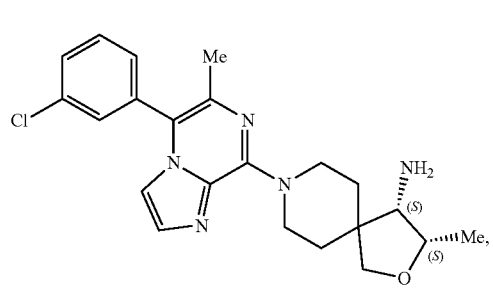
7
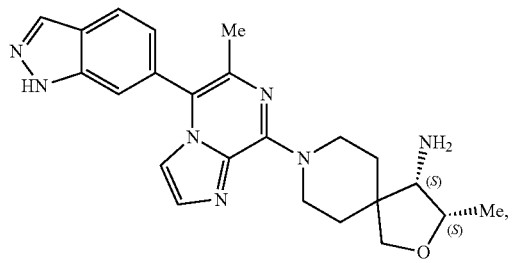
8
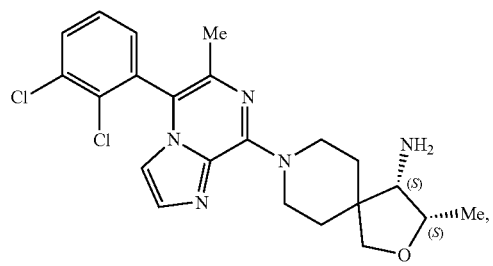
9
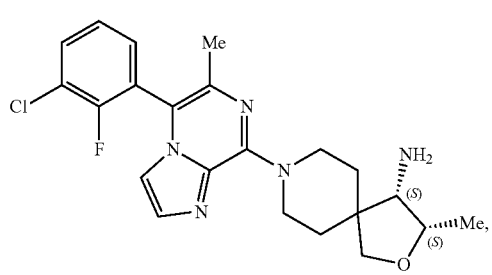
10
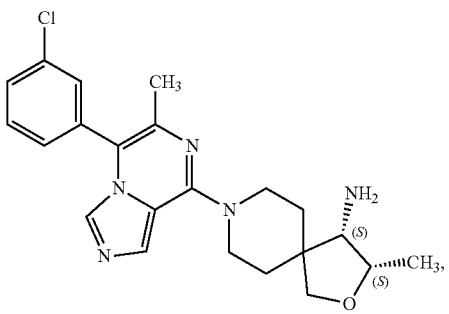
11
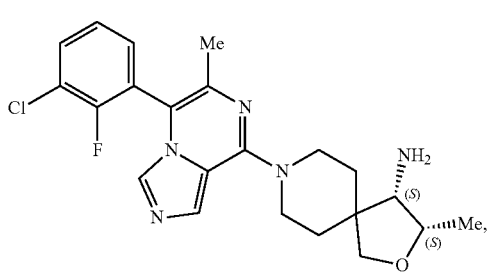
12
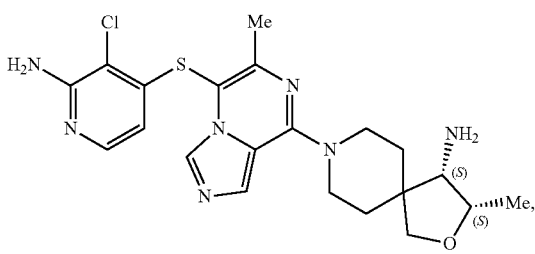
13
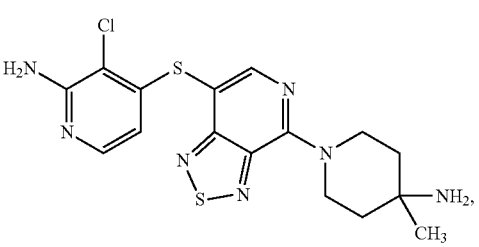
14
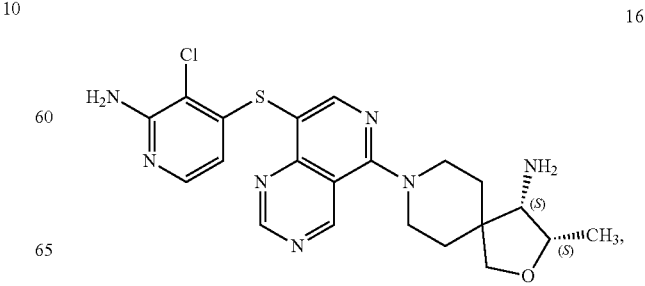
15

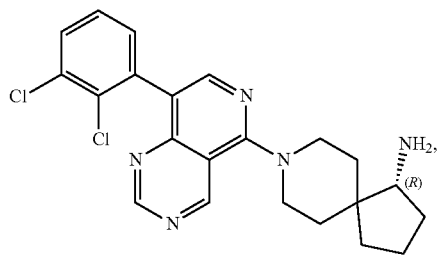
17
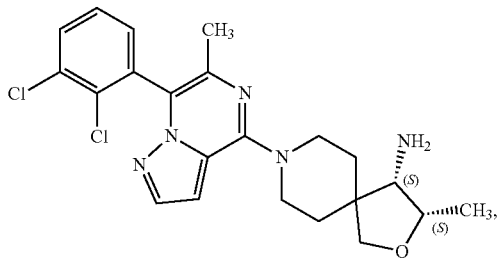
22
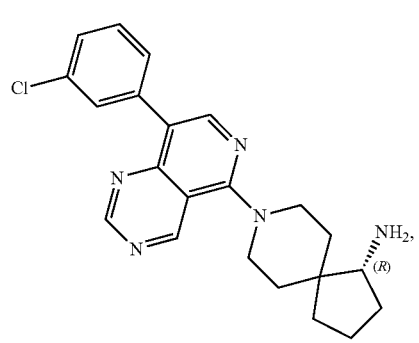
18
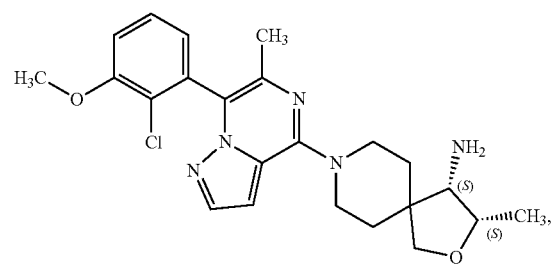
23
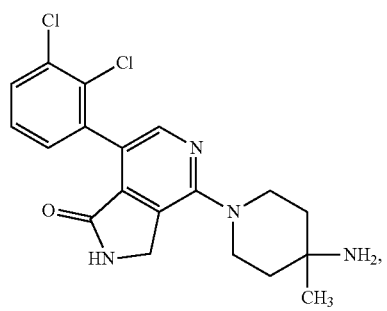
19
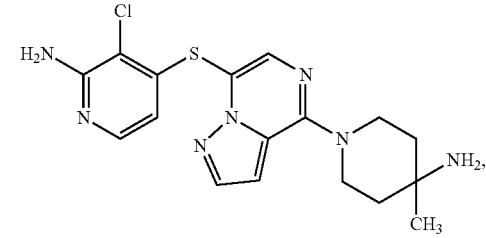
24
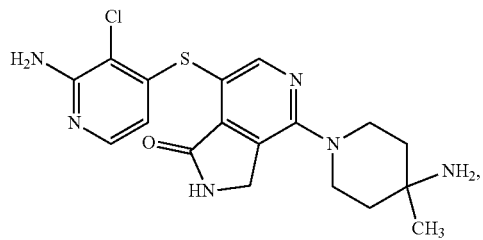
20
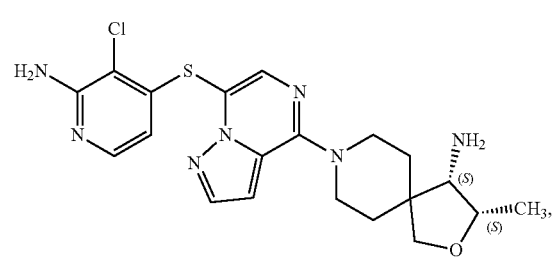
25
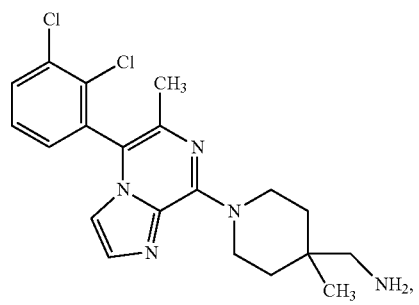
21
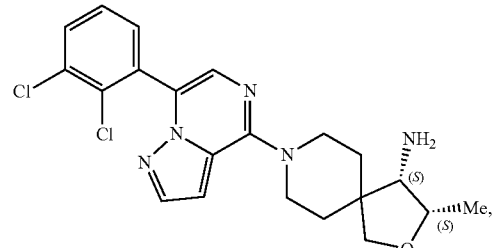
26
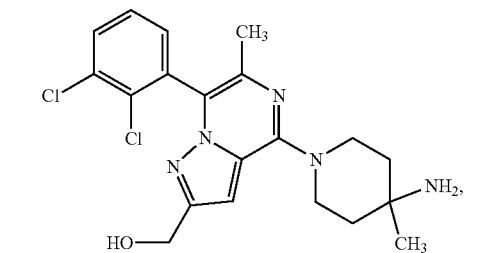
27

28
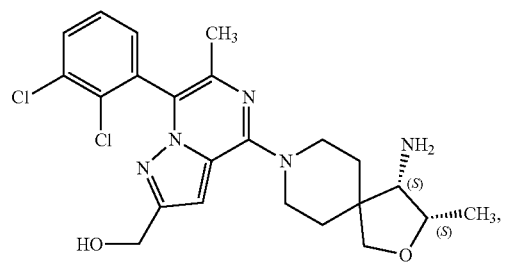
29
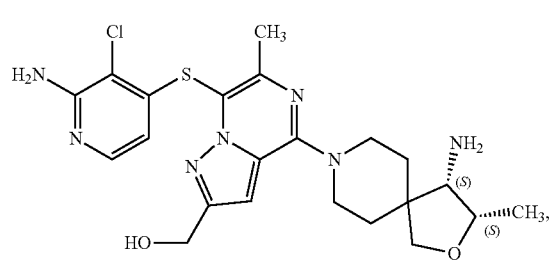
30
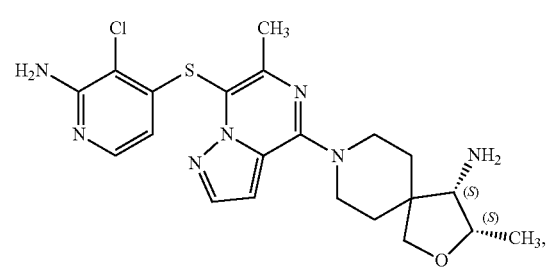
31
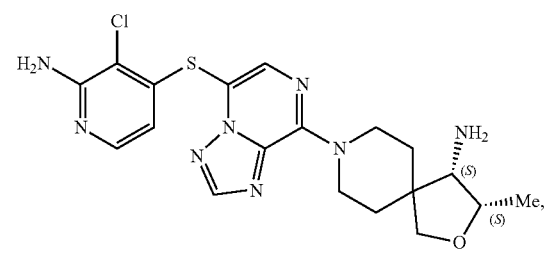
32
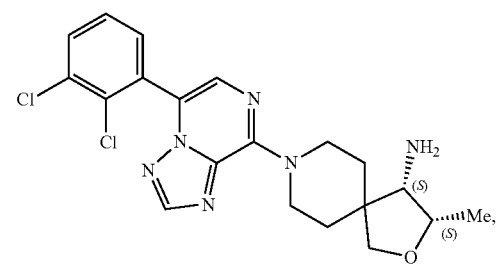
33
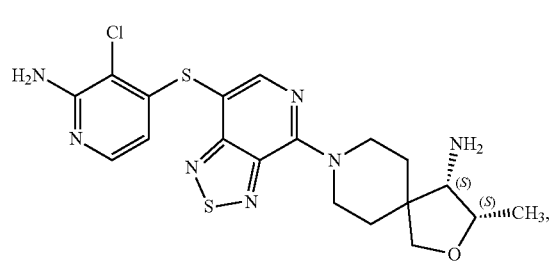
34
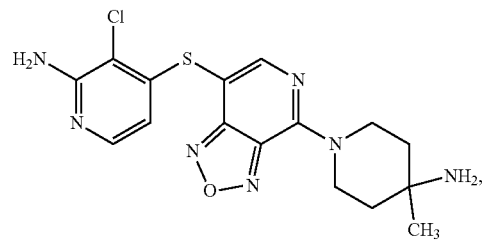
35
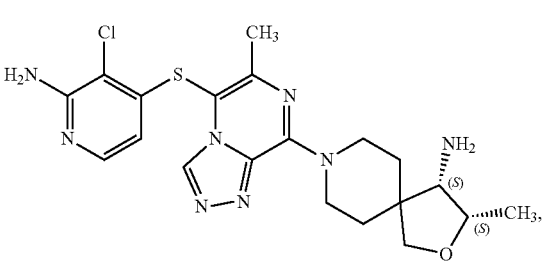
36
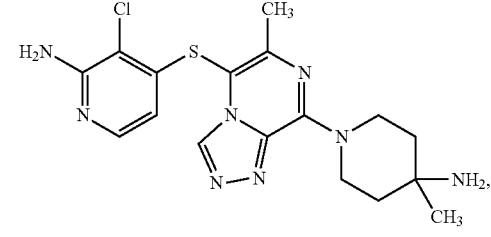
37
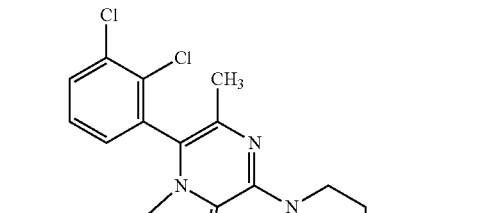
38
39
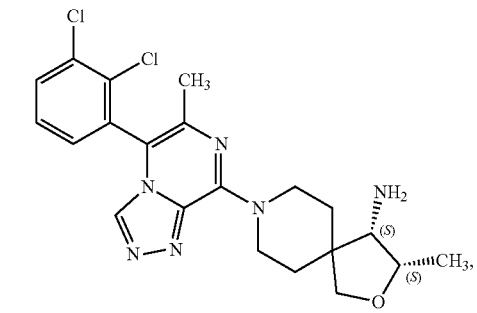

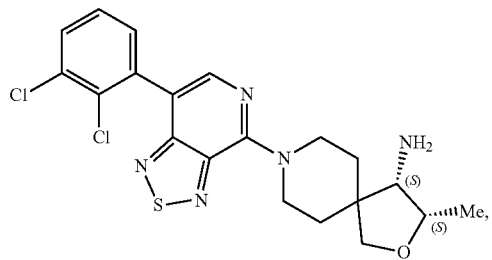
40
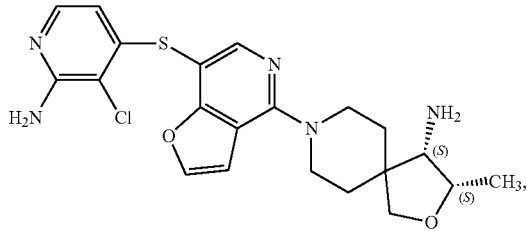
46
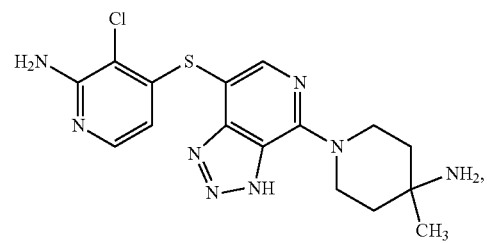
41
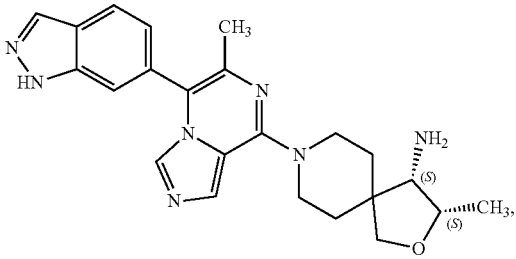
47
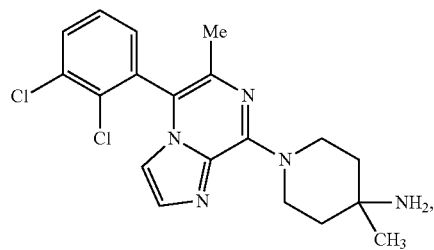
42
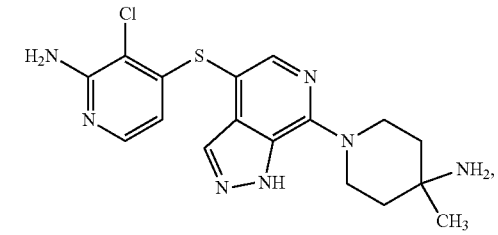
48
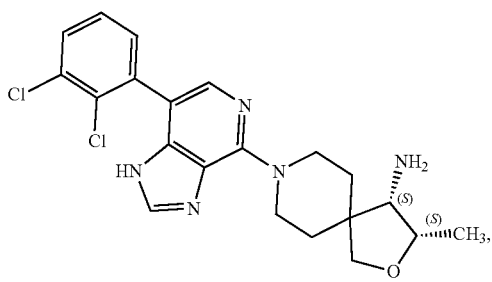
43
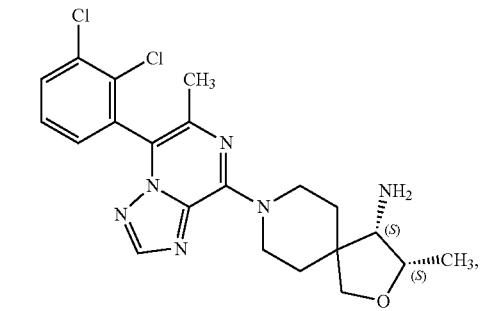
49
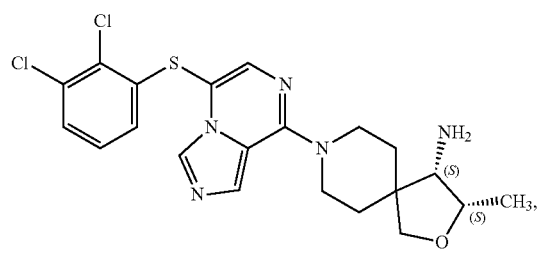
44
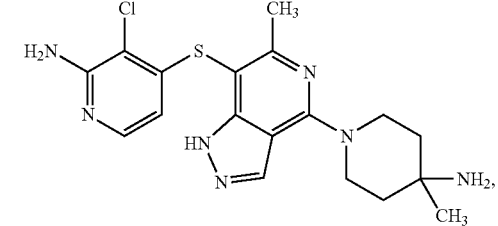
50
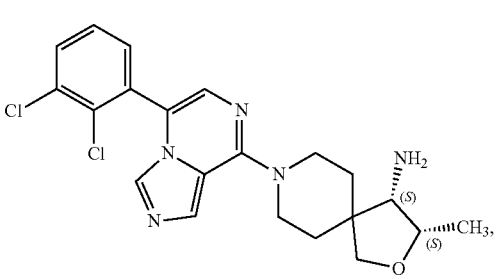
45
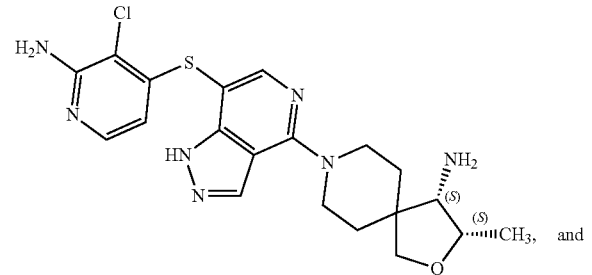
51

155

-continued

52

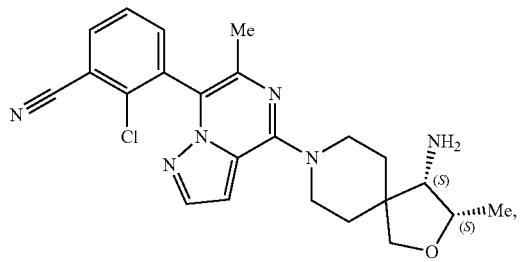

or a pharmaceutically acceptable salt, prodrug, solvate, hydrate, tautomer, or isomer of any of the foregoing.

Embodiment II-87. A pharmaceutical composition comprising a compound of any one of Embodiments II-1 to II-86, or a pharmaceutically acceptable salt, prodrug, solvate, hydrate, tautomer, or isomer thereof, and a pharmaceutically acceptable carrier.

Embodiment II-88. A method of treating a disease associated with SHP2 modulation in a subject in need thereof, comprising administering to the subject an effective amount of a compound of any one of Embodiments II-1 to II-86, or a pharmaceutically acceptable salt, prodrug, solvate, hydrate, tautomer, or isomer thereof.

Embodiment II-89. The method of Embodiment II-88, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment II-90. A compound of any one of Embodiments II-1 to II-86, or a pharmaceutically acceptable salt, prodrug, solvate, hydrate, tautomer, or isomer thereof, for use as a medicament.

Embodiment II-91. A compound of any one of Embodiments II-1 to II-86, or a pharmaceutically acceptable salt, prodrug, solvate, hydrate, tautomer, or isomer thereof, for use in treating or preventing a disease associated with SHP2 modulation.

Embodiment II-92. Use of a compound of any one of Embodiments II-1 to II-86, or a pharmaceutically acceptable salt, prodrug, solvate, hydrate, tautomer, or isomer thereof, in the manufacture of a medicament for treating or preventing a disease associated with SHP2 modulation.

Embodiment II-93. A method of treating a disease associated with SHP2 modulation in a subject in need thereof, comprising administering to the subject an effective amount of a pharmaceutical composition of Embodiment II-87.

Embodiment II-94. The method of Embodiment II-93, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment II-95. A pharmaceutical composition of Embodiment II-87 for use as a medicament.

Embodiment II-96. A pharmaceutical composition of Embodiment II-87 for use in treating or preventing a disease associated with SHP2 modulation.

Embodiment II-97. Use of a pharmaceutical composition of Embodiment II-87 in the manufacture of a medicament for treating or preventing a disease associated with SHP2 modulation.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Definitions used in the following examples and elsewhere herein are:

$CH_2Cl_2$, DCM Methylene chloride, Dichloromethane
$CH_3CN$, MeCN Acetonitrile
CuI Copper (I) iodide
DIPEA Diisopropylethyl amine
DMF N,N-Dimethylformamide
EtOAc Ethyl acetate
hr or h hour
$H_2O$ Water
HCl Hydrochloric acid
$K_3PO_4$ Potassium phosphate (tribasic)
MeOH Methanol
min minute
$Na_2SO_4$ Sodium sulfate
NBS N-bromosuccinimide
NMP N-methyl pyrrolidone
Pd(dppf)$Cl_2$ [1,1'-Bis(diphenylphosphino) ferrocene]dichloropalladium (II)
$POCl_3$ Phosphorous oxychloride Example 1

Synthesis of 4-methyl-1-(6-methylimidazo[1,5-a]pyrazin-8-yl) piperidin-4-amine

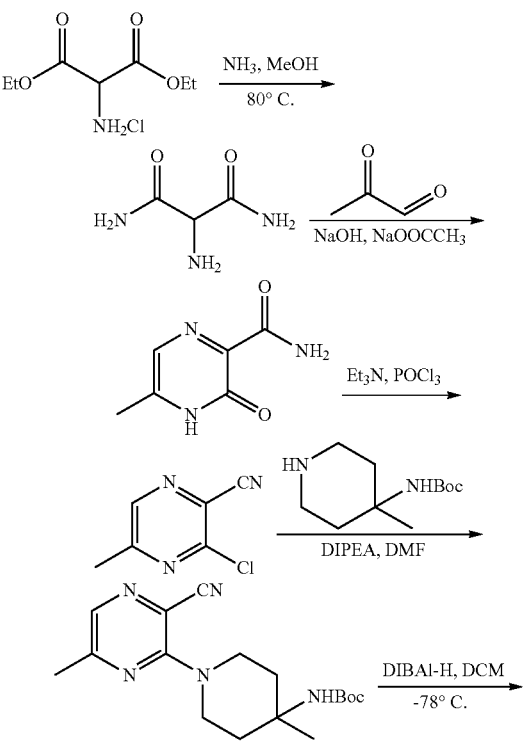

-continued

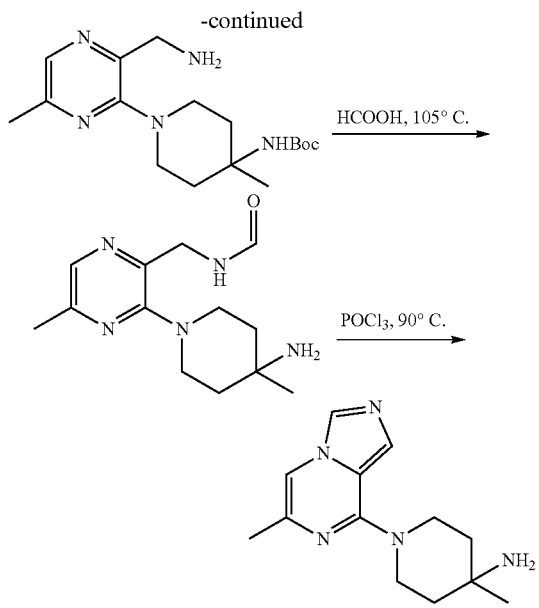

Step 1.
To a solution of diethylaminomalonate hydrochloride (25 g, 0.12 mol) in water (20 mL) was added solid sodium hydrogen carbonate until pH>7. After extraction with ethyl acetate, the organic phase was separated and evaporated under reduced pressure. The residue was taken into a methanolic ammonia solution (6M, 300 mL) and the reaction mixture was heated in a high pressure reactor at 80° C. overnight. The resulting mixture was concentrated under reduced pressure, the residue was washed successively with methanol and diethyl ether to afford aminomalonamide (10 g, 73%). $^1$H NMR (400 MHZ, DMSO-d6) δ 7.41 (s, 3H), 7.25 (s, 3H), 3.76 (s, 1H).
Step 2.
Sodium bisulfite (24 g, 0.23 mol) was added to 25 mL of 40% methylglyoxal solution followed by gradual addition of 86 mL of water containing sodium hydroxide (0.86 g, 0.021 mol). The solution was heated to 80° C. for 1 hr, aminomalonamide (18 g, 0.15 mol) was added and the temperature of the solution maintained at 80° C. for 2 more hrs with stirring. Sodium acetate (32.78 g, 0.4 mol) was added, the solution cooled to 20° C. and 25 mL of 30% hydrogen peroxide added gradually with stirring at 60-65° C. After cooling to room temperature, the product was removed, washed with cold water to give 5-methyl-3-oxo-3,4-dihydropyrazine-2-carboxamide (8.5 g, 36%) which was used in the next step without further purification. $^1$H NMR (400 MHZ, DMSO-d6) δ 13.21 (s, 1H), 8.75 (s, 1H), 8.03 (s, 1H), 7.83 (s, 1H), 2.37 (s, 3H).
Step 3.
5-Methyl-3-oxo-3,4-dihydropyrazine-2-carboxamide (2.0 g, 0.013 mol), was suspended in Et$_3$N (3.63 mL, 0.026 mol), cooled to 0° C. and reacted with 36.5 mL POCl$_3$. The mixture was heated to reflux for 2 hr and concentrated under reduced pressure. The resulting black oil was extracted with ether (5×50 mL), and the combined extracts were treated with 10% Na$_2$CO$_3$ (150 mL). The organic layers were separated, washed with water and brine, dried (Na$_2$SO$_4$), and concentrated under reduced pressure. The crude product was purified by flash column chromatography to afford 3-chloro-5-methylpyrazine-2-carbonitrile (1.5 g, 75%) as a fluffy solid. $^1$H NMR (400 MHZ, DMSO-d6) δ 8.77 (s, 1H), 2.63 (s, 3H).

Step 4.
3-Chloro-5-methylpyrazine-2-carbonitrile (1.1 g, 0.007 mol) was dissolved in anhydrous DMF (11 mL) and DIPEA (3.74 mL, 0.021 mol) was added. After stirring for 30 min at room temperature tert-butyl (4-methylpiperidin-4-yl) carbamate (1.84 g, 0.008 mol) was added in one portion. The reaction mixture was stirred overnight at room temperature, then diluted with EtOAc and extracted with 2% NaCl (aq.). The organic layer was dried over Na$_2$SO$_4$ and concentrated under reduced pressure. The desired product was purified via column chromatography (DCM/acetone 97:3) to yield tert-butyl N-[1-(3-cyano-6-methylpyrazin-2-yl)-4-methylpiperidin-4-yl]carbamate as a pale yellow solid (2.14 g, 90%). $^1$H NMR (400 MHZ, DMSO-d6) δ 7.97 (s, 1H), 6.67 (bs, 1H), 3.96 (dt, J=13.7, 4.3 Hz, 2H), 3.39 (dd, J=13.4, 10.3 Hz, 2H), 2.42 (s, 3H), 2.15 (d, J=13.4 Hz, 2H), 1.51 (ddd, J=14.1, 10.6, 3.9 Hz, 2H), 1.40 (s, 9H), 1.27 (s, 3H).
Step 5.
tert-Butyl N-[1-(3-cyano-6-methylpyrazin-2-yl)-4-methylpiperidin-4-yl]carbamate (1 g, 0.003 mol) was dissolved in anhydrous DCM (20 mL) and cooled to −78° C. and DIBAL-H 1 M in hexanes (9 mL, 0.009 mol) was added in small portions. After 1 hr, the reaction mixture was allowed to warm to room temperature and saturated solution of NH$_4$Cl (4 mL) and saturated solution of sodium potassium tartrate (30 mL) were added. This solution was stirred until organic and water layers separated. The water layer was removed and the organic layer was dried over Na$_2$SO$_4$ and concentrated under reduced pressure to give crude tert-butyl N-{1-[3-(aminomethyl)-6-methylpyrazin-2-yl]-4-methylpiperidin-4-yl}carbamate (1 g, 100%) which was used in next step without further purification. $^1$H NMR (400 MHZ, DMSO-d6) δ 8.01 (s, 1H), 6.53 (s, 2H), 3.72 (s, 2H), 3.19-3.08 (m, 3H), 3.04-2.95 (m, 2H), 2.35 (s, 3H), 2.18-2.10 (m, 2H), 1.60-1.50 (m, 2H), 1.39 (s, 9H), 1.27 (s, 3H).
Step 6.
tert-Butyl N-{1-[3-(aminomethyl)-6-methylpyrazin-2-yl]-4-methylpiperidin-4-yl}carbamate (0.88 g, 0.002 mol) was dissolved in formic acid (17.6 mL) and stirred at 105° C. for 2 hrs. Formic acid was removed under reduced pressure and obtained red oil was portioned between water and DCM. The organic layer was removed and the aqueous phase was basified with NaHCO$_3$ (aq.) to pH 11 then extracted with mixture of isopropyl alcohol and chloroform 1:3 (4×50 mL). The organic layers were combined, dried over MgSO$_4$ and concentrated under reduced pressure. The desired product was purified via column chromatography (MeOH with NH$_3$ 3M/DCM from 0:100 to 3:97) to give 4-methyl-1-{6-methylimidazo[1,5-a]pyrazin-8-yl}piperidin-4-amine as a yellow oil (0.224 g, 25%). $^1$H NMR (400 MHZ, DMSO-d6) δ 8.38 (s, 1H), 8.10 (s, 1H), 8.01 (s, 1H), 4.37 (d, J=5.5 Hz, 2H), 3.19 (ddd, J=12.7, 9.0, 3.5 Hz, 2H), 3.13-3.04 (m, 3H), 2.36 (s, 3H), 1.57 (ddd, J=12.9, 9.1, 3.8 Hz, 2H), 1.52-1.42 (m, 2H), 1.24 (s, 1H), 1.10 (s, 3H).
Step 7.
4-Methyl-1-{6-methylimidazo[1,5-a]pyrazin-8-yl}piperidin-4-amine (0.2 g, 0.55 mmol) was suspended in POCl$_3$ (10 mL) and stirred at 90° C. for 2 hr. POCl$_3$ was removed under reduced pressure and the obtained solid was portioned between water and DCM. The layers were separated, the aqueous layer was washed with NaHCO$_3$ (aq.), and extracted with mixture of isopropyl alcohol and chloroform 1:3. The organic layers were combined, dried over Na$_2$SO$_4$ and concentrated under reduced pressure. Purification by reparative TLC chromatography (1000 microns) (MeOH with NH$_3$ 3M/DCM 8:92; developed×2) resulted in 4-methyl-1-(6-methylimidazo[1,5-a]pyrazin-8-yl) piperidin-4-amine as yellow oil (16.6 mg, 9%). ¹H NMR (400 MHZ, DMSO-d6) δ 8.26 (s, 1H), 7.70 (s, 1H), 7.50 (t, J=1.1 Hz, 1H), 3.98-3.87 (m, 2H), 3.75-3.63 (m, 2H), 2.12 (d, J=1.1 Hz, 3H), 1.54-1.41 (m, 4H), 1.09 (s, 3H); LC-MS (ESI) m/z: [M+H] calculated for $C_{13}H_{20}N_5$: 246.2; found 246.3.

Example 2. Synthesis of 1-(5-(2,3-dichlorophenyl)-6-methylimidazo[1,5-a]pyrazin-8-yl)-4-methylpiperidin-4-amine

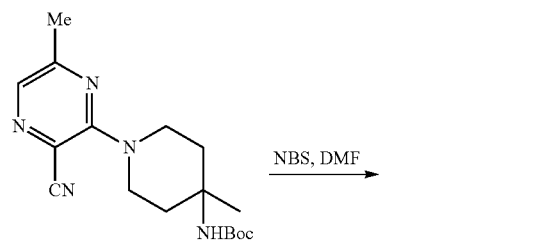

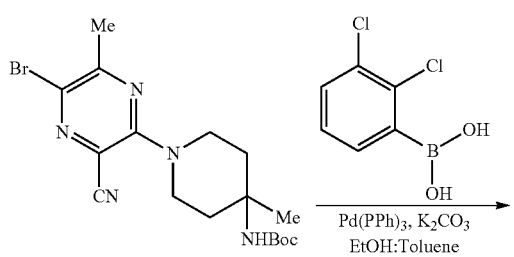

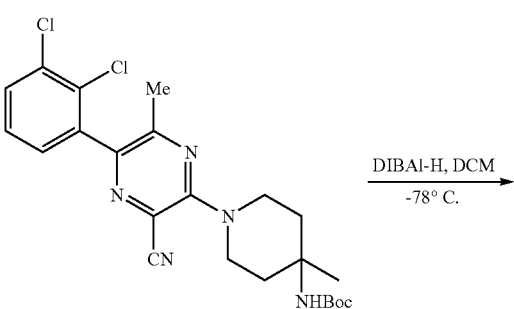

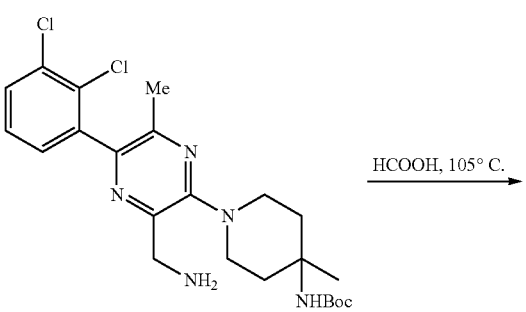

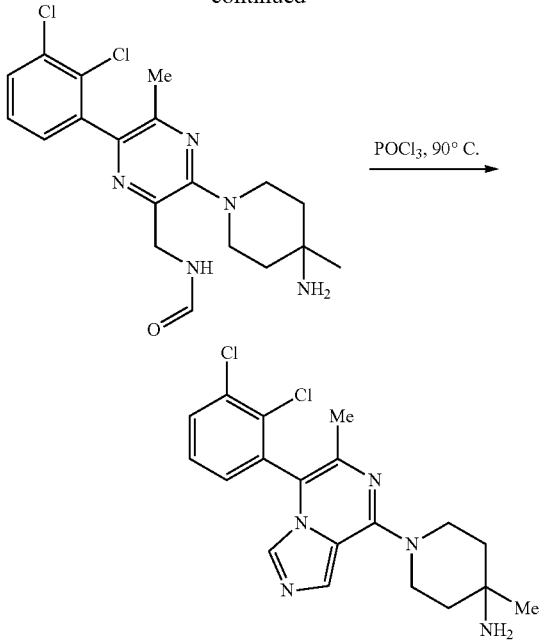

Step 1.

tert-Butyl N-[1-(3-cyano-6-methylpyrazin-2-yl)-4-methylpiperidin-4-yl]carbamate (1 g, 0.003 mol) was dissolved in anhydrous DMF (15 mL) and the reaction flask was protected from light with aluminum foil. The reaction mixture was cooled to 0° C. and NBS was added (0.8 g, 0.004 mol). The reaction mixture was stirred at room temperature for 72 hrs and then washed with water and EtOAc. The organic phase was extracted with 10% NaCl (aq.) (3×100 mL). The combined organic layers were dried over MgSO₄ and concentrated under reduced pressure to give tert-butyl N-[1-(5-bromo-3-cyano-6-methylpyrazin-2-yl)-4-methylpiperidin-4-yl]carbamate as a pale yellow solid (1 g, 81%). ¹H NMR (400 MHZ, DMSO-d6) δ 6.69 (s, 1H), 4.00 (dt, J=14.1, 4.2 Hz, 2H), 3.46-3.35 (m, 2H), 2.15 (d, J=13.5 Hz, 2H), 1.50 (ddd, J=14.0, 10.7, 3.9 Hz, 2H), 1.40 (s, 9H), 1.26 (s, 3H). UPLC [M+1]=409.9.

Step 2.

tert-Butyl N-[1-(5-bromo-3-cyano-6-methylpyrazin-2-yl)-4-methylpiperidin-4-yl]carbamate (0.2 g, 49 mmol) was suspended in EtOH (6.6 mL) and toluene (5 mL) and the received solution was degassed with argon for 15 min. Then K₂CO₃ (0.34 g, 0.002 mol) followed by 2,3-dichlorophenylboronic acid (0.1 g, 53 mmol) was added. The reaction mixture was degassed for another 15 min and tetrakis(triphenylphosphine) palladium (0) was added (0.03 g, 2 mmol). The reaction mixture was stirred at 80° C. overnight. The solvent was concentrated under reduced pressure and the resulting solid was portioned between water and DCM. The aqueous layer was extracted with DCM (2×100 mL). Purification with column chromatography (hexane/ethyl acetate 4:1) resulted in tert-butyl N-{1-[3-cyano-5-(2,3-dichlorophenyl)-6-methylpyrazin-2-yl]-4-methylpiperidin-4-yl}carbamate as a pale yellow solid (0.35 g, 10%). ¹H NMR (400 MHZ, DMSO-d6) δ 7.78 (dd, J=7.9, 1.8 Hz, 1H), 7.51 (t, J=7.7 Hz, 1H), 7.46 (dd, J=7.6, 1.8 Hz, 1H), 6.71 (s, 1H), 4.14-4.05 (m, 2H), 3.48 (t, J=11.9 Hz, 2H), 2.24 (s, 3H), 2.20 (d, J=14.0 Hz, 2H), 1.61-1.50 (m, 2H), 1.41 (s, 3H), 1.29 (s, 3H); UPLC [M+1]=475.55.

Step 3.

tert-Butyl N-{1-[3-cyano-5-(2,3-dichlorophenyl)-6-methylpyrazin-2-yl]-4-methylpiperidin-4-yl}carbamate (0.04 g, 8.4 mmol) was dissolved in anhydrous DCM (2 mL) under Ar, cooled to −78° C. and DIBAL-H 1 M in hexanes (0.3 mL, 25.1 mmol) was added in small portions. After 1 hr, the reaction mixture was allowed to warm to room temperature and saturated solution of NH$_4$Cl (1 mL) and saturated solution of sodium potassium tartare (7 mL) was added. The resulting solution was stirred until organic and water layers separated. The layers were separated and the organic layer was dried over Na$_2$SO$_4$ and concentrated under reduced pressure to give crude tert-butyl N-{1-[3-(aminomethyl)-5-(2,3-dichlorophenyl)-6-methylpyrazin-2-yl]-4-methylpiperidin-4-yl}carbamate (0.03 g, 75%) which was used in next step without further purification. $^1$H NMR (400 MHZ, DMSO-d6) δ 7.73 (dd, J=7.9, 1.7 Hz, 1H), 7.48 (t, J=7.8 Hz, 1H), 7.43 (dd, J=7.7, 1.8 Hz, 1H), 6.57 (s, 1H), 3.77 (s, 2H), 3.27 (m, 3H), 3.19-3.05 (m, 2H), 2.19 (d, J=1.9 Hz, 2H), 2.17-2.12 (m, 2H), 1.65-1.53 (m, 3H), 1.40 (s, 9H), 1.29 (d, J=3.9 Hz, 3H); UPLC [M+1]=480.15.

Step 4.

tert-Butyl N-{1-[3-(aminomethyl)-5-(2,3-dichlorophenyl)-6-methylpyrazin-2-yl]-4-methylpiperidin-4-yl}carbamate (0.08 g, 16.6 mmol) was dissolved in formic acid (1.6 mL) and stirred at 105° C. for 2 hrs. Formic acid was removed under reduced pressure, and the resulting red oil was portioned between water and DCM. An aqueous phase was basified with NaHCO$_3$ (aq.) to pH 11 then extracted with mixture of isopropyl alcohol and chloroform 1:3 (4×50) mL). The organic layers were combined, dried over MgSO$_4$, and concentrated under reduced pressure. Purification by preparative TLC (MeOH with NH$_3$ 3M/DCM 4:96) resulted in N-{[3-(4-amino-4-methylpiperidin-1-yl)-6-(2,3-dichlorophenyl)-5-methylpyrazin-2-yl]methyl}formamide (0.017 g, 25%) as an yellow oil. $^1$H NMR (400 MHZ, DMSO-d6) δ 8.07 (d, J=1.6 Hz, 1H), 7.74 (dd, J=7.9, 1.7 Hz, 1H), 7.48 (t, J=7.8 Hz, 1H), 7.43 (dd, J=7.7, 1.7 Hz, 1H), 4.42 (d, J=5.6 Hz, 2H), 3.31-3.14 (m, 3H), 2.20 (s, 3H), 1.66-1.47 (m, 4H), 1.13 (s, 3H). UPLC [M+1]=409.5.

Step 5.

N-{[3-(4-amino-4-methylpiperidin-1-yl)-6-(2,3-dichlorophenyl)-5-methylpyrazin-2-yl]methyl}formamide (0.017 g, 4.2 mmol) was suspended in POCl$_3$ (1 mL) and stirred at 90° C. for 2 hrs then at room temperature overnight. POCl$_3$ was removed under reduced pressure. Purification by preparative HPLC resulted in 3.4 mg (21%) of 1-(5-(2,3-dichlorophenyl)-6-methylimidazo[1,5-a]pyrazin-8-yl)-4-methylpiperidin-4-amine. $^1$H NMR (400 MHZ, DMSO-d6) δ 8.28 (s, 1H), 7.93-7.83 (m, 2H), 7.64-7.50 (m, 3H), 4.07-3.97 (m, 2H), 3.82-3.72 (m, 2H), 1.95 (s, 3H), 1.76-1.61 (m, 4H), 1.34-1.19 (m, 3H); LC-MS (ESI) m/z: [M+H] calculated for C$_{19}$H$_{22}$Cl$_2$N$_5$: 390.1; found 390.3.

Example 3. Synthesis of (1R)-8-[5-(2,3-dichlorophenyl)-6-methylimidazo[1,5-a]pyrazin-8-yl]-8-azaspiro[4.5]decan-1-amine (1R)-8-[5-(2,3-dichlorophenyl)-6-methylimidazo[1,5-a]pyrazin-8-yl]-8-azaspiro[4.5]decan-1-amine was synthesized in the was synthesized in the manner similar to Example 2, except tert-Butyl N-[1-(3-cyano-6-methylpyrazin-2-yl)-4-methylpiperidin-4-yl]carbamate was substituted with tert-butyl (R)-(8-azaspiro[4.5]decan-1-yl) carbamate. $^1$H NMR $^1$H NMR (400 MHZ, DMSO-d6) δ 7.89-7.80 (m, 2H), 7.61-7.52 (m, 3H), 4.48-4.33 (m, 2H), 2.73 (t, J=7.4 Hz, 1H), 1.94 (s, 3H), 1.92-1.79 (m, 2H), 1.78-1.16 (m, 8H). LC-MS (ESI) m/z: [M+H] calculated for C$_{22}$H$_{26}$Cl$_2$N$_5$: 431.3; found 431.5

Example 4. Synthesis of (1R)-8-[6-amino-5-(2,3-dichlorophenyl)imidazo[1,5-a]pyrazin-8-yl]-8-azaspiro[4.5]decan-1-amine

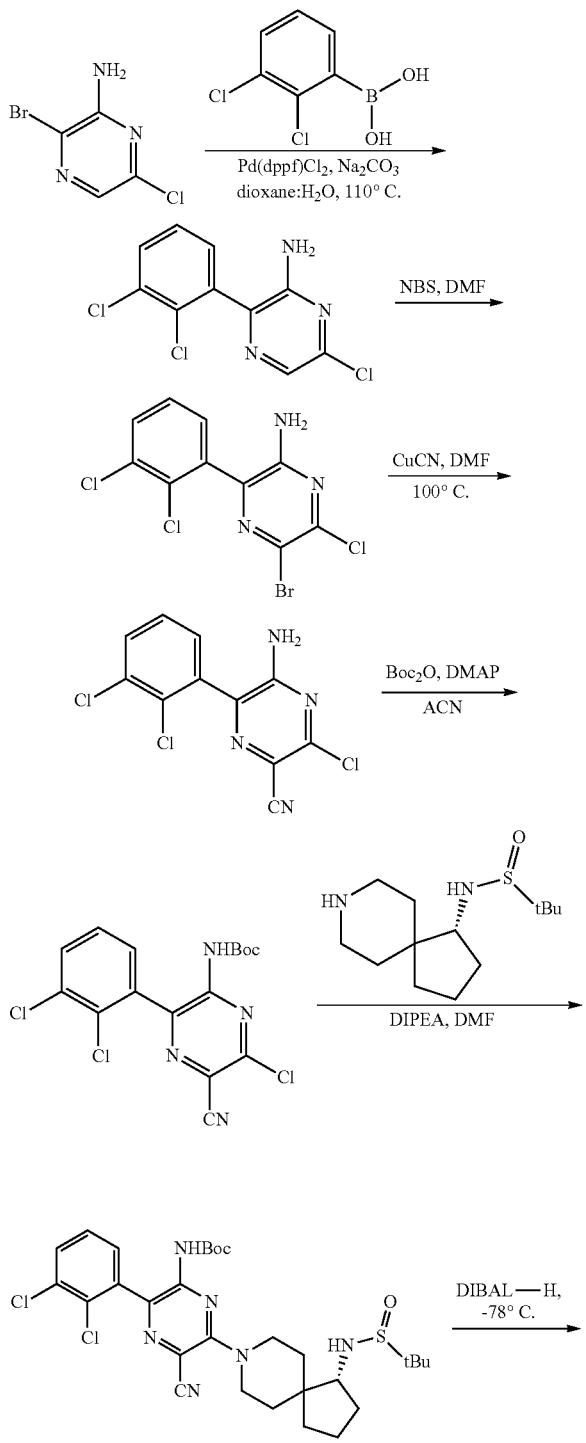

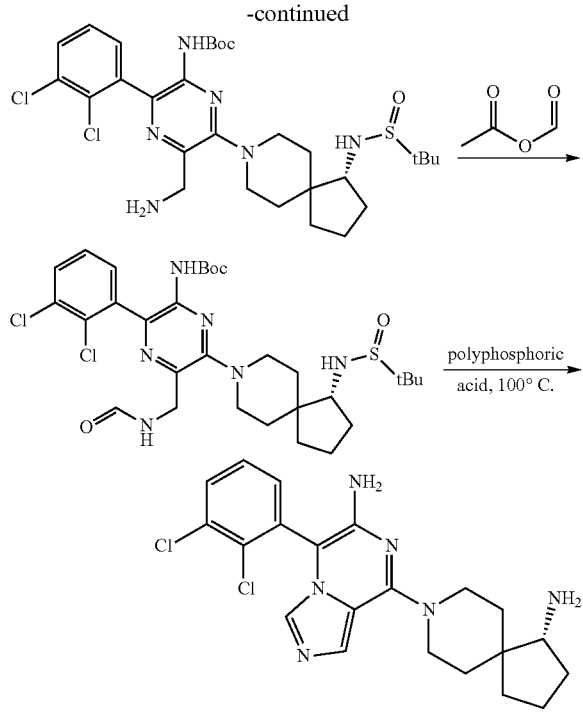

Step 1.

3-Bromo-6-chloropyrazine-2-amine (5.00 g, 24.0 mmol) and Na$_2$CO$_3$·10H$_2$O (20.6 g, 72.0 mmol) were suspended in mixture dioxane:water, 4:1. The solvent was degassed by passing argon through it and Pd(dppf)Cl$_2$ (0.88 g. 1.20 mmol) was added. The reaction was carried out 6 hrs at 110° C. The reaction mixture was filtered through celite pad (AcOEt). The residue was purified by column chromatography (hexane:AcOEt, 9:1→4:1) to give 4.63 g (70%) of 6-chloro-3-(2,3-dichlorophenyl) pyrazin-2-amine. $^1$H NMR (400 MHZ, DMSO-d6) δ 7.85 (s, 1H), 7.74 (dd, J=8.0, 1.6 Hz, 1H), 7.47 (t, J=7.8 Hz, 1H), 7.39 (dd, J=7.6, 1.6 Hz, 1H), 6.70 (s, 2H). LC-MS (ESI) m/z: [M+H] found 275.7.

Step 2.

6-Chloro-3-(2,3-dichlorophenyl) pyrazin-2-amine (1.8 g, 6.56 mmol) was dissolved in DMF, then cooled down to 0° C. At this temperature, NBS (1.75 g, 9.83 mmol) in one portion was added. The reaction was carried out at room temperature overnight. The reaction mixture was partitioned between DCM and water and the organic phase was washed with water and brine. Next, the combined water phases were extracted with DCM. The combined organic phases were dried over Na$_2$SO$_4$, filtered and concentrated under reduced pressure. The residue was purified by column chromatography to give 2.14 g (92%) of 5-bromo-6-chloro-3-(2,3-dichlorophenyl) pyrazin-2-amine. $^1$H NMR (400 MHZ, DMSO-d6) δ 7.76 (dd, J=7.8, 1.8 Hz, 1H), 7.52-7.43 (m, 2H), 6.92 (s, 2H).

Step 3.

5-Bromo-6-chloro-3-(2,3-dichlorophenyl) pyrazin-2-amine (2.14 g, 6.05 mmol) was dissolved in anhydrous DMF, then CuCN (1.09 g, 12.1 mmol) was added. The reaction was carried out overnight at 100° C. The reaction mixture was filtered through celite pad and the filtrate was concentrated under reduced pressure. The crude product (3.2 g, 176%) was used in next step without purification. $^1$H NMR (300 MHZ, DMSO-d6) δ 7.97 (s, 2H), 7.78 (d, J=7.6 Hz, 1H), 7.56-7.39 (m, 2H). LC-MS (ESI) m/z: [M−H] found 498.6 (negative ionization).

Step 4.

5-Amino-3-chloro-6-(2,3-dichlorophenyl) pyrazine-2-carbonitrile (1.81 g, 6.04 mmol) was suspended in ACN, then Boc$_2$O (4.62 g, 21.2 mmol) was added followed by DMAP (0.04 g, 0.30 mmol). The reaction was carried out at room temperature overnight, then the next portion of DMAP (0.22 g, 1.81 mmol) was added. The reaction was continued at room temperature for 4 hrs. The solvent was removed under reduced pressure and the residue was adsorbed on silica gel for purification. The crude product was purified by column chromatography to give 1.09 g (45%) tert-butyl N-[6-chloro-5-cyano-3-(2,3-dichlorophenyl) pyrazin-2-yl] carbamate. $^1$H NMR (300 MHz, DMSO-d6) δ 10.65 (s, 1H), 7.76 (dd, J=7.6, 2.0 Hz, 1H), 7.54-7.42 (m, 2H), 1.30 (s, 9H). LC-MS (ESI) m/z: [M−H] found 398.5 (negative ionization).

Step 5.

tert-Butyl N-[6-chloro-5-cyano-3-(2,3-dichlorophenyl) pyrazin-2-yl]carbamate (1.09 g, 2.73 mmol) and DIPEA (1.43 mL, 8.18 mmol) were dissolved in anhydrous DMF. After 15 minutes, N-{8-azaspiro[4.5]decan-1-yl}-2-methylpropane-2-sulfinamide (0.78 g, 3.00 mmol) was added and the reaction was carried out at room temperature overnight. The reaction mixture was partitioned between AcOEt and water. The separated water layer was extracted with AcOEt. The combined organic phases were dried over MgSO$_4$, filtered and concentrated under reduced pressure. The resulting residue was purified by a column chromatography to give tert-butyl N-[5-cyano-3-(2,3-dichlorophenyl)-6-[(1R)-1-[(2-methylpropane-2-sulfinyl)amino]-8-azaspiro[4.5]decan-8-yl]pyrazin-2-yl]carbamate (1.18 g, 70%). $^1$H NMR (400 MHZ, DMSO-d6) δ 9.80 (s, 1H), 7.66 (dd, J=6.9, 2.7 Hz, 1H), 7.46-7.39 (m, 2H), 5.05 (d, J=8.1 Hz, 1H), 4.55-4.40 (m, 2H), 3.28-3.12 (m, 3H), 2.01-1.82 (m, 4H), 1.76-1.61 (m, 3H), 1.53-1.45 (m, 1H), 1.42-1.32 (m, 2H), 1.28 (s, 9H), 1.12 (s, 9H). LC-MS (ESI) m/z: [M+H] found 622.9.

Step 6.

tert-Butyl N-[5-cyano-3-(2,3-dichlorophenyl)-6-[(1R)-1-[(2-methylpropane-2-sulfinyl)amino]-8-azaspiro[4.5]decan-8-yl]pyrazin-2-yl]carbamate (0.50 g, 0.80 mmol) was dissolved in anhydrous DCM and cooled to −78° C. A 1 M solution of DIBAL-H in hexane (2.41 mL, 2.41 mmol) was added dropwise and the reaction was carried out at −78° C. for 2 hrs and mixture was allowed to warm to 0° C. The reaction was then quenched by addition of NaHCO$_3$ sat. aq., followed by Rochelle's salt sat. aq. This resulting mixture was stirred until the organic and water layers separated. The aqueous layer was extracted with DCM. The combined organic phases were dried over Na$_2$SO$_4$ and concentrated under reduced pressure to give crude tert-butyl N-[5-(aminomethyl)-3-(2,3-dichlorophenyl)-6-[(1R)-1-[(2-methylpropane-2-sulfinyl)amino]-8-azaspiro[4.5]decan-8-yl] pyrazin-2-yl]carbamate (0.48 g, 95% yield) which was used in next step without further purification. $^1$H NMR (400 MHZ, DMSO-d6) δ 9.27 (s, 1H), 7.65-7.57 (m, 1H), 7.46-7.34 (m, 2H), 5.06-4.88 (m, 1H), 3.95-3.83 (m, 1H), 3.80 (s, 2H), 3.62-3.51 (m, 1H), 3.20 (q, J=7.7 Hz, 1H), 3.08-3.00 (m, 1H), 2.91 (q, J=12.7 Hz, 2H), 2.14-1.98 (m, 1H), 1.97-1.88 (m, 1H), 1.87-1.72 (m, 2H), 1.69-1.50 (m, 4H), 1.48-1.41 (m, 1H), 1.40-1.30 (m, 2H), 1.21 (s, 9H), 1.14 (s, 9H). LC-MS (ESI) m/z: [M+H] found 626.6.

Step 7.

tert-Butyl N-[5-(aminomethyl)-3-(2,3-dichlorophenyl)-6-[(1R)-1-[(2-methylpropane-2-sulfinyl)amino]-8-azaspiro[4.5]decan-8-yl]pyrazin-2-yl]carbamate (0.48 g, 0.77 mmol)

was dissolved in anhydrous DCM and cooled to 0° C. Acetic formic anhydride (0.39 mL, 5.37 mmol) was added dropwise and the reaction was allowed to stir overnight at 4° C. Water (5 mL) was added, the layers were separated, and aqueous phase was extracted with DCM. The combined organic phases were dried over $Na_2SO_4$, and concentrated under reduced pressure. The residue was purified by column column chromatography to give 0.27 g (54%) of tert-butyl N-[3-(2,3-dichlorophenyl)-5-(formamidomethyl)-6-[(1R)-1-[(2-methylpropane-2-sulfinyl)amino]-8-azaspiro[4.5]decan-8-yl]pyrazin-2-yl]carbamate as a pale yellow solid. $^1$H NMR (400 MHZ, DMSO-d6) δ 9.33 (s, 1H), 8.38-8.28 (m, 1H), 8.10 (d, J=1.6 Hz, 1H), 7.64-7.59 (m, 1H), 7.43-7.38 (m, 2H), 4.98 (d, J=7.8 Hz, 1H), 4.43 (d, J=5.6 Hz, 2H), 3.51 (s, 2H), 3.20 (q, J=7.8 Hz, 1H), 2.94 (q, J=12.1 Hz, 2H), 2.04-1.90 (m, 2H), 1.83-1.73 (m, 2H), 1.68-1.61 (m, 2H), 1.58-1.52 (m, 1H), 1.49-1.42 (m, 1H), 1.40-1.34 (m, 1H), 1.35-1.27 (m, 2H), 1.21 (s, 9H), 1.14 (s, 9H). LC-MS (ESI) m/z: [M+H] found 654.8.

Step 8.

tert-Butyl N-[3-(2,3-dichlorophenyl)-5-(formamidomethyl)-6-[(1R)-1-[(2-methylpropane-2-sulfinyl)amino]-8-azaspiro[4.5]decan-8-yl]pyrazin-2-yl]carbamate (0.10 g, 0.15 mmol) was mixed with polyphosphoric acid (1.00 g, 10.2 mmol). The reaction mixture was heated to 100° C. and reaction was carried out at this temperature for 1 hr. The resulting mixture was concentrated under reduced pressure. Purification by preparative HPLC resulted in (1R)-8-[6-amino-5-(2,3-dichlorophenyl)imidazo[1,5-a]pyrazin-8-yl]-8-azaspiro[4.5]decan-1-amine as a formate salt. $^1$H NMR (300 MHz, Methanol-d4) δ 8.49 (s, 3H), 7.81-7.67 (m, 2H), 7.55-7.46 (m, 2H), 7.41 (s, 1H), 4.45-4.25 (m, 2H), 3.66-3.54 (m, 2H), 2.35 (t, J=7.4 Hz, 2H), 2.14-1.96 (m, 5H), 1.89-1.78 (m, 2H), 1.65-1.55 (m, 2H), 1.39-1.27 (m, 2H). LC-MS (ESI) m/z: [M+1]$^+$ calculated for $C_{21}H_{25}N_6Cl_2$: 431.1; found 431.2.

Example 5. Synthesis of 1-[6-amino-5-(2,3-dichlorophenyl)imidazo[1,5-a]pyrazin-8-yl]-4-methylpiperidin-4-amine

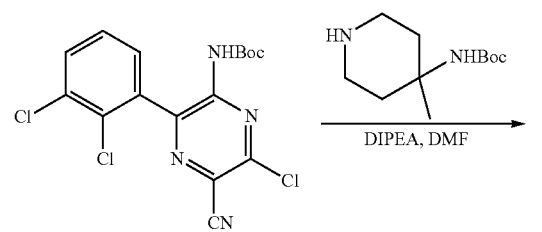

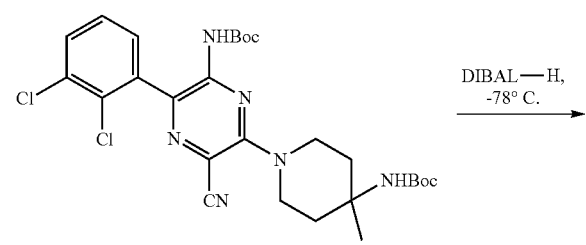

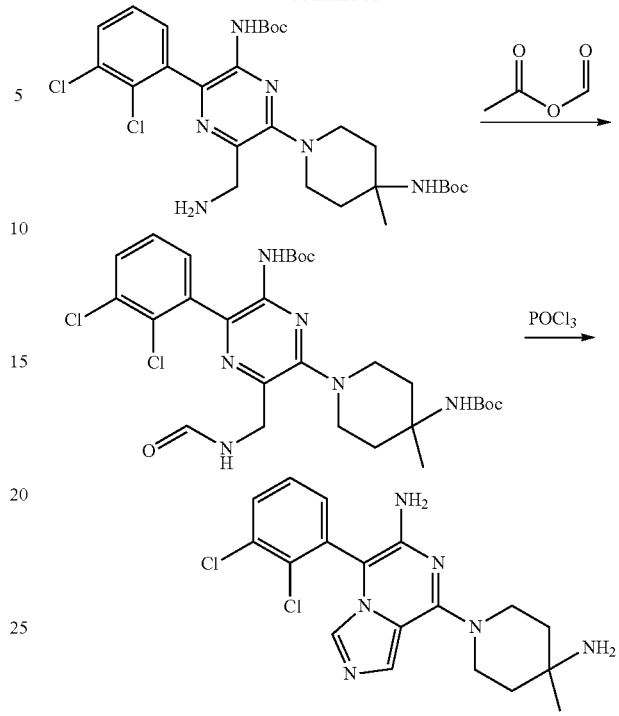

Step 1.

tert-Butyl N-[6-chloro-5-cyano-3-(2,3-dichlorophenyl) pyrazin-2-yl]carbamate (0.7 g, 1.75 mmol) and DIPEA (0.92 mL, 5.25 mmol) were dissolved in anhydrous DMF. After 15 minutes, tert-butyl (4-methylpiperidin-4-yl) carbamate (0.45 g, 0.21 mmol) was added and the reaction was allowed to stir at room temperature over 72 hrs. The reaction mixture was diluted with EtOAc and washed with 5% NaCl solution. The organic phase was dried over $Na_2SO_4$, filtered and concentrated under reduced pressure to give tert-butyl N-[6-(4-amino-4-methylpiperidin-1-yl)-5-cyano-3-(2,3-dichlorophenyl) pyrazin-2-yl]carbamate (0.99 g, 99%). $^1$H NMR (300 MHz, DMSO-d6) δ 7.66 (dd, J=7.4, 2.2 Hz, 1H), 7.47-7.36 (m, 2H), 6.70 (s, 1H), 4.13 (d, J=13.8 Hz, 2H), 3.45 (t, J=11.9 Hz, 2H), 2.18 (d, J=13.6 Hz, 2H), 1.63-1.47 (m, 2H), 1.41 (s, 9H), 1.28 (s, 12H).

Step 2.

tert-Butyl N-[6-(4-amino-4-methylpiperidin-1-yl)-5-cyano-3-(2,3-dichlorophenyl) pyrazin-2-yl]carbamate (0.83 g, 1.44 mmol) was dried overnight on vacuum pump and dissolved in anhydrous DCM. The solution was cooled to −60° C. and 1 M DIBAL-H in hexane (10 mL, 10.1 mmol) was added dropwise. The reaction was carried out at −30° C. for 4 hrs. After this time, the reaction mixture was allowed to warm to 0° C. The reaction was then quenched by addition of $NH_4Cl$ sat. aq., followed by sodium potassium tartrate sat. aq. This resulting mixture was stirred until organic and water layers separated. The water layer was extracted with DCM. The combined organic phases were dried over $Na_2SO_4$ and concentrated under reduced pressure to give crude tert-butyl N-[6-(4-amino-4-methylpiperidin-1-yl)-5-(aminomethyl)-3-(2,3-dichlorophenyl) pyrazin-2-yl]carbamate (0.6 g, 71% yield) which was used in next step without further purification. $^1$H NMR (400 MHZ, DMSO-d6) δ 7.68-7.55 (m, 1H), 7.46-7.35 (m, 2H), 6.56 (s, 1H), 3.77 (s, 2H), 3.62-3.47 (m, 2H), 3.09 (m, 2H), 2.16 (m, 2H), 1.58 (m, 2H), 1.39 (s, 9H), 1.28 (s, 3H). LC-MS (ESI) m/z: [M+H] found 582.4.

Step 3.

Tert-Butyl N-[6-(4-amino-4-methylpiperidin-1-yl)-5-(aminomethyl)-3-(2,3-dichlorophenyl) pyrazin-2-yl]carbamate (0.6 g, 1.38 mmol) was dissolved in anhydrous DCM and cooled to 0° C. in ice bath. Acetic formic anhydride (0.70 mL, 9.63 mmol) was added dropwise and the reaction was continued overnight at 4° C. The reaction was quenched by addition of water. The layers were separated and the next water phase was extracted with DCM. The combined organic phases were dried over $Na_2SO_4$ and concentrated under reduced pressure. The residue was purified by column chromatography to give 0.30 g (36%) of tert-butyl N-[6-(4-amino-4-methylpiperidin-1-yl)-3-(2,3-dichlorophenyl)-5-(formamidomethyl) pyrazin-2-yl]carbamate as a pale yellow solid. $^1$H NMR (400 MHZ, DMSO-d6) δ 9.35 (s, 1H), 8.34 (d, J=6.1 Hz, 1H), 8.09 (d, J=1.7 Hz, 1H), 7.62 (dt, J=7.6, 3.7 Hz, 1H), 7.47-7.34 (m, 2H), 6.59 (s, 1H), 4.43 (d, J=5.6 Hz, 2H), 3.30-3.21 (m, 3H), 3.10 (t, J=11.7 Hz, 2H), 2.17 (d, J=13.2 Hz, 2H), 1.70-1.54 (m, 3H), 1.41 (s, 9H), 1.30 (s, 3H). LC-MS (ESI) m/z: [M+H] found 610.2.

Step 4.

Tert-Butyl N-[6-(4-amino-4-methylpiperidin-1-yl)-3-(2,3-dichlorophenyl)-5-(formamidomethyl) pyrazin-2-yl]carbamate (0.15 g, 0.25 mmol) was mixed with $POCl_3$ (1.5 mL, 16.1 mmol). The reaction mixture was heated up to 90° C. and allowed to stir for 3 hrs. $POCl_3$ was removed under reduced pressure. Purification by preparative HPLC resulted in 4.5 mg of 1-[6-amino-5-(2,3-dichlorophenyl)imidazo[1,5-a]pyrazin-8-yl]-4-methylpiperidin-4-amine. $^1$H NMR (400 MHZ, DMSO-d6) δ 8.36 (s, 1H), 7.82-7.72 (m, 2H), 7.56-7.46 (m, 2H), 7.36 (s, 1H), 4.64 (s, 2H), 4.06 (s, 2H), 3.71 (s, 2H), 1.72 (s, 4H), 1.32 (s, 3H). LC-MS (ESI) m/z: [M+1]$^+$ calculated for $C_{18}H_{21}N_6Cl_2$: 391.1; found 391.2.

Example 6. Synthesis of (3S,4S)-8-{5-[(2-amino-3-chloropyridin-4-yl)sulfanyl]-6-methylimidazo[1,2-a]pyrazin-8-yl}-3-methyl-2-oxa-8-azaspiro[4.5]decan-4-amine

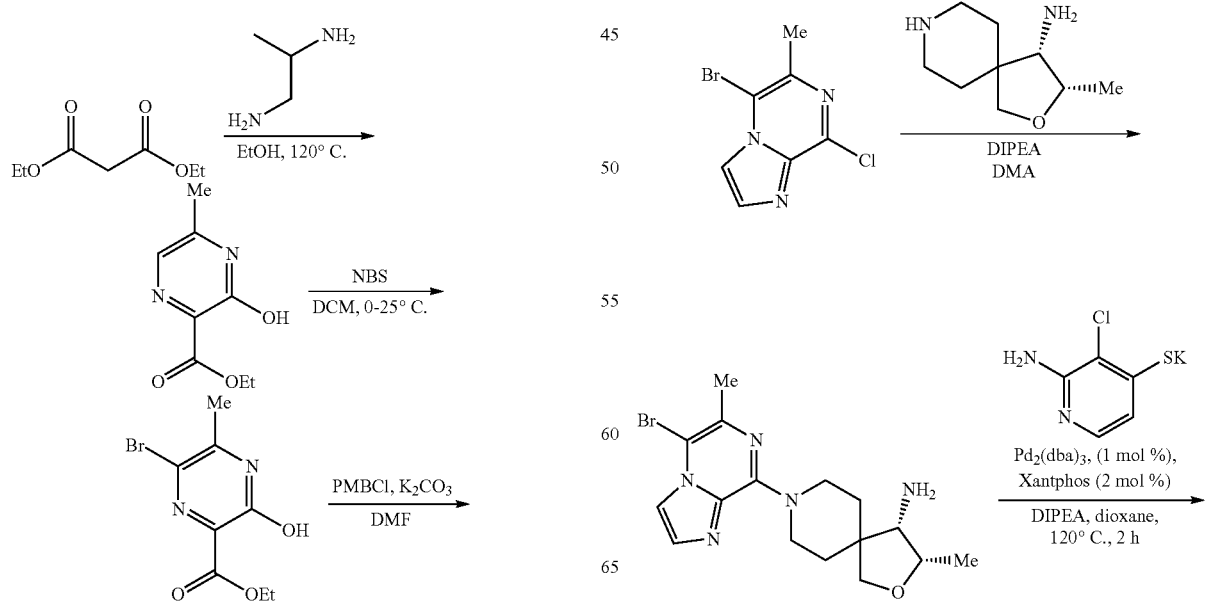

-continued

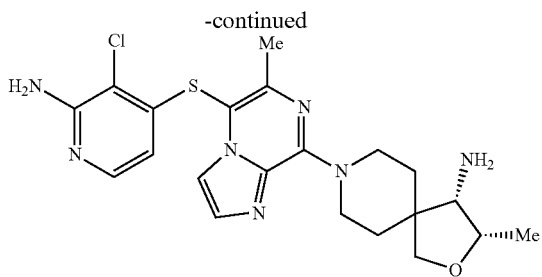

Step 1.

To a solution of propane-1,2-diamine (46.28 g, 624.34 mmol, 53.32 mL) in EtOH (2000 mL) was added diethyl propanedioate (100 g, 624.34 mmol, 94.34 mL) at 0° C. The mixture was stirred at 25° C. for 1.5 hrs, then heated to 120° C. and stirred for 20 hrs under $O_2$. The resulting mixture was concentrated under reduced pressure and the resulting residue was purified by column chromatography to afford ethyl 3-hydroxy-5-methyl-pyrazine-2-carboxylate (24 g, 658.70 mmol, 21.10% yield) as a white solid. LCMS (ESI): m/z: [M+H] calculated for $C_8H_{11}N_2O_3$: 183.07; found 183.1.

Step 2.

To a solution of ethyl 3-hydroxy-5-methyl-pyrazine-2-carboxylate (166 g, 911.21 mmol) in DCM (1500 mL) was added NBS (178.40 g, 1.00 mol) in one portion at 0° C. under $N_2$. The mixture was stirred at 25° C. for 10 min. The resulting mixture was diluted with saturated aq. $Na_2SO_3$ (1000 mL) and the aqueous phase was extracted with DCM. The combined organic phase was washed with brine (50 mL), dried with anhydrous $Na_2SO_4$, and concentrated under reduced pressure to afford ethyl 6-bromo-3-hydroxy-5-methyl-pyrazine-2-carboxylate (230 g, crude) as a dark brown solid. $^1$H NMR (400 MHZ, CDCl3-d) δ ppm 4.54 (q, J=7.13 Hz, 2H) 2.77 (s, 1H) 2.68 (s, 3H) 1.46 (t, J=7.09 Hz, 3H)

Step 3.

To a solution of ethyl 6-bromo-3-hydroxy-5-methyl-pyrazine-2-carboxylate (115 g. 440.49 mmol) and $K_2CO_3$ (182.64 g, 1.32 mol) in DMF (2.1 L) was added PMB-Cl (103.48 g, 660.74 mmol, 89.98 mL) in one portion at 20° C. under $N_2$. The mixture was stirred at 50° C. for 2 hr. The resulting mixture was diluted with water and the aqueous phase was extracted with EtOAc. The combined organic phase was washed with brine (200 mL), dried with anhydrous $Na_2SO_4$, and concentrated under reduced pressure. The remaining residue was purified by column chromatography to afford ethyl 6-bromo-3-[(4-methoxy phenyl) methoxy]-5-methyl-pyrazine-2-carboxy late (60 g, 35.73% yield) as a white solid. LCMS (ESI): m/z [M+Na] calculated for $C_{16}H_{17}BrN_2O_4Na$: 403.04; found 403.1.

Step 4.

To a solution of ethyl 6-bromo-3-[(4-methoxy phenyl) methoxy]-5-methyl-pyrazine-2-carboxy late (150 g, 393.47 mmol) in MeOH (1300 mL) was added a solution of LiOH (47.12 g, 1.97 mol) in $H_2O$ (400 mL) at 25° C. The mixture was stirred at 25° C. for 15 hrs. To the resulting mixture was added aqueous HCl (IM) drop wise into the reaction mixture until pH=6 was reached. The resulting mixture was diluted with $H_2O$ (2000 mL) and the aqueous phase was extracted with EtOAc. The combined organic phase was washed with brine (100 mL), dried with anhydrous $Na_2SO_4$, and concentrated under reduced pressure to afford 6-bromo-3-[(4-methoxyphenyl) methoxy]-5-methyl-pyrazine-2-carboxylic acid (138 g. crude) as a light yellow solid. LCMS (ESI): m/z [M+Na] calculated for $C_{14}H_{13}BrN_2O_4Na$: 375.01; found 375.1.

Step 5.

To a solution of 6-bromo-3-[(4-methoxyphenyl) methoxy]-5-methyl-pyrazine-2-carboxylic acid (100 g, 283.15 mmol) and DPPA (116.89 g, 424.73 mmol, 92.04 mL) in toluene (1800 mL) was added TEA (57.30 g, 566.30 mmol, 78.82 mL) and 1-BuOH (209.87 g, 2.83 mol, 270.80 mL) in one portion under $N_2$. The resulting mixture was stirred at 110° C. for 1 hr. The mixture was diluted with $H_2O$ (1000 mL) and the aqueous phase was extracted with EtOAc. The combined organic fractions were washed with brine (10 mL), dried with anhydrous $Na_2SO_4$, and concentrated under reduced pressure. The remaining residue was purified by column chromatography ($SiO_2$, petroleum ether/ethyl acetate=10:1 to 0:1) to give 6-bromo-3-[(4-methoxyphenyl) methoxy]-5-methyl-pyrazin-2-amine (5 g, 15.42 mmol, 5.45% yield) and tert-butyl N-[6-bromo-3-[(4-methoxyphenyl) methoxy]-5-methyl-pyrazin-2-yl]carbamate (90 g, 212.12 mmol, 74.91% yield) as white solids. LCMS (ESI): m/z [M+H] calculated for $C_{18}H_{23}BrN_3O_4$: 424.08; found 424.2.

Step 6.

To a solution of $K_2CO_3$ (87.95 g, 636.36 mmol) in MeOH (1000 mL) was added tert-butyl N-[6-bromo-3-[(4-methoxyphenyl) methoxy]-5-methyl-pyrazin-2-yl]carbamate (90 g, 212.12 mmol) in one portion at 70° C. The reaction was stirred at 70° C. for 15 hrs. The resulting reaction mixture was filtered and concentrated under reduced pressure to afford 6-bromo-3-[(4-methoxyphenyl) methoxy]-5-methyl-pyrazin-2-amine (90 g, crude) as a white solid. $^1$H NMR (400 MHZ, CDCl3-d) δ ppm 7.38 (d, J=8.68 Hz, 2H) 6.99-6.86 (m, 2H) 5.30 (s, 2H) 4.87 (br s, 2H) 3.87-3.77 (m, 3H) 2.49-2.38 (m, 3H).

Step 7.

To a 40% solution of 2-chloroacetaldehyde (272.42 g, 1.39 mol, 223.29 mL) in $H_2O$ was added 6-bromo-3-[(4-methoxyphenyl) methoxy]-5-methyl-pyrazin-2-amine (50 g, 154.24 mmol) at 25° C. The reaction was stirred at 120° C. for 1 hr. The resulting residue was purified by reverse phase column chromatography to afford 5-bromo-6-methyl-imidazo[1,2-a]pyrazine-8-ol (7 g, 30.70 mmol, 19.90% yield) as a white solid. LCMS (ESI): m/z [M+H] calculated for $C_7H_7BrN_3O$: 227.97; found 228.1.

Step 8.

A solution of 5-bromo-6-methyl-imidazo[1,2-a]pyrazin-8-ol (5 g, 21.93 mmol) and TEA (2.22 g, 21.93 mmol, 3.05 mL) in $POCl_3$ (100.86 g, 657.76 mmol, 61.12 mL) was heated to 120° C. for 0.5 h. The resulting reaction mixture was concentrated under reduced pressure. The resulting residue was diluted with ethyl acetate (200 mL) and sat.aq. $NaHCO_3$ (400 mL). The organic layer was removed, washed with water, dried over $Na_2SO_4$ and concentrated under reduced pressure. The remaining residue was purified by column chromatography ($SiO_2$, Petroleum ether/Ethyl acetate=15:1) to afford 5-bromo-8-chloro-6-methyl-imidazo [1,2-a]pyrazine (3.83 g, 10.78 mmol, 49.19% yield, 69.41% purity) as a white solid. $^1$H NMR (400 MHZ, CDCl3-d) δ ppm 7.93 (d, J=0.88 Hz, 1H) 7.87 (d, J=1.10 Hz, 1H) 2.66 (s, 3H) LCMS: m/z: [M+H] calculated for $C_7H_5BrClN_3$: 245.94; found 245.9.

Step 9.

To a solution of 5-bromo-8-chloro-6-methylimidazo[1,2-a]pyrazine (135 mg, 547 μmol) in DMA (5.46 mL) was added (3S,4S)-4-ammonio-3-methyl-2-oxa-8-azaspiro[4.5]decan-8-ium chloride (159 mg, 656 μmol) and DIPEA (474

µL, 2.73 mmol). The reaction mixture was stirred at 100° C. for 1 h. The resulting reaction mixture was concentrated under reduced pressure and the remaining residue was purified by column chromatography (0-10% MeOH/CH$_2$Cl$_2$) to afford (3S,4S)-8-(5-bromo-6-methylimidazo[1,2-a]pyrazin-8-yl)-3-methyl-2-oxa-8-azaspiro[4.5]decan-4-amine. LCMS (ESI): m/z: [M+H] calculated for C$_{16}$H$_{23}$BrN$_5$O: 380.1; found 380.4.

Step 10.

A vial was charged with (3S,4S)-8-(5-bromo-6-methylimidazo[1,2-a]pyrazin-8-yl)-3-methyl-2-oxa-8-azaspiro[4.5]decan-4-amine (162 mg, 425 µmol), potassium 2-amino-3-chloropyridine-4-thiolate (126 mg, 637 µmol), Pd$_2$(dba)$_3$ (23.2 mg, 25.4 µmol), Xantphos (24.5 mg, 42.5 µmol). The reaction vial was evacuated and purged with N$_2$ three times. Dioxane and DIPEA (221 µL, 1.27 mmol) were added and the reaction mixture was stirred at 140° C. for 2 hrs. The reaction mixture was filtered, and the filtrate was concentrated under reduced pressure. The remaining residue was purified by prep phase HPLC to afford (3S,4S)-8-(5-((2-amino-3-chloropyridin-4-yl)thio)-6-methylimidazo[1,2-a]pyrazin-8-yl)-3-methyl-2-oxa-8-azaspiro[4.5]decan-4-amine (60.0 mg, 130 µmol, 30.7%) as the formic acid salt. $^1$H NMR (500 MHZ, Methanol-d4) δ 8.53 (s, 1H), 7.73 (d, J=1.2 Hz, 1H), 7.55 (d, J=5.5 Hz, 1H), 7.51 (d, J=1.2 Hz, 1H), 5.74 (d, J=5.6 Hz, 1H), 5.23 (dd, J=31.5, 13.9 Hz, 3H), 4.38-4.24 (m, 1H), 4.02 (d, J=9.0 Hz, 1H), 3.90 (d, J=9.1 Hz, 1H), 3.69-3.51 (m, 2H), 2.50 (s, 3H), 1.97-1.86 (m, 3H), 1.75 (d, J=13.3 Hz, 1H), 1.31 (d, J=6.5 Hz, 3H). LCMS (ESI): m/z: [M+H] calculated for C$_{21}$H$_{27}$ClN$_7$OS: 460.2; found 460.5.

Example 7. Synthesis of (3S,4S)-8-(5-(3-chlorophenyl)-6-methylimidazo[1,2-a]pyrazin-8-yl)-3-methyl-2-oxa-8-azaspiro[4.5]decan-4-amine

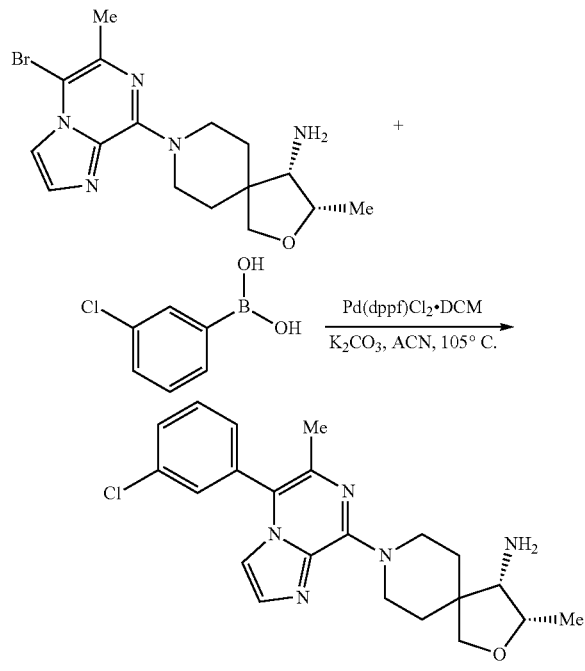

A vial was charged with (3S,4S)-8-(5-bromo-6-methylimidazo[1,2-a]pyrazin-8-yl)-3-methyl-2-oxa-8-azaspiro[4.5]decan-4-amine (125 mg, 328 µmol), (3-chlorophenyl) boronic acid (61.4 mg, 393 µmol), Pd(dppf)Cl$_2$·DCM (53.5 mg, 65.6 µmol), and K$_2$CO$_3$ (181 mg, 1.31 mmol). The vial was then evacuated and purged with N$_2$ three times. Degassed ACN (3.28 mL) was added and the reaction mixture was stirred at 105° C. for 2 hrs. The resulting reaction mixture was filtered and the filtrate was concentrated under reduced pressure. The remaining residue was purified by prep HPLC to afford (3S,4S)-8-(5-(3-chlorophenyl)-6-methylimidazo[1,2-a]pyrazin-8-yl)-3-methyl-2-oxa-8-azaspiro[4.5]decan-4-amine (48.0 mg, 116 µmol, 35.5%) as the formic acid salt. $^1$H NMR (500 MHZ, Methanol-d4) δ 8.53 (s, 1H), 7.61-7.53 (m, 2H), 7.48 (dd, J=4.8, 1.6 Hz, 2H), 7.39 (dt, J=7.0, 1.8 Hz, 1H), 7.20 (d, J=1.2 Hz, 1H), 5.06-4.89 (m, 3H), 4.31 (qd, J=6.6, 4.4 Hz, 1H), 4.00 (d, J=9.0 Hz, 1H), 3.89 (d, J=9.0 Hz, 1H), 3.45 (dddd, J=35.4, 13.9, 10.8, 3.1 Hz, 2H), 2.17 (s, 3H), 2.00-1.81 (m, 3H), 1.77-1.69 (m, 1H), 1.31 (d, J=6.5 Hz, 3H). LCMS (ESI): m/z: [M+H] calculated for C$_{22}$H$_{27}$ClN$_5$O: 412.2; found 412.4.

Example 8. Synthesis of (3S,4S)-8-(5-(1H-indazol-6-yl)-6-methylimidazo[1,2-a]pyrazin-8-yl)-3-methyl-2-oxa-8-azaspiro[4.5]decan-4-amine

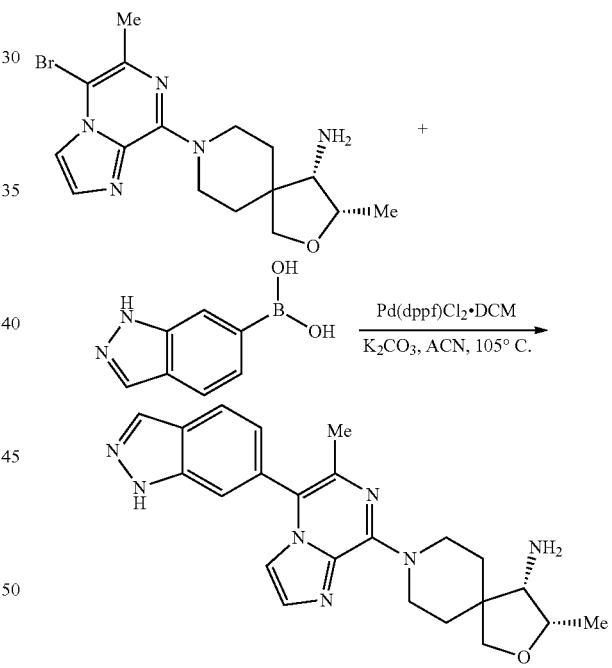

(3S,4S)-8-(5-(2,3-dichlorophenyl)-6-methylimidazo[1,2-a]pyrazin-8-yl)-3-methyl-2-oxa-8-azaspiro[4.5]decan-4-amine was synthesized in the manner similar to Example 7, except (3-chlorophenyl) boronic acid was replaced with (1H-indazol-6-yl) boronic acid. The product was isolated as the formic acid salt. $^1$H NMR (500 MHz, methanol-d4) δ 8.54 (s, 1H), 8.19 (d, J=1.0 Hz, 1H), 8.01 (dd, J=8.3, 0.9 Hz, 1H), 7.64 (q, J=1.1 Hz, 1H), 7.47 (d, J=1.2 Hz, 1H), 7.23-7.13 (m, 2H), 4.37-4.26 (m, 1H), 4.00 (d, J=8.9 Hz, 1H), 3.89 (d, J=8.9 Hz, 1H), 3.58-3.39 (m, 3H), 2.67 (s, 2H), 2.21 (s, 3H), 2.02-1.82 (m, 3H), 1.75 (d, J=13.2 Hz, 1H), 1.31 (d, J=6.5 Hz, 3H). LCMS (ESI): m/z [M+H] calculated for C$_{23}$H$_{28}$N$_7$O: 418.2; found 418.5.

Example 9. Synthesis of (3S,4S)-8-(5-(2,3-dichlorophenyl)-6-methylimidazo[1,2-a]pyrazin-8-yl)-3-methyl-2-oxa-8-azaspiro[4.5]decan-4-amine

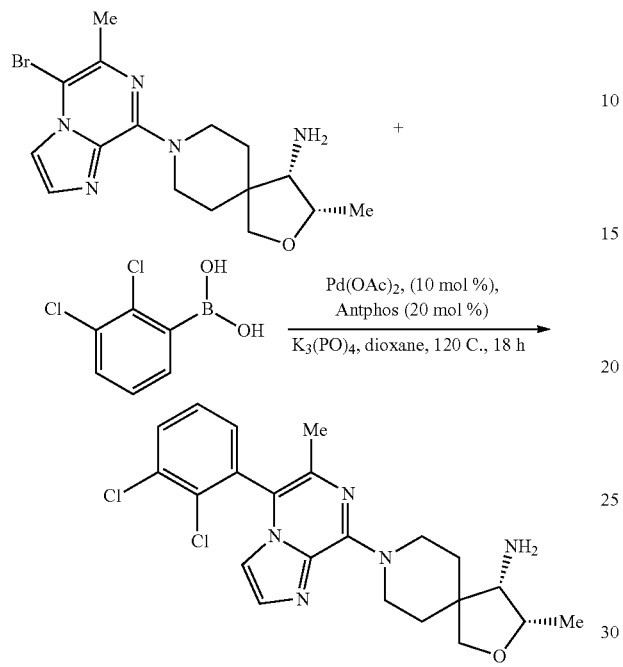

To a vial was added (3S,4S)-8-(5-bromo-6-methylimidazo[1,2-a]pyrazin-8-yl)-3-methyl-2-oxa-8-azaspiro[4.5]decan-4-amine (100 mg, 262 µmol), (2,3-dichlorophenyl) boronic acid (59.9 mg, 314 µmol), Antphos (19.4 mg, 52.4 µmol), Pd(OAc) 2 (5.88 mg, 26.2 µmol), and $K_3(PO)_4$ (166 mg, 786 µmol). The mixture was evacuated under reduced pressure for 10 min before adding in degassed dioxane (2.61 mL). The resulting mixture was degassed and allowed to stir at 125° C. overnight in the capped vial. The resulting reaction mixture was filtered through a pad of celite washing with DCM and MeOH. The filtrate was concentrated under reduced pressure and the residue was purified by prep HPLC to yield (3S,4S)-8-(5-(2,3-dichlorophenyl)-6-methylimidazo[1,2-a]pyrazin-8-yl)-3-methyl-2-oxa-8-azaspiro[4.5]decan-4-amine (17.0 mg, 38.0 µmol, 14.6%) as the formic acid salt. $^1$H NMR (500 MHZ, methanol-d4) δ 8.56 (s, 1H), 7.78 (dd, J=8.1, 1.6 Hz, 1H), 7.60-7.51 (m, 1H), 7.51-7.39 (m, 2H), 7.01 (d, J=1.2 Hz, 1H), 4.91 (d, J=2.1 Hz, 1H), 4.84-4.79 (m, 1H), 4.35-4.24 (m, 1H), 3.96 (d, J=8.8 Hz, 1H), 3.83 (d, J=8.7 Hz, 1H), 3.73-3.51 (m, 2H), 3.17 (d, J=4.7 Hz, 1H), 2.10 (s, 3H), 2.04-1.85 (m, 3H), 1.77 (dd, J=33.3, 13.4 Hz, 1H), 1.27 (d, J=6.5 Hz, 3H). LCMS (ESI): m/z [M+H] calculated for $C_{22}H_{26}Cl_2N_5O$: 446.1; found 446.3.

Example 10. Synthesis of (3S,4S)-8-(5-(3-chloro-2-fluorophenyl)-6-methylimidazo[1,2-a]pyrazin-8-yl)-3-methyl-2-oxa-8-azaspiro[4.5]decan-4-amine (3S,4S)-8-(5-(3-chloro-2-fluorophenyl)-6-methylimidazo[1,2-a]pyrazin-8-yl)-3-methyl-2-oxa-8-azaspiro[4.5]decan-4-amine was synthesized in the manner similar to Example 9, except (2,3-dichlorophenyl) boronic acid was substituted with (3-chloro-2-fluorophenyl) boronic acid. $^1$H NMR (500 MHZ, methanol-d6) δ 7.72 (ddd, J=7.8, 7.1, 1.9 Hz, 1H), 7.53-7.35 (m, 3H), 7.17 (q, J=1.5 Hz, 1H), 4.99-4.88 (m, 2H), 4.37-4.23 (m, 1H), 3.97 (d, J=8.8 Hz, 1H), 3.84 (d, J=8.7 Hz, 1H), 3.73-3.44 (m, 2H), 3.18 (d, J=5.0 Hz, 1H), 2.16 (d, J=1.6 Hz, 3H), 2.00-1.85 (m, 3H), 1.84-1.69 (m, 1H), 1.28 (dd, J=6.5, 1.6 Hz, 3H). LCMS (ESI): m/z [M+H] calculated for $C_{22}H_{26}ClFN_5O$: 430.2; found 430.4.

Example 11. Synthesis of (3S,4S)-8-[5-(3-chlorophenyl)-6-methylimidazo[1,5-a]pyrazin-8-yl]-3-methyl-2-oxa-8-azaspiro[4.5]decan-4-amine

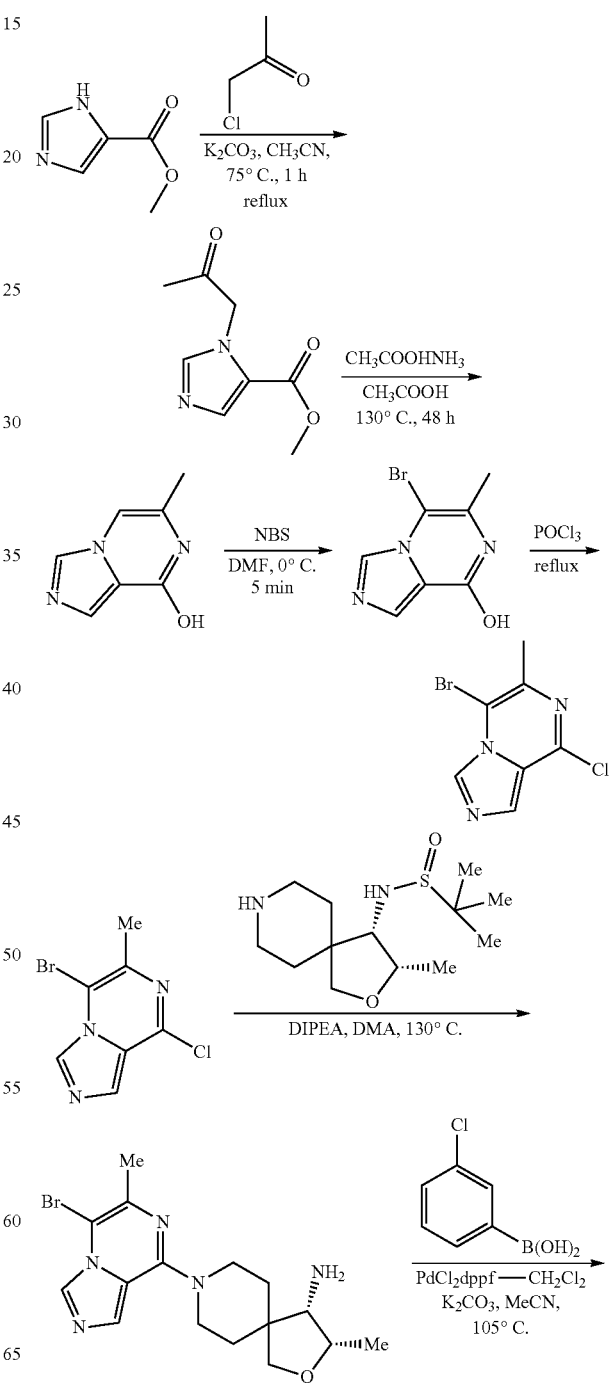

-continued

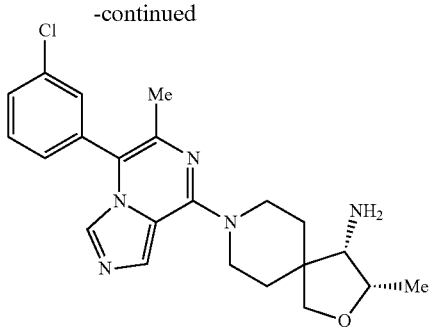

Step 1.

To a solution of methyl 1H-imidazole-5-carboxylate (96 g, 761.22 mmol) and 1-chloropropan-2-one (105.65 g, 1.14 mol) in ACN (2 L) was added $K_2CO_3$ (210.41 g, 1.52 mol) in one portion at 75° C. The mixture was stirred at 75° C. for 1 hr. Upon completion, the reaction mixture was filtered and the filtrate was evaporated under reduced pressure. The remaining residue was triturated with EtOAc (500 mL) and filtered. The resulting filtrate was concentrated under reduced pressure to afford methyl 3-acetonylimidazole-4-carboxylate (144 g, 41.54% yield) as a yellow solid. LCMS: m/z [M+H] calculated for $C_8H_{11}N_2O_3$:183.07; found 183.3.

Step 2.

To a solution of methyl 3-acetonylimidazole-4-carboxylate (130 g, 713.59 mmol) in $CH_3COOH$ (700 mL) was added $CH_3COONH_4$ (275.03 g, 3.57 mol) in one portion at 130° C. The reaction mixture was stirred at 130° C. for 48 hrs. Upon completion, the mixture was concentrated under reduced pressure, and the resulting residue was purified by reverse-phase column chromatography to afford 6-methylimidazo[1,5-a]pyrazin-8-ol (40 g, 230.64 mmol, 32.32% yield) as a yellow solid. LCMS: m/z [M+H] calculated for $CH_{11}N_2O_3$:150.06; found 150.02.

Step 3.

To a solution of 6-methylimidazo[1,5-a]pyrazin-8-ol (10 g, 67.05 mmol) in DMF (300 mL) was added NBS (12.17 g, 68.39 mmol) in one portion at 0° C. The mixture was stirred at 0° C. for 5 min. Upon completion, the reaction mixture was quenched by the addition of aq. $Na_2SO_3$ (60 mL), which caused the product to crash out as a white solid. The solid was filtered and the filter cake was dried under reduced pressure to afford 5-bromo-6-methyl-imidazo[1,5-a]pyrazin-8-ol (11.1 g. 72.6% yield) as a white solid. $^1$H NMR (400 MHz, DMSO-d6) δ ppm 11.13 (br s, 1H) 8.28 (s, 1H) 7.88 (s, 1H) 2.18 (s, 3H).

Step 4.

To a solution of 5-bromo-6-methyl-imidazo[1,5-a]pyrazin-8-ol (8.9 g, 39.03 mmol) was added $POCl_3$ (146.85 g, 957.73 mmol, 89 mL) in one portion at 25° C. under a positive pressure of nitrogen. The mixture was heated to 120° C. and stirred for 45 minutes at 120° C. Upon completion, the excess $POCl_3$ was removed under reduced pressure. The mixture was then quenched with sat.aq. $NaHCO_3$ (100 mL) to remove any remaining $POCl_3$. The resulting mixture was poured into water (300 mL) and stirred for 2 min. The aqueous phase was extracted with EtOAc and the combined organic layers were washed with water and concentrated under reduced pressure. The resulting residue was purified by column chromatography to afford 5-bromo-8-chloro-6-methyl-imidazo[1,5-a]pyrazine (7.8 g, 78.24% yield) as a yellow solid. $^1$H NMR (400 MHZ, methanol-d4) δ ppm 8.63 (s, 1H) 7.97 (s, 1H) 2.53 (s, 3H) LCMS: m/z: [M+H] calculated for $C_7H_6BrClN_3$:245.94; found 245.90.

Step 5.

5-bromo-8-chloro-6-methylimidazo[1,5-a]pyrazine (450 mg, 1.82 mmol) was added to a flask containing 2-methyl-N-((3S,4S)-3-methyl-2-oxa-8-azaspiro[4.5]decan-4-yl) propane-2-sulfinamide (842 mg, 2.18 mmol) and DMA (9.09 mL), followed by DIEA (1.58 mL, 9.10 mmol). The mixture was stirred at 130° C. for 20 min, at which point LCMS indicated almost complete conversion to product. The solvent was removed under reduced pressure and the residue was partitioned between water/$NH_4OH$ and EtOAc. The phases were separated and the aqueous phase was extracted with EtOAc. The combined organic phases were dried over $MgSO_4$ and the solvent was removed under reduced pressure. The crude residue was purified by silica gel chromatography to give N-[(3S,4S)-8-{5-bromo-6-methylimidazo[1,5-a]pyrazin-8-yl}-3-methyl-2-oxa-8-azaspiro[4.5]decan-4-yl]-2-methylpropane-2-sulfinamide (364 mg, 41.3%) as a yellow oil. LC-MS (ESI): m/z: [M+H] calculated for $C_{16}H_{22}BrN_5O$: 380.1; found 380.1.

Step 6.

N-[(3S,4S)-8-{5-bromo-6-methylimidazo[1,5-a]pyrazin-8-yl}-3-methyl-2-oxa-8-azaspiro[4.5]decan-4-yl]-2-methylpropane-2-sulfinamide (90 mg, 185 μmol), [1,1'-Bis(diphenylphosphino) ferrocene]dichloropalladium (II) complex with DCM (30.2 mg, 37.0 μmol), $K_2CO_3$ (102 mg, 740 μmol) and (3-chlorophenyl) boronic acid (37 mg, 240 μmol) were weighed into a 2 dram vial equipped with a screw cap septum and a stirbar. The reaction vessel was flushed 3 times with $N_2$. ACN (1.84 mL, degassed by purging with $N_2$ for 1 h) was added against $N_2$ and the headspace of the reaction vessel was flushed 3 times with $N_2$. The mixture was placed into a heating block preheated at 105° C. and stirred vigorously for 1.5 hrs. The mixture was filtered over celite, evaporated to dryness and redissolved in MeOH (4 mL). HCl (4 N in dioxane, 2 mL) was added and the mixture was stirred at room temperature for 10 min. The solvent was removed under reduced pressure and the crude product was purified by preparative HPLC to give (3S,4S)-8-[5-(3-chlorophenyl)-6-methylimidazo[1,5-a]pyrazin-8-yl]-3-methyl-2-oxa-8-azaspiro[4.5]decan-4-amine (22.1 mg, 53.6 μmol, 29%) as a white solid. $^1$H NMR (500 MHZ, methanol-d4) δ 8.56 (s, 1H), 7.81 (s, 1H), 7.69 (s, 1H), 7.65-7.56 (m, 2H), 7.52 (td, J=1.7, 0.6 Hz, 1H), 7.42 (dt, J=7.0, 1.7 Hz, 1H), 4.45-4.35 (m, 2H), 4.35-4.30 (m, 1H), 4.00 (d, J=9.0 Hz, 1H), 3.89 (d, J=9.0 Hz, 1H), 3.48 (ddd, J=13.8, 10.4, 3.5 Hz, 1H), 3.40 (ddd, J=13.8, 10.9, 2.9 Hz, 1H), 3.35-3.33 (m, 1H), 2.12 (s, 3H), 2.00-1.86 (m, 3H), 1.77 (d, J=13.2 Hz, 1H), 1.32 (d, J=6.5 Hz, 3H); LC-MS (ESI): m/z [M+H] calculated for $C_{22}H_{26}ClN_5O$: 412.2; found 412.3.

Example 12. Synthesis of (3S,4S)-8-(5-(3-chloro-2-fluorophenyl)-6-methylimidazo[1,5-a]pyrazin-8-yl)-3-methyl-2-oxa-8-azaspiro[4.5]decan-4-amine

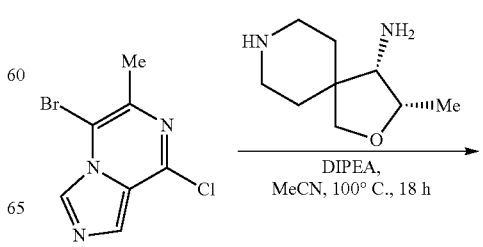

-continued

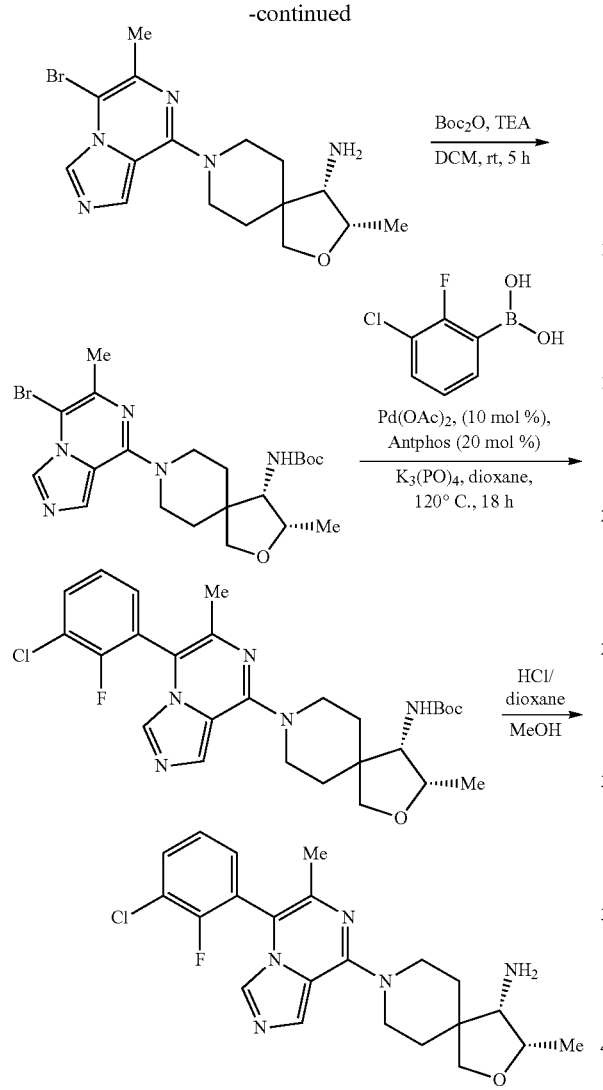

Step 1.

5-bromo-8-chloro-6-methylimidazo[1,5-a]pyrazine (850 mg, 3.44 mmol) and N-[(3S,4S)-8-chloro-3-methyl-2-oxa-8-azaspiro[4.5]decan-4-yl]chloranamine (903 mg, 3.78 mmol) were suspended in ACN (17.2 mL) and DIPEA (2.97 mL, 17.2 mmol) was added. The mixture was heated to 100° C. in a sealed 40 mL vial. The solvent was removed under reduced pressure and the crude residue was purified by column chromatography to give (3S,4S)-8-(5-bromo-6-methylimidazo[1,5-a]pyrazin-8-yl)-3-methyl-2-oxa-8-azaspiro[4.5]decan-4-amine (1.20 g, 92.3%). LCMS (ESI): m/z [M+H] calculated for $C_{16}H_{22}BrN_5O$: 380.1; found 380.1.

Step 2.

(3S,4S)-8-(5-bromo-6-methylimidazo[1,5-a]pyrazin-8-yl)-3-methyl-2-oxa-8-azaspiro[4.5]decan-4-amine (465 mg, 1.21 mmol) was dissolved in DCM (3.10 mL) and Boc₂O (414 µL, 1.81 mmol) was added, followed by TEA (250 µL, 1.81 mmol). The reaction was stirred at room temperature for 5 hrs and then concentrated under reduced pressure. The crude residue was purified by column chromatography to give 244 mg (42%) of tert-butyl ((3S,4S)-8-(5-bromo-6-methylimidazo[1,5-a]pyrazin-8-yl)-3-methyl-2-oxa-8-azaspiro[4.5]decan-4-yl) carbamate. LCMS (ESI): m/z [M+H] calculated for $C_{21}H_{30}BrN_5O_3$:480.1; found 480.2.

Step 3.

To a vial was added tert-butyl ((3S,4S)-8-(5-bromo-6-methylimidazo[1,5-a]pyrazin-8-yl)-3-methyl-2-oxa-8-azaspiro[4.5]decan-4-yl) carbamate (60 mg, 124 µmol), (3-chloro-2-fluorophenyl) boronic acid (25.8 mg, 148 µmol), Antphos (9.18 mg. 24.8 µmol), Pd(OAc) 2 (2.78 mg, 12.4 µmol) and $K_3(PO)_4$ (78.9 mg, 372 µmol). The mixture was evacuated under house vacuum for 10 min before adding in degassed dioxane (1.24 mL). The resulting mixture was filled with $N_2$ and evacuated three times before stirring at 125° C. overnight in the capped vial. The resulting reaction mixture was filtered through a pad of celite with DCM and MeOH. The filtrate was concentrated under reduced pressure and the residue was purified by column chromatography using 10% MeOH/DCM to yield tert-butyl ((3S,4S)-8-(5-(3-chloro-2-fluorophenyl)-6-methylimidazo[1,5-a]pyrazin-8-yl)-3-methyl-2-oxa-8-azaspiro[4.5]decan-4-yl) carbamate. LCMS (ESI): m/z [M+H] calculated for $C_{27}H_{34}ClFN_5O_3$:530.2; found 530.2.

Step 4.

To a solution tert-butyl ((3S,4S)-8-(5-(3-chloro-2-fluorophenyl)-6-methylimidazo[1,5-a]pyrazin-8-yl)-3-methyl-2-oxa-8-azaspiro[4.5]decan-4-yl) carbamate (28 mg, 52.8 µmol) in MeOH (264 µL) was added 4 M HCl in dioxane (132 µL, 528 µmol). The reaction mixture was stirred at 40° C. for 2 hrs. The resulting reaction mixture was concentrated under reduced pressure and the residue was purified by prep HPLC to yield (3S,4S)-8-(5-(3-chloro-2-fluorophenyl)-6-methylimidazo[1,5-a]pyrazin-8-yl)-3-methyl-2-oxa-8-azaspiro[4.5]decan-4-amine (3.0 mg, 13.2%) as the formic acid salt. $^1$H NMR (500 MHz, Methanol-d4) δ 8.56 (s, 3H), 7.83 (s, 1H), 7.76-7.66 (m, 2H), 7.50-7.38 (m, 2H), 4.91 (s, 1H), 4.83 (d, J=1.8 Hz, 1H), 4.44-4.24 (m, 1H), 3.96 (d, J=8.9 Hz, 1H), 3.82 (d, J=8.8 Hz, 1H), 3.63-3.43 (m, 2H), 3.17 (d, J=4.7 Hz, 1H), 2.10 (s, 3H), 2.01-1.87 (m, 1H), 1.79 (dd, J=36.5, 14.2 Hz, 3H), 1.28 (d, J=6.5 Hz, 3H). LCMS (ESI): m/z [M+H] calculated for $C_{22}H_{26}ClFN_5O$: 430.2; found 430.1.

Example 13. Synthesis of (3S,4S)-8-{5-[(2-amino-3-chloropyridin-4-yl)sulfanyl]-6-methylimidazo[1,5-a]pyrazin-8-yl}-3-methyl-2-oxa-8-azaspiro[4.5]decan-4-amine

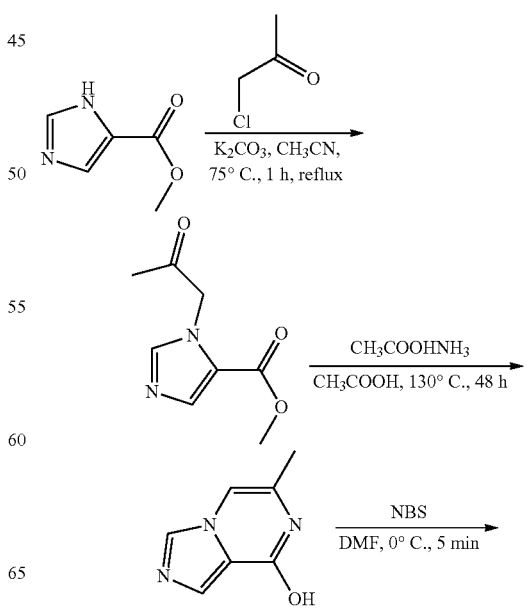

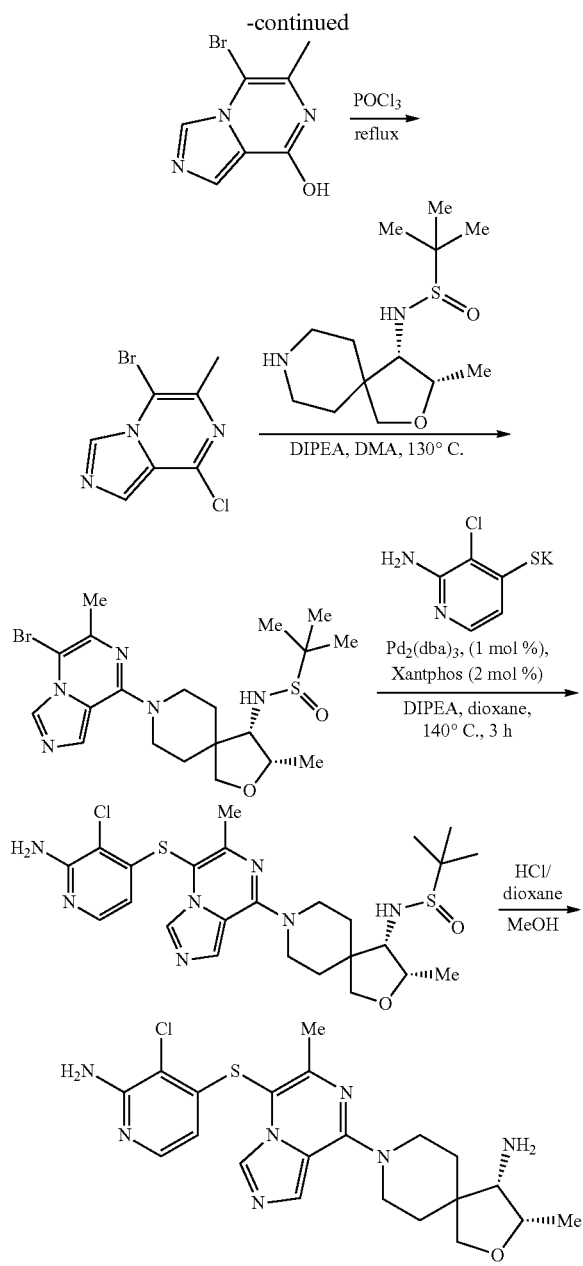

Step 1.

To a solution of methyl 1H-imidazole-5-carboxylate (96 g, 761.22 mmol) and 1-chloropropan-2-one (105.65 g, 1.14 mol) in ACN (2 L) was added $K_2CO_3$ (210.41 g, 1.52 mol) in one portion at 75° C. The mixture was stirred at 75° C. for 1 hr. Upon completion, the reaction mixture was filtered and the filtrate was evaporated under reduced pressure. The remaining residue was triturated with EtOAc (500 mL) and filtered. The resulting filtrate was concentrated under reduced pressure to afford methyl 3-acetonylimidazole-4-carboxylate (144 g, 41.54% yield) as a yellow solid. LCMS: m/z [M+H] calculated for $C_8H_{11}N_2O_3$:183.07; found 183.3.

Step 2.

To a solution of methyl 3-acetonylimidazole-4-carboxylate (130 g, 713.59 mmol) in $CH_3COOH$ (700 mL) was added $CH_3COOHNH_3$ (275.03 g, 3.57 mol) in one portion at 130° C. The reaction mixture was stirred at 130° C. for 48 hrs. Upon completion, the mixture was concentrated under reduced pressure, and the resulting residue was purified by reverse-phase column chromatography to afford 6-methyl-imidazo[1,5-a]pyrazin-8-ol (40 g, 32.3% yield) as a yellow solid. LCMS: m/z: [M+H] calculated for $C_8H_{11}N_2O_3$: 150.06; found 150.02.

Step 3.

To a solution of 6-methylimidazo[1,5-a]pyrazin-8-ol (10 g, 67.05 mmol) in DMF (300 mL) was added NBS (12.17 g, 68.39 mmol) in one portion at 0° C. The mixture was stirred at 0° C. for 5 min. Upon completion, the reaction mixture was quenched by the addition of aq. $Na_2SO_3$ (60 mL), which caused the product to crash out as a white solid. The solid was filtered and the filter cake was dried under reduced pressure to afford 5-bromo-6-methyl-imidazo[1,5-a]pyrazin-8-ol (11.1 g, 72.6% yield) as a white solid. $^1$H NMR (400 MHz, DMSO-d6) δ ppm 11.13 (br s, 1H) 8.28 (s, 1H) 7.88 (s, 1H) 2.18 (s, 3H).

Step 4.

To a solution of 5-bromo-6-methyl-imidazo[1,5-a]pyrazin-8-ol (8.9 g, 39.03 mmol) was added $POCl_3$ (146.85 g, 957.73 mmol, 89 mL) in one portion at 25° C. under a positive pressure of nitrogen. The mixture was heated to 120° C. and stirred for 45 minutes at 120° C. Upon completion, the excess $POCl_3$ was removed under reduced pressure. The mixture was then quenched with sat.aq. $NaHCO_3$ (100 mL) to remove any remaining $POCl_3$. The resulting mixture was poured into water (300 mL) and stirred for 2 min. The aqueous phase was extracted with EtOAc and the combined organic layers were washed with water and concentrated under reduced pressure. The resulting residue was purified by column chromatography to afford 5-bromo-8-chloro-6-methyl-imidazo[1,5-a]pyrazine (7.8 g, 78.24% yield) as a yellow solid. $^1$H NMR (400 MHZ, Methanol-d4) δ ppm 8.63 (s, 1H) 7.97 (s, 1H) 2.53 (s, 3H) LCMS: m/z: [M+H] calculated for $C_7H_6BrClN_3$:245.94; found 245.90.

Step 5.

To a solution of 5-bromo-8-chloro-6-methylimidazo[1,5-a]pyrazine (450 mg, 1.82 mmol) and 2-methyl-N-((3S,4S)-3-methyl-2-oxa-8-azaspiro[4.5]decan-4-yl) propane-2-sulfinamide (842 mg, 2.18 mmol) in DMA (9.09 mL) was added DIEA (1.58 mL, 9.10 mmol). The resultant reaction mixture was stirred at 130° C. for 20 min. The reaction mixture was concentrated under reduced pressure and the remaining residue was partitioned between water/$NH_4OH$ and EtOAc. The phases were separated and the aqueous phase was extracted with EtOAc. The combined organic phases were dried over $MgSO_4$ and the solvent was removed under reduced pressure. The crude residue was purified by silica gel chromatography to afford N-[(3S,4S)-8-{5-bromo-6-methylimidazo[1,5-a]pyrazin-8-yl}-3-methyl-2-oxa-8-azaspiro[4.5]decan-4-yl]-2-methylpropane-2-sulfinamide (364 mg, 41.3%) as a yellow oil. LC-MS (ESI): m/z: [M+H] calculated for $C_{16}H_{22}BrN_5O$: 380.1; found 380.1.

Step 6.

A vial was charged with N-((3S,4S)-8-(5-bromoimidazo[1,5-a]pyrazin-8-yl)-3-methyl-2-oxa-8-azaspiro[4.5]decan-4-yl)-2-methylpropane-2-sulfinamide (60 mg, 123 µmol), potassium 2-amino-3-chloropyridine-4-thiolate (36.5 mg, 184 µmol) $Pd_2(dba)_3$ (6.74 mg, 7.37 µmol), Xantphos (7.05 mg, 12.2 µmol), and DIPEA (64.1 µL, 369 µmol). The reaction vial was evacuated and purged with $N_2$ three times. Dioxane was added and the solution was stirred at 140° C. for 3 hrs. The resultant mixture was filtered and the filtrate was concentrated under reduced pressure. The resulting residue was purified by column chromatography (0-10% MeOH/DCM) to afford N-((3S,4S)-8-(5-((2-amino-3-chloropyridin-4-yl)thio)-6-methylimidazo[1,5-a]pyrazin-8-yl)-

3-methyl-2-oxa-8-azaspiro[4.5]decan-4-yl)-2-methylpropane-2-sulfinamide. LCMS (ESI): m/z [M+H] calculated for $C_{25}H_{35}ClN_7O_2S_2$:564.2; found 564.5.

Step 7.

To a solution of N-((3S,4S)-8-(5-((2-amino-3-chloropyridin-4-yl)thio)-6-methylimidazo[1,5-a]pyrazin-8-yl)-3-methyl-2-oxa-8-azaspiro[4.5]decan-4-yl)-2-methylpropane-2-sulfinamide (100 mg, 177 µmol) in MeOH (1.76 mL) was added 4 M HCl (440 µL, 1.76 mmol) in dioxane. The reaction mixture was stirred at 35° C. for 1 hr. The resulting reaction mixture was concentrated under reduced pressure and the resulting residue was purified by prep HPLC to afford (3S,4S)-8-{5-[(2-amino-3-chloropyridin-4-yl)sulfanyl]-6-methylimidazo[1,5-a]pyrazin-8-yl}-3-methyl-2-oxa-8-azaspiro[4.5]decan-4-amine (20.0 mg, 24.5%) as the formic acid salt. $^1$H NMR (500 MHZ, methanol-d4) δ 8.53 (s, 1H), 8.21 (s, 1H), 7.91 (s, 1H), 7.57 (d, J=5.6 Hz, 1H), 5.82 (d, J=5.5 Hz, 1H), 4.61-4.44 (m, 3H), 4.36-4.25 (m, 1H), 3.99 (d. J=9.0 Hz, 1H), 3.87 (d, J=9.0 Hz, 1H), 3.55 (dddd, J=38.4, 13.8, 10.1, 3.8 Hz, 2H), 2.44 (d, J=1.9 Hz, 3H), 2.01-1.84 (m, 3H), 1.77 (d, J=13.8 Hz, 1H), 1.30 (d, J=6.5 Hz, 3H). LCMS (ESI): m/z: [M+H] calculated for $C_{21}H_{27}ClN_7OS$: 460.2; found 460.5.

Example 14. Synthesis of 1-[7-(2,3-dichlorophenyl)-[1,2,5]thiadiazolo[3,4-c]pyridin-4-yl]-4-methylpiperidin-4-amine

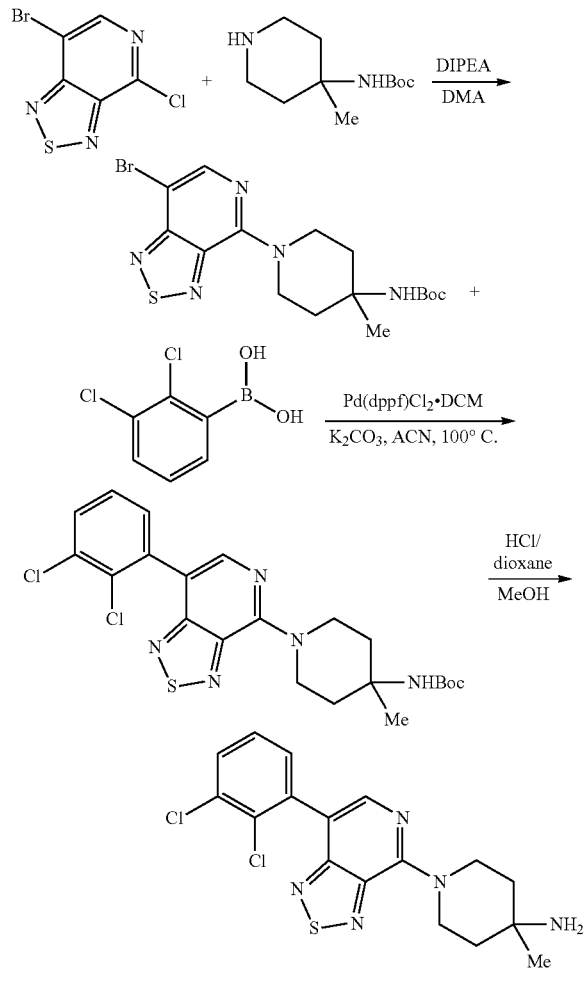

Step 1.

To a solution of 7-bromo-4-chloro-[1,2,5]thiadiazolo[3,4-c]pyridine (160 mg, 638 µmol) in DMA (3.18 mL) was added tert-butyl (4-methylpiperidin-4-yl) carbamate (409 mg, 1.91 mmol) and DIPEA (555 µL, 3.19 mmol). The reaction mixture was stirred in a capped vial at 100° C. for 1 hr. The resulting reaction mixture was concentrated under reduced pressure, removing as much of the DMA as possible. The residue was purified by column chromatography using 0-10% MeOH/DCM to yield the desired product tert-butyl (1-(7-bromo-[1,2,5]thiadiazolo[3,4-c]pyridin-4-yl)-4-methylpiperidin-4-yl) carbamate. LCMS (ESI): m/z [M+H] calculated for $C_{16}H_{22}BrN_5O_2S$: 427.07; found 427.9.

Step 2.

To a vial was added tert-butyl (1-(7-bromo-[1,2,5]thiadiazolo[3,4-c]pyridin-4-yl)-4-methylpiperidin-4-yl) carbamate (60 mg, 140 µmol), (2,3-dichlorophenyl) boronic acid (40.0 mg, 210 µmol), Pd(dppf)Cl$_2$·DCM (22.8 mg, 28.0 µmol), and K$_2$CO$_3$ (77.3 mg, 560 µmol). The vial was evacuated under house vacuum for 15 min before adding in degassed ACN (1.39 mL). The resulting mixture was filled with N$_2$ and evacuated three times before stirring at 100° C. for overnight in the capped vial. The resulting reaction mixture was filtered through a pad of celite. The filtrate was concentrated under reduced pressure and the residue was purified by column chromatography using 0-10% MeOH/DCM to yield the desired product tert-butyl (1-(7-(2,3-dichlorophenyl)-[1,2,5]thiadiazolo[3,4-c]pyridin-4-yl)-4-methylpiperidin-4-yl) carbamate. LCMS (ESI): m/z [M+H] calculated for $C_{22}H_{25}Cl_2N_5O_2S$: 493.11; found 493.9.

Step 3.

To a solution of tert-butyl (1-(7-(2,3-dichlorophenyl)-[1,2,5]thiadiazolo[3,4-c]pyridin-4-yl)-4-methylpiperidin-4-yl) carbamate (69 mg, 139 µmol) in methanol (1.38 mL) was added 4 M HCl in dioxane (347 µL, 1.39 mmol). The reaction was stirred in a capped vial at 35° C. for 1 hr. The resulting reaction mixture was concentrated under reduced pressure and the residue was purified by prep HPLC using 5-35% ACN+0.1% formic acid/H$_2$O+0.1% formic acid to yield the desired product 1-(7-(2,3-dichlorophenyl)-[1,2,5]thiadiazolo[3,4-c]pyridin-4-yl)-4-methylpiperidin-4-amine (30.0 mg, 54.7%) as the formic acid salt. $^1$H NMR (500 MHZ, methanol-d4) δ 8.54 (s, 2H), 8.00 (s, 1H), 7.63 (dd, J=7.3, 2.2 Hz, 1H), 7.48-7.31 (m, 2H), 4.01-3.83 (m, 4H), 1.97 (t, J=4.9 Hz, 4H), 1.57 (s, 3H). LCMS (ESI): m/z [M+H] calculated for $C_{17}H_{18}Cl_2N_5S$: 394.1; found 394.1.

Example 15. Synthesis of 4-((4-(4-amino-4-methylpiperidin-1-yl)-[1,2,5]thiadiazolo[3,4-c]pyridin-7-yl)thio)-3-chloropyridin-2-amine

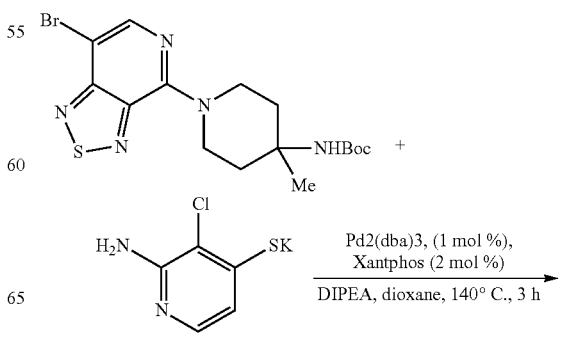

-continued

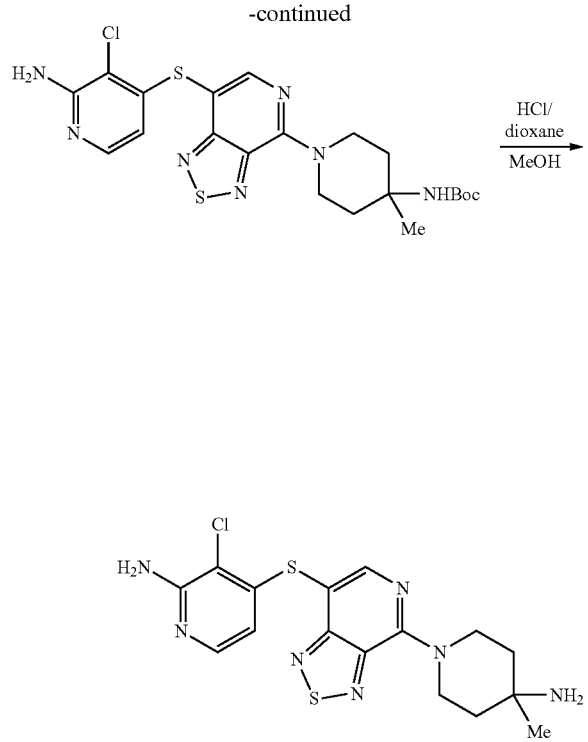

Step 1.

To a microwave vial was added tert-butyl (1-(7-bromo-[1,2,5]thiadiazolo[3,4-c]pyridin-4-yl)-4-methylpiperidin-4-yl) carbamate (60 mg, 140 µmol), 3-chloro-4-(potassiosulfanyl)pyridin-2-amine (36.5 mg, 184 µmol), potassium 2-amino-3-chloropyridine-4-thiolate (41.7 mg, 210 µmol), Pd$_2$(dba)$_3$ (12.8 mg, 14.0 µmol), Xantphos (16.2 mg, 28.0 µmol), and DIPEA (73.0 µL, 420 µmol). The mixture was degassed and degassed dioxane (1.39 mL) was added. The reaction vial was evacuated and purged with N$_2$ three times before stirring under microwave conditions at 140° C. for 3 hrs. The mixture was filtered through a pad of celite washing with DCM and MeOH. The filtrate was concentrated under reduced pressure and the residue was purified by column chromatography o yield the desired product tert-butyl (1-(7-((2-amino-3-chloropyridin-4-yl)thio)-[1,2,5]thiadiazolo[3,4-c]pyridin-4-yl)-4-methylpiperidin-4-yl) carbamate. LCMS (ESI): m/z: [M+H] calculated for C$_{21}$H$_{26}$ClN$_7$O$_2$S$_2$: 507.13; found 508.1.

Step 2.

To a solution of tert-butyl (1-(7-((2-amino-3-chloropyridin-4-yl)thio)-[1,2,5]thiadiazolo[3,4-c]pyridin-4-yl)-4-methylpiperidin-4-yl) carbamate (61 mg, 120 µmol) in methanol (1.20 mL) was added 4 M HCl in dioxane (300 µL, 1.20 mmol). The reaction was stirred in a capped vial at 35° C. for 1 hr. The resulting reaction mixture was concentrated under reduced pressure and the residue was purified by prep HPLC to yield 4-((4-(4-amino-4-methylpiperidin-1-yl)-[1,2,5]thiadiazolo[3,4-c]pyridin-7-yl)thio)-3-chloropyridin-2-amine (40.0 mg, 98.0 µmol, 81.7%) as the formic acid salt. $^1$H NMR (500 MHz, methanol-d4) δ 8.50 (d, J=37.7 Hz, 1H), 8.28 (s, 1H), 7.45 (d, J=5.6 Hz, 1H), 5.80 (d, J=5.5 Hz, 1H), 4.03-3.90 (m, 4H), 2.07-1.87 (m, 4H), 1.57 (d, J=0.9 Hz, 3H). LCMS (ESI): m/z [M+H] calculated for C$_{16}$H$_{19}$ClN$_7$S$_2$:408.1; found 408.2.

Example 16. Synthesis of (3S,4S)-8-{8-[(2-amino-3-chloropyridin-4-yl)sulfanyl]pyrido[4,3-d]pyrimidin-5-yl}-3-methyl-2-oxa-8-azaspiro[4.5]decan-4-amine

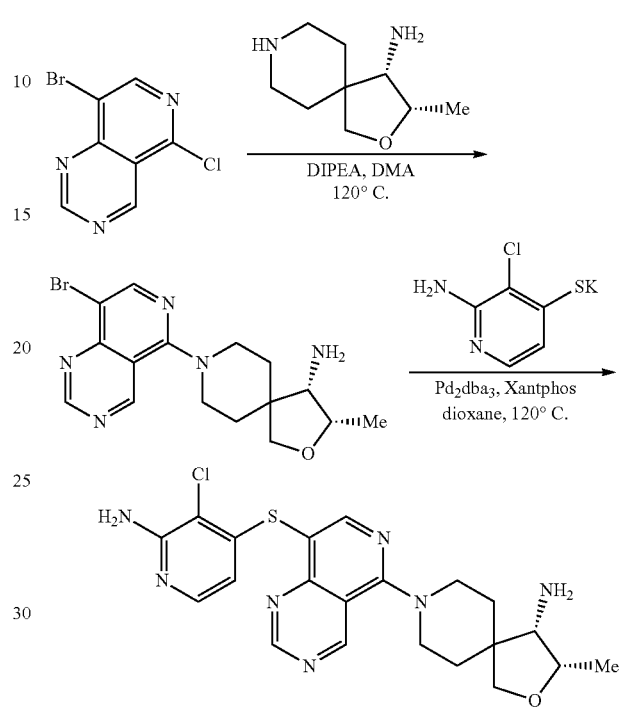

Step 1.

8-bromo-5-chloropyrido[4,3-d]pyrimidine (179 mg, 732 µmol) and (3S,4S)-3-methyl-2-oxa-8-azaspiro[4.5]decan-4-amine (175 mg, 732 µmol) were dissolved in DMA (3.66 mL) and DIPEA (1.27 mL, 7.32 mmol) was added at room temperature. The mixture was heated to 120° C. for 3 hrs. The solvent was removed under reduced pressure and the crude residue was purified by silica gel chromatography to give (3S,4S)-8-{8-bromopyrido[4,3-d]pyrimidin-5-yl}-3-methyl-2-oxa-8-azaspiro[4.5]decan-4-amine (182 mg, 65.9%) as a yellow solid. LC-MS (ESI): m/z [M+H] calculated for C$_{16}$H$_{20}$BrN$_5$O: 379.3; found 379.9.

Step 2.

3-chloro-4-(potassiosulfanyl)pyridin-2-amine (78.6 mg, 396 µmol), (3S,4S)-8-{8-bromopyrido[4,3-d]pyrimidin-5-yl}-3-methyl-2-oxa-8-azaspiro[4.5]decan-4-amine (100 mg, 264 µmol), Xantphos (30.5 mg, 52.8 µmol), Pd$_2$dba$_3$ (24.1 mg, 26.4 µmol) and DIEA (91.7 µL, 528 µmol) were weighed into a microwave vial equipped with a stir bar. The reaction vessel was purged with N$_2$ and dioxane (2.63 mL) was added, followed by DIEA (91.7 µL, 528 µmol). The headspace of the reaction vessel was backfilled 3 times with N$_2$ and the mixture was heated for 2 hrs at 120° C. under microwave irradiation. The resulting mixture was filtered over celite and the solvent was removed under reduced pressure. The crude residue was directly purified by preparative HPLC to give (3S,4S)-8-{8-[(2-amino-3-chloropyridin-4-yl)sulfanyl]pyrido[4,3-d]pyrimidin-5-yl}-3-methyl-2-oxa-8-azaspiro[4.5]decan-4-amine (5.70 mg, 4.75%) as a yellow solid. $^1$H NMR (500 MHZ, Methanol-d4) δ 9.57 (s, 1H), 9.25 (s, 1H), 8.65 (s, 1H), 8.42 (s, 1H), 7.46 (d, J=5.6 Hz, 1H), 5.72 (d, J=5.6 Hz, 1H), 4.38-4.30 (m, 2H), 4.27 (d, J=13.7 Hz, 1H), 4.05 (d, J=9.1 Hz, 1H), 3.94 (d, J=9.1 Hz, 1H), 3.62 (ddd, J=14.0, 11.1, 3.0 Hz, 1H), 3.52 (ddd, J=14.0, 11.3, 2.9 Hz, 1H), 3.49-3.47 (m, 1H), 2.13-2.04 (m, 2H), 1.98 (d, J=13.4 Hz, 1H), 1.83 (d, J=13.3 Hz, 1H), 1.35 (d, J=6.5 Hz, 3H); LC-MS (ESI): m/z: [M+H] calculated for $C_{21}H_{25}ClN_7OS$: 458.1; found 458.5.

Example 17. Synthesis of (1R)-8-[8-(2,3-dichlorophenyl)pyrido[4,3-d]pyrimidin-5-yl]-8-azaspiro[4.5]decan-1-amine

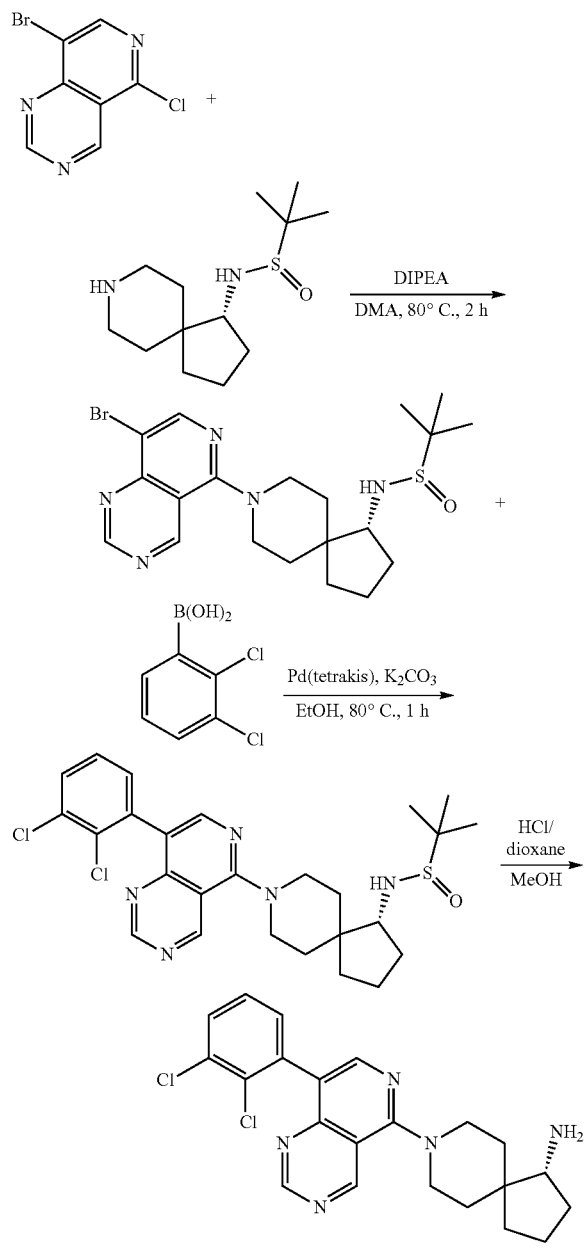

Step 1.

To a solution of 8-bromo-5-chloropyrido[4,3-d]pyrimidine (25 mg, 102 µmol) in DMA (1 mL) was added 2-methyl-N—((R)-8-azaspiro[4.5]decan-1-yl) propane-2-sulfinamide (28.9 mg, 112 µmol) and DIPEA (88.8 µL, 510 µmol). The mixture was capped and stirred at 80° C. for 2 hrs. The reaction was complete according to LCMS. The resulting reaction mixture was diluted with EtOAc and $H_2O$. The organic layer was separated and then washed three more times with $H_2O$. The resulting organic layer was separated, dried over $MgSO_4$, filtered, and concentrated under reduced pressure. The residue was purified by column chromatography using 0-100% EtOAc/heptane to yield the desired product N—((R)-8-(8-bromopyrido[4,3-d]pyrimidin-5-yl)-8-azaspiro[4.5]decan-1-yl)-2-methylpropane-2-sulfinamide (40.0 mg, 84.2%). LCMS (ESI): m/z [M+H] calculated for $C_{20}H_{29}BrN_5OS$: 466.12; found 466.3.

Step 2.

To a reaction vial was added N—((R)-8-(8-bromopyrido[4,3-d]pyrimidin-5-yl)-8-azaspiro[4.5]decan-1-yl)-2-methylpropane-2-sulfinamide (20 mg, 42.8 µmol), (2,3-dichlorophenyl) boronic acid (12.2 mg, 64.1 µmol), potassium carbonate (17.6 mg, 128 µmol), and tetrakis (2.95 mg, 2.56 µmol). The vial was evacuated under high vacuum for 10 min before adding in degassed ethyl alcohol (548 µL). The resulting mixture was purged and evacuated with $N_2$ three times and then stirred at 80° C. for 1 hr. The resulting reaction mixture was filtered through a pad of celite washing with DCM and MeOH. The resulting filtrate was purified by column chromatography to yield N—((R)-8-(8-(2,3-dichlorophenyl)pyrido[4,3-d]pyrimidin-5-yl)-8-azaspiro[4.5]decan-1-yl)-2-methylpropane-2-sulfinamide (11 mg, 48.4%). LCMS (ESI): m/z [M+H] calculated for $C_{27}H_{32}C_{12}N_5OS$: 533.5; found 533.3.

Step 3.

N—((R)-8-(8-(2,3-dichlorophenyl)pyrido[4,3-d]pyrimidin-5-yl)-8-azaspiro[4.5]decan-1-yl)-2-methylpropane-2-sulfinamide (25 mg, 46.9 µmol) was dissolved in MeOH (2 mL) and then added 4 M HCl in dioxane (1 mL, 4.00 mmol). The mixture was stirred in a capped vial for 1 hr. The resulting reaction mixture was concentrated under reduced pressure. The residue was purified by reverse phase chromatography to yield (1R)-8-[8-(2,3-dichlorophenyl)pyrido[4,3-d]pyrimidin-5-yl]-8-azaspiro[4.5]decan-1-amine (8.79 mg, 43.9%) as the formic acid salt. $^1$H NMR (500 MHZ, methanol-d4) δ 9.59 (s, 1H), 9.19 (s, 1H), 8.57 (s, 1H), 8.34 (s, 1H), 7.65 (dd, J=8.0, 1.6 Hz, 1H), 7.42 (t, J=7.8 Hz, 1H), 7.36 (dd, J=7.6, 1.6 Hz, 1H), 4.17 (dd, J=25.8, 13.6 Hz, 3H), 3.51 (d, J=12.9 Hz, 2H), 3.19 (d, J=14.3 Hz, 1H), 2.30-2.12 (m, 1H), 2.10-1.76 (m, 5H), 1.76-1.53 (m, 3H). LCMS (ESI): m/z [M+H] calculated for $C_{22}H_{24}C_{12}N_5$:428.1; found 428.4.

Example 18. Synthesis of (1R)-8-[8-(3-chlorophenyl)pyrido[4,3-d]pyrimidin-5-yl]-8-azaspiro[4.5]decan-1-amine

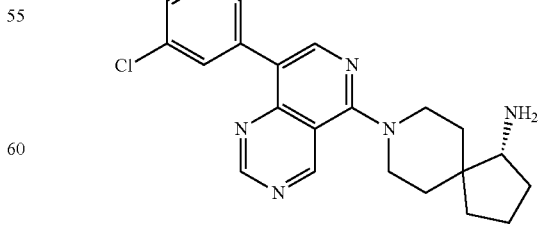

(1R)-8-[8-(3-chlorophenyl)pyrido[4,3-d]pyrimidin-5-yl]-8-azaspiro[4.5]decan-1-amine was synthesized in the manner similar to Example 17, except (2,3-dichlorophenyl)

boronic acid was substituted with (3-chlorophenyl) boronic acid. ¹H NMR (500 MHZ, methanol-d4) δ 9.58 (s, 1H), 9.29 (s, 1H), 8.56 (s, 1H), 8.49 (s, 1H), 7.73 (t, J=1.9 Hz, 1H), 7.59 (dt, J=7.6, 1.4 Hz, 1H), 7.48 (t, J=7.8 Hz, 1H), 7.43 (ddd, J=8.0, 2.1, 1.2 Hz, 1H), 4.18-4.01 (m, 3H), 3.52-3.41 (m, 2H), 3.23 (t, J=7.0 Hz, 1H), 2.29-2.17 (m, 1H), 2.07-1.78 (m, 5H), 1.78-1.53 (m, 3H). LCMS (ESI): m/z [M+H] calculated for $C_{22}H_{25}ClN_5$:394.2; found 394.3.

Example 19. Synthesis of 4-(4-amino-4-methylpiperidin-1-yl)-7-(2,3-dichlorophenyl)-1H,2H,3H-pyrrolo[3,4-c]pyridin-1-one

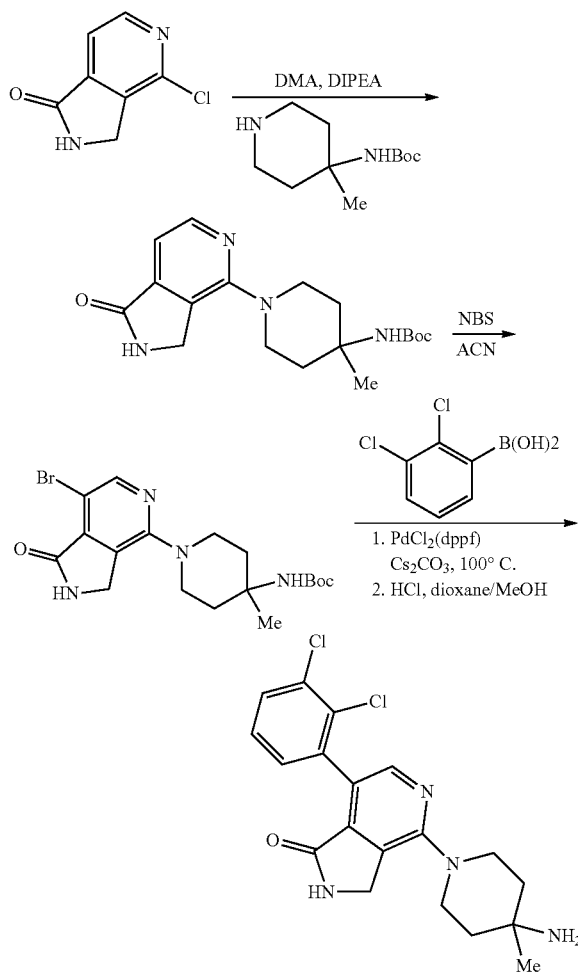

Step 1.

4-chloro-1H,2H,3H-pyrrolo[3,4-c]pyridin-1-one (50 mg, 296 μmol) and tert-butyl N-(4-methylpiperidin-4-yl) carbamate (317 mg, 1.48 mmol) were dissolved in DMA (1.47 mL) and DIPEA (514 μL, 2.96 mmol) was added. The mixture was heated to 110° C. for 4 hrs, the solvent was removed under reduced pressure and the crude residue was purified by silica gel chromatography to give tert-butyl N-(4-methyl-1-{1-oxo-1H,2H,3H-pyrrolo[3,4-c]pyridin-4-yl}piperidin-4-yl) carbamate (72.0 mg, 70.5%) as a brown solid. LC-MS (ESI): m/z [M+H] calculated for $C_{18}H_{26}N_4O_3$:347.2; found 347.5.

Step 2.

tert-Butyl-N-(4-methyl-1-{1-oxo-1H,2H,3H-pyrrolo[3,4-c]pyridin-4-yl}piperidin-4-yl) carbamate (100 mg, 288 μmol) was dissolved in MeCN (1.44 mL) and NBS (56.2 mg, 316 μmol) was added. After stirring for 30 min at room temperature the solvent was removed under reduced pressure and the crude residue was purified by silica gel chromatography to give tert-butyl-N-(1-{7-bromo-1-oxo-1H,2H,3H-pyrrolo[3,4-c]pyridin-4-yl}-4-methylpiperidin-4-yl) carbamate (98.0 mg, 80.3%) as a beige solid. LC-MS (ESI): m/z [M+H] calculated for $C_{18}H_{25}BrN_4O_3$:424.1; found 423.7.

Step 3.

To a solution of tert-butyl-N-(1-{7-bromo-1-oxo-1H,2H,3H-pyrrolo[3,4-c]pyridin-4-yl}-4-methylpiperidin-4-yl) carbamate (80 mg, 0.19 mmol) in dioxane (3 ml) was added (2,3-dichlorophenyl) boronic acid (72 mg, 0.38 mmol) and $PdCl_2$ (dppf) (15 mg, 0.019 mmol). An aqueous solution of $Cs_2CO_3$ (72 mg, 0.38 mmol) in 1 mL of water was added. The reaction was sealed and microwaved at 100° C. for 2 hrs. It was then cooled to room temperature, extracted with EtOAc (3×15 mL). The combined organic layers were combined, washed with brine (5 mL), dried ($MgSO_4$), filtered and concentrated under reduced pressure to provide the desired product as a white solid. The solid was taken up in dioxane (2 mL) and a solution of HCl in dioxane (1 M, 1 mL, excess) was added. The reaction was stirred at room temperature for 2 hrs to give a yellow precipitate, which was filtered and air-dried to furnish the HCl salt of 4-(4-amino-4-methylpiperidin-1-yl)-7-(2,3-dichlorophenyl)-1H,2H,3H-pyrrolo[3,4-c]pyridin-1-one (20 mg, 27%). ¹H NMR (500 MHz, methanol-d4) δ 8.00 (s, 1H), 7.65 (t, J=6.3 Hz, 1H), 7.44-7.34 (m, 2H), 4.16 (s, 1H), 3.79 (s, 1H), 3.37 (s, 2H), 3.32 (s, 3H), 2.18 (s, 1H), 2.12 (d, J=13.2 Hz, 2H), 1.60 (s, 3H); LC-MS (ESI): m/z [M+H] calculated for $C_{19}H_{21}Cl_2N_4O$: 391.1; found 391.3.

Example 20. Synthesis of 7-[(2-amino-3-chloropyridin-4-yl)sulfanyl]-4-(4-amino-4-methylpiperidin-1-yl)-1H,2H,3H-pyrrolo[3,4-c]pyridin-1-one

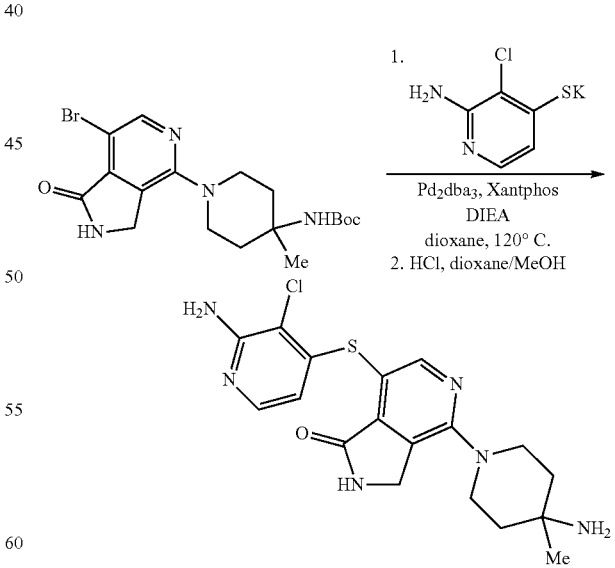

3-Chloro-4-(potassiosulfanyl)pyridin-2-amine (52.4 mg, 264 μmol), tert-butyl N-(1-{7-bromo-1-oxo-1H,2H,3H-pyrrolo[3,4-c]pyridin-4-yl}-4-methylpiperidin-4-yl) carbamate (75 mg, 176 μmol), Xantphos (20.3 mg, 35.2 μmol) and $Pd_2dba_3$ (16.1 mg, 17.6 μmol) were added into a microwave vial. The reaction vessel was purged with N₂ and dioxane (1.75 mL) was added, followed by DIEA (61.1 μL, 352 μmol). The headspace of the reaction vessel was backfilled 3 times with N₂ and the mixture was heated for 2 hrs at 120° C. under microwave irradiation. The crude mixture was cooled to room temperature and filtered over celite. The solvent was removed under reduced pressure and the residue was taken up in MeOH (1 mL). HCl in dioxane (4 M, 0.5 mL) was added and the mixture was stirred at room temperature for 2 h. The solvent was removed under reduced pressure and the product was purified by preparative HPLC to give 4.6 mg (6%) of 7-[(2-amino-3-chloropyridin-4-yl)sulfanyl]-4-(4-amino-4-methylpiperidin-1-yl)-1H,2H,3H-pyrrolo[3,4-c]pyridin-1-one. ¹H NMR (500 MHZ, Methanol-d4) δ 8.30 (d, J=0.7 Hz, 1H), 7.54 (d, J=6.4 Hz, 1H), 5.83 (d, J=5.6 Hz, 1H), 4.64 (s, 2H), 4.18 (dt, J=14.2, 4.6 Hz, 2H), 3.58-3.45 (m, 2H), 1.97-1.90 (m, 4H), 1.54 (s, 3H); LC-MS (ESI): m/z [M+H] calculated for $C_{18}H_{22}ClN_6OS$: 405.1; found 405.3.

Example 21. Synthesis of 1-{1-[5-(2,3-dichlorophenyl)-6-methylimidazo[1,2-a]pyrazin-8-yl]-4-methylpiperidin-4-yl}methanamine

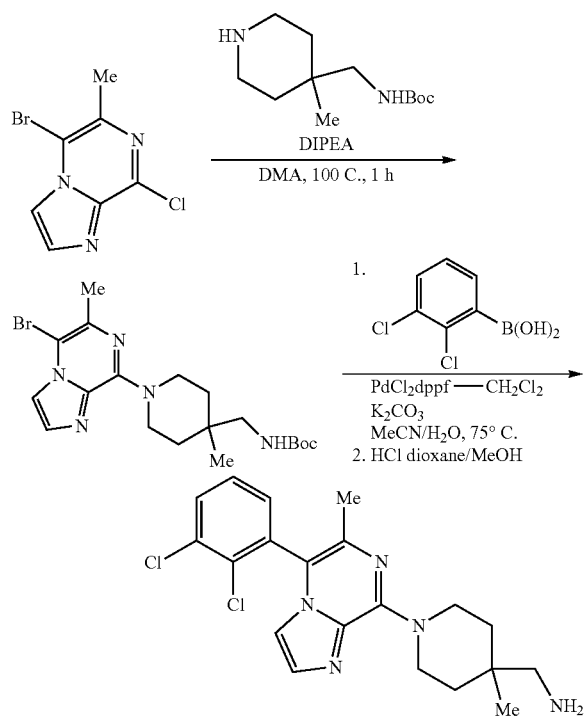

Step 1.
To a solution of 5-bromo-8-chloro-6-methylimidazo[1,2-a]pyrazine (500 mg, 2.02 mmol) in DMA (10.1 mL) was added tert-butyl N-[(1-chloro-4-methylpiperidin-4-yl)methyl]carbamate (583 mg, 2.21 mmol) and DIPEA (1.75 mL, 10.1 mmol). The reaction mixture was stirred in a capped vial at 100° C. for 1 hr. The resulting reaction mixture was concentrated under reduced pressure. The residue was purified by column chromatography to yield tert-butyl N-[(1-{5-bromo-6-methylimidazo[1,2-a]pyrazin-8-yl}-4-methylpiperidin-4-yl)methyl]carbamate (580 mg, 65%) LCMS (ESI): m/z [M+H] calculated for $C_{19}H_{29}BrN_5O_2$:438.1; found 438.4.

Step 2.
To a vial was added (2,3-dichlorophenyl) boronic acid (121 mg, 638 μmol), (2,3-dichlorophenyl) boronic acid (121 mg, 638 μmol), AntPhos (34 mg, 91.2 μmol), K₃PO₄ (288 mg, 1.36 mmol) and Pd(OAc) 2 (10 mg, 45.6 μmol). The mixture was evacuated under house vacuum for 10 min before adding in degassed dioxane (4.56 mL). The resulting mixture was filled with N₂ and degassed three times before stirring at 110° C. for 2 hrs. The resulting reaction mixture was filtered through a pad of celite washing with DCM and MeOH. The filtrate was concentrated under reduced pressure and the residue was taken up in MeOH (2 mL). HCl (4 M in dioxane, 1 mL) was added and the mixture was stirred at room temperature for 2 h. The solvent was removed under reduced pressure and the crude residue was purified by preparative HPLC to give 1-{1-[5-(2,3-dichlorophenyl)-6-methylimidazo[1,2-a]pyrazin-8-yl]-4-methylpiperidin-4-yl}methanamine (4.40 mg, 2.39%) as a colorless solid. ¹H NMR (500 MHZ, Methanol-d4) δ 8.57 (s, 1H), 7.79 (dd, J=8.1, 1.6 Hz, 1H), 7.58-7.52 (m, 1H), 7.49 (d. J=1.3 Hz, 1H), 7.45 (dd, J=7.7, 1.6 Hz, 1H), 7.03 (d, J=1.2 Hz, 1H), 4.85-4.76 (m, 2H), 3.80 (dtd, J=13.6, 10.3, 3.2 Hz, 2H), 2.92 (s, 2H), 2.11 (s, 3H), 1.72 (ddt, J=13.4, 10.1, 3.7 Hz, 2H), 1.67-1.55 (m, 2H), 1.24 (s, 3H); LC-MS (ESI): m/z [M+H] calculated for $C_{20}H_{24}Cl_2N_5$: 404.1; found 404.1.

Example 22. Synthesis of (3S,4S)-8-[7-(2,3-dichlorophenyl)-6-methylpyrazolo[1,5-a]pyrazin-4-yl]-3-methyl-2-oxa-8-azaspiro[4.5]decan-4-amine

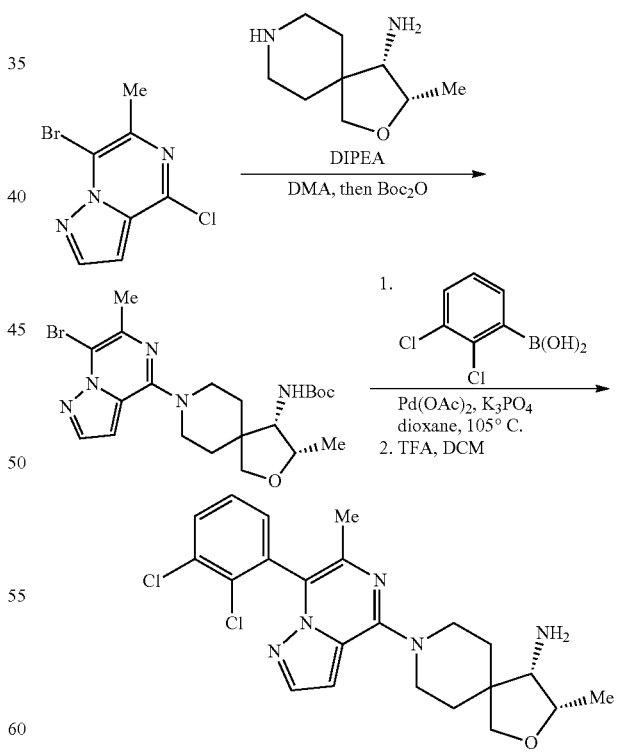

Step 1.
A 20 mL vial was charged with 7-bromo-4-chloro-6-methylpyrazolo[1,5-a]pyrazine (300 mg, 1.21 mmol), N-[(3S,4S)-8-chloro-3-methyl-2-oxa-8-azaspiro[4.5]decan-4-yl]chloranamine (352 mg, 1.45 mmol), DMA (6 mL), and N,N-diisopropylethylamine (1.05 mL, 6.04 mmol), sequentially. The flask was then sealed and warmed to 85° C. After stirring for 16 hrs, the reaction was cooled to room temperature and di-tert-butyl dicarbonate (1.05 g, 4.84 mmol) was added in one portion. After stirring for 1 hr, the reaction mixture was diluted with ethyl acetate (30 mL) and water (10 mL), and the layers were separated. The organic solution was then washed with water (10 mL), half-saturated aqueous sodium chloride (10 mL), and saturated aqueous sodium chloride (10 mL) sequentially. The organic solution was then dried over sodium sulfate. The dried solution was filtered, and the filtrate was concentrated to give an orange oil. This crude oil was purified by column chromatography to give tert-butyl N-[(3S,4S)-8-{7-bromo-6-methylpyrazolo[1,5-a]pyrazin-4-yl}-3-methyl-2-oxa-8-azaspiro[4.5]decan-4-yl]carbamate (475.7 mg, 82% yield) as a pale pink foam. LC-MS (ESI): m/z: [M+H] calculated for $C_{21}H_{31}BrN_5O_3$: 480.1; found 480.0.

Step 2.

A 20 mL vial was charged with tert-butyl N-[(3S,4S)-8-{7-bromo-6-methylpyrazolo[1,5-a]pyrazin-4-yl}-3-methyl-2-oxa-8-azaspiro[4.5]decan-4-yl]carbamate (200 mg, 0.4 mmol), (2,3-dichlorophenyl) boronic acid (95.3 mg, 0.5 mmol), tripotassium phosphate (263 mg, 1.24 mmol), 4-(anthracen-9-yl)-3-tert-butyl-2,3-dihydro-1,3-benzoxaphosphole (30.8 mg, 0.08 mmol), and degassed dioxane (4 mL). The resulting slurry was then degassed for 10 min before palladium (II) acetate (9.34 mg, 0.04 mmol) was added, and the orange mixture was degassed for an additional 5 min. After this time, the vial was sealed and warmed to 105° C. After stirring for 2 hrs, the reaction was filtered through a short pad of celite, and the filtrate was then concentrated under reduced pressure. The crude residue obtained was purified by column chromatography to give tert-butyl N-[(3S,4S)-8-[7-(2,3-dichlorophenyl)-6-methylpyrazolo[1,5-a]pyrazin-4-yl]-3-methyl-2-oxa-8-azaspiro[4.5]decan-4-yl]carbamate as an impure orange oil. This oil was carried into the next step without further manipulation. LC-MS (ESI): m/z [M+H] calculated for $C_{27}H_{34}Cl_2N_5O_3$:546.2; found 546.1.

Step 3.

A 20 mL vial was charged with tert-butyl N-[(3S,4S)-8-[7-(2,3-dichlorophenyl)-6-methylpyrazolo[1,5-a]pyrazin-4-yl]-3-methyl-2-oxa-8-azaspiro[4.5]decan-4-yl]carbamate (227 mg, 0.4 mmol), DCM (2 mL), and TFA (0.5 mL), sequentially, at room temperature. The resulting yellow solution was left to stir for 1 hr before the reaction mixture was concentrated under reduced pressure to give an orange residue. This crude material was purified by preparative HPLC to give (3S,4S)-8-[7-(2,3-dichlorophenyl)-6-methylpyrazolo[1,5-a]pyrazin-4-yl]-3-methyl-2-oxa-8-azaspiro[4.5]decan-4-amine (6.9 mg, 3.7% yield) as a fluffy white solid. (3S,4S)-8-[7-(2,3-dichlorophenyl)-6-methylpyrazolo[1,5-a]pyrazin-4-yl]-3-methyl-2-oxa-8-azaspiro[4.5]decan-4-amine as a formate salt. $^1$H NMR (500 MHz, methanol-d4) δ 8.53 (s, 1H), 7.80 (d, J=2.5 Hz, 1H), 7.70 (dd, J=8.1, 1.5 Hz, 1H), 7.46 (t, J=8.1, 7.6 Hz, 1H), 7.36 (dd, J=7.7, 1.5 Hz, 1H), 6.92 (d, J=2.5 Hz, 1H), 4.41-4.26 (m, 3H), 3.99 (d, J=8.9 Hz, 1H), 3.87 (d, J=9.0 Hz, 1H), 3.48-3.34 (m, 2H), 2.13 (s, 3H), 2.02-1.91 (m, 2H), 1.91-1.84 (m, 1H), 1.79-1.73 (m, 1H), 1.30 (d, J=6.5 Hz, 3H). LC-MS (ESI): m/z [M+H] calculated for $C_{22}H_{26}Cl_2N_5O$: 446.1; found 446.4.

Example 23. Synthesis of (3S,4S)-8-[7-(2-chloro-3-methoxyphenyl)-6-methylpyrazolo[1,5-a]pyrazin-4-yl]-3-methyl-2-oxa-8-azaspiro[4.5]decan-4-amine

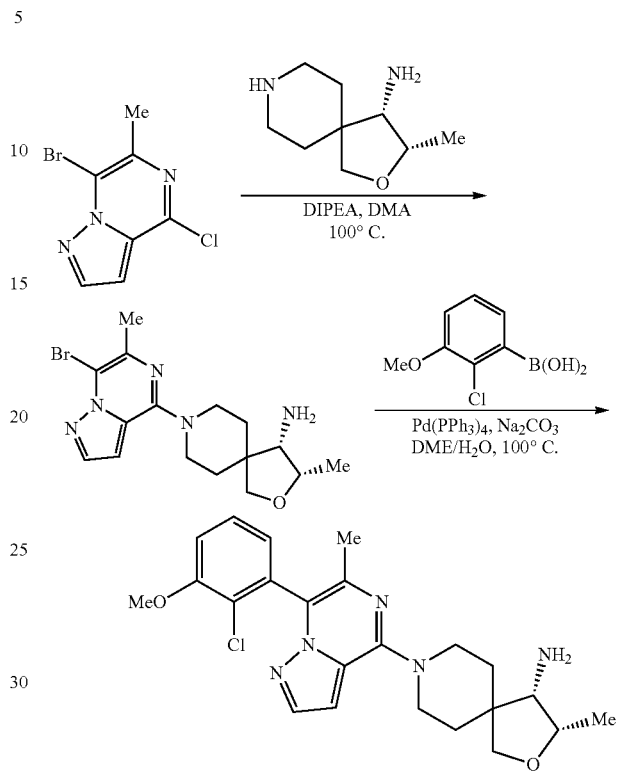

Step 1.

A 20 mL vial was charged with 7-bromo-4-chloro-6-methylpyrazolo[1,5-a]pyrazine (300 mg, 1.2 mmol), N-[(3S,4S)-8-chloro-3-methyl-2-oxa-8-azaspiro[4.5]decan-4-yl] chloranamine (352 mg, 1.5 mmol), DMA (6 mL), and N,N-diisopropylethylamine (1.05 mL, 6.04 mmol), sequentially. The flask was then sealed and warmed to 85° C. After stirring for 16 hrs, the reaction was cooled to room temperature, concentrated under reduced pressure and the resulting residue was purified by column chromatography to give (3S,4S)-8-{8-bromo-7-methylimidazo[1,2-c]pyrimidin-5-yl}-3-methyl-2-oxa-8-azaspiro[4.5]decan-4-amine (360 mg, 78%). LC-MS (ESI): m/z [M+H] calculated for $C_{16}H_{23}BrN_5O$: 380.1; found 380.1.

Step 2.

To a solution of (3S,4S)-8-{8-bromo-7-methylimidazo[1,2-c]pyrimidin-5-yl}-3-methyl-2-oxa-8-azaspiro[4.5]decan-4-amine (75 mg, 0.2 mmol) and (2,3-dichlorophenyl) boronic acid (56 mg, 0.29 mmol) in DME (990 µL) and H$_2$O (197 µL) was added sodium carbonate (42 mg, 0.3944 mmol) then tetrakis(triphenylphosphine) palladium (0) (23 mg, 0.02 mmol) was added to the reaction mixture. The mixture was stirred at 100° C. for 1 hr. After cooling to room temperature the mixture was filtered through a pad of celite and the solvent was removed under reduced pressure. The crude residue was purified by preparative HPLC to give 10 mg (17%) of (3S,4S)-8-[7-(2-chloro-3-methoxyphenyl)-6-methylpyrazolo[1,5-a]pyrazin-4-yl]-3-methyl-2-oxa-8-azaspiro[4.5]decan-4-amine. $^1$H NMR (500 MHZ, methanol-d4) δ 7.76 (d, J=2.5 Hz, 1H), 7.43 (dd, J=8.3, 7.6 Hz, 1H), 7.23 (dd, J=8.4, 1.4 Hz, 1H), 6.97 (dd, J=7.7, 1.4 Hz, 1H), 6.90 (d, J=2.5 Hz, 1H), 4.30-4.17 (m, 2H), 3.96 (s, 3H), 3.92 (d, J=8.7 Hz, 1H), 3.79 (d, J=8.7 Hz, 1H), 3.49 (ddt, J=13.8, 10.3, 3.5 Hz, 1H), 3.46-3.37 (m, 1H), 3.11 (d, J=4.9 Hz, 1H), 2.11 (s, 3H), 1.94 (dddd, J=27.6, 14.1, 10.3, 3.9 Hz, 2H), 1.84-1.69 (m, 2H), 1.25 (d, J=6.5 Hz, 3H); LC-MS (ESI): m/z: [M+H] calculated for $C_{23}H_{29}ClN_5O_2$:442.2; found 442.4.

Example 24. Synthesis of 4-{[4-(4-amino-4-methylpiperidin-1-yl) pyrazolo[1,5-a]pyrazin-7-yl]sulfanyl}-3-chloropyridin-2-amine

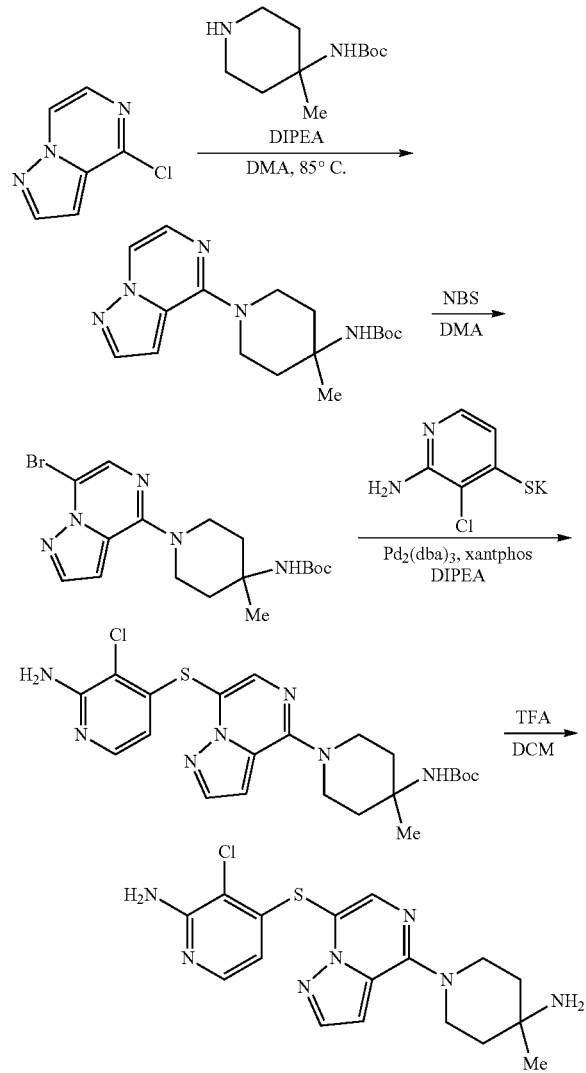

Step 1.

A 4 mL vial was charged with 4-chloropyrazolo[1,5-a]pyrazine (50 mg, 0.3 mmol), tert-butyl N-(4-methylpiperidin-4-yl) carbamate (83 mg, 0.39 mmol), DMA (2 mL), and N,N-diisopropylethylamine (281 µL, 1.6 mmol), sequentially. The flask was then sealed and warmed to 120° C. After 16 hrs, the reaction was diluted with ethyl acetate (10 mL) and water (5 mL). The layers were separated, and the organic phase was washed with water (5 mL) and saturated aqueous sodium chloride (5 mL), sequentially. The washed organic solution was then dried over sodium sulfate. The dried solution was then filtered, and the filtrate was concentrated to give an orange oil. The crude material was purified by column chromatography to give to give tert-butyl N-(4-methyl-1-{pyrazolo[1,5-a]pyrazin-4-yl}piperidin-4-yl) carbamate (101 mg, 94.3% yield) as a pale yellow oil. LC-MS (ESI): m/z [M+H] calculated for $C_{17}H_{26}N_5O_2$:332.2; found 332.0.

Step 2.

A 20 mL vial was charged with tert-butyl N-(4-methyl-1-{pyrazolo[1,5-a]pyrazin-4-yl}piperidin-4-yl) carbamate (101 mg, 0.3 mmol) and DMA (2.54 mL) before it was cooled to 0° C. Once cool, a solution of N-bromosuccinimide (57 mg, 0.3 mmol) in DMA (0.5 mL) was added to the mixture dropwise over 10 min to give a burgandy solution. After 0.5 hr, the reaction was diluted with water (5 mL) and ethyl acetate (10 mL). The biphasic mixture was separated, and the organic solution was washed with water (5 mL) and saturated aqueous sodium chloride (5 mL), sequentially. The combined aqueous washes were then extracted with ethyl acetate (10 mL), and the combined organic solutions were dried over sodium sulfate. The dried solution was filtered, and the filtrate was concentrated to an orange oil that was purified by column chromatography to give tert-butyl N-(1-{7-bromopyrazolo[1,5-a]pyrazin-4-yl}-4-methylpiperidin-4-yl) carbamate (37.3 mg, 30% yield) as a white solid. LC-MS (ESI): m/z [M+H] calculated for $C_{17}H_{25}BrN_5O_2$: 410.1; found 409.9.

Step 3.

A 2 mL microwave vial was charged with tert-butyl N-(1-{7-bromopyrazolo[1,5-a]pyrazin-4-yl}-4-methylpiperidin-4-yl) carbamate (37 mg, 0.09 mmol), 3-chloro-4-(potassiosulfanyl)pyridin-2-amine (22 mg, 0.11 mmol), xantphos (10 mg, 0.02 mmol), degassed dioxane (910 µL), and N,N-diisopropylethylamine (47.4 µL, 0.27 mmol), sequentially. The resulting mixture was degassed by bubbling nitrogen gas through the solution for 10 min, and then tris(dibenzylideneacetone) dipalladium (8 mg, 0.01 mmol) was added to the vial in one portion. The mixture was then degassed for an additional 5 min before it was sealed. The mixture was then warmed to 120° C. via microwave radiation and stirred for 1.5 hrs. After this time, the mixture was then filtered through a pad of celite and concentrated to an orange oil. This oil was purified by column chromatography to give tert-butyl (1-(7-((2-amino-3-chloropyridin-4-yl)thio) pyrazolo[1,5-a]pyrazin-4-yl)-4-methylpiperidin-4-yl) carbamate as an impure orange oil that was carried forward to the next step without further purification. LC-MS (ESI): m/z [M+H] calculated for $C_{22}H_{29}ClN_7O_2S$: 490.2; found 490.5.

Step 4.

A 20 mL vial was charged with tert-butyl N-(1-{7-[(2-amino-3-chloropyridin-4-yl)sulfanyl]pyrazolo[1,5-a]pyrazin-4-yl}-4-methylpiperidin-4-yl) carbamate (45 mg, 0.09 mmol), DCM (2 mL), and TFA (0.5 mL), sequentially, to give a bright red-orange solution. This solution was left to stir at 23° C. for 1 hr. After this time, the reaction mixture was concentrated to a red-orange oil that was purified by preparative HPLC to give 4-{[4-(4-amino-4-methylpiperidin-1-yl) pyrazolo[1,5-a]pyrazin-7-yl]sulfanyl}-3-chloropyridin-2-amine (17 mg, 0.04 mmol, 46%) as a white solid. 4-{[4-(4-amino-4-methylpiperidin-1-yl) pyrazolo[1,5-a]pyrazin-7-yl]sulfanyl}-3-chloropyridin-2-amine as a formate salt. $^1$H NMR (500 MHZ, Methanol-d4) δ 8.13 (s, 1H), 7.96 (d, J=2.5 Hz, 1H), 7.82 (s, 1H), 7.47 (d, J=5.6 Hz, 1H), 7.14 (d, J=2.5 Hz, 1H), 5.67 (d, J=5.6 Hz, 1H), 4.43 (dt, J=13.9, 4.6 Hz, 2H), 3.67 (dt, J=14.0, 6.9 Hz, 2H), 1.96 (dd, J=6.8, 4.6 Hz, 4H), 1.55 (s, 3H); LC-MS (ESI): m/z: [M+H] calculated for $C_{17}H_{21}ClN_7S$: 390.1; found 390.4.

Example 25. Synthesis of (3S,4S)-8-{7-[(2-amino-3-chloropyridin-4-yl)sulfanyl]pyrazolo[1,5-a]pyrazin-4-yl}-3-methyl-2-oxa-8-azaspiro[4.5]decan-4-amine

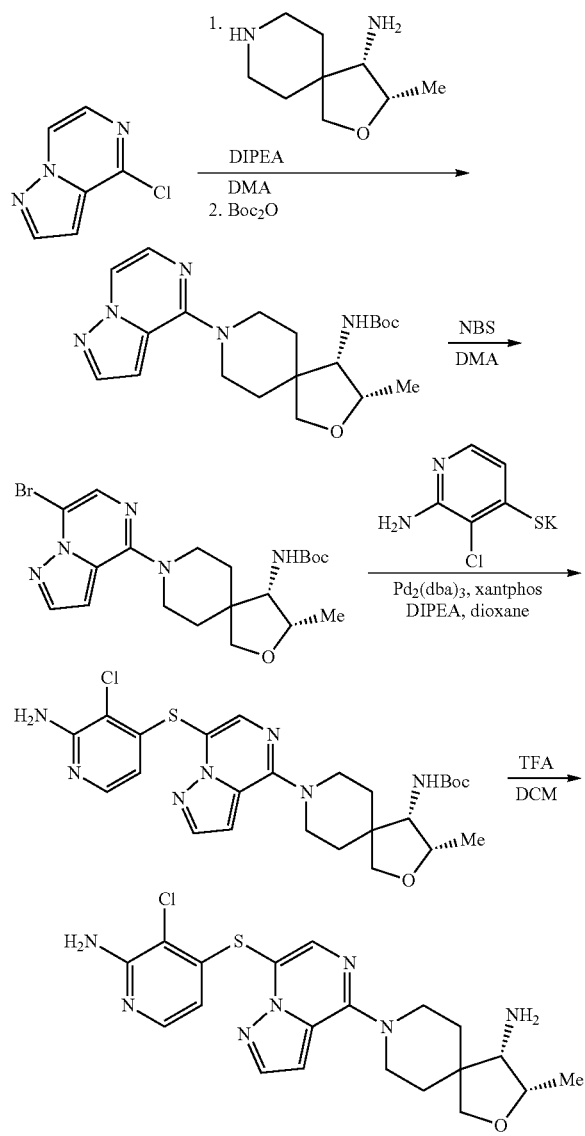

Step 1.

A 20 mL vial was charged with 4-chloropyrazolo[1,5-a]pyrazine (200 mg, 1.30 mmol), (3S,4S)-3-methyl-2-oxa-8-azaspiro[4.5]decan-4-amine (379 mg, 1.5 mmol), DMA (7 mL), and N,N-diisopropylethylamine (1 mL, 6.5 mmol), sequentially. The flask was then sealed and warmed to 120° C. After stirring for 60 hrs, the reaction was cooled to room temperature, and di-tert-butyl dicarbonate (1.41 g, 6.5 mmol) was added in one portion. After stirring for 1 hr, the reaction mixture was diluted with ethyl acetate (20 mL) and water (5 mL), and the layers were separated. The organic solution was then washed with water (5 mL) and saturated aqueous sodium chloride (5 mL) sequentially. The combined aqueous washes were then extracted with ethyl acetate (20 mL), and the combined organic solutions were dried over sodium sulfate. The dried solution was then filtered, and the filtrate was concentrated to give an orange oil. This crude oil was purified by column chromatography to give tert-butyl N-[(3S,4S)-3-methyl-8-{pyrazolo[1,5-a]pyrazin-4-yl}-2-oxa-8-azaspiro[4.5]decan-4-yl]carbamate (503 mg, 100% yield) as a green oil. LC-MS (ESI): m/z [M+H] calculated for $C_{20}H_{30}N_5O_3$:388.2; found 388.1.

Step 2.

A 20 mL vial was charged with tert-butyl N-[(3S,4S)-3-methyl-8-{pyrazolo[1,5-a]pyrazin-4-yl}-2-oxa-8-azaspiro[4.5]decan-4-yl]carbamate (555 mg, 1.4 mmol) and DMA (11 mL). The resulting pale tan solution was then cooled to 0° C. Once cool, a solution of N-bromosuccinimide (227 mg, 1.28 mmol) in DMA (3 mL) was added to the reaction in a slow, dropwise fashion. The resulting solution was left to stir for 1 hr at 0° C. After this time, the reaction mixture was diluted with water (15 mL) and ethyl acetate (15 mL), and the layers were separated. The aqueous phase was extracted with ethyl acetate (10 mL), and the combined organic solution was washed with water (2×10 mL) and saturated aqueous sodium chloride (10 mL), sequentially. The washed organic solution was then dried over sodium sulfate. The dried solution was filtered, and the filtrate was concentrated to give an orange oil that was purified by column chromatography to give tert-butyl N-[(3S,4S)-8-{7-bromopyrazolo[1,5-a]pyrazin-4-yl}-3-methyl-2-oxa-8-azaspiro[4.5]decan-4-yl]carbamate (92 mg, 14% yield) as a white foam. LC-MS (ESI): m/z [M+H] calculated for $C_{20}H_{29}BrN_5O_3$:466.1; found 466.2.

Step 3.

A 2 mL microwave vial was charged with tert-butyl N-[(3S,4S)-8-{7-bromopyrazolo[1,5-a]pyrazin-4-yl}-3-methyl-2-oxa-8-azaspiro[4.5]decan-4-yl]carbamate (53 mg, 0.1 mmol), 3-chloro-4-(potassiosulfanyl)pyridin-2-amine (27 mg, 0.1 mmol), xantphos (13.1 mg, 0.02 mmol), degassed dioxane (1 mL), and N,N-diisopropylethylamine (59.2 μL, 0.3 mmol), sequentially. The resulting mixture was degassed by bubbling nitrogen gas through the solution for 10 min, and then tris(dibenzylideneacetone) dipalladium (10 mg, 0.01 mmol) was added to the vial in one portion. The mixture was then degassed for an additional 5 min before it was sealed. The mixture was then warmed to 120° C. via microwave radiation and stirred for 1.5 hrs. After this time, the reaction mixture was filtered through a pad of celite and concentrated to an orange oil. This oil was purified by column chromatography to give tert-butyl-N-[(3S,4S)-8-{7-[(2-amino-3-chloropyridin-4-yl)sulfanyl]pyrazolo[1,5-a]pyrazin-4-yl}-3-methyl-2-oxa-8-azaspiro[4.5]decan-4-yl]carbamate as an impure orange oil that was carried forward to the next step without further purification. LC-MS (ESI): m/z [M+H] calculated for $C_{25}H_{33}ClN_7O_3S$: 546.2; found 546.5.

Step 4.

A 20 mL vial was charged with tert-butyl N-[(3S,4S)-8-{7-[(2-amino-3-chloropyridin-4-yl)sulfanyl]pyrazolo[1,5-a]pyrazin-4-yl}-3-methyl-2-oxa-8-azaspiro[4.5]decan-4-yl]carbamate (62 mg, 0.1 mmol) and DCM (2 mL), giving an orange solution. TFA (0.5 mL) was added to the solution, and the resulting mixture was left to stir for 1 hr. After this time, the reaction mixture was concentrated to an orange-red residue which was purified by preparative HPLC to give (3S,4S)-8-{7-[(2-amino-3-chloropyridin-4-yl)sulfanyl]pyrazolo[1,5-a]pyrazin-4-yl}-3-methyl-2-oxa-8-azaspiro[4.5]decan-4-amine (23.4 mg, 46.2% yield) as a formate salt. $^1$H NMR (500 MHZ, Methanol-d4) δ 8.16 (s, 1H), 7.95 (d, J=2.5 Hz, 1H), 7.80 (s, 1H), 7.47 (d, J=5.6 Hz, 1H), 7.11 (d, J=2.5 Hz, 1H), 5.67 (d, J=5.5 Hz, 1H), 4.58-4.47 (m, 2H), 4.37-4.28 (m, 1H), 4.04 (d, J=9.2 Hz, 1H), 3.93 (d, J=9.3 Hz, 1H), 3.52-3.44 (m, 2H), 3.40 (ddd, J=14.0, 11.3, 2.9 Hz, 1H), 2.00-1.90 (m, 3H), 1.78 (d, J=13.3 Hz, 1H), 1.33 (d, J=6.5 Hz, 3H); LC-MS (ESI): m/z [M+H] calculated for $C_{20}H_{25}ClN_7OS$: 446.1; found 446.2.

Example 26. Synthesis of (3S,4S)-8-[7-(2,3-dichlorophenyl) pyrazolo[1,5-a]pyrazin-4-yl]-3-methyl-2-oxa-8-azaspiro[4.5]decan-4-amine

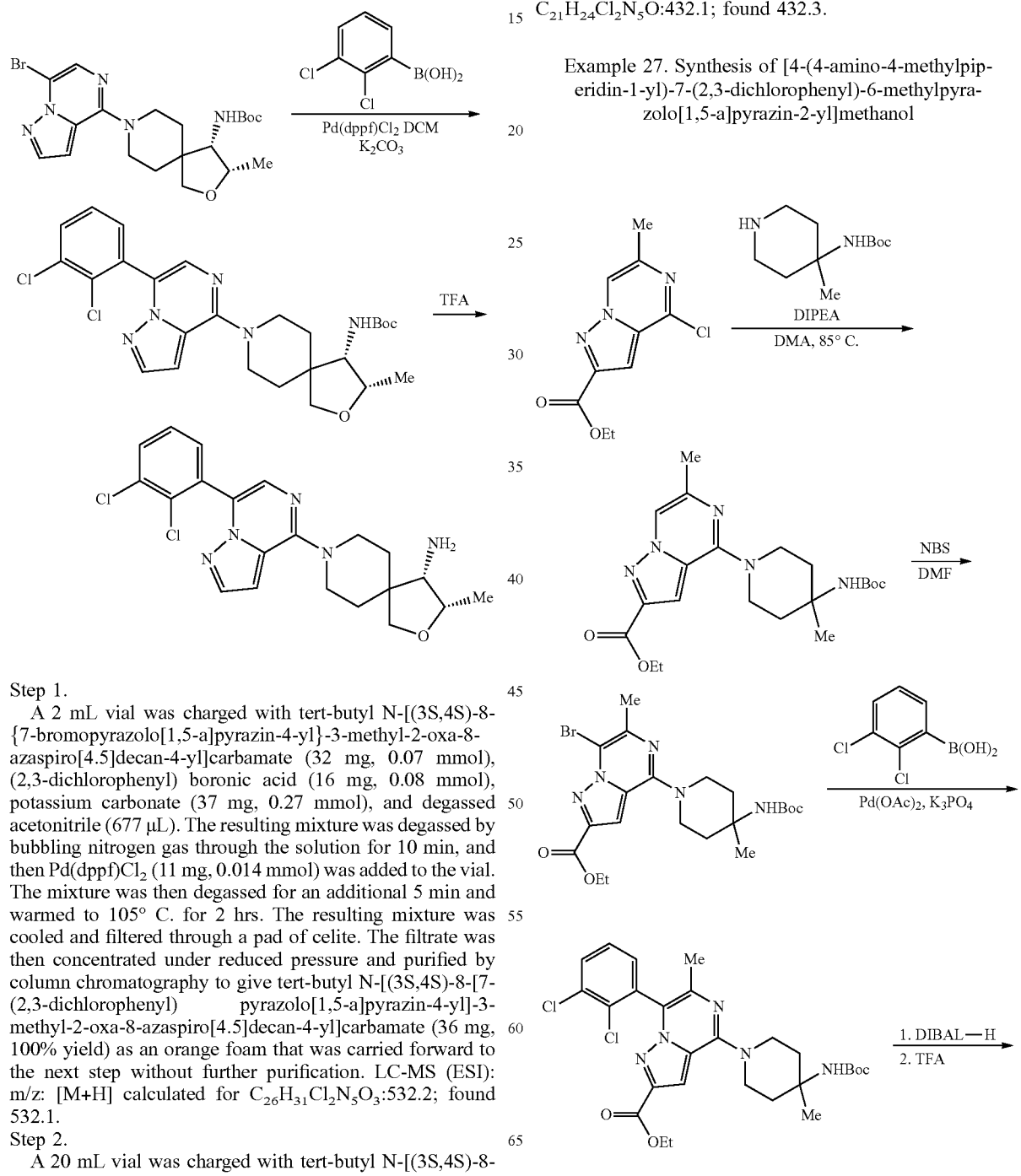

Step 1.

A 2 mL vial was charged with tert-butyl N-[(3S,4S)-8-{7-bromopyrazolo[1,5-a]pyrazin-4-yl}-3-methyl-2-oxa-8-azaspiro[4.5]decan-4-yl]carbamate (32 mg, 0.07 mmol), (2,3-dichlorophenyl) boronic acid (16 mg, 0.08 mmol), potassium carbonate (37 mg, 0.27 mmol), and degassed acetonitrile (677 μL). The resulting mixture was degassed by bubbling nitrogen gas through the solution for 10 min, and then Pd(dppf)Cl₂ (11 mg, 0.014 mmol) was added to the vial. The mixture was then degassed for an additional 5 min and warmed to 105° C. for 2 hrs. The resulting mixture was cooled and filtered through a pad of celite. The filtrate was then concentrated under reduced pressure and purified by column chromatography to give tert-butyl N-[(3S,4S)-8-[7-(2,3-dichlorophenyl) pyrazolo[1,5-a]pyrazin-4-yl]-3-methyl-2-oxa-8-azaspiro[4.5]decan-4-yl]carbamate (36 mg, 100% yield) as an orange foam that was carried forward to the next step without further purification. LC-MS (ESI): m/z: [M+H] calculated for $C_{26}H_{31}Cl_2N_5O_3$:532.2; found 532.1.

Step 2.

A 20 mL vial was charged with tert-butyl N-[(3S,4S)-8-[7-(2,3-dichlorophenyl) pyrazolo[1,5-a]pyrazin-4-yl]-3-methyl-2-oxa-8-azaspiro[4.5]decan-4-yl]carbamate (36 mg, 0.06 mmol), DCM (2 mL), and TFA (0.5 mL), sequentially. After stirring for 1 hr, the reaction mixture was concentrated under reduced pressure to give a thick red-orange oil that was purified by preparative HPLC to give (3S,4S)-8-[7-(2, 3-dichlorophenyl) pyrazolo[1,5-a]pyrazin-4-yl]-3-methyl-2-oxa-8-azaspiro[4.5]decan-4-amine (5.54 mg, 18.9% yield). ¹H NMR (500 MHZ, Methanol-d4) δ 7.94 (d, J=2.4 Hz, 1H), 7.74-7.69 (m, 1H), 7.47-7.44 (m, 2H), 7.38 (s, 1H), 7.04 (d, J=2.5 Hz, 1H), 4.46-4.29 (m, 3H), 4.04 (d, J=9.2 Hz, 1H), 3.93 (d, J=9.1 Hz, 1H), 3.48 (d, J=4.1 Hz, 1H), 3.46-3.32 (m, 2H), 2.05-1.92 (m, 3H), 1.79 (d, J=13.1 Hz, 1H), 1.34 (d, J=6.5 Hz, 3H); LC-MS (ESI): m/z [M+H] calculated for $C_{21}H_{24}Cl_2N_5O$:432.1; found 432.3.

Example 27. Synthesis of [4-(4-amino-4-methylpiperidin-1-yl)-7-(2,3-dichlorophenyl)-6-methylpyrazolo[1,5-a]pyrazin-2-yl]methanol -continued

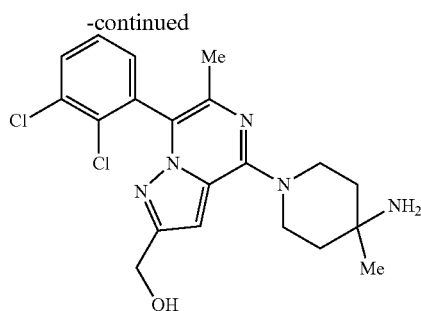

Step 1.

A 40 mL vial was charged with ethyl 4-chloro-6-methylpyrazolo[1,5-a]pyrazine-2-carboxylate (500 mg, 2.08 mmol), tert-butyl N-(4-methylpiperidin-4-yl) carbamate (533 mg, 2.4 mmol), DMA (10 mL), and N,N-diisopropylethylamine (2 mL, 10.4 mmol), sequentially. The flask was then sealed and warmed to 120° C. After stirring for 16 hrs, the reaction was cooled and diluted with ethyl acetate (40 mL) and water (10 mL). The layers were separated, and the organic phase was washed with water (10 mL) and saturated aqueous sodium chloride (10 mL), sequentially. The washed organic solution was then dried over sodium sulfate. The dried solution was filtered and the filtrate was concentrated to an orange oil. This crude material was purified by column chromatography to give ethyl 4-(4-{[(tert-butoxy) carbonyl]amino}-4-methylpiperidin-1-yl)-6-methylpyrazolo[1,5-a]pyrazine-2-carboxylate (836 mg, 96.3% yield) as a pale yellow oil. LC-MS (ESI): m/z [M+H] calculated for $C_{21}H_{32}N_5O_4$:418.2; found 418.1.

Step 2.

An 8 mL vial was charged with ethyl 4-(4-{[(tert-butoxy) carbonyl]amino}-4-methylpiperidin-1-yl)-6-methylpyrazolo[1,5-a]pyrazine-2-carboxylate (200 mg, 0.4 mmol) and DMF (3 mL). The resulting pale tan solution was cooled to 0° C. Once cool, a solution of N-bromosuccinimide (76 mg, 0.43 mmol) in DMF (2.0 mL) was added to the reaction in a slow; dropwise fashion. The resulting solution was left to stir for 1 hr at 0° C. After this time, the reaction mixture was diluted with water (10 mL) and ethyl acetate (10 mL), and the layers were separated. The aqueous phase was extracted with ethyl acetate (10 mL), and the combined organic extracts were washed with water (2×5 mL) and saturated aqueous sodium chloride (5 mL), sequentially. The washed organic solution was then dried over sodium sulfate. The dried solution was filtered, and the filtrate was concentrated to a pink oil that was purified by column chromatography to give ethyl 7-bromo-4-(4-{[(tert-butoxy)carbonyl]amino}-4-methylpiperidin-1-yl)-6-methylpyrazolo[1,5-a]pyrazine-2-carboxylate (165.7 mg, 69.6% yield) as a white foam. LC-MS (ESI): m/z [M+H] calculated for $C_{21}H_{31}BrCl_2N_5O_4$:496.11; found 496.0.

Step 3.

A 20 mL vial was charged with ethyl 7-bromo-4-(4-{[(tert-butoxy) carbonyl]amino}-4-methylpiperidin-1-yl)-6-methylpyrazolo[1,5-a]pyrazine-2-carboxy late (100 mg, 0.2 mmol), (2,3-dichlorophenyl) boronic acid (46 mg, 0.24 mmol), tripotassium phosphate (128 mg, 0.6 mmol), 4-(anthracen-9-yl)-3-tert-butyl-2,3-dihydro-1,3-benzoxaphosphole (15 mg, 0.04 mmol), and degassed dioxane (2 mL). The resulting slurry was then degassed for 10 min before palladium (II) acetate (4.51 mg, 0.02 mmol) was added, and the orange mixture was degassed for an additional 5 min. After this time, the vial was sealed and warmed to 105° C. After 2 hrs, the reaction mixture was cooled and filtered through a pad of celite. The filtrate was then concentrated and purified by column chromatography to give ethyl 4-(4-{[(tert-butoxy) carbonyl]amino}-4-methylpiperidin-1-yl)-7-(2,3-dichlorophenyl)-6-methylpyrazolo[1,5-a]pyrazine-2-carboxylate (75.8 mg, 67% yield). LC-MS (ESI): m/z [M+H] calculated for $C_{27}H_{34}Cl_2N_5O_4$:562.2; found 562.2.

Step 4.

A 20 mL vial was charged with ethyl 4-(4-{[(tert-butoxy) carbonyl]amino}-4-methylpiperidin-1-yl)-7-(2,3-dichlorophenyl)-6-methylpyrazolo[1,5-a]pyrazine-2-carboxylate (76 mg, 0.13 mmol) and DCM (1.3 mL) before it was cooled to −78° C. Once cool, DIBAL-H (1 M in DCM, 538 µL, 0.53 mmol) was added in a dropwise fashion. After complete addition, the reaction was left to stir at −78° C. for 30 min before it was warmed to 0° C. and stirred for an additional 30 min. After this time, the reaction was once again cooled to −78° C. At this time, the reaction solution was poured into a saturated aqueous solution of Rochelle's salt (10 mL) pre-cooled to 0° C., and the reaction mixture was allowed to warm to room temperature and left to stir vigorously overnight. The layers were then separated, and the aqueous phase was extracted with DCM. The combined organic extracts were dried over sodium sulfate. The dried solution was filtered, and the filtrate was concentrated under reduced pressure. The crude residue was then purified by column chromatography to give tert-butyl N-{1-[7-(2,3-dichlorophenyl)-2-(hydroxymethyl)-6-methylpyrazolo[1,5-a]pyrazin-4-yl]-4-methylpiperidin-4-yl}carbamate as a clear, colorless glaze that was submitted to the next reaction without further purification.

Step 5.

A 20 mL vial was charged with tert-butyl N-{1-[7-(2,3-dichlorophenyl)-2-(hydroxymethyl)-6-methylpyrazolo[1,5-a]pyrazin-4-yl]-4-methylpiperidin-4-yl}carbamate (46 mg, 0.09 mmol), DCM (2 mL), and TFA (0.5 mL), sequentially. The resulting pale yellow solution was left to stir for 1 hr. After this time, the reaction mixture was concentrated under reduced pressure, and the crude residue was purified by preparative HPLC to give [4-(4-amino-4-methylpiperidin-1-yl)-7-(2,3-dichlorophenyl)-6-methylpyrazolo[1,5-a]pyrazin-2-yl]methanol (20.6 mg, 56% yield) as a fluffy white solid. [4-(4-amino-4-methylpiperidin-1-yl)-7-(2,3-dichlorophenyl)-6-methylpyrazolo[1,5-a]pyrazin-2-yl]methanol was isolated as its formate salt. $^1$H NMR (500 MHZ, Methanol-d4) δ 8.50 (s, 1H), 7.70 (dd, J=8.1, 1.5 Hz, 1H), 7.46 (t, 1H), 7.35 (dd, J=7.6, 1.5 Hz, 1H), 6.90 (s, 1H), 4.67 (s, 2H), 4.37-4.27 (m, 2H), 3.63-3.51 (m, 2H), 2.12 (s, 3H), 2.05-1.90 (m, 4H), 1.54 (s, 3H); LC-MS (ESI): m/z [M+H] calculated for $C_{20}H_{24}Cl_2N_5O$: 420.13; found 420.1.

Example 28. Synthesis of {4-[(3S,4S)-4-amino-3-methyl-2-oxa-8-azaspiro[4.5]decan-8-yl]-7-(2,3-dichlorophenyl)-6-methylpyrazolo[1,5-a]pyrazin-2-yl}methanol {4-[(3S,4S)-4-amino-3-methyl-2-oxa-8-azaspiro[4.5]decan-8-yl]-7-(2,3-dichlorophenyl)-6-methylpyrazolo[1,5-a]pyrazin-2-yl}methanol was synthesized in the manner similar to Example 27, except tert-butyl (4-methylpiperidin-4-yl) carbamate was substituted for (3S,4S)-3-methyl-2-oxa-8-azaspiro[4.5]decan-4-amine $^1$H NMR (500 MHZ, methanol-d4) δ 8.53 (s, 1H), 7.70 (dd, J=8.1, 1.6 Hz, 1H), 7.48-7.43 (m, 1H), 7.35 (dd, J=7.7, 1.5 Hz, 1H), 6.88 (s, 1H), 4.66 (s, 2H), 4.37-4.25 (m, 3H), 3.97 (d, J=9.0 Hz, 1H), 3.85 (d, J=9.0 Hz, 1H), 3.49-3.34 (m, 2H), 3.27 (d, J=4.5 Hz, 1H), 2.11 (s, 3H), 2.02-1.90 (m, 2H), 1.90-1.82 (m, 1H), 1.79-

1.72 (m, 1H), 1.29 (d, J=6.5 Hz, 3H); LC-MS (ESI): m/z [M+H] calculated for $C_{23}H_{28}Cl_2N_5O_2$:476.2; found 476.4.

Example 29. Synthesis of {7-[(2-amino-3-chloro-pyridin-4-yl)sulfanyl]-4-[(3S,4S)-4-amino-3-methyl-2-oxa-8-azaspiro[4.5]decan-8-yl]-6-methylpyrazolo[1,5-a]pyrazin-2-yl}methanol

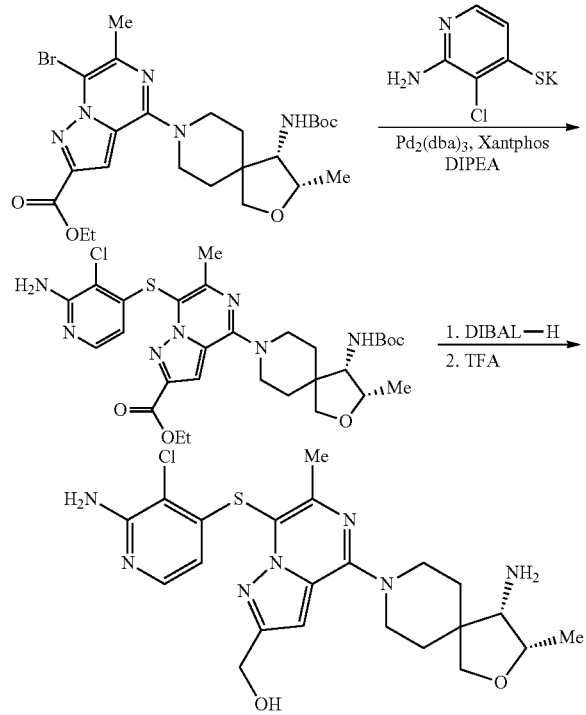

Step 1.

A 5 mL microwave vial was charged with ethyl 7-[(2-amino-3-chloropyridin-4-yl)sulfanyl]-4-[(3S,4S)-4-{[(tert-butoxy) carbonyl]amino}-3-methyl-2-oxa-8-azaspiro[4.5]decan-8-yl]-6-methylpyrazolo[1,5-a]pyrazine-2-carboxylate (200 mg, 0.36 mmol), 3-chloro-4-(potassiosulfanyl)pyridin-2-amine (86 mg, 0.4 mmol), Xantphos (42 mg, 0.07 mmol), degassed dioxane (3.6 mL), and N,N-diisopropylethylamine (187 μL, 1.08 mmol), sequentially. The resulting mixture was degassed by bubbling nitrogen gas through the solution for 10 min, and then tris(dibenzylideneacetone) dipalladium (33.1 mg, 0.0362 mmol) was added to the vial in one portion. The mixture was then degassed for an additional 5 min before it was sealed. The mixture was then warmed to 120° C. via microwave radiation and stirred for 1.5 hrs. After this time, the reaction mixture was filtered through a pad of Celite, and the filtrate was concentrated under reduced pressure to an orange oil. This oil was purified by column chromatography to give ethyl 7-[(2-amino-3-chloropyridin-4-yl)sulfanyl]-4-[(3S,4S)-4-{[(tert-butoxy) carbonyl]amino}-3-methyl-2-oxa-8-azaspiro[4.5]decan-8-yl]-6-methylpyrazolo[1,5-a]pyrazine-2-carboxylate (197 mg, 86% yield) as an orange foam. LC-MS (ESI): m/z [M+H] calculated for $C_{29}H_{39}ClN_7O_5S$: 632.2; found 632.5.

Step 2.

A 20 mL vial was charged with ethyl 7-[(2-amino-3-chloropyridin-4-yl)sulfanyl]-4-[(3S,4S)-4-{[(tert-butoxy) carbonyl]amino}-3-methyl-2-oxa-8-azaspiro[4.5]decan-8-yl]-6-methylpyrazolo[1,5-a]pyrazine-2-carboxylate (197 mg, 0.31 mmol) and DCM (3 mL). The resulting orange solution was then cooled to −78° C. Once cool, DIBAL-H (1 M in DCM, 1.2 mL, 1.2 mmol) was added to the solution in a dropwise manner, and the resulting mixture was left to stir at −78° C. for 30 min. After this time, the reaction mixture was warmed to 0° C. and stirred for an additional 30 min. The reaction mixture was then cooled to −78° C. once again. The reaction mixture was then poured into saturated aqueous Rochelle's salt solution (10 mL) pre-cooled to 0° C., and the biphasic mixture was stirred vigorously overnight while letting the mixture warm to room temperature. After this time, the biphasic mixture was transferred to a separatory funnel, and the layers were separated. The aqueous phase was then extracted with DCM, and the combined organic extracts were dried over sodium sulfate. The dried solution was filtered, and the filtrate was concentrated under reduced pressure. The crude residue so obtained was then purified by column chromatography to give tert-butyl N-[(3S,4S)-8-{7-[(2-amino-3-chloropyridin-4-yl)sulfanyl]-2-(hydroxymethyl)-6-methylpyrazolo[1,5-a]pyrazin-4-yl}-3-methyl-2-oxa-8-azaspiro[4.5]decan-4-yl]carbamate (93 mg, 51% yield) as a tan solid. LC-MS (ESI): m/z [M+H] calculated for $C_{27}H_{37}ClN_7O_4S$: 590.2; found 590.6.

Step 3.

A 20 mL vial at room temperature was charged with tert-butyl N-[(3S,4S)-8-{7-[(2-amino-3-chloropyridin-4-yl)sulfanyl]-2-(hydroxymethyl)-6-methylpyrazolo[1,5-a]pyrazin-4-yl}-3-methyl-2-oxa-8-azaspiro[4.5]decan-4-yl]carbamate (93 mg, 0.158 mmol), DCM (2 mL), and TFA (0.5 mL), sequentially. The resulting yellow solution was left to stir for 1 hr before the reaction mixture was concentrated under reduced to give a thick golden oil that was purified by preparative HPLC to give {7-[(2-amino-3-chloropyridin-4-yl)sulfanyl]-4-[(3S,4S)-4-amino-3-methyl-2-oxa-8-azaspiro[4.5]decan-8-yl]-6-methylpyrazolo[1,5-a]pyrazin-2-yl}methanol (40.2 mg, 52% yield) as its formate salt. $^1$H NMR (500 MHZ, Methanol-d4) δ 8.11 (s, 1H), 7.47 (d, J=5.6 Hz, 1H), 6.99 (s, 1H), 5.65 (d, J=5.6 Hz, 1H), 4.70 (s, 2H), 4.58 (ddt, J=13.5, 5.4, 2.6 Hz, 1H), 4.55-4.48 (m, 1H), 4.33 (qd, J=6.5, 4.1 Hz, 1H), 4.04 (d, J=9.2 Hz, 1H), 3.93 (d, J=9.2, 0.8 Hz, 1H), 3.48-3.42 (m, 2H), 3.37 (ddd, J=14.0, 11.3, 2.9 Hz, 1H), 2.51 (s, 3H), 1.99-1.89 (m, J=4.2 Hz, 3H), 1.82-1.74 (m, 1H), 1.33 (d, J=6.5 Hz, 3H); LC-MS (ESI): m/z [M+H] calculated for $C_{22}H_{29}ClN_7O_2S$: 490.2; found 490.4.

Example 30. Synthesis of (3S,4S)-8-{7-[(2-amino-3-chloropyridin-4-yl)sulfanyl]-6-methylpyrazolo[1,5-a]pyrazin-4-yl}-3-methyl-2-oxa-8-azaspiro[4.5]decan-4-amine

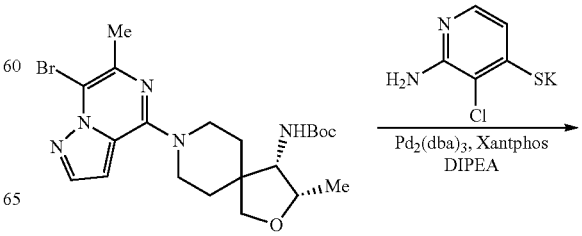

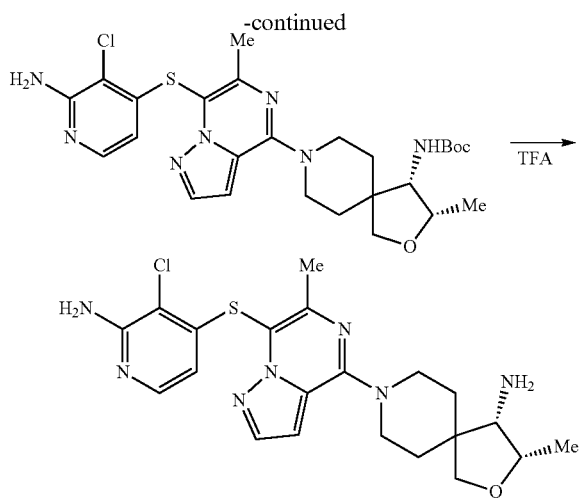

Step 1.

An 8 mL microwave vial was charged with tert-butyl N-[(3S,4S)-8-{7-bromo-6-methylpyrazolo[1,5-a]pyrazin-4-yl}-3-methyl-2-oxa-8-azaspiro[4.5]decan-4-yl]carbamate (200 mg, 0.4163 mmol), 3-chloro-4-(potassiosulfanyl)pyridin-2-amine (99.2 mg, 0.49 mmol), Xantphos (48 mg, 0.08 mmol), degassed dioxane (4.16 mL), and N,N-diisopropylethylamine (215 μL, 1.24 mmol), sequentially. The resulting mixture was degassed by bubbling nitrogen gas through the solution for 10 min, and then tris(dibenzylideneacetone)dipalladium (38.1 mg, 0.04163 mmol) was added to the vial in one portion. The mixture was then degassed for an additional 5 min before it was sealed. The mixture was then warmed to 120° C. via microwave radiation and stirred for 1.5 hrs. After this time, the reaction mixture was filtered through a pad of celite, and the filtrate was concentrated under reduced pressure to an orange oil. Purification by column chromatography resulted in tert-butyl N-[(3S,4S)-8-{7-[(2-amino-3-chloropyridin-4-yl)sulfanyl]-6-methylpyrazolo[1,5-a]pyrazin-4-yl}-3-methyl-2-oxa-8-azaspiro[4.5]decan-4-yl]carbamate (233 mg, 100% yield) as an orange oil. LC-MS (ESI): m/z [M+H] calculated for $C_{26}H_{34}ClN_7O_3S$: 560.2; found 560.3.

Step 2.

A 20 mL vial at room temperature was charged with tert-butyl N-[(3S,4S)-8-{7-[(2-amino-3-chloropyridin-4-yl)sulfanyl]-6-methylpyrazolo[1,5-a]pyrazin-4-yl}-3-methyl-2-oxa-8-azaspiro[4.5]decan-4-yl]carbamate (233 mg, 0.41 mmol), DCM (2 mL), and TFA (1 mL), sequentially. The resulting red-orange solution was left to stir for 1 h before the reaction mixture was concentrated under reduced to give a thick red oil that was purified by preparative HPLC to give (3S,4S)-8-{7-[(2-amino-3-chloropyridin-4-yl)sulfanyl]-6-methylpyrazolo[1,5-a]pyrazin-4-yl}-3-methyl-2-oxa-8-azaspiro[4.5]decan-4-amine (54 mg, 26% yield) as formate salt. $^1$H NMR (500 MHZ, methanol-d4) δ 8.21 (s, 1H), 7.86 (d, J=2.5 Hz, 1H), 7.46 (d, J=5.5 Hz, 1H), 7.03 (d, J=2.5 Hz, 1H), 5.61 (d, J=5.6 Hz, 1H), 4.62-4.56 (m, 1H), 4.56-4.49 (m, 1H), 4.32 (qd, J=6.5, 4.2 Hz, 1H), 4.04 (d, J=9.2 Hz, 1H), 3.93 (d, J=9.3, 0.9 Hz, 1H), 3.50-3.42 (m, 2H), 3.38 (ddd, J=14.0, 11.3, 2.9 Hz, 1H), 2.53 (s, 3H), 1.99-1.91 (m, J=4.2 Hz, 4H), 1.81-1.75 (m, 1H), 1.33 (d, J=6.6 Hz, 3H); LC-MS (ESI): m/z [M+H] calculated for $C_{21}H_{27}ClN_7OS$: 460.2; found 460.4.

Example 31. Synthesis of (3S,4S)-8-{5-[(2-amino-3-chloropyridin-4-yl)sulfanyl]-[1,2,4]triazolo[1,5-a]pyrazin-8-yl}-3-methyl-2-oxa-8-azaspiro[4.5]decan-4-amine

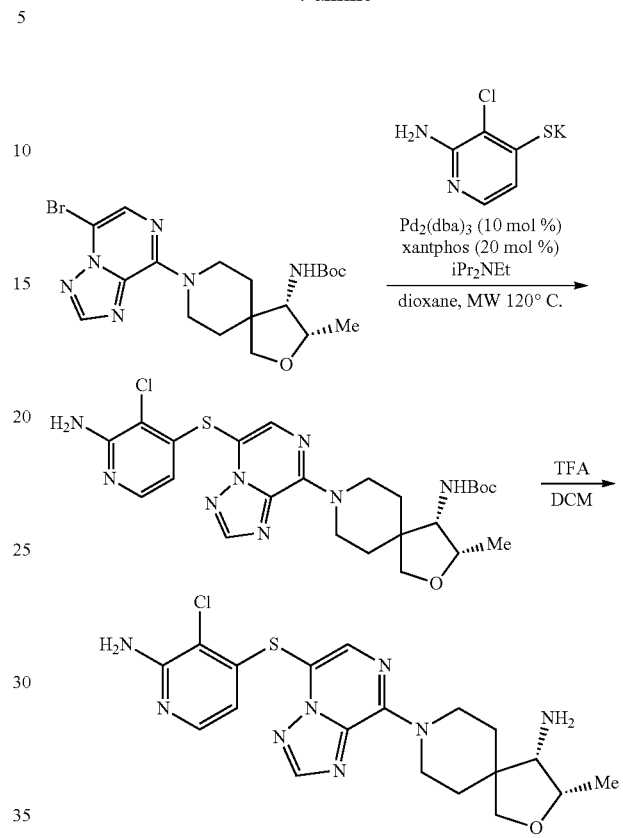

Step 1.

tert-Butyl N-[(3S,4S)-8-{5-bromo-[1,2,4]triazolo[1,5-a]pyrazin-8-yl}-3-methyl-2-oxa-8-azaspiro[4.5]decan-4-yl]carbamate (50 mg, 106 μmol), 3-chloro-4-(potassiosulfanyl)pyridin-2-amine (31.5 mg, 159 μmol), [5-(diphenylphosphanyl)-9,9-dimethyl-9H-xanthen-4-yl]diphenylphosphane (known as XantPhos) (12.2 mg, 21.2 μmol), tris(dibenzylideneacetone)dipalladium (10 mg, 10.6 μmol) and a Teflon coated magnetic stir bar were sequentially added to a 2.5 mL microwave vial. The vial was capped, and then purged with nitrogen gas for 3 min. To this vial was then added dioxane (1.1 mL), which had been purged with nitrogen gas for 30 minutes, followed by the addition of N,N-diisopropylethylamine (36.7 μL, 212 μmol). This heterogeneous mixture was then heated in a microwave to 120° C. for 1.5 hrs. The reaction was filtered over a pad of celite, washed with EtOAc. The filtrate was concentrated under reduced pressure and the resulting residue was purified via silica gel chromatography. LCMS (ESI): m/z: [M+H] calculated for $C_{24}H_{32}ClN_8O_3S$: 547.2; found 547.2.

Step 2.

To a solution of tert-butyl N-[(3S,4S)-8-{5-[(2-amino-3-chloropyridin-4-yl)sulfanyl]-[1,2,4]triazolo[1,5-a]pyrazin-8-yl}-3-methyl-2-oxa-8-azaspiro[4.5]decan-4-yl]carbamate (58 mg, 106 μmol) in DCM (3 mL) was added TFA (706 μL). The reaction mixture was stirred at 25° C. for 1 hr. The resulting solution was concentrated under reduced pressure and the residue was purified by prep HPLC to yield (3S,4S)-8-{5-[(2-amino-3-chloropyridin-4-yl)sulfanyl]-[1,2,4]triazolo[1,5-a]pyrazin-8-yl}-3-methyl-2-oxa-8-azaspiro

[4.5]decan-4-amine (20 mg, 38.6%) as formic acid salt. $^1$H NMR (500 MHZ, Methanol-d4) δ 8.38 (s, 1H), 7.99 (s, 1H), 7.52 (d, J=5.5 Hz, 1H), 5.79 (d, J=5.5 Hz, 1H), 5.39-5.20 (m, 2H), 4.35 (qd, J=6.5, 4.2 Hz, 1H), 4.06 (d, J=9.2 Hz, 1H), 3.95 (d, J=9.2 Hz, 1H), 3.70-3.51 (m, 2H), 3.46 (d, J=4.2 Hz, 1H), 2.00-1.89 (m, 3H), 1.81 (dt, J=14.1, 3.6 Hz, 2H), 1.35 (d, J=6.5 Hz, 3H). LCMS (ESI): m/z [M+H] calculated for $C_{19}H_{24}ClN_8OS$: 447.1; found 447.4.

Example 32. Synthesis of (3S,4S)-8-[5-(2,3-dichlorophenyl)-[1,2,4]triazolo[1,5-a]pyrazin-8-yl]-3-methyl-2-oxa-8-azaspiro[4.5]decan-4-amine

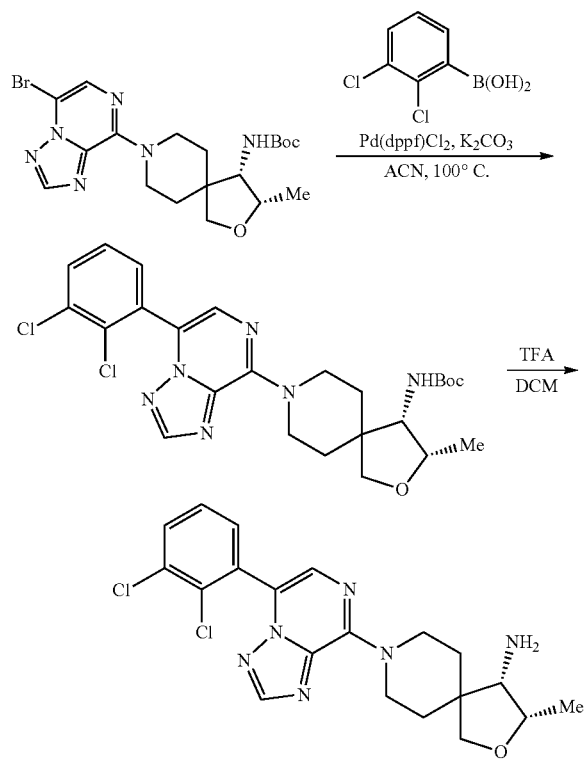

Step 1.

To a reaction vial was added tert-butyl N-[(3S,4S)-8-{5-bromo-[1,2,4]triazolo[1,5-a]pyrazin-8-yl}-3-methyl-2-oxa-8-azaspiro[4.5]decan-4-yl]carbamate (100 mg, 213 μmol), (2,3-dichlorophenyl) boronic acid (60.8 mg, 319 μmol), Pd(dppf)Cl$_2$·CH$_2$Cl$_2$ (34.7 mg, 42.6 μmol), and K$_2$CO$_3$ (117 mg, 852 μmol). The mixture was sparged with N$_2$ for 10 minutes before adding in ACN (2.1 mL). The reaction was stirred at 100° C. for 1 hr. The resulting mixture was filtered through a pad of celite and washed with EtOAc. The filtrate was concentrated under reduced pressure and purified by column chromatography to yield the desired product. LCMS (ESI): m/z [M+H] calculated for $C_{25}H_{31}Cl_2N_6O_3$:533.2; found 533.5.

Step 2.

To a solution of tert-butyl N-[(3S,4S)-8-[5-(2,3-dichlorophenyl)-[1,2,4]triazolo[1,5-a]pyrazin-8-yl]-3-methyl-2-oxa-8-azaspiro[4.5]decan-4-yl]carbamate (56 mg, 104 μmol) in DCM (1 mL) was added TFA (260 μL). The reaction mixture was stirred at 25° C. for 1.5 hrs. The resulting solution was concentrated under reduced pressure and the residue was purified by prep HPLC to yield (3S,4S)-8-[5-(2,3-dichlorophenyl)-[1,2,4]triazolo[1,5-a]pyrazin-8-yl]-3-methyl-2-oxa-8-azaspiro[4.5]decan-4-amine (18.5 mg, 38.5 μmol, 37%) as the formic acid salt. $^1$H NMR (500 MHZ, Methanol-d4) δ 8.36 (s, 1H), 7.74 (dd, J=7.7, 2.0 Hz, 1H), 7.65 (s, 1H), 7.54-7.44 (m, 2H), 5.15 (ddt, J=28.2, 13.7, 3.2 Hz, 2H), 4.33 (qd, J=6.5, 4.4 Hz, 1H), 4.04 (d, J=9.1 Hz, 1H), 3.92 (d, J=9.1 Hz, 1H), 3.62 (ddd, J=14.1, 9.9, 4.3 Hz, 1H), 3.55 (ddd, J=13.8, 11.0, 2.9 Hz, 1H), 3.38 (d, J=4.4 Hz, 1H), 2.00-1.89 (m, 3H), 1.83-1.75 (m, 1H), 1.33 (d, J=6.5 Hz, 3H). LCMS (ESI): m/z [M+H] calculated for $C_{20}H_{23}Cl_2N_6O$: 433.1; found 433.2.

Example 33. Synthesis of (3S,4S)-8-{7-[(2-amino-3-chloropyridin-4-yl)sulfanyl]-[1,2,5]thiadiazolo[3,4-c]pyridin-4-yl}-3-methyl-2-oxa-8-azaspiro[4.5]decan-4-amine

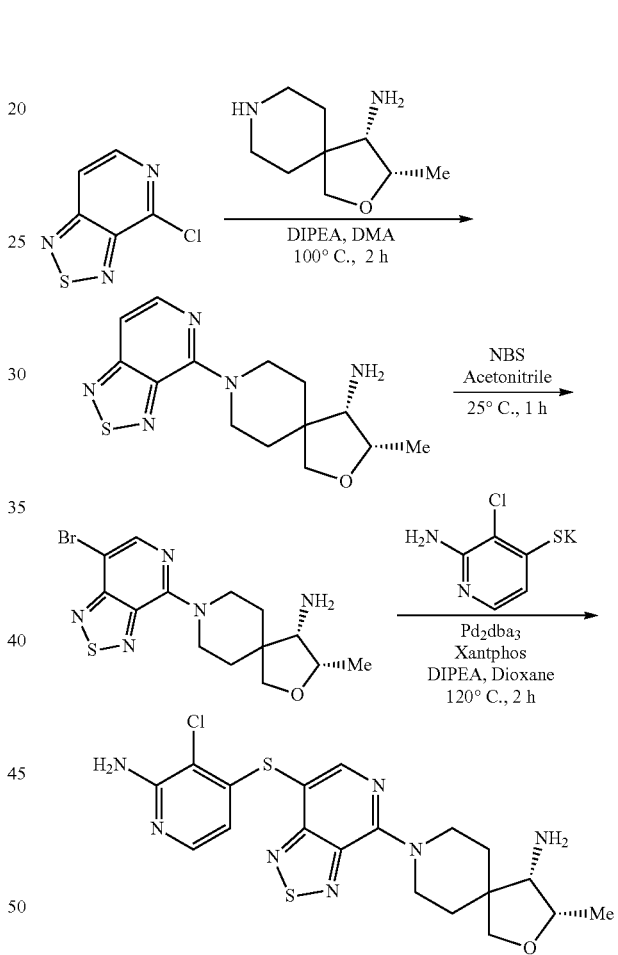

Step 1.

To a solution of 4-chloro-[1,2,5]thiadiazolo[3,4-c]pyridine (230 mg, 1.34 mmol) and N-[(3S,4S)-8-chloro-3-methyl-2-oxa-8-azaspiro[4.5]decan-4-yl]chloranamine (454 mg, 1.87 mmol) in DMA (7 mL) was added DIPEA (1 mL, 6.70 mmol) at 25° C. The mixture was capped and heated to 110° C. for 2 hrs. After this time, the reaction was cooled to 25° C. and concentrated under reduced pressure. The crude product was submitted to the next step without further purification. LC-MS (ESI): m/z [M+H] calculated for $C_{14}H_{20}N_5OS$: 306.14; found 306.1.

Step 2.

To a solution of (3S,4S)-3-methyl-8-{[1,2,5]thiadiazolo[3,4-c]pyridin-7-yl}-2-oxa-8-azaspiro[4.5]decan-4-amine (409 mg, 1.34 mmol) in ACN (3.94 mL) was added N-bromosuccinimide (261 mg, 1.47 mmol) and the reaction mixture was stirred at room temperature for 1 hr, concentrated under reduced pressure. The residue was diluted with EtOAc (6 mL), washed with saturated NaHCO$_3$ (2×3 mL), dried over Na$_2$SO$_4$, filtered, and concentrated under reduced pressure. The crude material submitted to the next step without further purification. LC-MS (ESI): m/z [M+H] calculated for C$_{14}$H$_{19}$BrN$_5$OS: 384.04; found 384.2.

Step 3.

To a microwave vial was added (3S,4S)-8-{7-bromo-[1,2,5]thiadiazolo[3,4-c]pyridin-4-yl}-3-methyl-2-oxa-8-azaspiro[4.5]decan-4-amine (80 mg, 208 μmol), 3-chloro-4-(potassiosulfanyl)pyridin-2-amine (82.6 mg, 416 μmol), Pd$_2$dba$_3$ (19.0 mg, 20.8 μmol), Xantphos (24 mg, 41.6 μmol), and DIEPA (53 mg, 416 μmol), and degassed dioxane (1 mL). The mixture was purged with N$_2$ and evacuated three times. The reaction mixture was stirred under microwave conditions at 130° C. for 2 hrs. The resulting mixture was filtered and concentrated under reduced pressure. The residue was purified by column chromatography to give (3S,4S)-8-{7-[(2-amino-3-chloropyridin-4-yl)sulfanyl]-[1,2,5]thiadiazolo[3,4-c]pyridin-4-yl}-3-methyl-2-oxa-8-azaspiro[4.5]decan-4-amine (78.0 mg, 168 μmol, 80.8%) as a yellow solid. $^1$H NMR (500 MHZ, Methanol-d4) δ 8.41 (s, 1H), 8.22 (s, 1H), 7.42 (d, J=5.6 Hz, 1H), 5.78 (d, J=5.6 Hz, 1H), 4.33 (dd, J=6.6, 4.2 Hz, 1H), 4.06 (d, J=9.2 Hz, 1H), 3.94 (dd, J=9.2, 0.8 Hz, 1H), δ 3.73-3.56 (m, 2H), 3.45 (d, J=4.2 Hz, 1H), 2.01-1.91 (m, 3H), 1.85-1.78 (m, 1H), 1.33 (d, J=6.5 Hz, 3H). LC-MS (ESI): m/z [M+H] calculated for C$_{19}$H$_{23}$ClN$_7$OS$_2$:464.10; found 464.3.

Example 34. Synthesis of 4-{[4-(4-amino-4-methylpiperidin-1-yl)-[1,2,5]oxadiazolo[3,4-c]pyridin-7-yl]sulfanyl}-3-chloropyridin-2-amine

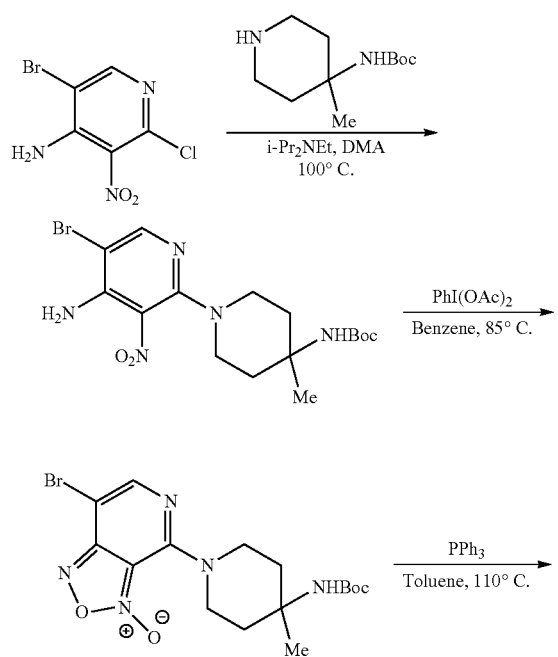

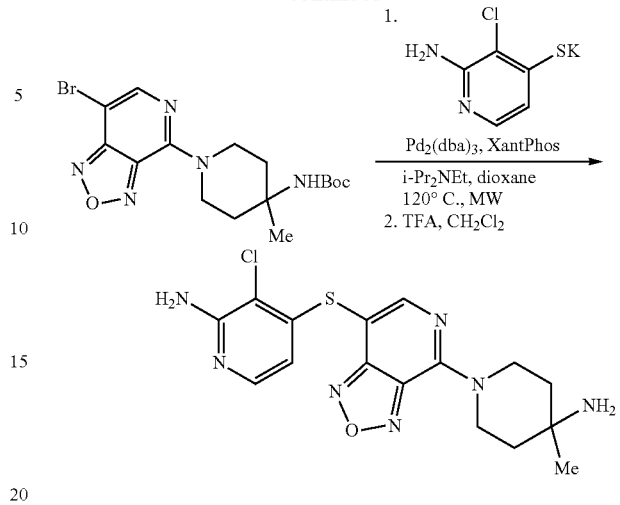

Step 1.

To a solution of 5-bromo-2-chloro-3-nitropyridin-4-amine (0.50 g, 1.98 mmol) in DMA (9.90 mL) was added tert-butyl N-(4-methylpiperidin-4-yl) carbamate (0.63 g, 2.96 mmol) and N,N-diisopropylethylamine (1.7 mL, 9.89 mmol) at room temperature. The reaction was heated to 100° C. for 1 hr, concentrated under reduced pressure and the resulting residue was submitted to next step without purification. LC-MS (ESI): m/z [M+H]$^+$ calculated for C$_{16}$H$_{25}$BrN$_5$O$_4$:430.1; found 430.1.

Step 2.

tert-Butyl N-[1-(4-amino-5-bromo-3-nitropyridin-2-yl)-4-methylpiperidin-4-yl]carbamate (650 mg, 1.51 μmol) was in benzene (7.55 mL, 0.2 M). (acetyloxy) (phenyl)-λ$^3$-iodanyl acetate (0.53 g, 1.66 mmol) was added. The resulting mixture was stirred at 85° C. for 4 hrs. The mixture was concentrated under reduced pressure and diluted with DCM, washed with NaHCO$_3$ until pH 8, and dried over Na$_2$SO$_4$. The solvent was removed under reduced pressure, and the residue was subjected to next step. LC-MS (ESI): m/z [M+H]$^+$ calculated for C$_{16}$H$_{23}$BrN$_5$O$_4$:428.1; found 427.9.

A solution of triphenylphosphine (0.12 g, 0.46 mmol) in PhMe (0.5 mL) was added to a solution of tert-butyl 7-bromo-4-(4-(((tert-butoxycarbonyl)amino)-4-methylpiperidin-1-yl)-[1,2,5]oxadiazolo[3,4-c]pyridine 3-oxide (0.15 g, 0.35 mmol) in PhMe (1.24 mL). The reaction mixture was stirred for 4 hrs at 110° C., filtered through a silica-gel pad, and the filtrate was concentrated under reduced pressure. The resulting product was subjected to next step without further purification. LC-MS (ESI): m/z: [M+H] calculated for C$_{16}$H$_{23}$BrN$_5$O$_3$:412.1; found 412.0.

Step 4.

A microwave vial was charged with tert-butyl N-(1-{7-bromo-[1,2,5]oxadiazolo[3,4-c]pyridin-4-yl}-4-methylpiperidin-4-yl) carbamate (0.075 g, 0.181 mmol), 3-chloro-4-(potassiosulfanyl)pyridin-2-amine (0.072 g. 0.362 mmol), tris(dibenzylideneacetone) dipalladium (0.016 g, 0.0181 mmol), xantphos (0.02 g, 0.0362 mmol), and N,N-diisopropylethylamine (0.0944 mL, 0.543 mmol). The mixture was degassed before adding in degassed dioxane (1.80 mL 0.1 M). The reaction vial was evacuated and purged with N$_2$ three times before stirring under microwave conditions at 130° C. for 2 hrs. After 1.5 hrs, LCMS showed full conversion. The reaction mixture was filtered through a celite pad and then concentrated under reduced pressure. The residue was dissolved in DCM (3 mL), and TFA (1 mL) was added at 0° C. The reaction mixture was warmed to room temperature and stirred for 1 hr at that temperature. The reaction mixture was concentrated under reduced pressure and subjected to column. Purification by reverse phase column chromatography afforded 4-{[4-(4-amino-4-methylpiperidin-1-yl)-[1,2,5]oxadiazolo[3,4-c]pyridin-7-yl]sulfanyl}-3-chloropyridin-2-amine (52.7 mg, 61% yield). $^1$H NMR (500 MHZ, DMSO-d6) δ 8.11 (s, 1H), 7.59 (d, J=5.4 Hz, 1H), 6.37 (s, 2H), 5.97 (d, J=5.4 Hz, 1H), 3.33 (s, 4H), 1.89 (s, 4H), 1.42 (s, 3H). LC-MS (ESI): m/z [M+H]$^+$ calculated for $C_{16}H_{19}ClN_7OS$: 392.1; found 392.3.

Example 35. Synthesis of (3S,4S)-8-{5-[(2-amino-3-chloropyridin-4-yl)sulfanyl]-6-methyl-[1,2,4]triazolo[4,3-a]pyrazin-8-yl}-3-methyl-2-oxa-8-azaspiro[4.5]decan-4-amine

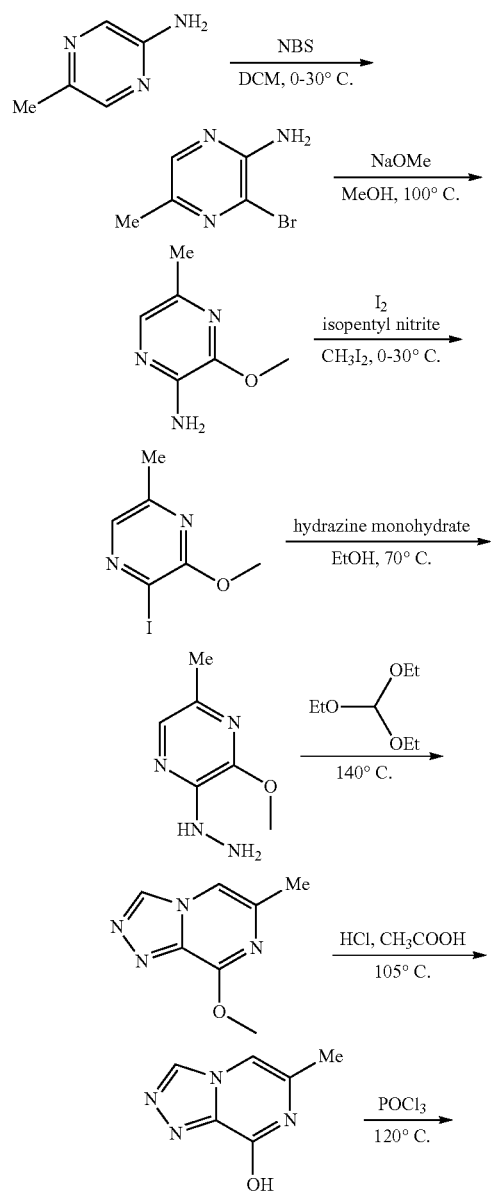

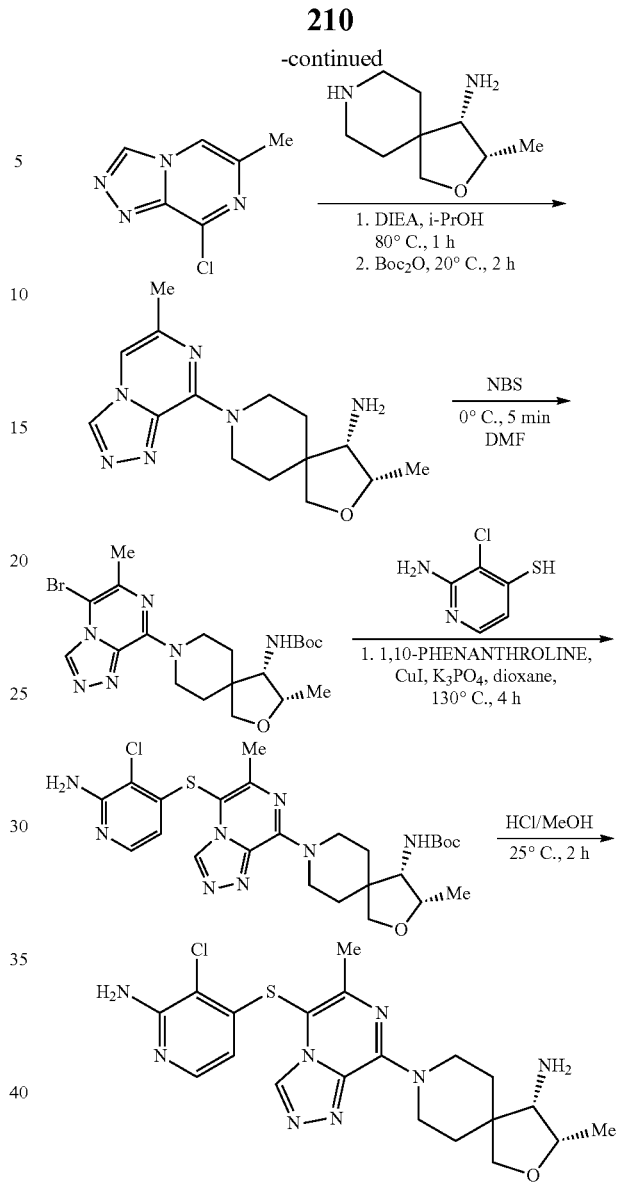

Step 1.

To a mixture of 5-methylpyrazin-2-amine (10 g, 92 mmol) in DCM (300 mL) was added NBS (16 g, 91.63 mmol) in one portion at 0° C. under $N_2$. The mixture was stirred at 30° C. for 1 hr. The resulting mixture was poured into saturated aq. $Na_2SO_3$ (100 mL) and the aqueous phase was extracted with EtOAc. The combined organic layers were washed with brine, dried with $Na_2SO_4$, filtered and concentrated under reduced pressure. The residue was purified by column chromatography to afford 3-bromo-5-methyl-pyrazin-2-amine (12 g, 69% yield.) as a light yellow solid. $^1$H NMR (400 MHZ, CDCl$_3$-d) δ ppm 7.82 (s, 1H) 4.79-5.03 (m, 2H) 2.39 (s, 3H).

Step 2.

To a mixture of 3-bromo-5-methyl-pyrazin-2-amine (31 g, 164.87 mmol) in MeOH (150 mL) was added NaOMe (14 g, 263.79 mmol) in one portion at 30° C. under $N_2$. The mixture was stirred at 100° C. for 6 hrs. The mixture was concentrated under reduced pressure and the resulting residue was dissolved in water (100 mL). The mixture was extracted with EtOAc and the combined organic layers were washed with brine (20 mL), dried with $Na_2SO_4$, filtered and concentrated under reduced pressure. The resulting residue was purified by column chromatography (to afford 3-methoxy-5-methyl-pyrazin-2-amine (21 g, 92% yield) as a white solid. $^1$H NMR (400 MHZ, CDCl$_3$-d) δ ppm 7.39 (s, 1H) 4.59 (br s, 2H) 3.97 (s, 3H) 2.29 (s, 3H)

To a solution of 3-methoxy-5-methyl-pyrazin-2-amine (21 g, 150.91 mmol) in CH$_2$I$_2$ (40 mL) was added isopentyl nitrite (35.36 g, 301.82 mmol, 40.64 mL) and I$_2$ (45.96 g, 181.09 mmol, 36.48 mL) at 0° C. The mixture was warmed to 30° C. and stirred at 30° C. for 3 hrs. The reaction mixture was poured into 300 mL of saturated aq. Na$_2$SO$_3$ and the aqueous phase was extracted with DCM. The combined organic layers were washed with brine, dried with anhydrous Na$_2$SO$_4$, filtered and concentrated under reduced pressure. The resulting residue was purified by column chromatography to afford 2-iodo-3-methoxy-5-methyl-pyrazine (21 g, 55.65% yield) as a yellow solid. $^1$H NMR (400 MHZ, CDCl$_3$-d) δ ppm 7.81 (s, 1H) 3.99 (s, 3H) 2.40 (s, 3H)
Step 4.

To a mixture of 2-iodo-3-methoxy-5-methyl-pyrazine (5 g, 20 mmol) in EtOH (50 mL) at 70° C. under N$_2$ was added hydrazine monohydrate (5.01 g, 100 mmol, 4.9 mL) in one portion. The mixture was stirred at 70° C. for 48 hrs. The mixture was concentrated under reduced pressure and purified by column chromatography to afford (3-methoxy-5-methyl-pyrazin-2-yl) hydrazine (2.16 g, 14.01 mmol, 70% yield) as a light yellow solid. LCMS (ESI): m/z [M+H] calculated for C$_6$H$_1$N$_4$O: 155.1; found 155.2.
Step 5.

A mixture of (3-methoxy-5-methyl-pyrazin-2-yl) hydrazine (2 g, 12.97 mmol) and triethyl orthoformate (17.8 g, 120.24 mmol, 20 mL) was heated at 140° C. under N$_2$ for 1 hr. The reaction solution was filtered and the filter cake was dried under reduced pressure to give 8-methoxy-6-methyl-[1,2,4]triazolo[4,3-a]pyrazine (1.5 g, 70.4% yield) as a light yellow solid. LCMS (ESI): m/z [M+H] calculated for C$_7$H$_9$N$_4$O: 165.1; found 165.1.
Step 6.

To a mixture of 8-methoxy-6-methyl-[1,2,4]triazolo[4,3-a]pyrazine (740 mg, 4.51 mmol) in CH$_3$COOH (18 mL) was added HCl (1N, 6 mL) in one portion. The mixture was stirred at 105° C. for 1 hr. The resulting mixture was concentrated under reduced pressure to give 6-methyl-[1,2,4]triazolo[4,3-a]pyrazin-8-ol (740 mg) as a brown solid. LCMS (ESI): m/z [M+H] calculated for C$_6$H$_7$N$_4$O: 151.1; found 151.1.
Step 7.

A mixture of 6-methyl-[1,2,4]triazolo[4,3-a]pyrazin-8-ol (900 mg, 5.99 mmol) in POCl$_3$ (29.70 g, 193.70 mmol, 18.00 mL) was heated at 120° C. for 1 hr. The excess POCl$_3$ was removed under reduced pressure. The mixture was then quenched with saturated aq. NaHCO$_3$ (100 mL) to remove any remaining POCl$_3$. The resulting mixture was poured into water (300 mL) and stirred for 2 min. The aqueous phase was extracted with EtOAc and the combined organic layers were washed with water and concentrated under reduced pressure. The resulting residue was purified by column chromatography to afford 8-chloro-6-methyl-[1,2,4]triazolo[4,3-a]pyrazine (900 mg, 84.61% yield,) as a black brown solid.
Step 8.

To a mixture of 8-chloro-6-methyl-[1,2,4]triazolo[4,3-a]pyrazine (400 mg, 2.37 mmol) and (3S,4S)-3-methyl-2-oxa-8-azaspiro[4.5]decan-4-amine (403.49 mg, 2.37 mmol) in i-PrOH (20 mL) was added DIEA (1.53 g, 11.85 mmol, 2.06 mL). The mixture was heated at 80° C. and stirred for 1 hr. After 1 hr, Boc$_2$O (517.25 mg, 2.37 mmol, 544.47 μL) was added and the reaction mixture was stirred at 20° C. for 2 hrs. The reaction mixture was concentrated under reduced pressure and purified by column chromatography (SiO$_2$, petroleum ether/ethyl acetate=5/1 to 0:1) to afford tert-butyl N-[(3S,4S)-3-methyl-8-(6-methyl-[1,2,4]triazolo[4,3-a]pyrazin-8-yl)-2-oxa-8-azaspiro[4.5]decan-4-yl]carbamate (800 mg. 1.95 mmol, 82.1% yield) as a white solid. $^1$H NMR (400 MHZ, CDCl3-d) δ ppm 8.61 (s. 1H) 7.23 (s, 1H) 4.63 (br d, J=10.80 Hz, 2H) 4.17-4.24 (m, 1H) 4.01 (br dd, J=10.69, 4.30 Hz, 1H) 3.68-3.77 (m, 2H) 2.26 (s, 2H) 1.82-1.96 (m, 2H) 1.53-1.59 (m, 4H) 1.52 (s, 1H) 1.49 (s, 1H) 1.45 (s, 9H) 1.18-1.25 (m, 4H).
Step 9.

To a mixture of tert-butyl N-[(3S,4S)-3-methyl-8-(6-methyl-[1,2,4]triazolo[4,3-a]pyrazin-8-yl)-2-oxa-8-azaspiro[4.5]decan-4-yl]carbamate (700 mg, 1.74 mmol) in DMF (7 mL) was added NBS (309 mg, 1.74 mmol). The mixture was stirred at 0° C. for 5 min. The resulting mixture was quenched by addition saturated aq. Na$_2$SO$_3$ (10 mL) and concentrated under reduced pressure. The remaining residue was purified by column chromatography to afford tert-butyl N-[(3S,4S)-8-(5-bromo-6-methyl-[1,2,4]triazolo[4,3-a]pyrazin-8-yl)-3-methyl-2-oxa-8-azaspiro[4.5]decan-4-yl]carbamate (500 mg, 59.7% yield) as a red solid. LCMS (ESI): m/z [M+H] calculated for C$_{20}$H$_{30}$BrN$_6$O$_3$:481.15; found 481.3.
Step 10.

To a solution of tert-butyl N-[(3S,4S)-8-(5-bromo-6-methyl-[1,2,4]triazolo[4,3-a]pyrazin-8-yl)-3-methyl-2-oxa-8-azaspiro[4.5]decan-4-yl]carbamate (200 mg, 415 μmol) in dioxane (3 mL) was added 2-amino-3-chloro-pyridine-4-thiol (166 mg, 1.04 mmol), K$_3$PO$_4$ (176 mg, 830 μmol), 1,10-phenanthroline (14.9 mg, 83.1 μmol) and CuI (7.91 mg, 41.5 μmol). The reaction mixture was stirred at 130° C. for 4 hrs. The reaction was monitored by LCMS. The reaction was filtered and concentrated, the residue was purified by silica gel chromatography (petroleum ether:ethyl acetate=5:1, 0:1) to give tert-butyl N-[(3S,4S)-8-[5-[(2-amino-3-chloro-4-pyridyl)sulfanyl]-6-methyl-[1,2,4]triazolo[4,3-a]pyrazin-8-yl]-3-methyl-2-oxa-8-azaspiro[4.5]decan-4-yl]carbamate (80 mg, 32.7% yield) as white solid. LCMS (ESI): m/z [M+H] calculated for C$_{25}$H$_{34}$ClN$_8$O$_3$S: 561.2; found 561.3.
Step 11.

A mixture of tert-butyl N-[(3S,4S)-8-[5-[(2-amino-3-chloro-4-pyridyl)sulfanyl]-6-methyl-[1,2,4]triazolo[4,3-a]pyrazin-8-yl]-3-methyl-2-oxa-8-azaspiro[4.5]decan-4-yl]carbamate (20 mg, 35.6 μmol) in HCl/MeOH (1 mL) was stirred at 25° C. for 2 hrs. The reaction was monitored by LCMS and HPLC. The reaction mixture was concentrated to dryness, and adjusted to pH=7 with NaOH in MeOH at −78° C., then filtered and concentrated. The residue was purified by pre-HPLC to give (3S,4S)-8-[5-[(2-amino-3-chloro-4-pyridyl)sulfanyl]-6-methyl-[1,2,4]triazolo[4,3-a]pyrazin-8-yl]-3-methyl-2-oxa-8-azaspiro[4.5]decan-4-amine (10 mg, 60% yield,) as white solid. LCMS (ESI): m/z [M+H] calculated for C$_{20}$H$_{26}$ClN$_8$OS: 461.16; found 461.2.1H NMR (400 MHZ, Methanol-d4) δ ppm 8.99 (s, 1H) 7.60 (d, J=5.50 Hz, 1H) 5.88 (d, J=5.50 Hz, 1H) 5.26-4.96 (m, 1H) 4.57 (s, 1H) 4.34-4.21 (m, 1H) 4.05-3.71 (m, 4H) 3.07 (d, J=5.01 Hz, 1H) 2.48 (s, 3H) 2.03-1.67 (m, 4H) 1.25 (d, J=6.48 Hz, 3H).

Example 36. Synthesis of 4-[[8-(4-amino-4-methyl-1-piperidyl)-6-methyl-[1,2,4]triazolo[4,3-a]pyrazin-5-yl]sulfanyl]-3-chloro-pyridin-2-amine

Example 37. Synthesis of 1-[5-(2,3-dichlorophenyl)-6-methyl-[1,2,4]triazolo[4,3-a]pyrazin-8-yl]-4-methyl-piperidin-4-amine

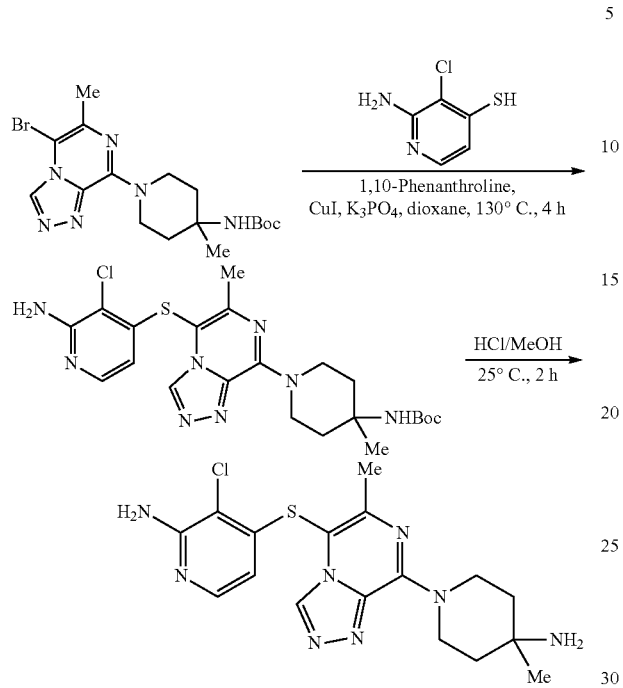

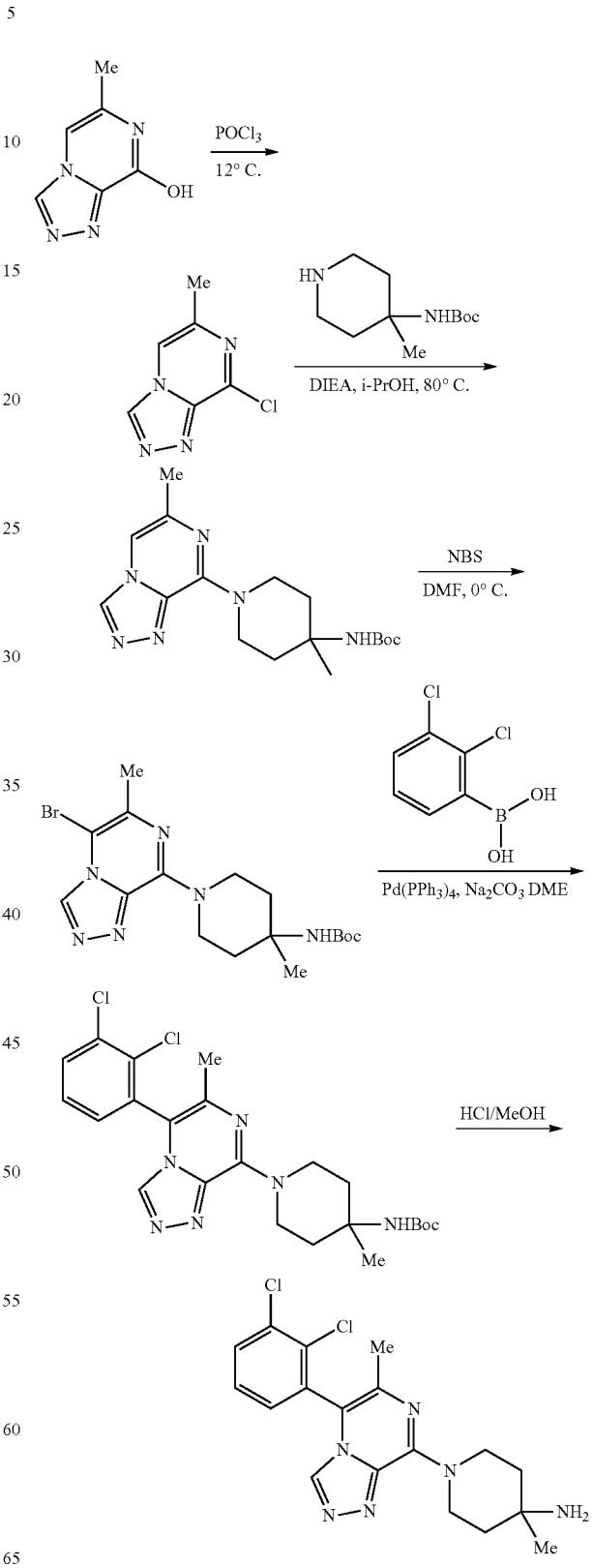

Step 1.

To a solution of 2-amino-3-chloro-pyridine-4-thiol (122 mg, 764 μmol) in dioxane (2 mL) was added tert-butyl N-[1-(5-bromo-6-methyl-[1,2,4]triazolo[4,3-a]pyrazin-8-yl)-4-methyl-4-piperidyl]carbamate (130 mg, 305 μmol), $K_3PO_4$ (129 mg, 611 μmol), 1,10-phenanthroline (11.0 mg, 61.1 μmol) and CuI (6 mg, 30.5 μmol). The reaction mixture was stirred at 130° C. for 4 hrs. The reaction mixture was filtered and concentrated under reduced pressure. The remaining residue was purified by column chromatography to afford tert-butyl N-[1-[5-[(2-amino-3-chloro-4-pyridyl)sulfanyl]-6-methyl-[1,2,4]triazolo[4,3-a]pyrazin-8-yl]-4-methyl-4-piperidyl]carbamate (60 mg, 37% yield) as a white solid. LCMS (ESI): m/z [M+H] calculated for $C_{22}H_{30}ClN_8O_2S$: 505.18; found 505.3.

Step 2.

A mixture of tert-butyl N-[1-[5-[(2-amino-3-chloro-4-pyridyl)sulfanyl]-6-methyl-[1,2,4]triazolo[4,3-a]pyrazin-8-yl]-4-methyl-4-piperidyl]carbamate (30 mg, 59 μmol) in HCl/MeOH (2 mL) was stirred at 25° C. for 2 hrs. The reaction mixture was concentrated under reduced pressure. The remaining residue was dissolved in MeOH (2 mL) and the pH of the solution was adjusted to pH 7 by the addition of NaOH in MeOH at −78° C. The mixture was filtered and the filtrate was concentrated under reduced pressure to afford 4-[[8-(4-amino-4-methyl-1-piperidyl)-6-methyl-[1,2,4]triazolo[4,3-a]pyrazin-5-yl]sulfanyl]-3-chloro-pyridin-2-amine (10 mg, 40% yield) as a white solid; found 405.3. $^1$H NMR (400 MHZ, methanol-d4) δ ppm 8.96 (s, 1H) 7.57 (d, J=5.50 Hz, 1H) 5.85 (d, J=5.50 Hz, 1H) 4.47 (s, 2H) 3.34 (s, 2H) 2.45 (s, 3H) 1.79-1.59 (m, 4H) 1.25 (s, 2H); LCMS (ESI): m/z [M+H] calculated for $C_{17}H_{22}ClN_8S$: 405.1; found 405.1.

Step 1.

A mixture of 6-methyl-[1,2,4]triazolo[4,3-a]pyrazin-8-ol (120 mg, 799.27 µmol) and POCl₃ (3.30 g, 21.52 mmol, 2.00 mL) was heated to 120° C. and stirred for 1 hr. The excess POCl₃ was removed under reduced pressure. The mixture was then quenched with saturated aq. NaHCO₃ (100 mL) to remove any remaining POCl₃. The resulting mixture was poured into water (300 mL) and stirred for 2 min. The aqueous phase was extracted with EtOAc and the combined organic layers were washed with water and concentrated under reduced pressure. The resulting residue was purified by column chromatography to afford 8-chloro-6-methyl-[1,2,4]triazolo[4,3-a]pyrazine (120 mg, 80.2% yield) as a black brown solid. ¹H NMR (400 MHZ, DMSO-d6) δ ppm 9.05 (s, 1H) 7.32 (s, 1H) 2.09 (s, 3H).

Step 2.

To a mixture of 8-chloro-6-methyl-[1,2,4]triazolo[4,3-a]pyrazine (120 mg, 711.81 µmol) and tert-butyl N-(4-methyl-4-piperidyl) carbamate (198 mg, 925.36 µmol) in i-PrOH (2 mL) was added DIEA (460 mg, 3.56 mmol, 619.93 µL). The mixture was heated to 80° C. and stirred for 1 hr. The reaction mixture was concentrated under reduced pressure and the remaining residue was purified by column chromatography to afford tert-butyl N-[4-methyl-1-(6-methyl-[1,2,4]triazolo[4,3-a]pyrazin-8-yl)-4-piperidyl]carbamate (160 mg, 55% yield) as a red solid. ¹H NMR (400 MHZ, methanol-d4) δ ppm 8.99 (s, 1H) 7.55 (d, J=0.98 Hz, 1H) 3.68 (br t, J=11.13 Hz, 2H) 2.26 (d, J=0.98 Hz, 3H) 2.21 (br d, J=13.08 Hz, 2H) 2.02 (s, 1H) 1.58-1.67 (m, 2H) 1.43-1.51 (m, 9H) 1.37 (s, 3H).

Step 3.

To a mixture of tert-butyl N-[4-methyl-1-(6-methyl-[1,2,4]triazolo[4,3-a]pyrazin-8-yl)-4-piperidyl]carbamate (160 mg, 461.86 µmol) in DMF (2 mL) was added NBS (82.20 mg, 461.86 µmol) in one portion at 0° C. The mixture was stirred at 0° C. for 10 min. The mixture was quenched by addition sat.aq. Na₂SO₃ (10 mL) and concentrated under reduced pressure. The remaining residue was purified by column chromatography to afford tert-butyl N-[1-(5-bromo-6-methyl-[1,2,4]triazolo[4,3-a]pyrazin-8-yl)-4-methyl-4-piperidyl]carbamate (180 mg, 91.6% yield) as a red solid. ¹H NMR (400 MHZ, CDCl3-d) δ ppm 8.82 (s, 1H) 4.83 (br s, 2H) 4.46 (br s, 1H) 3.82 (br s, 2H) 2.41 (s, 3H) 2.16 (br d, J=15.21 Hz, 2H) 2.06 (s, 1H) 1.70 (ddd, J=14.22, 10.47, 3.97 Hz, 2H) 1.46 (s, 9H) 1.42 (s, 3H)

Step 4.

To a mixture of tert-butyl N-[1-(5-bromo-6-methyl-[1,2,4]triazolo[4,3-a]pyrazin-8-yl)-4-methyl-4-piperidyl]carbamate (180 mg, 423.21 µmol) and (2,3-dichlorophenyl) boronic acid (121 mg, 634.81 µmol) in DME (2 mL) and H₂O (1 mL) was added Pd(PPh₃)₄ (63.58 mg, 55.02 µmol) and Na₂CO₃ (112 mg, 1.06 mmol). The reaction mixture was heated to 80° C. and stirred for 5 hrs. The reaction mixture was concentrated under reduced pressure and the remaining residue was purified by column chromatography to afford tert-butyl N-[1-[5-(2,3-dichlorophenyl)-6-methyl-[1,2,4]triazolo[4,3-a]pyrazin-8-yl]-4-methyl-4-piperidyl]carbamate (100 mg, 47.6% yield) as a light yellow solid. LCMS (ESI): m/z [M+H] calculated for C₂₃H₂₉Cl₂N₆O₂:491.2; found 491.2.

Step 5.

A mixture of tert-butyl N-[1-[5-(2,3-dichlorophenyl)-6-methyl-[1,2,4]triazolo[4,3-a]pyrazin-8-yl]-4-methyl-4-piperidyl]carbamate (100 mg, 203.5 µmol) in HCl/MeOH (6 mL) was stirred at 20° C. for 1 hr. The reaction mixture was concentrated under reduced pressure to afford 1-[5-(2,3-dichlorophenyl)-6-methyl-[1,2,4]triazolo[4,3-a]pyrazin-8-yl]-4-methyl-piperidin-4-amine (66 mg, 160.24 µmol, 78% yield) as a light yellow solid. ¹H NMR (400 MHz, methanol-d4) δ ppm 8.86 (s, 1H) 7.84 (dd, J=7.89, 1.75 Hz, 1H) 7.55-7.60 (m, 1H) 7.50-7.55 (m, 1H) 5.10 (br s, 2H) 3.99 (br s, 2H) 2.17 (s, 3H) 2.05 (br t, J=5.26 Hz, 5H) 1.59 (s, 3H). LCMS (ESI): m/z [M+H] calculated for C₁₈H₂₁Cl₂N₆: 391.11; found 391.1.

Example 38. Synthesis of (3S,4S)-8-[5-(2,3-dichlorophenyl)-6-methyl-[1,2,4]triazolo[4,3-a]pyrazin-8-yl]-3-methyl-2-oxa-8-azaspiro[4.5]decan-4-amine

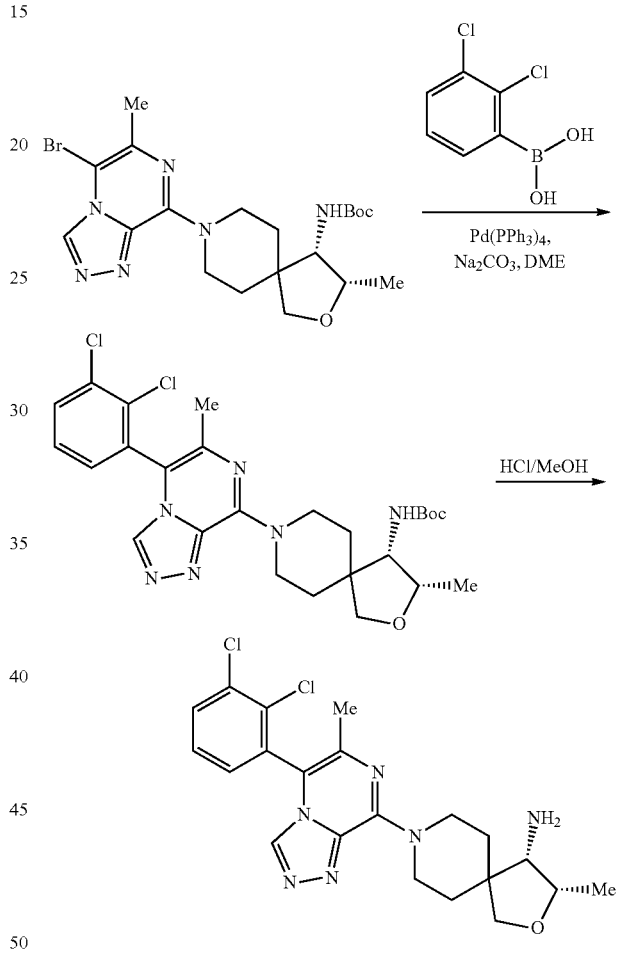

Step 1.

To a mixture of tert-butyl N-[(3S,4S)-8-(5-bromo-6-methyl-[1,2,4]triazolo[4,3-a]pyrazin-8-yl)-3-methyl-2-oxa-8-azaspiro[4.5]decan-4-yl]carbamate (150 mg, 311.60 µmol) and (2,3-dichlorophenyl) boronic acid (89.19 mg, 467.40 µmol) in DME (2 mL) was added Pd(PPh₃)₄ (46.81 mg, 40.51 µmol) and Na₂CO₃ (82.57 mg, 779.00 µmol). The mixture was heated and stirred at 80° C. for 2 hrs. The reaction was concentrated under reduced pressure and the residue was purified by column chromatography to afford tert-butyl N-[(3S,4S)-8-[5-(2,3-dichlorophenyl)-6-methyl-[1,2,4]triazolo[4,3-a]pyrazin-8-yl]-3-methyl-2-oxa-8-azaspiro[4.5]decan-4-yl]carbamate (90 mg, 51.70% yield) as a white solid. LCMS (ESI): m/z [M+H] calculated for C₂₆H₃₂Cl₂N₆O₃:547.19; found 547.3.

Step 2.

A solution of tert-butyl N-[(3S,4S)-8-[5-(2,3-dichlorophenyl)-6-methyl-[1,2,4]triazolo[4,3-a]pyrazin-8-yl]-3-methyl-2-oxa-8-azaspiro[4.5]decan-4-yl]carbamate (40 mg, 73.06 μmol) in HCl/MeOH (3 mL) was stirred at 25° C. for 1.5 hrs. The reaction mixture was concentrated under reduced pressure to afford (3S,4S)-8-[5-(2,3-dichlorophenyl)-6-methyl-[1,2,4]triazolo[4,3-a]pyrazin-8-yl]-3-methyl-2-oxa-8-azaspiro[4.5]decan-4-amine (29 mg, 77.94% yield HCl salt) as a white solid. $^1$H NMR (400 MHZ, Methanol-d4) δ ppm 8.92 (s, 1H) 7.86 (dd, J=7.64, 1.65 Hz, 1H) 7.57-7.61 (m, 1H) 7.56 (d, J=3.30 Hz, 1H) 5.36 (br s, 1H) 5.17 (br s, 1H) 4.36 (dd, J=6.42, 4.10 Hz, 1H) 4.08 (d, J=9.29 Hz, 1H) 3.96 (d, J=9.17 Hz, 1H) 3.80 (br s, 2H) 3.55 (d, J=4.16 Hz, 1H) 2.20 (s, 3H) 2.07-2.17 (m, 3H) 1.91 (br d, J=12.47 Hz, 1H) 1.32-1.39 (m, 3H). LMS (ESI): m/z [M+H] calculated for $C_{21}H_{25}Cl_2N_6O$:447.1; found 447.1.

Example 39. Synthesis of 1-[7-(2,3-dichlorophenyl)-6-methyl-1H-pyrazolo[4,3-c]pyridin-4-yl]-4-methyl-piperidin-4-amine

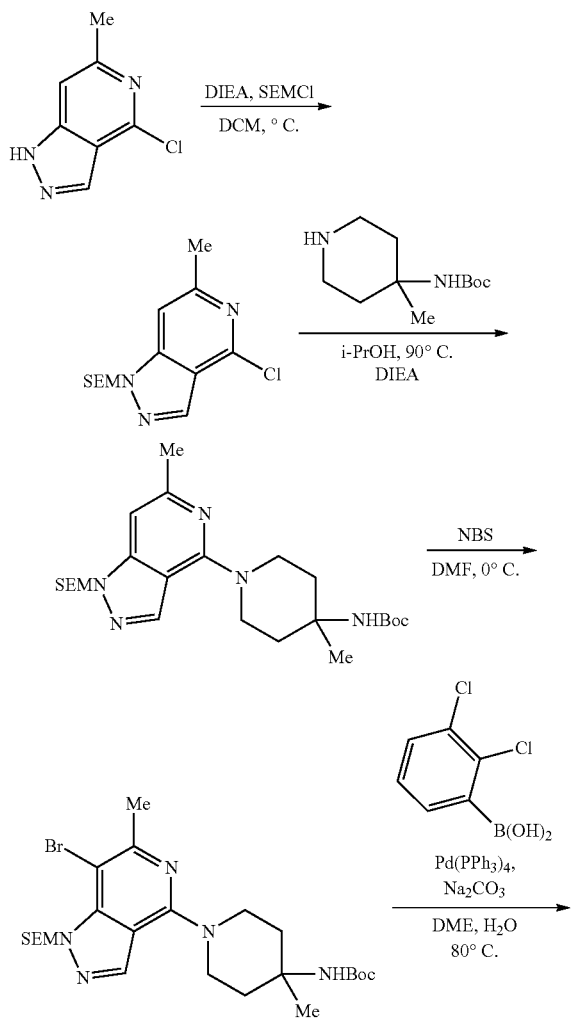

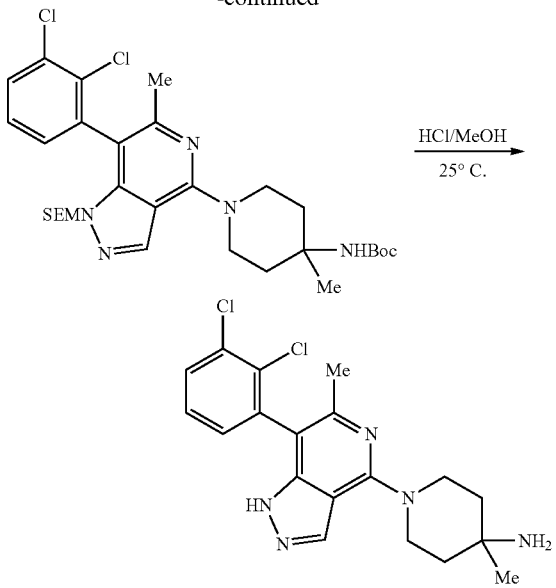

Step 1.

To a solution of 4-chloro-6-methyl-1H-pyrazolo[4,3-c]pyridine (0.5 g, 2.98 mmol) in DCM (3 mL) was added SEM-Cl (1.24 g, 7.46 mmol, 1.32 mL) and DIEA (3.86 g, 29.8 mmol, 5.20 mL) at 0° C. and the mixture was stirred at 0° C. for 4 hrs. The reaction was poured into ice-water and stirred for 5 min. The aqueous phase was extracted with EtOAc and the combined organic phases were washed with brine, dried with anhydrous $Na_2SO_4$, filtered and concentrated under reduced pressure. The residue was purified by silica gel chromatography to give 2-[(4-chloro-6-methyl-pyrazolo[4,3-c]pyridin-1-yl) methoxy]ethyl-trimethyl-silane (365 mg, 41.1% yield). $^1$H NMR (400 MHZ, CDCl3-d) δ ppm 8.22 (s, 1H), 7.24 (s, 1H), 5.69 (s, 2H) 3.66-3.60 (m, 2H), 2.57 (s, 3H), 0.98-0.91 (m, 2H), 0.01-0.05 (m, 9H); LCMS (ESI): m/z [M+H] calculated for $C_{13}H_{21}ClN_3OSi$: 298.1; found 298.3;

Step 2.

To a solution of 2-[(4-chloro-6-methyl-pyrazolo[4,3-c]pyridin-1-yl) methoxy]ethyl-trimethyl-silane (350 mg, 1.18 mmol) in i-PrOH (1 mL) was added DIEA (911 mg, 7.05 mmol, 1.23 mL) and tert-butyl N-(4-methyl-4-piperidyl) carbamate (755 mg, 3.53 mmol) and the mixture was stirred at 90° C. for 24 hrs. The mixture was cooled to room temperature and concentrated under reduced pressure. The crude residue was purified by column chromatography to give tert-butyl N-[4-methyl-1-[6-methyl-1-(2-trimethylsilylethoxymethyl) pyrazolo[4,3-c]pyridin-4-yl]-4-piperidyl] carbamate (384 mg, 68.7% yield). $^1$H NMR (400 MHz, Methanol-d4) δ ppm 8.52 (s, 1H) 6.51 (s, 1H) 5.54-5.49 (m, 2H) 4.01-3.96 (m, 1H) 3.53 (t, J=8.11 Hz, 1H) 3.48-3.30 (m, 3H) 2.25 (s, 2H) 2.09 (d, J=12.72 Hz, 2H) 1.91 (s, 1H) 1.59-1.49 (m, 2H) 1.34 (s, 9H) 1.26 (s, 3H) 0.85-0.72 (m, 2H)-0.12 (s, 9H); LCMS (ESI): m/z [M+H] calculated for: $C_{24}H_{42}N_5O_3Si$ 476.3; found 476.3.

Step 3.

To a solution of tert-butyl N-[4-methyl-1-[6-methyl-1-(2-trimethylsilylethoxymethyl) pyrazolo[4,3-c]pyridin-4-yl]-4-piperidyl]carbamate (250 mg, 525 μmol) in DMF (3 mL) was added NBS (112 mg, 630 μmol) at 0° C. and the mixture was stirred at 0° C. for 0.5 h. and then poured into sat.aq. $Na_2SO_3$ (9 mL) and filtered. The aqueous phase was extracted with EtOAc and the combined organic phases were washed with brine, dried over Na₂SO₄, filtered and concentrated under reduced pressure. The crude residue was purified by silica gel chromatography to give tert-butyl N-[1-[7-bromo-6-methyl-1-(2-trimethylsilylethoxy methyl) pyrazolo[4,3-c]pyridin-4-yl]-4-methyl-4-piperidyl]carbamate (160 mg, 54.9% yield). ¹H NMR (400 MHZ, CDCl3-d) δ ppm 8.19 (s, 1H) 5.68 (s, 2H) 4.43 (s, 1H) 4.04 (d, J=12.96 Hz, 2H) 3.71-3.63 (m, 2H) 3.45-3.55 (m, 2H) 2.51 (s, 3H) 2.19-2.07 (m, 2H) 1.78-1.66 (m, 2H) 1.44 (s, 9H) 1.41 (s, 3H) 0.99-0.80 (m, 2H) 0.09-0.01 (m, 9H); LCMS (ESI): m/z [M+H] calculated for $C_{24}H_{41}BrN_5O_3Si$: 556.2; found 556.0.
Step 4.

To a solution of tert-butyl N-[1-[7-bromo-6-methyl-1-(2-trimethylsilylethoxymethyl) pyrazolo[4,3-c]pyridin-4-yl]-4-methyl-4-piperidyl]carbamate (50 mg, 90.2 μmol) in H₂O (0.2 mL) and DME (1 mL) was added (2,3-dichlorophenyl) boronic acid (18.9 mg. 99.2 μmol), Na₂CO₃ (19.1 mg, 180 μmol) and Pd(PPh₃)₄ (10.4 mg, 9.02 μmol). The mixture was stirred under under N₂ at 80° C. for 6 hrs, cooled to room temperature and filtered. The solvent was removed under reduced pressure and the crude residue was purified by column chromatography to give tert-butyl N-[1-[7-(2,3-dichlorophenyl)-6-methyl-1-(2-trimethylsilylethoxymethyl) pyrazolo[4,3-c]pyridin-4-yl]-4-methyl-4-piperidyl]carbamate (20.0 mg, 32.2 μmol, 35.7% yield). LCMS (ESI): m/z [M+H] calculated for $C_{30}H_{43}Cl_2NO_3Si$: 620.3; found 620.3.
Step 5.

A mixture of tert-butyl-N-[1-[7-(2,3-dichlorophenyl)-6-methyl-1-(2-trimethylsilylethoxymethyl) pyrazolo[4,3-c]pyridin-4-yl]-4-methyl-4-piperidyl]carbamate (40 mg, 64.5 μmol) in HCl/MeOH (2 mL each) was stirred at 25° C. for 0.5 hr. The mixture was concentrated under reduced pressure and the crude residue was purified by preparative HPLC to give 1-[7-(2,3-dichlorophenyl)-6-methyl-1H-pyrazolo[4,3-c]pyridin-4-yl]-4-methyl-piperidin-4-amine (2.7 mg, 10.70% yield,). ¹H NMR (400 MHZ, methanol-d4) δ ppm 8.37 (s, 1H) 8.10 (s, 1H) 7.53 (J=8.07, 1.34 Hz, 1H) 7.30 (t, J=7.89 Hz, 1H) 7.16 (J=7.58, 1.47 Hz, 1H) 4.31 (t, J=14.12 Hz, 2H) 3.58-3.33 (m, 2H) 2.06 (s, 3H) 1.92-1.75 (m, 4H) 1.42 (s, 3H); LCMS (ESI): m/z [M+H] calculated for $C_{19}H_{22}Cl_2N_5$:390.1; found 390.3.

Example 40. Synthesis of (3S,4S)-8-[7-(2,3-dichlorophenyl)-[1,2,5]thiadiazolo[3,4-c]pyridin-4-yl]-3-methyl-2-oxa-8-azaspiro[4.5]decan-4-amine

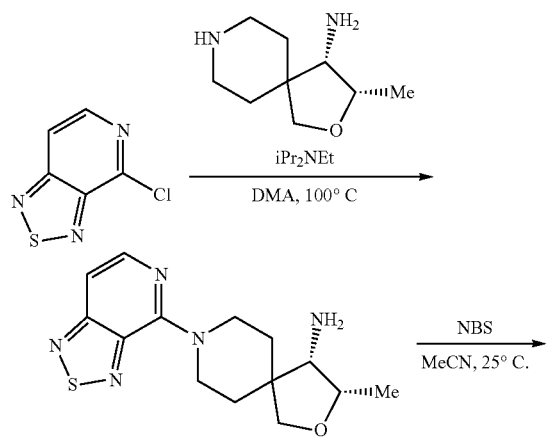

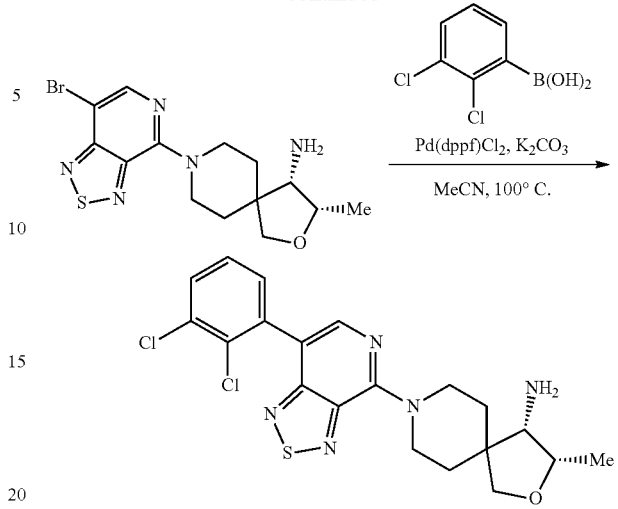

Step 1.

To a solution of 4-chloro-[1,2,5]thiadiazolo[3,4-c]pyridine (230 mg, 1.34 mmol) and (3S,4S)-3-methyl-2-oxa-8-azaspiro[4.5]decan-4-amine (454 mg, 1.87 mmol) in DMA (6.7 mL) was added DIPEA (1.19 mL, 6.70 mmol) at 25° C. The mixture was capped and heated to 110° C. for 2 hrs, cooled to 25° C., and concentrated under reduced pressure. The crude product was submitted to the next step without further purification. LC-MS (ESI): m/z [M+H] calculated for $C_{14}H_{20}N_5OS$: 306.14; found 306.1.
Step 2.

To a solution of (3S,4S)-3-methyl-8-{[1,2,5]thiadiazolo[3,4-c]pyridin-7-yl}-2-oxa-8-azaspiro[4.5]decan-4-amine (409 mg, 1.34 mmol) in acetonitrile (3.94 mL) was added N-bromosuccinimide (261 mg, 1.47 mmol) and the reaction mixture was stirred at room temperature for 1 hr. After concentration under reduced pressure, the crude residue was diluted with EtOAc (6 mL), washed with saturated NaHCO₃ (2×3 mL), dried over Na₂SO₄, filtered, and concentrated under reduced pressure. The crude material so obtained was used into the next step without further purification. LC-MS (ESI): m/z [M+H] calculated for $C_{14}H_{19}BrN_5OS$: 384.04; found 384.2.
Step 3.

To a 20 mL vial containing (3S,4S)-8-{7-bromo-[1,2,5]thiadiazolo[3,4-c]pyridin-4-yl}-3-methyl-2-oxa-8-azaspiro[4.5]decan-4-amine (166 mg, 431 μmol) was added (2,3-dichlorophenyl) boronic acid (123 mg, 646 μmol), palladium (2+)bis(cyclopenta-1,3-dien-1-yldiphenylphosphane)methylene chloride iron dichloride (70.3 mg, 86.2 μmol), and potassium carbonate (237 mg, 1.72 mmol). The vial was flushed with N₂, ACN (4.31 mL) was added and the vial was sealed and heated to 100° C. After 1 hr, the reaction was cooled to 25° C., filtered through celite, eluted with EtOAc and concentrated under reduced pressure. The crude residue was purified by prep-HPLC to give (3S,4S)-8-[7-(2,3-dichlorophenyl)-[1,2,5]thiadiazolo[3,4-c]pyridin-4-yl]-3-methyl-2-oxa-8-azaspiro[4.5]decan-4-amine (12.1 mg, 5.7% yield) as a white solid. ¹H NMR (500 MHZ, Methanol-d4) δ 8.55 (s, 1H), 7.97 (s, 1H), 7.62 (dd, J=7.6, 2.0 Hz, 1H), 7.51-7.33 (m, 2H), 5.19-5.08 (m, 2H), 4.38-4.25 (m, 1H), 4.03 (d, J=8.9 Hz, 1H), 3.90 (d, J=9.0 Hz, 1H), 3.77 (ddd, J=13.9, 10.4, 3.4 Hz, 1H), 3.69 (ddd, J=13.9, 10.5, 2.9 Hz, 1H), 3.29 (d, J=4.6 Hz, 1H), 2.68 (s, 3H), 2.06-1.86 (m, 3H), 1.80 (d, J=13.8 Hz, 1H), 1.31 (d, J=6.5 Hz, 3H); LC-MS (ESI): m/z [M+H] calculated for $C_{20}H_{22}Cl_2N_5OS$: 450.1; found 450.3.

Example 41. Synthesis of 4-{[4-(4-amino-4-methylpiperidin-1-yl)-3H-[1,2,3]triazolo[4,5-c]pyridin-7-yl]sulfanyl}-3-chloropyridin-2-amine

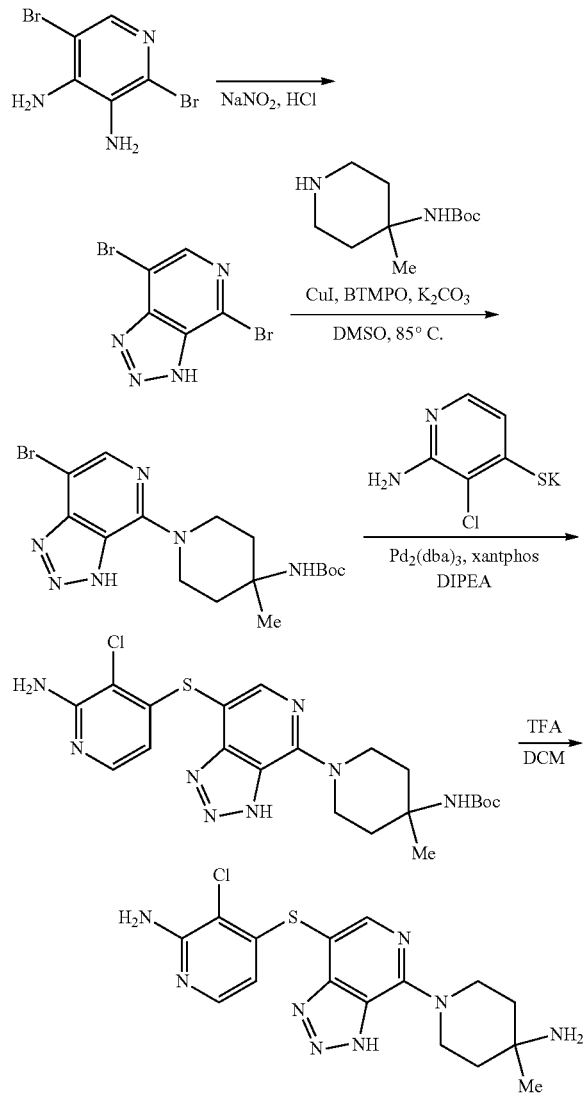

Step 1.

To a suspension of 2,5-dibromopyridine-3,4-diamine (2.5 g, 9.36 mmol) in aqueous 2 N HCl (12.4 mL) at 0° C. was added an aqueous solution of sodium nitrite (3.7 mL water, 965 mg). Upon completion of addition, the solution was vigorously stirred for 2 hrs while maintaining the reaction temperature at 0° C. After this time, the reaction mixture was filtered, and the collected solid was washed with ice cold water and dried under reduced pressure to afford 4,7-dibromo-3H-[1,2,3]triazolo[4,5-c]pyridine (2.38 g, 91% yield) as a light tan solid. LC-MS (ESI): m/z [M+H] calculated for $C_5H_2Br_2N_4$:276.9; found 277.0.

Step 2.

A vial was charged with 4,7-dibromo-3H-[1,2,3]triazolo[4,5-c]pyridine (753 mg, 2.70 mmol), tert-butyl N-(4-methylpiperidin-4-yl) carbamate (867 mg, 4.05 mmol), copper iodide (51.4 mg, 0.27 mmol), tripotassium phosphate (573 mg, 2.70 mmol), N,N-bis(2,4,6-trimethoxyphenyl) oxalamide (BTMPO, 113 mg, 0.27 mmol), and degassed DMSO (5 mL), sequentially. The vial was then sealed, and the reaction headspace was evacuated and filled with $N_2$. This procedure was repeated two times and the vial was then placed in a preheated reaction block at 120° C. After stirring for 16 hrs, the reaction mixture was diluted with ethyl acetate and filtered through a pad of celite. The filtrate was further diluted with ethyl acetate and washed with water (4×50 ml) and saturated aqueous sodium chloride (1×25 mL), sequentially. The washed solution was dried over magnesium sulfate. The dried solution was filtered, and the filtrate was concentrated under reduced pressure. The crude residue was purified column chromatography to give tert-butyl (1-(7-bromo-3H-[1,2,3]triazolo[4,5-c]pyridin-4-yl)-4-methylpiperidin-4-yl) carbamate (213 mg, 19% yield) as a yellow solid. LC-MS (ESI): m/z: [M+H] calculated for $C_{16}H_{23}BrN_6O_2$:411.1; found 410.9.

Step 3.

A 5 mL microwave vial was charged with tert-butyl N-(1-{7-bromopyrazolo[1,5-a]pyrazin-4-yl}-4-methylpiperidin-4-yl) carbamate (37.3 mg, 0.09 mmol), 3-chloro-4-(potassiosulfanyl)pyridin-2-amine (21.6 mg, 0.10 mmol), Xantphos (10.5 mg, 0.018 mmol), degassed dioxane (909 μL), and N,N-diisopropylethylamine (47.4 μL, 0.27 mmol), sequentially. The resulting mixture was degassed by bubbling nitrogen gas through the solution for 10 min, and then tris(dibenzylideneacetone) dipalladium (8.32 mg, 0.01 mmol) was added to the vial in one portion. The mixture was then degassed for an additional 5 min before it was sealed, and the mixture was warmed to 120° C. via microwave radiation and stirred for 1.5 hrs. After this time, the reaction mixture was filtered through a pad of celite, and the filtrate was concentrated under reduced pressure to an orange oil. This oil was purified by column chromatography to give tert-butyl N-(1-{7-[(2-amino-3-chloropyridin-4-yl)sulfanyl]-3H-[1,2,3]triazolo[4,5-c]pyridin-4-yl}-4-methylpiperidin-4-yl) carbamate as an impure orange oil that was submitted to the next step without further purification. LC-MS (ESI): m/z [M+H] calculated for $C_{21}H_{27}ClN_8O_2S$: 491.2; found 491.4.

Step 4.

A 20 mL vial was charged with tert-butyl N-(1-{7-[(2-amino-3-chloropyridin-4-yl)sulfanyl]-3H-[1,2,3]triazolo[4,5-c]pyridin-4-yl}-4-methylpiperidin-4-yl) carbamate (33 mg, 0.07 mmol), DCM (2 mL), and TFA (0.5 mL), sequentially, at room temperature. The resulting yellow solution was left to stir for 1 hr. After this time, the reaction mixture was concentrated under reduced pressure to give an orange residue. This crude residue was purified by preparative HPLC to give 4-{[4-(4-amino-4-methylpiperidin-1-yl)-3H-[1,2,3]triazolo[4,5-c]pyridin-7-yl]sulfanyl}-3-chloropyridin-2-amine (7.7 mg, 29% yield) as a fluffy white solid. 4-{[4-(4-amino-4-methylpiperidin-1-yl)-3H-[1,2,3]triazolo[4,5-c]pyridin-7-yl]sulfanyl}-3-chloropyridin-2-amine was isolated as its formate salt. $^1$H NMR (500 MHZ, Methanol-d4) δ 8.34 (s, 1H), 8.08 (s, 1H), 7.50 (d, J=5.5 Hz, 1H), 5.70 (d, J=5.6 Hz, 1H), 5.13 (d, J=14.1 Hz, 2H), 3.88 (ddd, J=14.0, 9.5, 4.0 Hz, 2H), 2.01-1.88 (m, 4H), 1.57 (s, 3H); LC-MS (ESI): m/z [M+H] calculated for $C_{16}H_{20}ClN_8S$: 391.1; found 391.2.

Example 42. Synthesis of 1-[5-(2,3-dichlorophenyl)-6-methylimidazo[1,2-a]pyrazin-8-yl]-4-methylpiperidin-4-amine

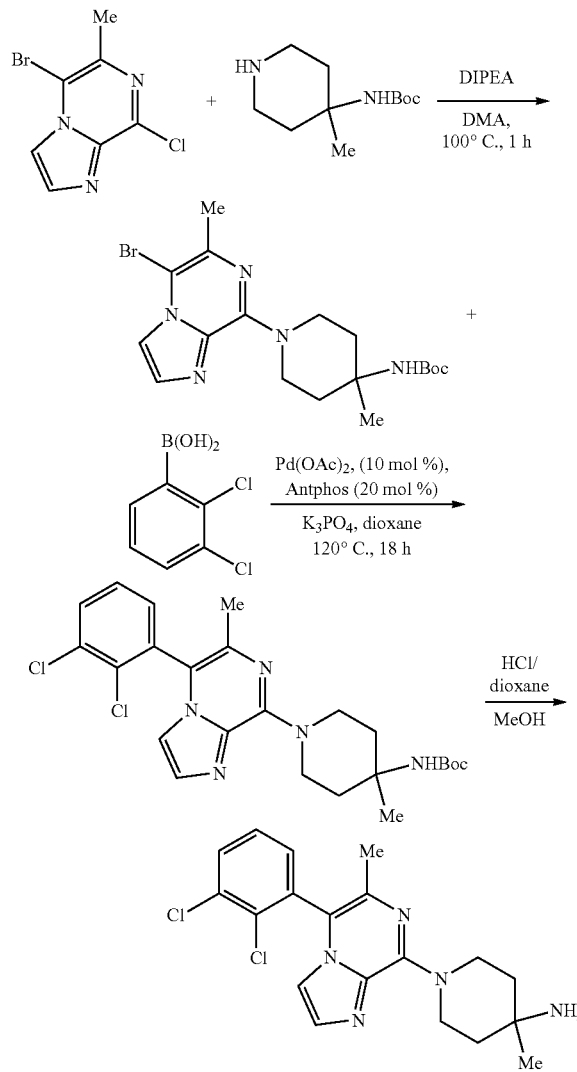

Step 1.

To a solution of 5-bromo-8-chloro-6-methylimidazo[1,2-a]pyrazine (800 mg, 3.24 mmol) in DMA (16.2 mL) was added tert-butyl N-(4-methylpiperidin-4-yl) carbamate (762 mg, 3.56 mmol) and DIPEA (16.2 mmol). The reaction mixture was stirred in a capped vial at 100° C. for 1 hr. The resulting reaction mixture was concentrated under reduced pressure, removing as much of the DMA as possible. The residue was purified by column chromatography to yield tert-butyl N-(1-{5-bromo-6-methylimidazo[1,2-a]pyrazin-8-yl}-4-methylpiperidin-4-yl) carbamate (1.10 g, 80%). LCMS (ESI): m/z [M+H] calculated for $C_{18}H_{27}BrN_5O_2$: 424.13; found 424.4.

Step 2.

To a vial was added tert-butyl N-(1-{5-bromo-6-methylimidazo[1,2-a]pyrazin-8-yl}-4-methylpiperidin-4-yl) carbamate (100 mg, 235 μmol), (2,3-dichlorophenyl) boronic acid (53.8 mg, 282 μmol), Antphos (17.4 mg, 47.0 μmol), $K_3PO_4$ (149 mg, 705 μmol), and Pd(OAc)$_2$ (5.27 mg, 23.5 μmol). The mixture was evacuated under house vacuum for 10 min before adding in degassed dioxane (2.34 mL). The resulting mixture was filled with $N_2$ and degassed three times before stirring at 105° C. for 2 hrs. The resulting reaction mixture was filtered through a pad of celite washing with DCM and MeOH. The filtrate was concentrated under reduced pressure and the residue was purified by column chromatography to yield tert-butyl N-{1-[5-(2,3-dichlorophenyl)-6-methylimidazo[1,2-a]pyrazin-8-yl]-4-methylpiperidin-4-yl}carbamate (95.0 mg, 82.6%). LCMS (ESI): m/z [M+H] calculated for $C_{24}H_{30}Cl_2N_5O_2$: 490.2; found 490.4.

Step 3.

To a solution of tert-butyl N-{1-[5-(2,3-dichlorophenyl)-6-methylimidazo[1,2-a]pyrazin-8-yl]-4-methylpiperidin-4-yl}carbamate (115 mg, 234 μmol) in methanol (1.9 mL) was added 4 M hydrogen chloride in dioxane (482 μL, 1.93 mmol). The reaction was stirred in capped vial for 4 hrs. The resulting reaction mixture was concentrated under reduced pressure. The residue was purified by reverse phase HPLC (Biotage) to yield the desired product 1-[5-(2,3-dichlorophenyl)-6-methylimidazo[1,2-a]pyrazin-8-yl]-4-methylpiperidin-4-amine (10.0 mg, 25.6 μmol, 13.2%) as the formic acid salt. $^1$H NMR (500 MHZ, methanol-d) δ 8.56 (s, 1H), 7.79 (dd, J=8.1, 1.5 Hz, 1H), 7.54 (t, J=7.9 Hz, 1H), 7.50 (d, J=1.2 Hz, 1H), 7.44 (dd, J=7.7, 1.6 Hz, 1H), 7.04 (d, J=1.3 Hz, 1H), 3.92-3.77 (m, 2H), 2.11 (s, 3H), 1.90 (dt, J=11.7, 4.8 Hz, 6H), 1.49 (s, 3H). LCMS (ESI): m/z [M+H] calculated for $C_{19}H_{22}Cl_2N_5$: 390.1; found 390.1.

Example 43. Synthesis of (3S,4S)-8-[7-(2,3-dichlorophenyl)-3H-imidazo[4,5-c]pyridin-4-yl]-3-methyl-2-oxa-8-azaspiro[4.5]decan-4-amine

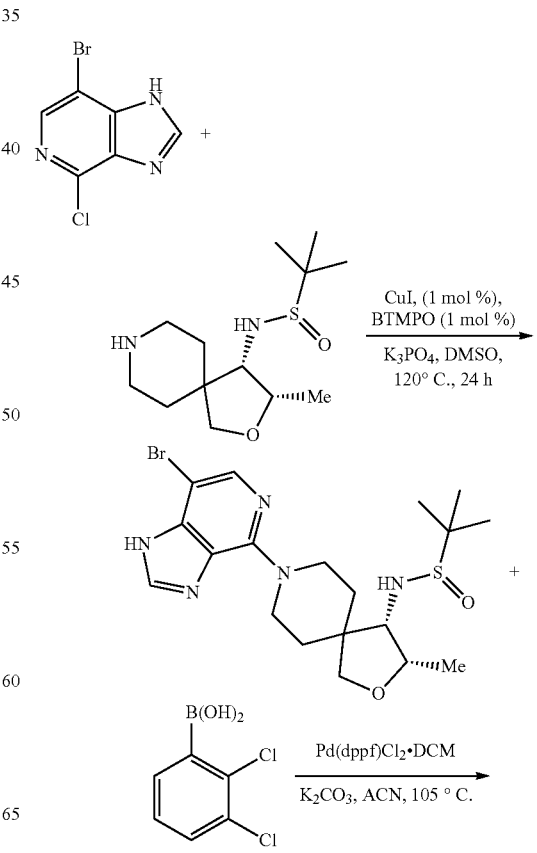

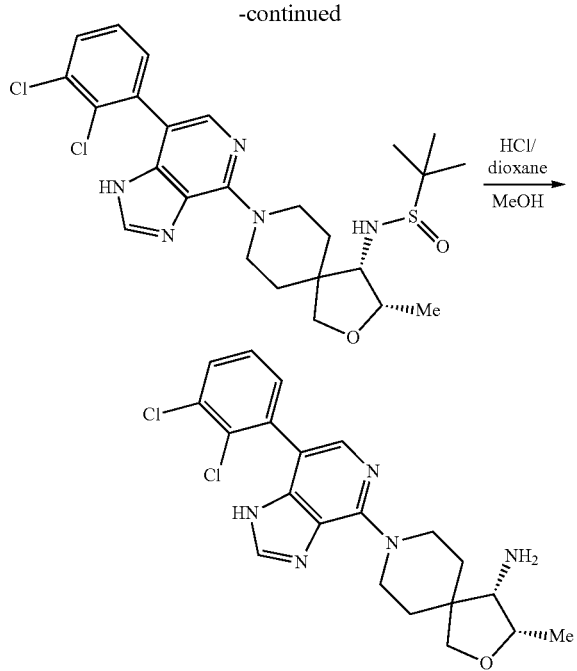

Step 1.

To a reaction vial was added 7-bromo-4-chloro-1H-imidazo[4,5-c]pyridine (130 mg, 559 µmol), 2-methyl-N-[(3S,4S)-3-methyl-2-oxa-8-azaspiro[4.5]decan-4-yl]propane-2-sulfinamide (153 mg, 559 µmol), CuI (106 mg, 559 µmol), $K_3PO_4$ (118 mg, 559 µmol), and BTMPO (235 mg, 559 µmol). The vial was evacuated and filled with $N_2$ three times before adding in dimethyl sulfoxide (1 mL). The reaction was stirred in the capped vial at 120° C. for 24 hrs. The resulting reaction mixture was diluted with EtOAc and $H_2O$. The aqueous layer was extracted three times with EtOAc. The combined organic layers were washed with brine. The resulting organic layer was dried over $MgSO_4$, filtered, and concentrated under reduced pressure. The residue was purified by column chromatographyto yield the desired product, N-[(3S,4S)-8-{7-bromo-1H-imidazo[4,5-c]pyridin-4-yl}-3-methyl-2-oxa-8-azaspiro[4.5]decan-4-yl]-2-methylpropane-2-sulfinamide (60 mg, 22.9%). LCMS (ESI): m/z [M+H] calculated for $C_{19}H_{29}BrN_5O_2S$: 470.1; found 470.2.

Step 2.

To a reaction vial was added N-[(3S,4S)-8-{7-bromo-1H-imidazo[4,5-c]pyridin-4-yl}-3-methyl-2-oxa-8-azaspiro[4.5]decan-4-yl]-2-methylpropane-2-sulfinamide (50 mg, 106 µmol), (2,3-dichlorophenyl) boronic acid (30.3 mg, 159 µmol), Pd(dppf)Cl$_2$·DCM (17.3 mg, 21.2 µmol), and $K_2CO_3$ (43.9 mg, 318 µmol). The mixture was evacuated and filled with $N_2$ three times before adding in acetonitrile (1.05 mL). The reaction was stirred at 100° C. for 2 hrs. The resulting reaction mixture was filtered through a pad of celite. The filtrate was concentrated under reduced pressure and the residue was purified by column chromatography to yield N-[(3S,4S)-8-[7-(2,3-dichlorophenyl)-1H-imidazo[4,5-c]pyridin-4-yl]-3-methyl-2-oxa-8-azaspiro[4.5]decan-4-yl]-2-methylpropane-2-sulfinamide (25.0 mg, 44.0%). LCMS (ESI): m/z [M+H] calculated for $C_{25}H_{32}Cl_2N_5O_2S$: 536.1; found 536.3.

Step 3.

To a solution of N-((3S,4S)-8-(7-(2,3-dichlorophenyl)-1H-imidazo[4,5-c]pyridin-4-yl)-3-methyl-2-oxa-8-azaspiro[4.5]decan-4-yl)-2-methylpropane-2-sulfinamide (25 mg, 46.5 µmol) in methanol (1 mL) was added a 4 M solution of hydrogen chloride (34.7 µL, 139 µmol) in dioxane. The reaction mixture was stirred in a capped vial at room temperature for 2 hrs. The resulting reaction mixture was concentrated under reduced pressure. The residue was purified by reverse phase HPLC to yield (3S,4S)-8-[7-(2,3-dichlorophenyl)-3H-imidazo[4,5-c]pyridin-4-yl]-3-methyl-2-oxa-8-azaspiro[4.5]decan-4-amine (5.00 mg, 24.8%). $^1$H NMR (500 MHZ, Methanol-d4) δ 8.57 (s, 1H), 8.05 (s, 1H), 7.75 (s, 1H), 7.64 (dd, J=7.6, 2.0 Hz, 1H), 7.50-7.32 (m, 2H), 4.30 (dd, J=6.5, 4.8 Hz, 1H), 3.96 (d, J=8.7 Hz, 1H), 3.83 (d, J=8.8 Hz, 1H), 3.54 (d, J=41.6 Hz, 2H), 3.16 (d, J=4.9 Hz, 2H), 1.96 (dd, J=16.0, 10.6 Hz, 2H), 1.82 (s, 1H), 1.76 (s, 1H), 1.28 (d, J=6.5 Hz, 4H). LCMS (ESI): m/z [M+H] calculated for $C_{21}H_{24}Cl_2N_5O$:432.1; found 432.2.

Example 44. Synthesis of (3S,4S)-8-{5-[(2,3-dichlorophenyl)sulfanyl]imidazo[1,5-a]pyrazin-8-yl}-3-methyl-2-oxa-8-azaspiro[4.5]decan-4-amine

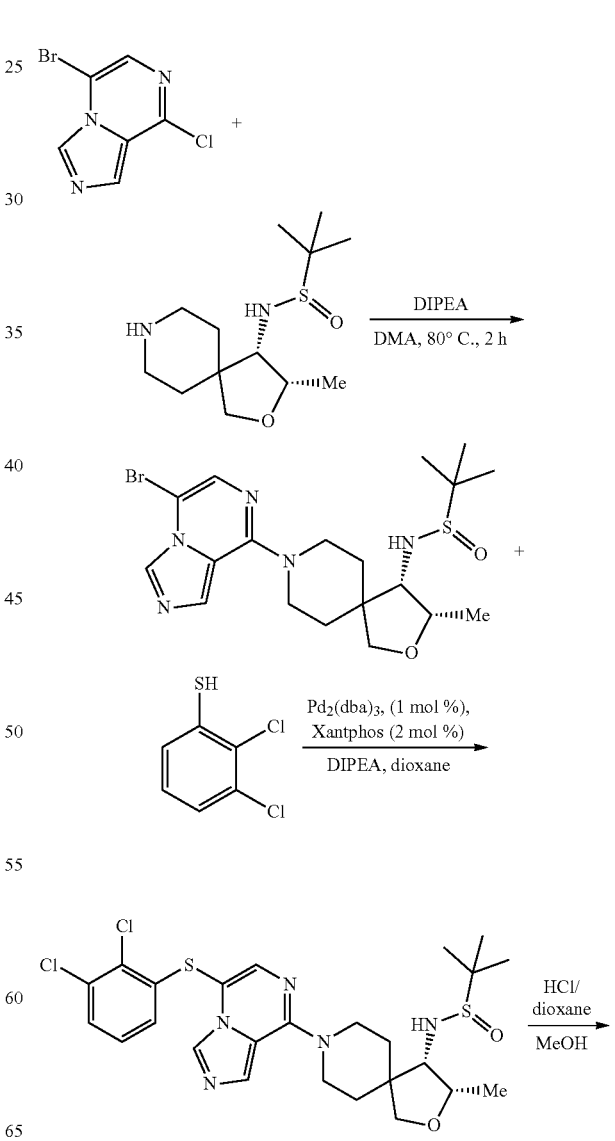

-continued

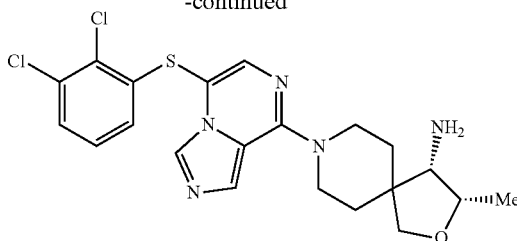

Step 1.

To a solution of 5-bromo-8-chloroimidazo[1,5-a]pyrazine (30 mg, 129 µmol) in DMA (1 mL) was added 2-methyl-N-((3S,4S)-3-methyl-2-oxa-8-azaspiro[4.5]decan-4-yl) propane-2-sulfinamide (38.6 mg, 141 µmol) and DIPEA (112 µL, 645 µmol). The mixture was capped and stirred at 80° C. for 2 hrs. The resulting mixture was diluted with EtOAc and H$_2$O. The organic layer was separated and then washed 3 more times with H$_2$O. The combined organic layer was separated, dried over MgSO$_4$, filtered, and concentrated under reduced pressure. The residue was purified by column chromatography to yield N-((3S,4S)-8-(5-bromoimidazo[1,5-a]pyrazin-8-yl)-3-methyl-2-oxa-8-azaspiro[4.5]decan-4-yl)-2-methylpropane-2-sulfinamide (30.0 mg, 49.5%). LCMS (ESI): m/z [M+H] calculated for C$_{19}$H$_{29}$BrN$_5$O$_2$S: 470.1; found 470.3.

Step 2.

In a microwave vial was added N-((3S,4S)-8-(5-bromo-imidazo[1,5-a]pyrazin-8-yl)-3-methyl-2-oxa-8-azaspiro [4.5]decan-4-yl)-2-methylpropane-2-sulfinamide (30 mg, 63.7 µmol), 2,3-dichlorobenzenethiol (22.7 mg, 127 µmol), Xantphos (7.34 mg, 12.7 µmol), Pd$_2$(dba)$_3$ (2.84 mg, 6.37 µmol) and DIPEA (16.4 mg, 127 µmol). The vial was evacuated for 10 min before adding in degassed dioxane (637 µL). The mixture was purged and evacuated with N$_2$ gas three times. The reaction was subjected to microwave conditions for 2 hrs at 110° C. The resulting reaction mixture was filtered through a pad of celite. The filtrate was concentrated under reduced pressure and residue was purified by column chromatographyto yield N-((3S,4S)-8-(5-((2,3-dichlorophenyl)thio)imidazo[1,5-a]pyrazin-8-yl)-3-methyl-2-oxa-8-azaspiro[4.5]decan-4-yl)-2-methylpropane-2-sulfinamide (23.0 mg, 63.5%). LCMS (ESI): m/z [M+H] calculated for C$_{25}$H$_{32}$Cl$_2$N$_5$O$_2$S$_2$:568.1; found 568.3.

Step 3.

To a solution of N-((3S,4S)-8-(5-((2,3-dichlorophenyl)thio)imidazo[1,5-a]pyrazin-8-yl)-3-methyl-2-oxa-8-azaspiro[4.5]decan-4-yl)-2-methylpropane-2-sulfinamide (23 mg, 40.4 µmol), in methanol (2 mL) was added 4 M HCl in dioxane (1 mL, 4.00 mmol). The reaction mixture was stirred in a capped vial at room temperature for 1 hr. The resulting reaction mixture was concentrated under reduced pressure and the residue was purified by reverse phase HPLC to yield (3S,4S)-8-{5-[(2,3-dichlorophenyl)sulfanyl]imidazo[1,5-a]pyrazin-8-yl}-3-methyl-2-oxa-8-azaspiro [4.5]decan-4-amine (7.00 mg, 37.4%). $^1$H NMR (500 MHZ, Methanol-d4) δ 8.53 (s, 1H), 8.21 (s, 1H), 7.99 (s, 1H), 7.61 (s, 1H), 7.40 (dd, J=8.0, 1.4 Hz, 1H), 7.11 (t, J=8.1 Hz, 1H), 6.69 (dd, J=8.1, 1.4 Hz, 1H), 4.53-4.41 (m, 2H), 4.37-4.25 (m, 1H), 3.99 (d, J=9.0 Hz, 1H), 3.86 (d, J=8.9 Hz, 1H), 3.70-3.50 (m, 2H), 2.04-1.84 (m, 4H), 1.78 (d, J=13.2 Hz, 1H), 1.30 (d, J=6.5 Hz, 3H). LCMS (ESI): m/z [M+H] calculated for C$_{21}$H$_{24}$Cl$_2$N$_5$OS: 464.1; found 464.2.

Example 45. Synthesis of (3S,4S)-8-[5-(2,3-dichlorophenyl)imidazo[1,5-a]pyrazin-8-yl]-3-methyl-2-oxa-8-azaspiro[4.5]decan-4-amine

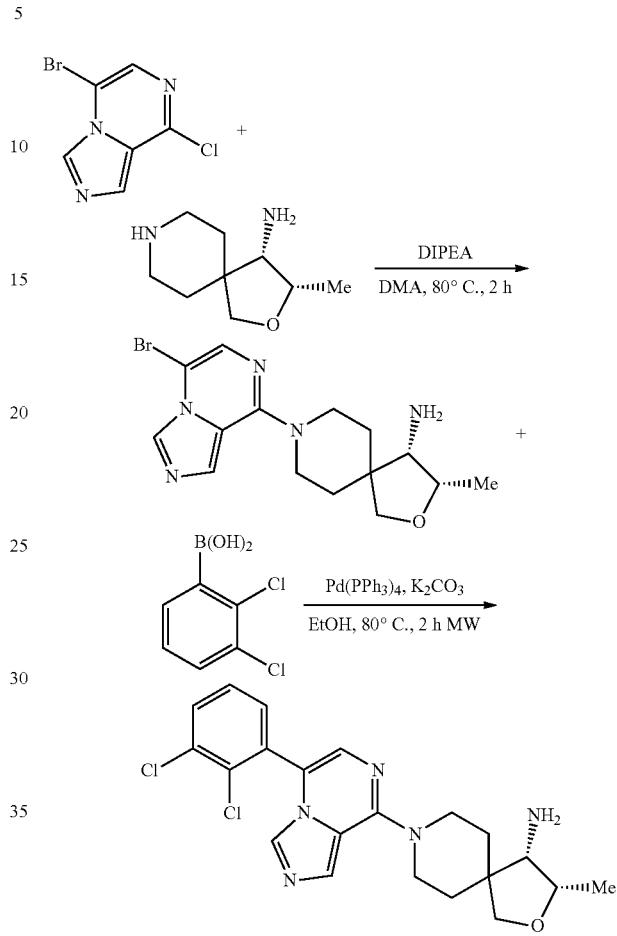

Step 1.

To a solution of 5-bromo-8-chloroimidazo[1,5-a]pyrazine (120 mg, 516 µmol) in DMA (2 mL) was added (3S,4S)-3-methyl-2-oxa-8-azaspiro[4.5]decan-4-amine (135 mg, 567 µmol) and DIPEA (447 µL, 2.57 mmol). The mixture was capped and stirred at 80° C. for 2 hrs. The resulting reaction mixture was diluted with EtOAc and NH$_4$OH. The organic layer was separated and then washed three more times with H$_2$O. The resulting organic layer was separated, dried over MgSO$_4$, filtered, and concentrated under reduced pressure. The residue was purified by column chromatographyto yield (3S,4S)-8-(5-bromoimidazo[1,5-a]pyrazin-8-yl)-3-methyl-2-oxa-8-azaspiro[4.5]decan-4-amine (113 mg, 60.1%). LCMS (ESI): m/z [M+H] calculated for C$_{15}$H$_{21}$BrNO: 366.09; found 366.2.

Step 2.

(3S,4S)-8-(5-Bromoimidazo[1,5-a]pyrazin-8-yl)-3-methyl-2-oxa-8-azaspiro[4.5]decan-4-amine (113 mg, 308 µmol), (2,3-dichlorophenyl) boronic acid (88.1 mg, 462 µmol), tetrakis (21.2 mg, 18.4 µmol), and potassium carbonate (127 mg, 924 µmol) were added to a microwave vial. The vial was flashed with N$_2$ before adding in degassed EtOH (3.94 mL). The mixture was purged and evacuated with N$_2$ three times. The reaction was heated under microwave irradiation for 2 h at 110° C. The resulting reaction mixture was filtered through a pad of celite, concentrated under reduced pressure and residue was purified by reverse phase to yield the (3S,4S)-8-[5-(2,3-dichlorophenyl)imidazo[1,5-a]pyrazin-8-yl]-3-methyl-2-oxa-8-azaspiro[4.5]decan-4-amine (35.0 mg, 26.3%) as formic acid salt. $^1$H NMR (500 MHZ, Methanol-d4) δ 8.40 (s, 2H), 7.91 (s, 1H), 7.83 (s, 1H), 7.81-7.74 (m, 1H), 7.56-7.49 (m, 2H), 7.12 (s, 1H), 4.58-4.39 (m, 2H), 4.33 (qd, J=6.5, 4.1 Hz, 1H), 4.04 (d, J=9.2 Hz, 1H), 3.99-3.87 (m, 1H), 3.49-3.45 (m, 2H), 1.95 (s, 4H), 1.79 (d, J=13.5 Hz, 1H), 1.34 (d, J=6.5 Hz, 3H). LCMS (ESI): m/z [M+H] calculated for $C_{21}H_{24}Cl_2N_5O$: 432.1; found 432.2.

Example 46. Synthesis of (3S,4S)-8-{7-[(2-amino-3-chloropyridin-4-yl)sulfanyl]furo[3,2-c]pyridin-4-yl}-3-methyl-2-oxa-8-azaspiro[4.5]decan-4-amine

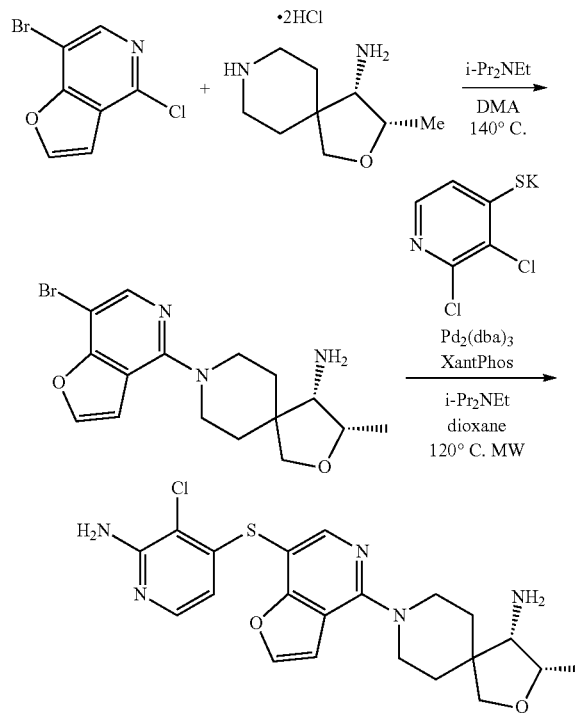

Step 1.
To a solution of 7-bromo-4-chlorofuro[3,2-c]pyridine (250 mg, 1.07 mmol) and (3S,4S)-3-methyl-2-oxa-8-azaspiro[4.5]decan-4-amine (311 mg, 1.28 mmol, HCl salt) in dimethylacetamide (5.35 mL) was added N,N-diisopropylethylamine (931 μL, 5.35 mmol) at room temperature. The solution was then heated at 140° C. for 18 hrs. The resulting solution was concentrated under reduced pressure and purified via flash column chromatography to yield (3S,4S)-8-{7-bromofuro[3,2-c]pyridin-4-yl}-3-methyl-2-oxa-8-azaspiro[4.5]decan-4-amine (390 mg, 100%) as a viscous yellow oil. LC-MS (ESI): m/z [M+H]$^+$ calculated for $C_{16}H_{21}BrN_3O_2$:366.1; found 366.2.
Step 2.
To a 5 mL microwave vial was added (3S,4S)-8-{7-bromofuro[3,2-c]pyridin-4-yl}-3-methyl-2-oxa-8-azaspiro[4.5]decan-4-amine (100 mg, 273 μmol), 3-chloro-4-(potassiosulfanyl)pyridin-2-amine (81 mg, 409 μmol), XantPhos (32 mg, 54.6 μmol), and tris(dibenzylideneacetone) dipalladium (25 mg, 27.3 μmol). The vial was then capped and purged with N$_2$, followed by addition of degassed dioxane (3 mL) and DIPEA (95 μL, 546 μmol). The mixture was heated to 120° C. for 2 hrs under microwave irradiation. The resulting mixture was filtered through a pad of celite, washed with 20% MeOH/DCM, and concentrated under reduced pressure. Purification by silica gel chromatography, followed by purification by preparatory HPLC yielded (3S,4S)-8-{7-[(2-amino-3-chloropyridin-4-yl)sulfanyl]furo[3,2-c]pyridin-4-yl}-3-methyl-2-oxa-8-azaspiro[4.5]decan-4-amine (7.9 mg, 7% yield) as a formic acid salt. $^1$H NMR (500 MHZ, methanol-d4) δ 8.49 (s, 1H), 8.08 (s, 1H), 7.77 (d, J=2.3 Hz, 1H), 7.49 (d, J=5.6 Hz, 1H), 7.13 (d, J=2.3 Hz, 1H), 5.71 (d, J=5.6 Hz, 1H), 4.39 (dt, J=14.2, 4.5 Hz, 1H), 4.36-4.26 (m, 2H), 4.00 (d, J=9.1 Hz, 1H), 3.88 (d, J=9.0 Hz, 1H), 3.44 (ddd, J=14.0, 10.0, 4.1 Hz, 1H), 3.41-3.33 (m, 2H), 2.02-1.87 (m, 3H), 1.75 (d, J=13.3 Hz, 1H), 1.31 (d, J=6.5 Hz, 3H). LC-MS (ESI): m/z [M+H]$^+$ calculated for $C_{21}H_{25}ClN_5O_2S$: 446.1; found 446.3.

Example 47. Synthesis of (3S,4S)-8-[5-(2H-indazol-6-yl)-6-methylimidazo[1,5-a]pyrazin-8-yl]-3-methyl-2-oxa-8-azaspiro[4.5]decan-4-amine

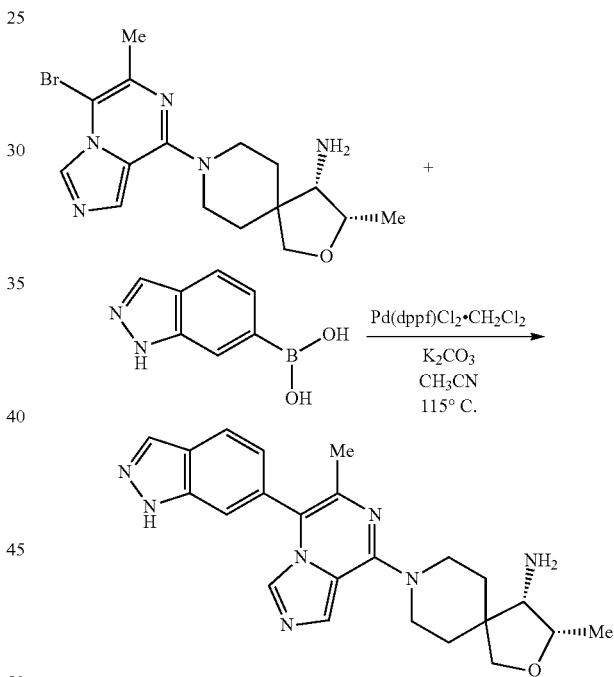

To a 40 mL scintillation vial was added (3S,4S)-8-{5-bromo-6-methylimidazo[1,5-a]pyrazin-8-yl}-3-methyl-2-oxa-8-azaspiro[4.5]decan-4-amine (0.1 g, 262 μmol), (1H-indazol-6-yl) boronic acid (50.8 mg, 314 μmol), Pd(dppf)Cl$_2$·DCM (21.3 mg, 26.2 μmol) and potassium carbonate (143 mg, 1.04 mmol). The vial was capped and the headspace was then purged with nitrogen gas for 3 min. To the mixture of solids was then added ACN (3.61 mL) that had been sparged with nitrogen gas for 45 minutes. The heterogeneous solution was then heated to 100° C. for 1 hr. Dimethylacetamide (0.5 mL), ACN (0.5 mL), Pd(dppf)Cl$_2$·DCM (21.3 mg, 26.2 μmol), and (1H-indazol-6-yl) boronic acid (20 mg, 123 μmol) were added to the solution. The solution was then sparged with nitrogen gas for 10 minutes. The reaction was then allowed to stir at 115° C. for additional 16 hrs. The resulting mixture was filtered through a pad of celite, which was washed with 20% MeOH/DCM and the filtrate was concentrated under reduced pressure. The residue was purified via preparatory HPLC to afford (3S,4S)-8-[5-(1H-indazol-6-yl)-6-methylimidazo[1,5-a]pyrazin-8-yl]-3-methyl-2-oxa-8-azaspiro[4.5]decan-4-amine (8.0 mg, 7% yield) as formic acid salt. $^1$H NMR (500 MHZ, methanol-d4) δ 8.55 (s, 2H), 8.17 (s, 1H), 8.00 (dt, J=8.3, 0.9 Hz, 1H), 7.79 (d, J=0.9 Hz, 1H), 7.65 (dd, J=2.7, 1.0 Hz, 2H), 7.19 (dt, J=8.3, 1.2 Hz, 1H), 4.43-4.21 (m, 3H), 3.95 (d, J=8.7 Hz, 1H), 3.81 (d, J=8.8 Hz, 1H), 3.54 (dd, J=14.4, 9.3 Hz, 1H), 3.50-3.38 (m, 1H), 3.24-3.09 (m, 1H), 2.13 (d, J=0.8 Hz, 3H), 2.06-1.87 (m, 2H), 1.86-1.79 (m, 1H), 1.78-1.70 (m, 1H), 1.27 (d, J=6.5 Hz, 3H). LC-MS (ESI): m/z [M+H] calculated for $C_{23}H_{28}N_7O$: 418.2; found 418.4.

Example 48. Synthesis of 4-((7-(4-amino-4-methylpiperidin-1-yl)-1H-pyrazolo[3,4-c]pyridin-4-yl)thio)-3-chloropyridin-2-amine

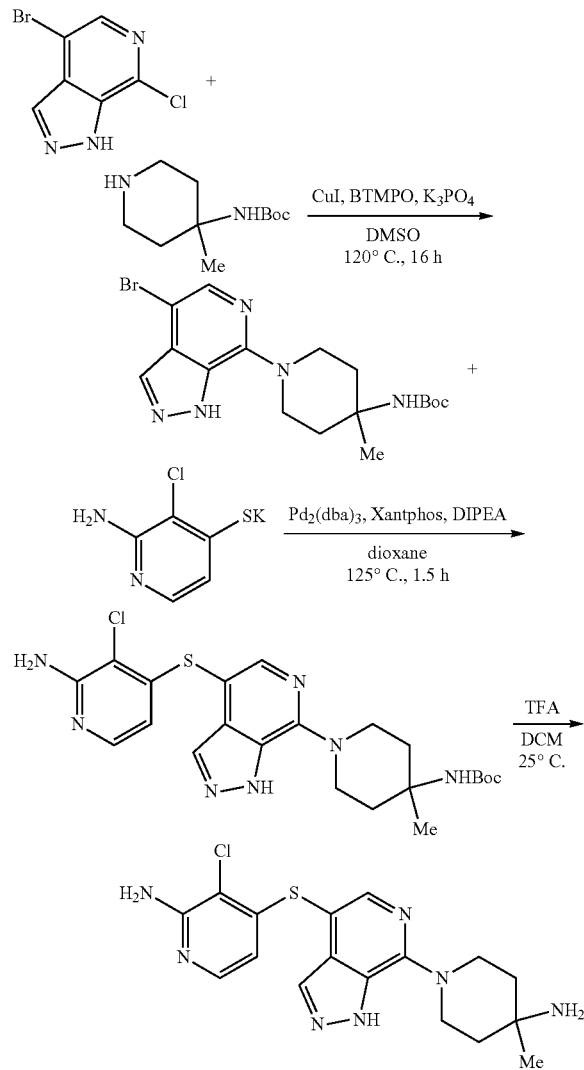

Step 1.
To a vial charged with 4-bromo-7-chloro-1H-pyrazolo[3,4-c]pyridine (200 mg, 0.860 mmol), tert-butyl N-(4-methylpiperidin-4-yl) carbamate (276 mg, 1.29 mmol), copper iodide (16.3 mg, 0.08603 mmol), tripotassium phosphate (182 mg, 0.860 mmol), and N,N-bis(2,4,6-trimethoxyphenyl) oxalamide (BTMPO) (36.1 mg, 0.08603 mmol), was added degassed DMSO (860 μL). The vial was capped and reaction headspace was evacuated and filled with N$_2$ and mixture was allowed to stir at 120° C. overnight. The resulting mixture was diluted with ethyl acetate, filtered through a pad of celite, and the filtrate concentrated under reduced pressure. The crude material was purified via column chromatography to afford tert-butyl (1-(4-bromo-1H-pyrazolo[3,4-c]pyridin-7-yl)-4-methylpiperidin-4-yl) carbamate (240 mg, 68%). LC-MS (ESI): m/z [M+H] calculated for $C_{17}H_{24}BrN_5O_2$:410.1; found 409.9.
Step 2.
To a microwave vial charged with tert-butyl (1-(4-bromo-1H-pyrazolo[3,4-c]pyridin-7-yl)-4-methylpiperidin-4-yl) carbamate (47 mg, 0.115 mmol), potassium 2-amino-3-chloropyridine-4-thiolate (34.1 mg, 0.1717 mmol), Pd$_2$(dba)$_3$ (6.29 mg, 0.0069 mmol), and xantphos (6.62 mg, 0.0115 mmol), was added degassed dioxane (1.14 mL) followed by DIPEA (60 μL, 0.343 mmol). The vial was capped and the reaction headspace evacuated and filled with N$_2$. The vial was capped and reaction headspace was evacuated and filled with N$_2$ and mixture was allowed to stir at 125° C. for 1.5 hrs. The resulting mixture was then diluted with ethyl acetate, filtered through a celite pad and concentrated under reduced pressure. The crude product was purified by column chromatography to afford tert-butyl (1-(4-((2-amino-3-chloropyridin-4-yl)thio)-1H-pyrazolo[3,4-c]pyridin-7-yl)-4-methylpiperidin-4-yl) carbamate, 19 mg (33%) as a light yellow film. LC-MS (ESI): m/z [M+H] calculated for $C_{22}H_{28}ClN_7O_2S$: 490.2; found 490.5.

To a dichloromethane (3 mL) solution of tert-butyl (1-(4-((2-amino-3-chloropyridin-4-yl)thio)-1H-pyrazolo[3,4-c]pyridin-7-yl)-4-methylpiperidin-4-yl) carbamate (19 mg, 0.038 mmol) was added trifluoroacetic acid (500 μL). The resulting homogenous solution was stirred at room temperature for 1.5 hrs. The reaction mixture was concentrated and the crude product was purified by preparative HPLC to afford 4-((7-(4-amino-4-methylpiperidin-1-yl)-1H-pyrazolo[3,4-c]pyridin-4-yl)thio)-3-chloropyridin-2-amine, (10.7 mg, 71%) as formate salt. $^1$H NMR (500 MHz, methanol-d4) δ 8.26 (br s, 1H), 7.83 (br s, 1H), 7.48 (d, J=5.6 Hz, 1H), 5.83 (d, J=5.6 Hz, 1H), 5.06 (br s, 1H), 3.77 (m, 2H), 1.96 (m, 4H), 1.58 (s, 3H). LC-MS (ESI): m/z [M+H] calculated for $C_{17}H_{21}ClN_7S$: 390.1; found 390.4.

Example 49. Synthesis of (3S,4S)-8-[6-amino-5-(2,3-dichlorophenyl)-[1,2,4]triazolo[1,5-a]pyrazin-8-yl]-3-methyl-2-oxa-8-azaspiro[4.5]decan-4-amine

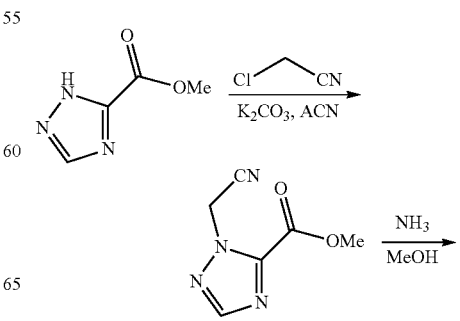

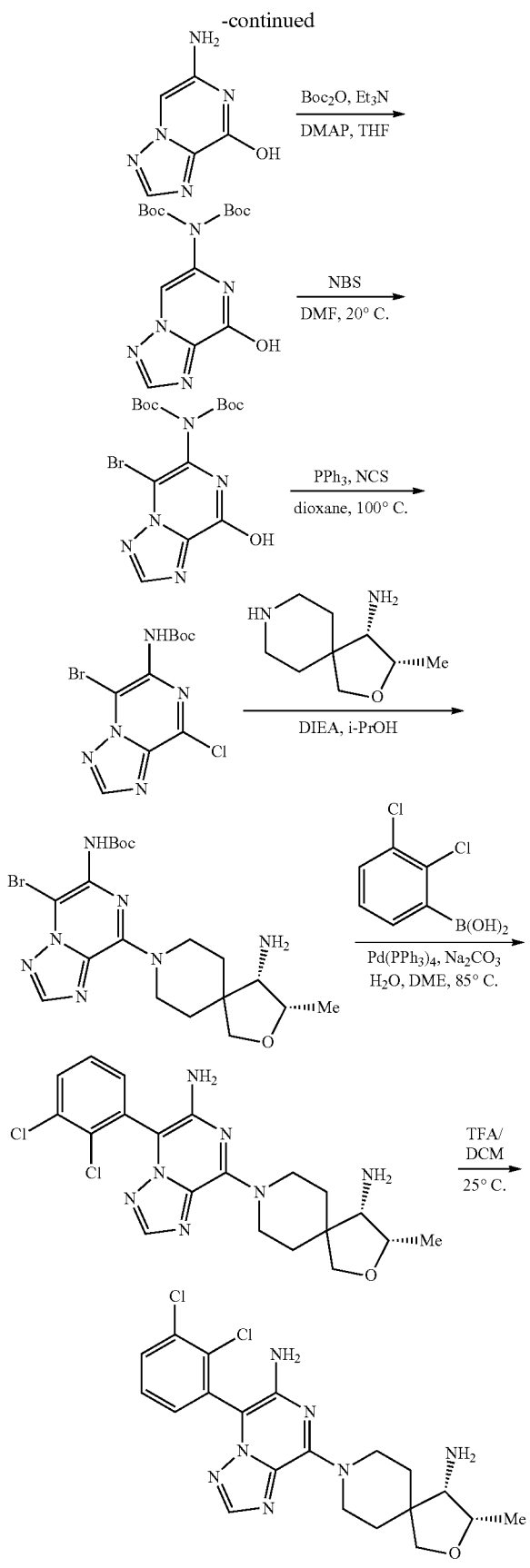

Step 1.
To a mixture of methyl 4H-1,2,4-triazole-3-carboxylate (15 g, 118.02 mmol) and 2-chloroacetonitrile (13 g, 177.02 mmol, 11.23 mL) in ACN (200 mL) was added K$_2$CO$_3$ (32 g, 236 mmol). The mixture was heated to 80° C. for 24 hrs. After cooling to room temperature the mixture was filtered and the solvent was removed under reduced pressure. The crude residue was purified by silica gel chromatography to give methyl 2-(cyanomethyl)-1,2,4-triazole-3-carboxylate (5 g, 25.50% yield). LCMS (ESI): m/z [M+H] calculated for C$_6$H$_7$N$_4$O$_2$:167.1; found 167.0. $^1$H NMR (400 MHZ, DMSO-d6) δ ppm 8.30 (s, 1H) 5.79 (s, 2H) 3.94 (s, 3H).

Step 2.
A mixture of methyl 2-(cyanomethyl)-1,2,4-triazole-3-carboxylate (5 g, 30.10 mmol) in NH$_3$/MeOH (100 mL, 30%) was stirred at 25° C. for 24 hr. MTBE (100 mL) was added dropwise into the reaction mixture and the forming precipitate was isolated by filtration to give 6-amino-[1,2,4]triazolo[1,5-a]pyrazin-8-ol (3.4 g, 22.5 mmol, 74% yield). LCMS (ESI): m/z: [M+H] calculated for C$_5$H$_6$N$_5$O:152.1; found 152.3. $^1$H NMR (400 MHZ, DMSO-d6) δ ppm 11.24 (br s, 1H) 8.17 (s, 1H) 6.94 (s, 1H) 5.35 (s, 2H)

Step 3.
To a mixture of 6-amino-[1,2,4]triazolo[1,5-a]pyrazin-8-ol (3 g, 19.8 mmol) in THF (60 mL) was added TEA (6.03 g, 59.55 mmol, 8.3 mL), Boc$_2$O (13.00 g, 59.55 mmol, 13.68 mL) and DMAP (242.52 mg, 1.99 mmol). The mixture was stirred at 30° C. for 3 hrs and then concentrated under reduced pressure. The crude residue was purified by silica gel chromatography to give tert-butyl-N-tert-butoxycarbonyl-N-(8-hydroxy-[1,2,4]triazolo[1,5-a]pyrazin-6-yl) carbamate (700 mg, 10.04% yield). LCMS (ESI): m/z [M+H] calculated for C$_{15}$H$_{22}$N$_5$O$_5$:352.1; found 352.2: $^1$H NMR (400 MHz, DMSO-d6) δ ppm 12.51 (br s, 1H) 8.55 (s, 1H) 8.34 (s, 1H) 1.41 (s, 18H).

Step 4.
To a mixture of tert-butyl N-tert-butoxycarbonyl-N-(8-hydroxy-[1,2,4]triazolo[1,5-a]pyrazin-6-yl) carbamate (400 mg, 1.14 mmol) in DMF (4 mL) was added NBS (222.88 mg, 1.25 mmol) at 0° C. under N$_2$. The mixture was stirred at 0° C. for 5 min and then quenched with Na$_2$SO$_3$ (aq. sat.). A yellow precipitate formed and was isolated by filtration to give tert-butyl N-(5-bromo-8-hydroxy-[1,2,4]triazolo[1,5-a]pyrazin-6-yl)-N-tert-butoxycarbonyl-carbamate (430 mg, 83.40% yield). $^1$H NMR (400 MHZ, DMSO-d6) δ ppm 13.01 (br s, 1H) 8.64 (s, 1H) 1.41 (s, 18H).

Step 5.
To a mixture of tert-butyl N-(5-bromo-8-hydroxy-[1,2,4]triazolo[1,5-a]pyrazin-6-yl)-N-tert-butoxycarbonyl-carbamate (430 mg, 999.41 μmol) in dioxane (17 mL) was added PPh$_3$ (521.65 mg, 1.99 mmol) and NCS (272.25 mg, 2.04 mmol). The mixture was stirred at 100° C. for 8 h and then cooled to room temperature. TEA (5 mL) was added over 15 min, followed by MTBE (10 mL). The forming precipitate was isolated by filtration and purified by column chromatography to give tert-butyl N-(5-bromo-8-chloro-[1,2,4]triazolo[1,5-a]pyrazin-6-yl) carbamate (100 mg, 28.70% yield) as a yellow solid. $^1$H NMR (400 MHZ, DMSO-d6) δ ppm 8.99-9.04 (m, 1H) 1.40 (s, 9H).

Step 6.
To a mixture of tert-butyl N-(5-bromo-8-chloro-[1,2,4]triazolo[1,5-a]pyrazin-6-yl) carbamate (50 mg, 143.44 μmol) and (3S,4S)-3-methyl-2-oxa-8-azaspiro[4.5]decan-4-amine hydrochloride (29 mg, 143.4 μmol, HCl) in i-PrOH (3 mL) was added DIEA (92 mg, 717 μmol, 124 μL). The mixture was stirred at 80° C. for 2 h and then concentrated under reduced pressure. The crude residue was purified by silica gel chromatography to give tert-butyl N-[8-[(3S,4S)-4-amino-3-methyl-2-oxa-8-azaspiro[4.5]decan-8-yl]-5-bromo-[1,2,4]triazolo[1,5-a]pyrazin-6-yl]carbamate (20 mg, 28.91% yield). LCMS (ESI): m/z [M+H] calculated for $C_{19}H_{29}BrN_7O_3$:482.1, found 482.2.

Step 7.

To a solution of tert-butyl N-[8-[(3S,4S)-4-amino-3-methyl-2-oxa-8-azaspiro[4.5]decan-8-yl]-5-bromo-[1,2,4]triazolo[1,5-a]pyrazin-6-yl]carbamate (22 mg, 45.6 µmol) in DME (1 mL) was added (2,3-dichlorophenyl) boronic acid (13.0 mg. 68.4 µmol), $Na_2CO_3$ (9.67 mg, 91.2 µmol, 3.11 µL) in $H_2O$ (0.2 mL) and $Pd(PPh_3)_4$ (5.27 mg, 4.56 µmol). The reaction mixture was stirred at 85° C. for 0.5 hrs. The reaction mixture was cooled to room temperature and filtered. The solvent was removed under reduced pressure and the residue was purified by column chromatography to give tert-butyl-N-[8-[(3S,4S)-4-amino-3-methyl-2-oxa-8-azaspiro[4.5]decan-8-yl]-5-(2,3-dichlorophenyl)-[1,2,4]triazolo[1,5-a]pyrazin-6-yl]carbamate (12 mg, 47.9% yield). LCMS (ESI): m/z [M+H] calculated for $C_{25}H_{32}Cl_2N_7O_3$: 548.2; found 548.2.

Step 8.

To a solution of tert-butyl N-[8-[(3S,4S)-4-amino-3-methyl-2-oxa-8-azaspiro[4.5]decan-8-yl]-5-(2,3-dichlorophenyl)-[1,2,4]triazolo[1,5-a]pyrazin-6-yl]carbamate (10 mg, 18.2 µmol) in DCM (2 mL) was added TFA (1 mL). The reaction mixture was stirred at 25° C. for 48 hrs. The reaction mixture was then concentrated to dryness and redissolved in MeOH. The solution was adjusted to pH 7 with NaOH/MeOH (0.5 N) at −78° C. The mixture was then concentrated and any solids were removed by filtration. The final filtrate was dissolved with MeOH and stirred with anion exchange resin for 4 hrs. The resin was then filtered and the filtrate was concentrated under reduced pressure. The residue was purified by preparative HPLC to give (3S,4S)-8-[6-amino-5-(2,3-dichlorophenyl)-[1,2,4]triazolo[1,5-a]pyrazin-8-yl]-3-methyl-2-oxa-8-azaspiro[4.5]decan-4-amine (1 mg, 12.2% yield). $^1$H NMR (400 MHZ, methanol-d4) δ ppm 8.66-8.36 (m, 1H) 8.07 (s, 1H) 7.68 (d, J=7.02 Hz, 1H) 7.51-7.37 (m, 1H) 5.23-5.00 (m, 1H) 4.61 (s, 1H) 4.35-4.24 (m, 1H) 4.04-3.99 (m, 1H) 3.89 (d, J=9.65 Hz, 1H) 3.60-3.53 (m, 2H) 1.93-1.88 (m, 2H) 1.74-1.71 (m, 1H) 1.30 (d, J=6.14 Hz, 3H); LCMS (ESI): m/z [M+H] calculated for: $C_{20}H_{24}Cl_2N_7O$:448.1; found 448.2.

Example 50. Synthesis of 4-[[4-(4-amino-4-methyl-1-piperidyl)-6-methyl-1H-pyrazolo[4,3-c]pyridin-7-yl]sulfanyl]-3-chloro-pyridin-2-amine

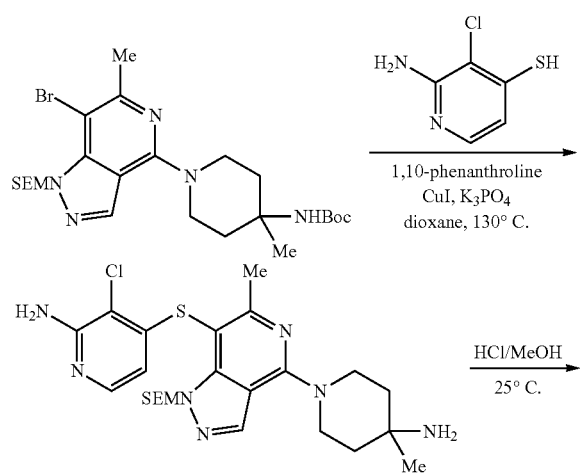

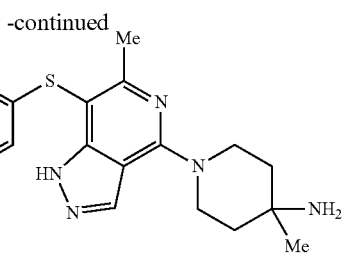
-continued

Step 1.

Degassed dioxane (4.00 mL) was added to a mixture of tert-butyl N-[1-[7-bromo-6-methyl-1-(2-trimethylsilylethoxymethyl) pyrazolo[4,3-c]pyridin-4-yl]-4-methyl-4-piperidyl]carbamate (60 mg, 108 µmol), 2-amino-3-chloropyridine-4-thiol (34.8 mg, 216 µmol), 1,10-phenanthroline (5.85 mg, 32.5 µmol), $K_3PO_4$ (45.9 mg, 216 µmol) and CuI (4.12 mg, 21.6 µmol) under $N_2$ and the mixture was stirred at 130° C. for 12 hrs. The solvent was removed under reduced pressure and the crude residue was purified by preparative HPLC to give tert-butyl N-[1-[7-[(2-amino-3-chloro-4-pyridyl)sulfanyl]-6-methyl-1-(2-trimethylsilylethoxymethyl) pyrazolo[4,3-c]pyridin-4-yl]-4-methyl-4-piperidyl]carbamate (15.0 mg, 15.8 µmol, 21.9% yield). LCMS (ESI): m/z: [M+H] calculated for $C_{29}H_{45}ClN_7O_3SSi$ 634.27; found 634.4.

Step 2.

A solution of tert-butyl N-[1-[7-[(2-amino-3-chloro-4-pyridyl)sulfanyl]-6-methyl-1-(2-trimethylsilylethoxymethyl) pyrazolo[4,3-c]pyridin-4-yl]-4-methyl-4-piperidyl]carbamate (15 mg, 23.7 µmol) in HCl/MeOH (2 mL) was stirred at 25° C. for 1 hr. The solvent was removed under reduced pressure the residue was dissolved in MeOH (0.5 mL). The resulting mixture was adjusted to PH~8 with NaOH/MeOH (0.5 M). The solvent was removed under reduced pressure and the residue was suspended in DCM/MeOH (2 mL). The mixture was filtered and the filtrate was to give 4-[[4-(4-amino-4-methyl-1-piperidyl)-6-methyl-1H-pyrazolo[4,3-c]pyridin-7-yl]sulfanyl]-3-chloro-pyridin-2-amine (3.30 mg, 7.86 µmol, 33.2% yield). $^1$H NMR (400 MHZ, methanol-d4) δ ppm 8.25 (s, 1H) 7.49 (d, J=5.26 Hz, 1H) 5.68 (d, J=5.70 Hz, 1H) 4.40 (d, J=13.15 Hz, 2H) 3.75 (s, 2H) 2.51 (s, 3H) 1.87 (s, 4H) 1.46 (s, 3H); LCMS (ESI): m/z [M+H] calculated for $C_{18}H_{23}ClN_7S$ 404.13; found 404.3.

Example 51. Synthesis of (3S,4S)-8-(7-((2-amino-3-chloropyridin-4-yl)thio)-1H-pyrazolo[4,3-c]pyridin-4-yl)-3-methyl-2-oxa-8-azaspiro[4.5]decan-4-amine

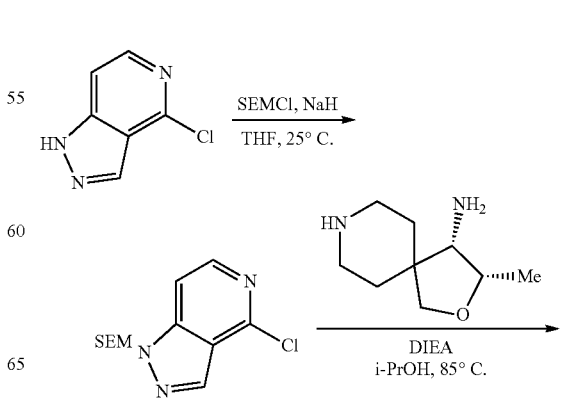

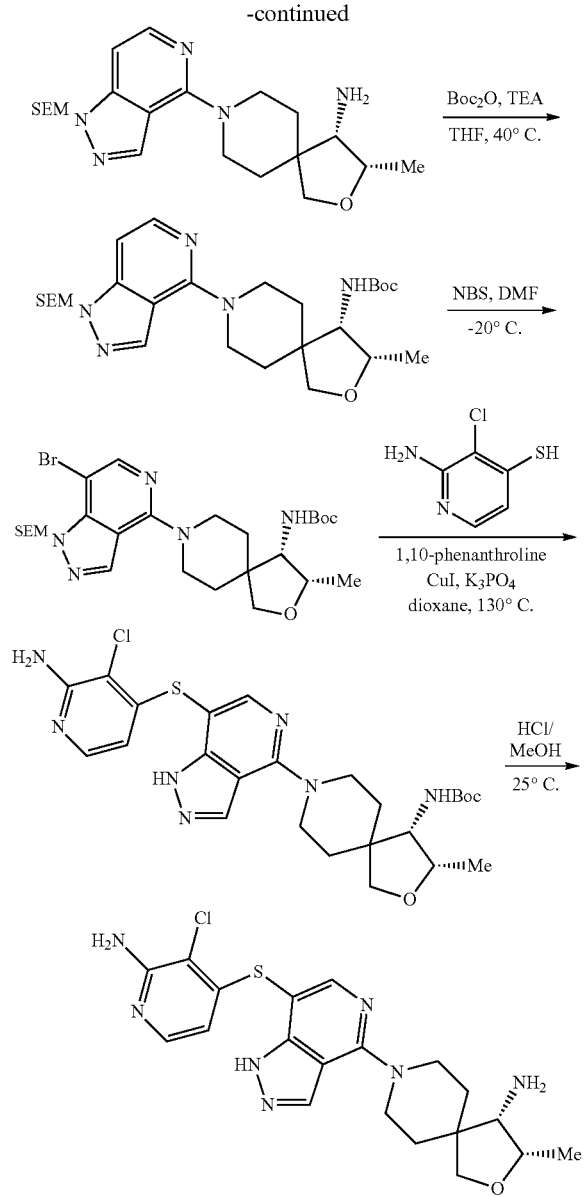

Step 1.

To a solution of 4-chloro-1H-pyrazolo[4,3-c]pyridine (2 g, 13.02 mmol) in anhydrous THF (25 mL) was added NaH (625 mg, 15.6 mmol, 60%) at 0° C. After stirring at 25° C. for 20 min SEM-Cl (2.82 g, 16.93 mmol, 3 mL) was added dropwise at 0° C. The reaction was stirred at 25° C. for 2 hrs and then quenched by slowly adding $H_2O$. After extraction with EtOAc the combined organic phases were washed with brine, dried over anhydrous $Na_2SO_4$, filtered and concentrated under reduced pressure. The crude residue was purified by column chromatography to give 4-chloro-1-((2-(trimethylsilyl) ethoxy)methyl)-1H-pyrazolo[4,3-c]pyridine (1.7 g, 5.99 mmol, 46% yield). LCMS (ESI): m/z [M+H] calculated for $C_{12}H_{19}ClN_3OSi$: 284.1; found 284.1.

Step 2.

To a solution of 4-chloro-1-((2-(trimethylsilyl) ethoxy)methyl)-1H-pyrazolo[4,3-c]pyridine (400 mg, 1.41 mmol) in i-PrOH (8 mL) was added (3S,4S)-3-methyl-2-oxa-8-azaspiro[4.5]decan-4-amine bis-hydrochloride (377 mg, 1.55 mmol) and DIEA (1.27 g, 9.87 mmol, 1.72 mL). The reaction mixture was stirred at 85° C. for 16 hrs and then concentrated to give (3S,4S)-3-methyl-8-(1-((2-(trimethylsilyl) ethoxy)methyl)-1H-pyrazolo[4,3-c]pyridin-4-yl)-2-oxa-8-azaspiro[4.5]decan-4-amine (600 mg, crude) as yellow solid which was used for the next step without further purification. LCMS (ESI): m/z [M+H] calculated for $C_{21}H_{36}N_5O_2Si$: 418.3; found 418.3.

Step 3.

To a solution of (3S,4S)-3-methyl-8-[1-(2-trimethylsilylethoxymethyl) pyrazolo[4,3-c]pyridin-4-yl]-2-oxa-8-azaspiro[4.5]decan-4-amine (600 mg, 1.44 mmol) in DCM (10 mL) was added TEA (290 mg, 2.87 mmol, 399 μL) and $Boc_2O$ (627 mg, 2.87 mmol, 660 μL). The reaction mixture was stirred at 40° C. for 1 hr and then concentrated under reduced pressure. The crude residue was purified by silica gel chromatography to give tert-butyl ((3S,4S)-3-methyl-8-(1-((2-(trimethylsilyl) ethoxy)methyl)-1H-pyrazolo[4,3-c]pyridin-4-yl)-2-oxa-8-azaspiro[4.5]decan-4-yl) carbamate (300 mg, 40% yield). $^1$H NMR (400 MHZ, CDCl3-d) δ ppm 8.06 (s, 1H) 8.01 (d, J=5.99 Hz, 1H) 6.86 (d, J=5.87 Hz, 1H) 5.69 (s, 2H) 4.67 (d, J=10.64 Hz, 1H) 4.20-4.04 (m, 3H) 3.81-3.74 (m, 3H) 3.70-3.56 (m, 3H) 2.22 (s, 1H) 2.03-1.82 (m, 3H) 1.77-1.68 (m, 1H) 1.50 (s, 9H) 1.26 (d, J=6.36 Hz, 3H) 0.00 (s, 9H); LCMS (ESI): m/z: [M+H] calculated for $C_{26}H_{44}N_5O_4Si$: 518.3; found 518.4.

Step 4.

To a solution of tert-butyl N-[(3S,4S)-3-methyl-8-[1-(2-trimethylsilylethoxymethyl) pyrazolo[4,3-c]pyridin-4-yl]-2-oxa-8-azaspiro[4.5]decan-4-yl]carbamate (300 mg, 579 μmol) in DMF (5 mL) was added NBS (123 mg, 695 μmol) at −20° C. The reaction mixture was stirred at −20° C. for 30 min and then quenched by adding $Na_2SO_3$ (sa.aq.). The mixture was filtered and concentrated under reduced pressure. The crude residue was purified by silica gel chromatography to give tert-butyl N-[(3S,4S)-8-[7-bromo-1-(2-trimethylsilylethoxymethyl) pyrazolo[4,3-c]pyridin-4-yl]-3-methyl-2-oxa-8-azaspiro[4.5]decan-4-yl]carbamate (250 mg, 72% yield). $^1$H NMR (400 MHZ, CDCl3-d) δ ppm 8.06 (d, J=1.34 Hz, 1H) 6.05 (s, 1H) 4.66 (d, J=10.64 Hz, 1H) 4.27-4.20 (m, 1H) 4.09-3.94 (m, 3H) 3.79-3.71 (m, 3H) 3.69-3.61 (m, 3H) 2.01-1.81 (m, 3H) 1.76-1.67 (m, 1H) 1.50 (s, 9H) 1.26 (d, J=6.36 Hz, 3H) 1.02-0.892 (m, 2H)-0.02-0.05 (m, 8H); LCMS (ESI): m/z [M+H] calculated for $C_{26}H_{43}BrN_5O_4Si$: 598.2; found 598.4.

Step 5.

To a solution of tert-butyl N-[(3S,4S)-8-[7-bromo-1-(2-trimethylsilylethoxymethyl) pyrazolo[4,3-c]pyridin-4-yl]-3-methyl-2-oxa-8-azaspiro[4.5]decan-4-yl]carbamate (250 mg, 419 μmol) in dioxane (3.5 mL) was added 2-amino-3-chloro-pyridine-4-thiol (134 mg, 838 μmol), $K_3PO_4$ (177 mg, 838 μmol), 1,10-phenanthroline (15.1 mg, 83.8 μmol) and CuI (7.98 mg, 41.9 μmol). The reaction mixture was stirred at 130° C. for 48 hrs under $N_2$. After cooling to room temperature the reaction mixture was filtered and concentrated under vacuum. The crude residue was purified by preparative TLC to give tert-butyl N-[(3S,4S)-8-[7-[(2-amino-3-chloro-4-pyridyl)sulfanyl]-1-(2-trimethylsilylethoxymethyl) pyrazolo[4,3-c]pyridin-4-yl]-3-methyl-2-oxa-8-azaspiro[4.5]decan-4-yl]carbamate (50 mg, 73.9 μmol, 17% yield). LCMS (ESI): m/z [M+H] calculated for $C_{31}H_{47}ClN_7O_4SSi$: 676.3; found 676.1.

Step 6.

A solution of tert-butyl N-[(3S,4S)-8-[7-[(2-amino-3-chloro-4-pyridyl)sulfanyl]-1-(2-trimethylsilylethoxymethyl) pyrazolo[4,3-c]pyridin-4-yl]-3-methyl-2-oxa-8-azaspiro[4.5]decan-4-yl]carbamate (40 mg, 59.1 μmol) in HCl/MeOH (2 mL) was stirred at 25° C. for 1 hr and then concentrated under reduced pressure. The crude residue was purified by preparative HPLC to give (3S,4S)-8-(7-((2-amino-3-chloropyridin-4-yl)thio)-1H-pyrazolo[4,3-c]pyridin-4-yl)-3-methyl-2-oxa-8-azaspiro[4.5]decan-4-amine (16 mg, 60% yield). $^1$H NMR (400 MHZ, Methanol-d4) δ ppm 8.61-8.42 (m, 1H) 8.33 (s, 1H) 7.97 (s, 1H) 7.48 (d, J=5.50 Hz, 1H) 5.72 (d, J=5.62 Hz, 1H) 4.61-4.42 (m, 2H) 4.36-4.25 (m, 1H) 4.00 (d, J=9.05 Hz, 1H) 3.88 (d, J=9.05 Hz, 1H) 3.60-3.37 (m, 2H) 3.34 (d, J=4.40 Hz, 1H) 1.97-1.84 (m, 3H) 1.76 (d, J=13.08 Hz, 1H) 1.30 (d, J=6.48 Hz, 3H); LCMS (ESI): m/z [M+H] calculated for $C_{20}H_{25}ClN_7OS$: 446.2; found 446.0.

Example 52: Synthesis of 3-{4-[(3S,4S)-4-amino-3-methyl-2-oxa-8-azaspiro[4.5]decan-8-yl]-6-methylpyrazolo[1,5-a]pyrazin-7-yl}-2-chlorobenzonitrile 3-{4-[(3S,4S)-4-amino-3-methyl-2-oxa-8-azaspiro[4.5]decan-8-yl]-6-methylpyrazolo[1,5-a]pyrazin-7-yl}-2-chlorobenzonitrile was synthesized in the manner similar to Example 22, except (2-chloro-3-cyanophenyl) boronic acid was used instead of (2,3-dichlorophenyl) boronic acid. $^1$H NMR (500 MHZ, Methanol-d4) δ 7.99 (dd, J=7.8, 1.7 Hz, 1H), 7.82 (d, J=2.5 Hz, 1H), 7.76 (dd, J=7.8, 1.6 Hz, 1H), 7.67 (t, J=7.7 Hz, 1H), 6.96 (d, J=2.5 Hz, 1H), 4.37-4.20 (m, 1H), 3.94 (d, J=8.7 Hz, 1H), 3.81 (d, J=8.7 Hz, 1H), 3.63-3.42 (m, 2H), 3.12 (d, J=4.8 Hz, 1H), 2.14 (s, 3H), 1.95 (dtd, J=28.8, 9.9, 5.0 Hz, 2H), 1.79 (dd, J=27.2, 13.3 Hz, 2H), 1.27 (d, J=6.5 Hz, 3H). LC-MS (ESI): m/z [M+H] calcd for $C_{23}H_{26}ClN_6O$: 437.2; found 437.4.

Biological Examples—SHP2 Allosteric Inhibition Assay

Without wishing to be bound by theory, SHP is allosterically activated through binding of bis-tyrosyl-phosphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

The phosphatase reactions were performed at room temperature in 96-well black polystyrene plate, flat bottom, non-binding surface (Corning, Cat #3650) using a final reaction volume of 100 μL and the following assay buffer conditions: 50 mM HEPES, pH 7.2, 100 mM NaCl, 0.5 mM EDTA, 0.05% P-20, 1 mM DTT.

The inhibition of SHP2 by compounds of the disclosure (concentrations varying from 0.00005-10 μM) was monitored using an assay in which 0.2 nM of SHP2 was incubated with 0.5 μM of Activating Peptide 1 (sequence: H2N-LN(pY)IDLDLV(dPEG8)LST(pY)ASINFQK-amide) or Activating Peptide 2 (sequence: H$_2$N-LN(pY)AQLWHA(dPEG8)LTI(pY)ATIRRF-amide). After 30-60-minutes incubation at 25° C., the surrogate substrate DiFMUP (Invitrogen, Cat #D6567) was added to the reaction and activity was determined by a kinetic read using a microplate reader (Envision, Perkin-Elmer or Spectramax M5, Molecular Devices). The excitation and emission wavelengths were 340 nm and 450 nm, respectively. Initial rates were determined from a linear fit of the data, and the inhibitor dose response curves were analyzed using normalized IC$_{50}$ regression curve fitting with control based normalization.

Using the above-protocol, SHP2 inhibition measured as set forth in Table 1.

TABLE 1

| SHP2 Inhibition of Tested Compounds | |
|---|---|
| Compound | SHP2 IC$_{50}$, nM |
| Compound 2 (Example 2) | 190 |
| Compound 3 (Example 3) | 34 |
| Compound 6 (Example 6) | 1100 |
| Compound 15 (Example 15) | 340 |
| Compound 16 (Example 16) | 83 |

In some embodiments, compounds of the disclosure can have an activity of less than 1000 nM. In some embodiments, compounds of the disclosure can have an activity of about 1 nM to about 10 nM. In some embodiments, compounds of the disclosure can have an activity of less than about 1 nM. In some embodiments, compounds of the disclosure can have an activity of about 10 nM to about 100 nM. In some embodiments, compounds of the disclosure can have an activity of about 100 nM to about 10 μM.

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

The invention claimed is:

1. A method for modulating SH2 domain-containing protein tyrosine phosphatase-2 (SHP2) activity in a subject in need thereof, wherein the method comprises administering to the subject a therapeutically effective amount of a compound of Formula IV:

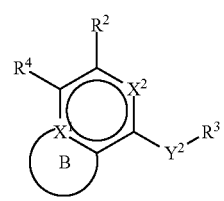

IV or a pharmaceutically acceptable salt, stereoisomer, or tautomer thereof, wherein:

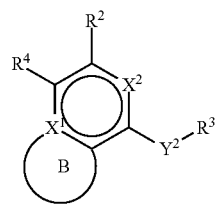

is:

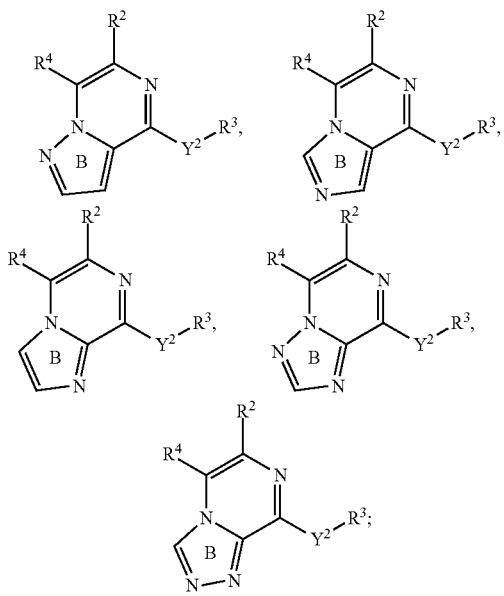

wherein ring B is optionally substituted on any available carbon with one or two substituents independently selected from the group consisting of $C_1$-$C_6$ alkyl, $CH_2F$, $CHF_2$, $CF_3$, $(CH_2)_nNH_2$, $(CH_2)_nOH$, heterocyclyl, and heteroaryl;

$R^2$ is H, halogen, $C_1$-$C_6$ alkyl, $C_2$-$C_6$ alkenyl, $C_2$-$C_6$ alkynyl, $NR^5R^6$, OH, $C_3$-$C_8$ cycloalkyl, $C_4$-$C_8$ cycloalkenyl, or heterocyclyl;

wherein the heterocyclyl contains 1, 2, 3, 4, or 5 heteroatoms independently selected from the group consisting of nitrogen, phosphorous, oxygen, and sulfur;

wherein the heterocyclyl is not attached via a nitrogen atom; and wherein the $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, or heterocyclyl is optionally substituted with one or more substituents independently selected from the group consisting of halogen, CN, $NO_2$, $NR^5R^6$, $NR^5S(O)R^6$, $NR^5S(O)NR^5R^6$, $NR^5S(O)_2R^6$, $NR^5S(O)_2NR^5R^6$, $OR^5$, =O, $SR^5$, $S(O)R^5$, $S(O)NR^5R^6$, $S(O)_2R^5$, $S(O)_2 NR^5R^6$, heterocyclyl, aryl, heteroaryl, and $R^5$;

$Y^2$ is $-NR^a-$, $-NR^aC(O)-$, $-NR^aC(O)NR^a-$, $-NR^aC(O)O-$, $-NR^aC(S)-$, $-NR^aC(S)NR^a-$, or $-NR^aS(O)_2-$, wherein the bond on the left side of $Y^2$ is bound to the ring and the bond on the right side of $Y^2$ is bound to $R^3$;

$R^3$ and $R^a$, together with the atom(s) to which they are attached, form a monocyclic or polycyclic 3- to 12-membered heterocyclyl or a spirocyclic 5- to 12-membered heterocyclyl, wherein the monocyclic or polycyclic 3- to 12-membered heterocyclyl or spirocyclic 5- to 12-membered heterocyclyl is optionally substituted with one or more substituents independently selected from the group consisting of $C_1$-$C_6$ alkyl, $CH_2F$, $CHF_2$, $CF_3$, $(CH_2)_nNH_2$, $(CH_2)_nOH$, =O, heterocyclyl, and heteroaryl;

$R^4$ is:

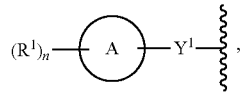

wherein:
$Y^1$ is a direct bond, $-CH_2-$, $-C(=CH_2)-$, $-NH-$, $-S-$, $-S(O)-$, $-S(O)_2-$, or $-S(O)_2NH-$;

ring A is a monocyclic or polycyclic 5- to 12-membered cycloalkyl, heterocycloalkyl, aryl, or heteroaryl; and each $R^1$ is independently H, D, halogen, CN, $NO_2$, $C_1$-$C_6$ alkyl, $C_2$-$C_6$ alkenyl, $C_2$-$C_6$ alkynyl, $C(O)R^5$, $C(O)OR^5$, $NR^5R^6$, $NR^5S(O)R^6$, $NR^5S(O)NR^5R^6$, $NR^5S(O)_2R^6$, $NR^5S(O)_2NR^5R^6$, $OR^5$, $SR^5$, $S(O)R^5$, $S(O)NR^5R^6$, $S(O)_2R^5$, $S(O)_2NR^5R^6$, $C_3$-$C_8$ cycloalkyl, or $C_4$-$C_8$ cycloalkenyl, wherein each $C_1$-$C_6$ alkyl, $C_2$-$C_6$ alkenyl, $C_2$-$C_6$ alkynyl, $C_3$-$C_8$ cycloalkyl, and $C_4$-$C_8$ cycloalkenyl is optionally and independently substituted with one or more substituents independently selected from the group consisting of halogen, CN, $NO_2$, $NR^5R^6$, $NR^5S(O)R^6$, $NR^5S(O)NR^5R^6$, $NR^5S(O)_2R^6$, $NR^5S(O)^2NR^5R^6$, $OR^5$, =O, $SR^5$, $S(O)R^5$, $S(O)NR^5R^6$, $S(O)_2R^5$, $S(O)_2NR^5R^6$, heterocyclyl, aryl, heteroaryl, and $R^5$;

each $R^5$ is independently H, D, halogen, CN, $NO_2$, $C_1$-$C_6$ alkyl, $C_2$-$C_6$ alkenyl, $C_2$-$C_6$ alkynyl, $NR^7R^8$, $OR^7$, $SR^7$, $C_3$-$C_8$ cycloalkyl, $C_4$-$C_8$ cycloalkenyl, or a monocyclic or polycyclic 3- to 12-membered heterocyclyl;

each $R^6$ is independently H, D, halogen, CN, $NO_2$, $C_1$-$C_6$ alkyl, $C_2$-$C_6$ alkenyl, $C_2$-$C_6$ alkynyl, $NR^7R^8$, $OR^7$, $SR^7$, $C_3$-$C_8$ cycloalkyl, $C_4$-$C_8$ cycloalkenyl, or a monocyclic or polycyclic 3- to 12-membered heterocyclyl;

each $R^7$ is independently H, D, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, or a monocyclic or polycyclic 3- to 12-membered heterocyclyl, wherein each $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, and monocyclic or polycyclic 3- to 12-membered heterocyclyl is optionally and independently substituted with one or more substituents independently selected from the group consisting of CN, $NO_2$, $NH_2$, OH, and SH;

each $R^8$ is independently H, D, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, or a monocyclic or polycyclic 3- to 12-membered heterocyclyl, wherein each $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, and monocyclic or polycyclic 3- to 12-membered heterocyclyl is optionally and independently substituted with one or more substituents independently selected from the group consisting of CN, $NO_2$, $NH_2$, OH, and SH; and each n is independently 0, 1, 2, 3, 4, 5, 6, 7, 8, 9, or 10;

with the provisos that:
(1) the heteroaryl of ring A is not furanyl or thiophenyl; and
(2) $R^a$ and $R^3$, together with the atom(s) to which they are attached, do not form an optionally substituted piperazinyl.

2. The method of claim 1, wherein the subject has a disease associated with modulation of SHP2 activity selected from the group consisting of acute myeloid leukemia, breast cancer, colon cancer, juvenile myelomonocytic leukemia, LEOPARD syndrome, lung cancer, melanoma, neuroblastoma, and Noonan syndrome.

3. The method of claim 1, wherein ring B is optionally substituted on any available carbon with one or two substituents independently selected from the group consisting of $C_1$-$C_6$ alkyl, $CH_2F$, $CHF_2$, $CF_3$, $(CH_2)_nNH_2$, and $(CH_2)_nOH$.

4. The method of claim 1, wherein $R^2$ is $C_1$-$C_6$ alkyl, wherein the $C_1$-$C_6$ alkyl is optionally substituted with one or more substituents independently selected from the group consisting of halogen, $NR^5R^6$, and $OR^5$.

5. The method of claim 1, wherein $R^2$ is $CH_3$.

6. The method of claim 1, wherein $Y^2$ is —$NR^a$—, wherein the bond on the left side of $Y^2$ is bound to the ring and the bond on the right side of $Y^2$ is bound to $R^3$.

7. The method of claim 1, wherein $R^3$ and $R^a$, together with the atom(s) to which they are attached, form a monocyclic or polycyclic 3- to 12-membered heterocyclyl, wherein the monocyclic or polycyclic 3- to 12-membered heterocyclyl is optionally substituted with one or more substituents independently selected from the group consisting of $C_1$-$C_6$ alkyl, $CH_2F$, $CHF_2$, $CF_3$, $(CH_2)_nNH_2$, and $(CH_2)_nOH$.

8. The method of claim 1, wherein $R^3$ and $R^a$, together with the atom(s) to which they are attached, form a spirocyclic 5- to 12-membered heterocyclyl, wherein the spirocyclic 5- to 12-membered heterocyclyl is optionally substituted with one or more substituents independently selected from the group consisting of $C_1$-$C_6$ alkyl, $CH_2F$, $CHF_2$, $CF_3$, $(CH_2)_nNH_2$, and $(CH_2)_nOH$.

9. The method of claim 8, wherein the spirocyclic 5- to 12-membered heterocyclyl is optionally substituted with one or more independently selected $C_1$-$C_6$ alkyl substituents.

10. The method of claim 8, wherein the spirocyclic 5- to 12-membered heterocyclyl is optionally substituted with one or more $NH_2$ substituents.

11. The method of claim 1, wherein $Y^1$ is a direct bond.

12. The method of claim 1, wherein $Y^1$ is —S—.

13. The method of claim 1, wherein ring A is a monocyclic or polycyclic aryl.

14. The method of claim 1, wherein ring A is a monocyclic or polycyclic heteroaryl.

15. The method of claim 1, wherein each $R^1$ is independently H, halogen, or $NR^5R^6$.

16. The method of claim 1, wherein the compound is of Formula IV-Q:

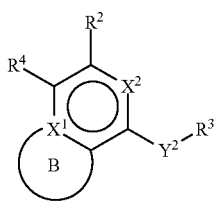

IV-Q or a pharmaceutically acceptable salt, stereoisomer, or tautomer thereof,
wherein:

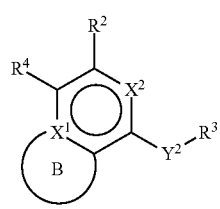

is:

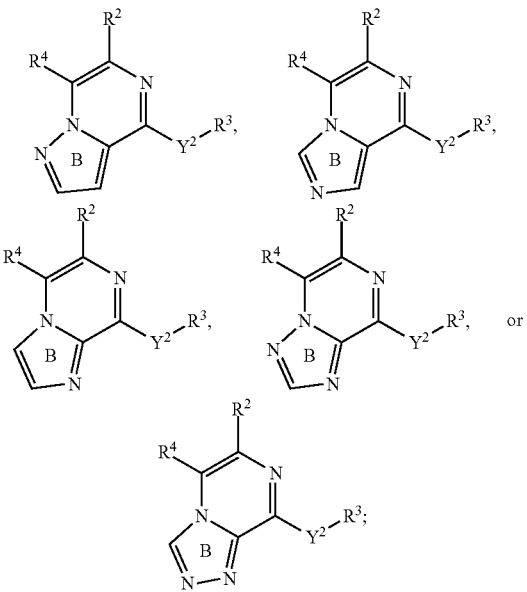

wherein ring B is optionally substituted on any available carbon with one or two substituents independently selected from the group consisting of $C_1$-$C_6$ alkyl, $CH_2F$, $CHF_2$, $CF_3$, $(CH_2)_nNH_2$, and $(CH_2)_nOH$;

$R^2$ is H, $C_1$-$C_6$ alkyl, $NR^5R^6$, or OH, wherein the $C_1$-$C_6$ alkyl is optionally substituted with one or more substituents independently selected from the group consisting of halogen, $NR^5R^6$, or $OR^5$;

$Y^2$ is —$NR^a$—, wherein the bond on the left side of $Y^2$ is bound to the ring and the bond on the right side of $Y^2$ is bound to $R^3$;

$R^3$ and $R^a$, together with the atom(s) to which they are attached, form a monocyclic or polycyclic 3- to 12-membered heterocyclyl or a spirocyclic 5- to 12-membered heterocyclyl, wherein the monocyclic or polycyclic 3- to 12-membered heterocyclyl or spirocyclic 5- to 12-membered heterocyclyl is optionally substituted with one or more substituents independently selected from the group consisting of $C_1$-$C_6$ alkyl, $CH_2F$, $CHF_2$, $CF_3$, $(CH_2)_nNH_2$, and $(CH_2)_nOH$;

$R^4$ is:

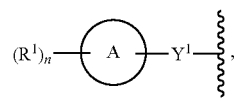

wherein:
Y$^1$ is a direct bond or —S—;
ring A is a monocyclic or polycyclic aryl or heteroaryl; and
each $R^1$ is independently H, halogen, CN, $C_1$-$C_6$ alkyl, $NR^5R^6$, or $OR^5$;
each $R^5$ is independently H or $C_1$-$C_6$ alkyl; and
each $R^6$ is independently H or $C_1$-$C_6$ alkyl.

17. The method of claim 1, wherein the compound, or stereoisomer thereof, is selected from the group consisting of:

2
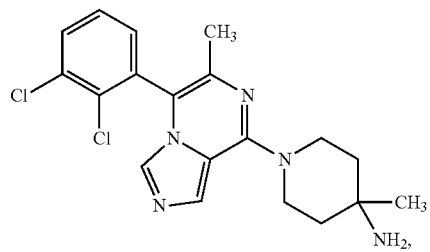
3
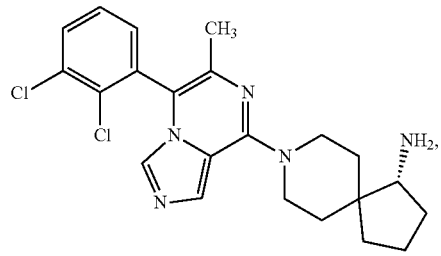
4
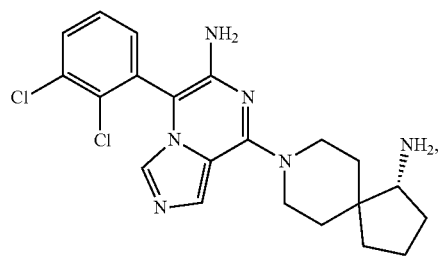
5
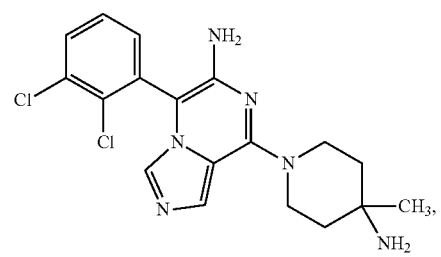
6
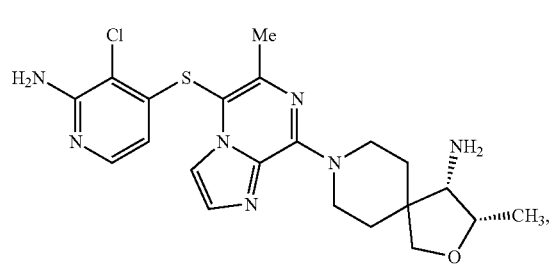
7
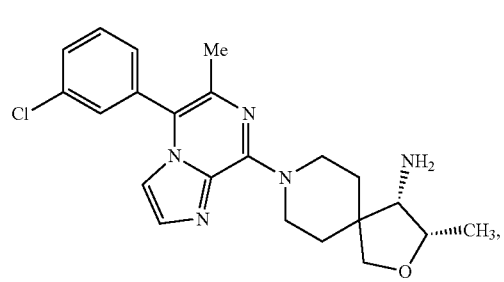
8
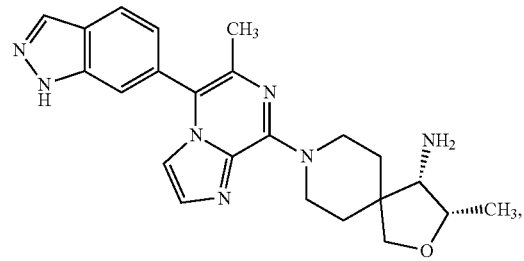
9
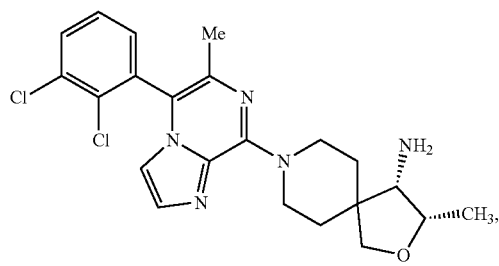
10
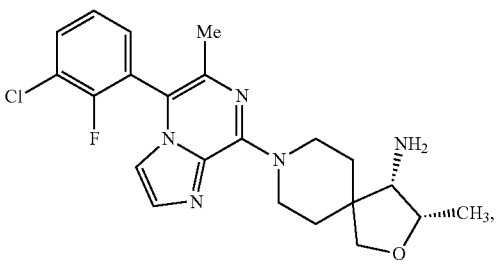
11
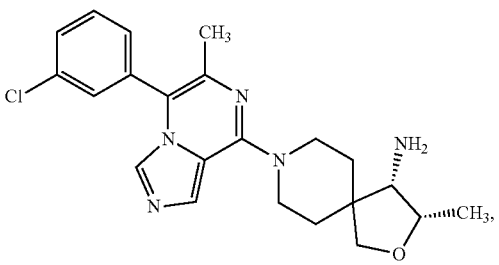
12
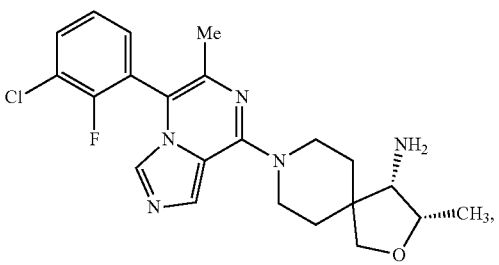
13
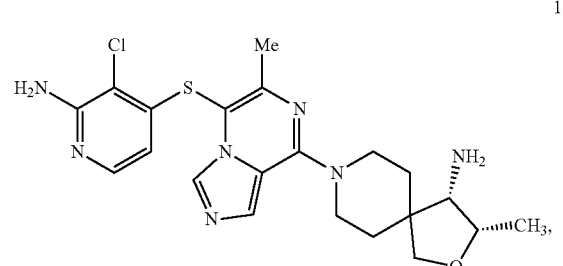

21
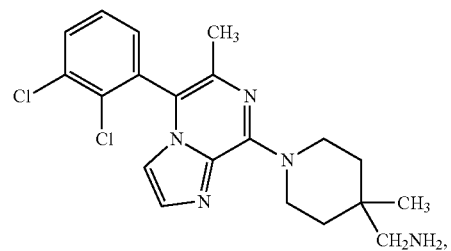
22
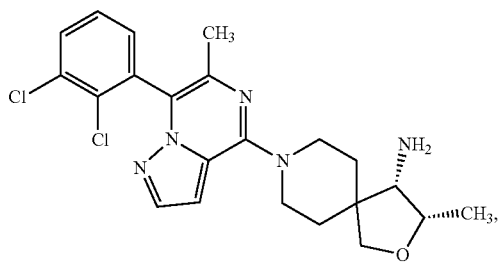
23
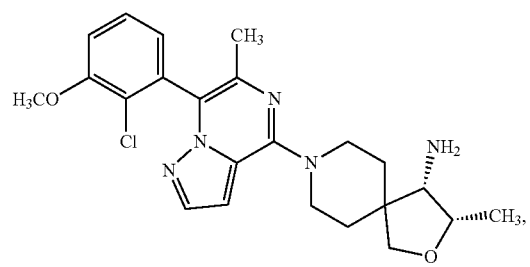
24
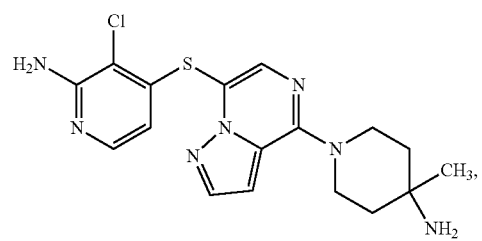
25
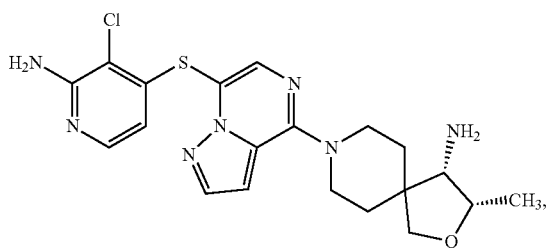
26
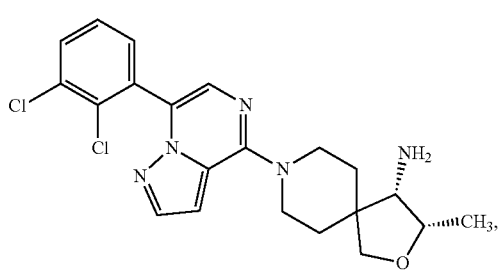
27
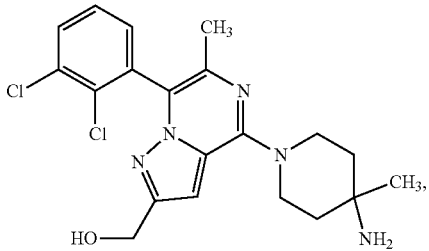
28
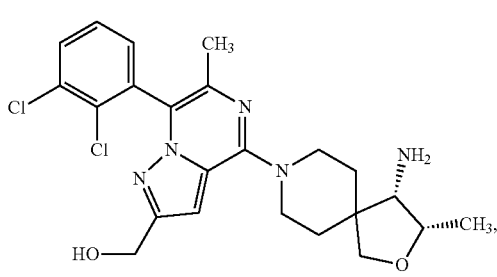
29
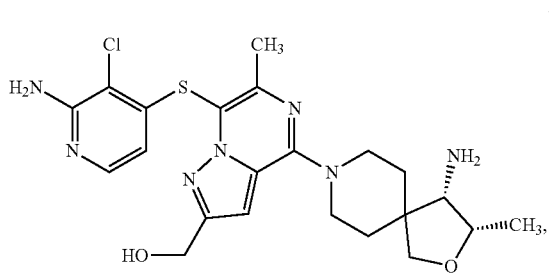
30
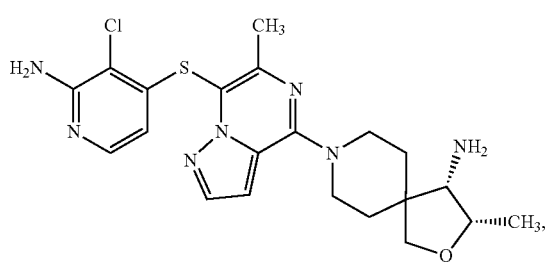
31
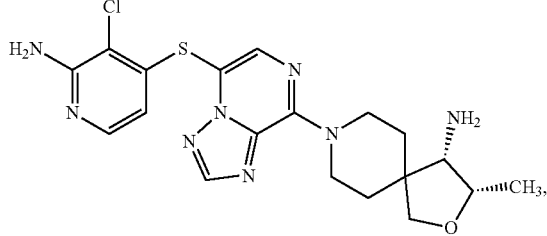
32
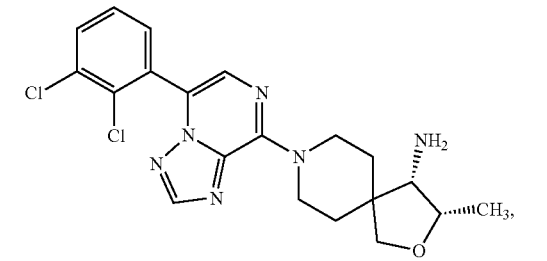

35
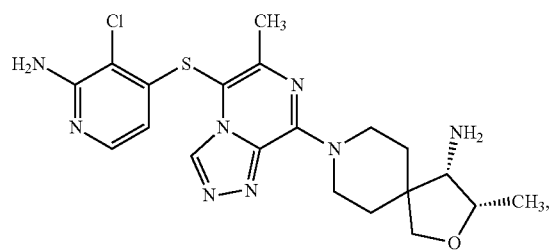
36
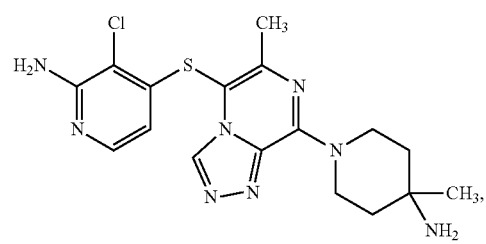
37
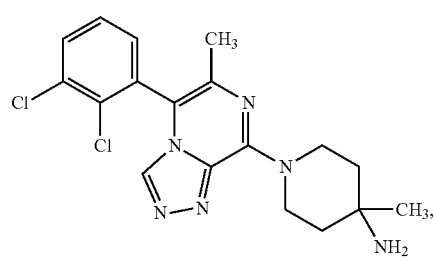
38
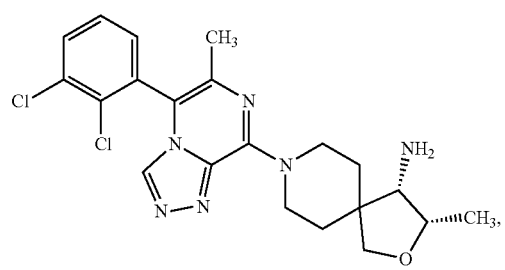
42
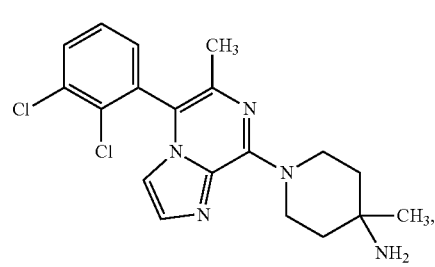
44
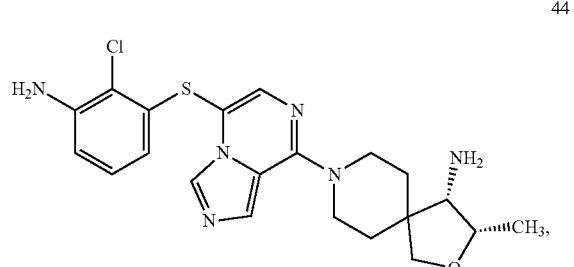
45
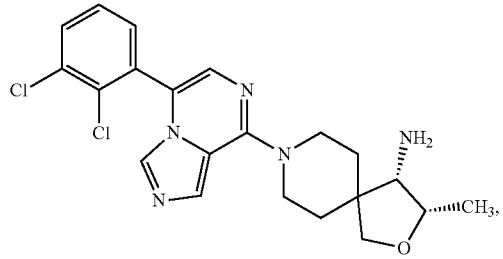
47
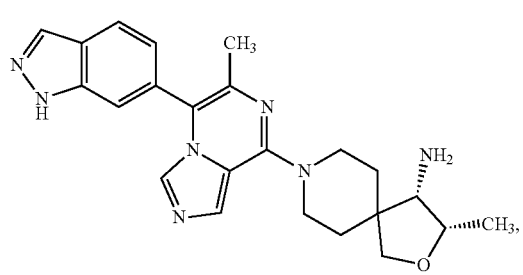
49
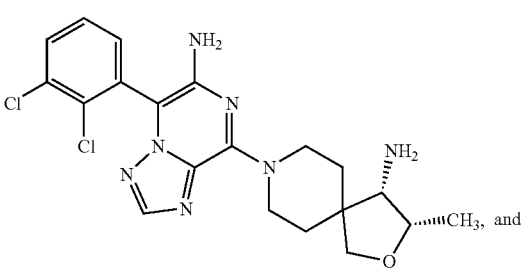
52
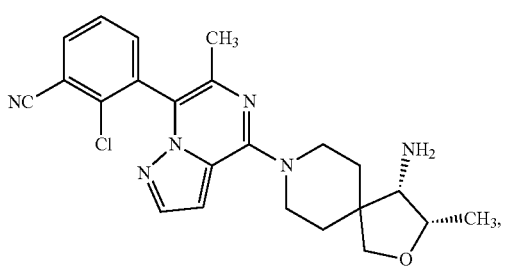
or a pharmaceutically acceptable salt or tautomer thereof.
18. The method of claim 17, wherein the compound, or stereoisomer thereof, is selected from the group consisting of:
2
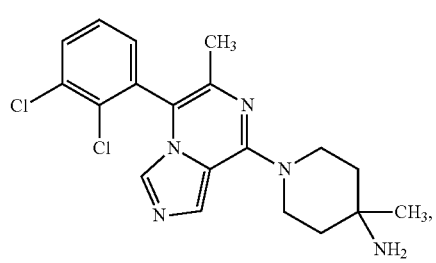

3

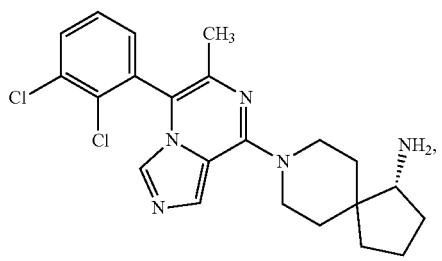

6

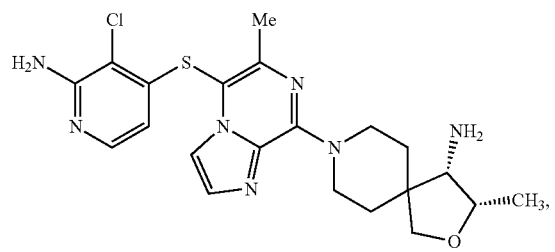

22

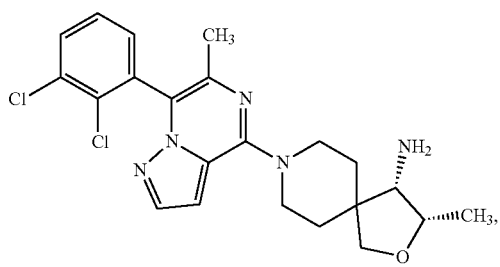

25

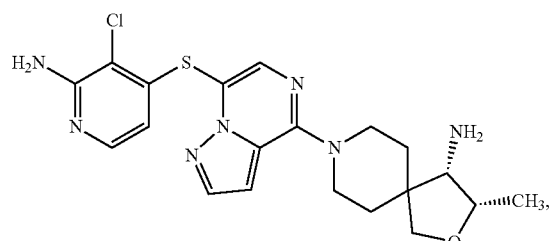

28

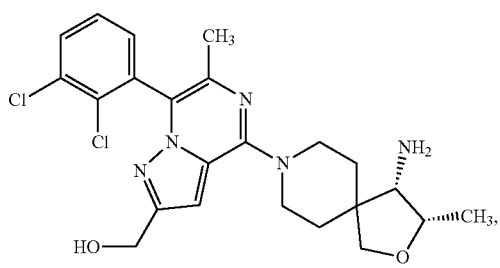

29

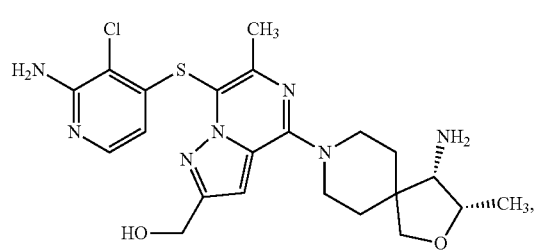 and

30

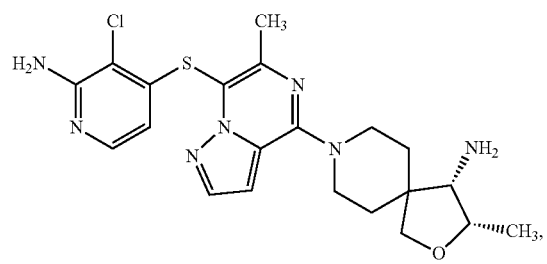

or a pharmaceutically acceptable salt or tautomer thereof.

19. A method for modulating SH2 domain-containing protein tyrosine phosphatase-2 (SHP2) activity in a subject in need thereof, wherein the method comprises administering to the subject a therapeutically effective amount of a pharmaceutical composition comprising a pharmaceutically acceptable carrier and a compound of Formula IV:

IV

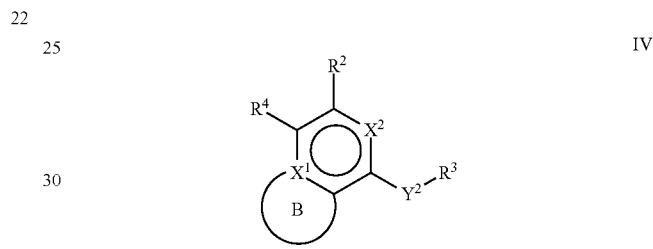

or a pharmaceutically acceptable salt, stereoisomer, or tautomer thereof, wherein:

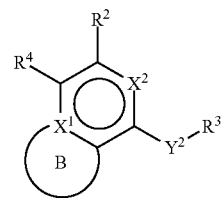

is:

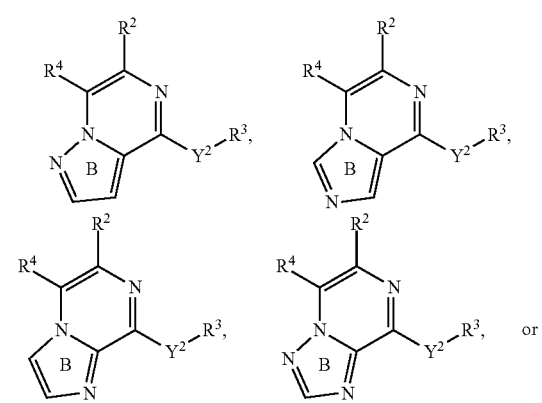

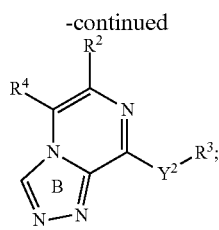

wherein ring B is optionally substituted on any available carbon with one or two substituents independently selected from the group consisting of $C_1$-$C_6$ alkyl, $CH_2F$, $CHF_2$, $CF_3$, $(CH_2)_nNH_2$, $(CH_2)_nOH$, heterocyclyl, and heteroaryl;

$R^2$ is H, halogen, $C_1$-$C_6$ alkyl, $C_2$-$C_6$ alkenyl, $C_2$-$C_6$ alkynyl, $NR^5R^6$, OH, $C_3$-$C_8$ cycloalkyl, $C_4$-$C_8$ cycloalkenyl, or heterocyclyl;

wherein the heterocyclyl contains 1, 2, 3, 4, or 5 heteroatoms independently selected from the group consisting of nitrogen, phosphorous, oxygen, and sulfur;

wherein the heterocyclyl is not attached via a nitrogen atom; and wherein the $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, or heterocyclyl is optionally substituted with one or more substituents independently selected from the group consisting of halogen, CN, $NO_2$, $NR^5R^6$, $NR^5S(O)R^6$, $NR^5S(O)NR^5R^6$, $NR^5S(O)_2R^6$, $NR^5S(O)_2NR^5R^6$, $OR^5$, =O, $SR^5$, $S(O)R^5$, $S(O)NR^5R^6$, $S(O)_2R^5$, $S(O)_2 NR^5R^6$, heterocyclyl, aryl, heteroaryl, and $R^5$;

$Y^2$ is —$NR^a$—, —$NR^aC(O)$—, —$NR^aC(O)NR^a$—, —$NR^aC(O)O$—, —$NR^aC(S)$—, —$NR^aC(S)NR^a$—, or —$NR^aS(O)_2$—, wherein the bond on the left side of $Y^2$ is bound to the ring and the bond on the right side of $Y^2$ is bound to $R^3$;

$R^3$ and $R^a$, together with the atom(s) to which they are attached, form a monocyclic or polycyclic 3- to 12-membered heterocyclyl or a spirocyclic 5- to 12-membered heterocyclyl, wherein the monocyclic or polycyclic 3- to 12-membered heterocyclyl or spirocyclic 5- to 12-membered heterocyclyl is optionally substituted with one or more substituents independently selected from the group consisting of $C_1$-$C_6$ alkyl, $CH_2F$, $CHF_2$, $CF_3$, $(CH_2)_nNH_2$, $(CH_2)_nOH$, =O, heterocyclyl, and heteroaryl;

$R^4$ is:

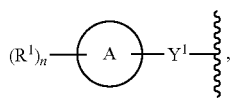

wherein:

$Y^1$ is a direct bond, —$CH_2$—, —$C(=CH_2)$—, —NH—, —S—, —S(O)—, —$S(O)_2$—, or —$S(O)_2$NH—;

ring A is a monocyclic or polycyclic 5- to 12-membered cycloalkyl, heterocycloalkyl, aryl, or heteroaryl; and each $R^1$ is independently H, D, halogen, CN, $NO_2$, $C_1$-$C_6$ alkyl, $C_2$-$C_6$ alkenyl, $C_2$-$C_6$ alkynyl, $C(O)R^5$, $C(O)OR^5$, $NR^5R^6$, $NR^5S(O)R^6$, $NR^5S(O)NR^5R^6$, $NR^5S(O)_2R^6$, $NR^5S(O)_2NR^5R^6$, $OR^5$, $SR^5$, $S(O)R^5$, $S(O)NR^5R^6$, $S(O)_2R^5$, $S(O)_2NR^5R^6$, $C_3$-$C_8$ cycloalkyl, or $C_4$-$C_8$ cycloalkenyl, wherein each $C_1$-$C_6$ alkyl, $C_2$-$C_6$ alkenyl, $C_2$-$C_6$ alkynyl, $C_3$-$C_8$ cycloalkyl, and $C_4$-$C_8$ cycloalkenyl is optionally and independently substituted with one or more substituents independently selected from the group consisting of halogen, CN, $NO_2$, $NR^5R^6$, $NR^5S(O)R^6$, $NR^5S(O)NR^5R^6$, $NR^5S(O)_2R^6$, $NR^5S(O)_2NR^5R^6$, $OR^5$, =O, $SR^5$, $S(O)R^5$, $S(O)NR^5R^6$, $S(O)_2R^5$, $S(O)_2NR^5R^6$, heterocyclyl, aryl, heteroaryl, and $R^5$;

each $R^5$ is independently H, D, halogen, CN, $NO_2$, $C_1$-$C_6$ alkyl, $C_2$-$C_6$ alkenyl, $C_2$-$C_6$ alkynyl, $NR^7R^8$, $OR^7$, $SR^7$, $C_3$-$C_8$ cycloalkyl, $C_4$-$C_8$ cycloalkenyl, or a monocyclic or polycyclic 3- to 12-membered heterocyclyl;

each $R^6$ is independently H, D, halogen, CN, $NO_2$, $C_1$-$C_6$ alkyl, $C_2$-$C_6$ alkenyl, $C_2$-$C_6$ alkynyl, $NR^7R^8$, $OR^7$, $SR^7$, $C_3$-$C_8$ cycloalkyl, $C_4$-$C_8$ cycloalkenyl, or a monocyclic or polycyclic 3- to 12-membered heterocyclyl;

each $R^7$ is independently H, D, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, or a monocyclic or polycyclic 3- to 12-membered heterocyclyl, wherein each $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, and monocyclic or polycyclic 3- to 12-membered heterocyclyl is optionally and independently substituted with one or more substituents independently selected from the group consisting of CN, $NO_2$, $NH_2$, OH, and SH;

each $R^8$ is independently H, D, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, or a monocyclic or polycyclic 3- to 12-membered heterocyclyl, wherein each $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, and monocyclic or polycyclic 3- to 12-membered heterocyclyl is optionally and independently substituted with one or more substituents independently selected from the group consisting of CN, $NO_2$, $NH_2$, OH, and SH; and each n is independently 0, 1, 2, 3, 4, 5, 6, 7, 8, 9, or 10;

with the provisos that:

(1) the heteroaryl of ring A is not furanyl or thiophenyl; and (2) $R^a$ and $R^3$, together with the atom(s) to which they are attached, do not form an optionally substituted piperazinyl.

20. The method of claim 19, wherein the subject has a disease associated with modulation of SHP2 activity selected from the group consisting of acute myeloid leukemia, breast cancer, colon cancer, juvenile myelomonocytic leukemia, LEOPARD syndrome, lung cancer, melanoma, neuroblastoma, and Noonan syndrome.

21. The method of claim 19, wherein ring B is optionally substituted on any available carbon with one or two substituents independently selected from the group consisting of $C_1$-$C_6$ alkyl, $CH_2F$, $CHF_2$, $CF_3$, $(CH_2)_nNH_2$, and $(CH_2)_nOH$.

22. The method of claim 19, wherein $R^2$ is $C_1$-$C_6$ alkyl, wherein the $C_1$-$C_6$ alkyl is optionally substituted with one or more substituents independently selected from the group consisting of halogen, $NR^5R^6$, and $OR^5$.

23. The method of claim 19, wherein $R^2$ is $CH_3$.

24. The method of claim 19, wherein $Y^2$ is —$NR^a$—, wherein the bond on the left side of $Y^2$ is bound to the ring and the bond on the right side of $Y^2$ is bound to $R^3$.

25. The method of claim 19, wherein $R^3$ and $R^a$, together with the atom(s) to which they are attached, form a monocyclic or polycyclic 3- to 12-membered heterocyclyl, wherein the monocyclic or polycyclic 3- to 12-membered heterocyclyl is optionally substituted with one or more substituents independently selected from the group consisting of $C_1$-$C_6$ alkyl, $CH_2F$, $CHF_2$, $CF_3$, $(CH_2)_nNH_2$, and $(CH_2)_nOH$.

26. The method of claim 19, wherein $R^3$ and $R^a$, together with the atom(s) to which they are attached, form a spirocyclic 5- to 12-membered heterocyclyl, wherein the spirocyclic 5- to 12-membered heterocyclyl is optionally substituted with one or more substituents independently selected from the group consisting of $C_1$-$C_6$ alkyl, $CH_2F$, $CHF_2$, $CF_3$, $(CH_2)_nNH_2$, and $(CH_2)_nOH$.

27. The method of claim 26, wherein the spirocyclic 5- to 12-membered heterocyclyl is optionally substituted with one or more independently selected $C_1$-$C_6$ alkyl substituents.

28. The method of claim 26, wherein the spirocyclic 5- to 12-membered heterocyclyl is optionally substituted with one or more $NH_2$ substituents.

29. The method of claim 19, wherein $Y^1$ is a direct bond.

30. The method of claim 19, wherein $Y^1$ is —S—.

31. The method of claim 19, wherein ring A is a monocyclic or polycyclic aryl.

32. The method of claim 19, wherein ring A is a monocyclic or polycyclic heteroaryl.

33. The method of claim 19, wherein each $R^1$ is independently H, halogen, or $NR^5R^6$.

34. The method of claim 19, wherein the compound is of Formula IV-Q:

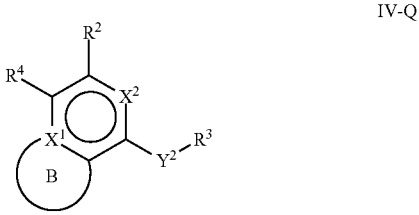

IV-Q or a pharmaceutically acceptable salt, stereoisomer, or tautomer thereof, wherein:

is:

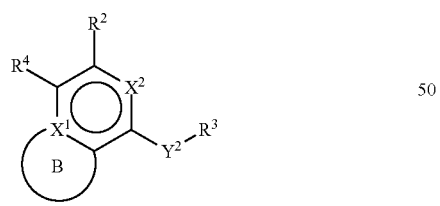

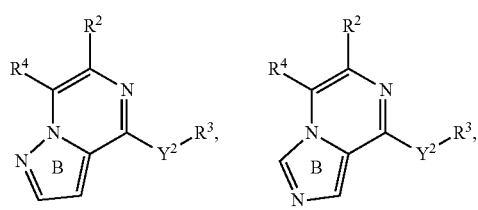

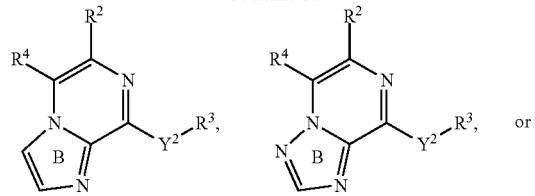

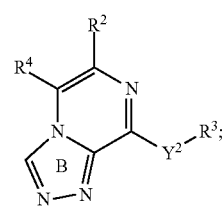

wherein ring B is optionally substituted on any available carbon with one or two substituents independently selected from the group consisting of $C_1$-$C_6$ alkyl, $CH_2F$, $CHF_2$, $CF_3$, $(CH_2)_nNH_2$, and $(CH_2)_nOH$;

$R^2$ is H, $C_1$-$C_6$ alkyl, $NR^5R^6$, or OH, wherein the $C_1$-$C_6$ alkyl is optionally substituted with one or more substituents independently selected from the group consisting of halogen, $NR^5R^6$, or $OR^5$;

$Y^2$ is —$NR^a$—, wherein the bond on the left side of $Y^2$ is bound to the ring and the bond on the right side of $Y^2$ is bound to $R^3$;

$R^3$ and $R^a$, together with the atom(s) to which they are attached, form a monocyclic or polycyclic 3- to 12-membered heterocyclyl or a spirocyclic 5- to 12-membered heterocyclyl, wherein the monocyclic or polycyclic 3- to 12-membered heterocyclyl or spirocyclic 5- to 12-membered heterocyclyl is optionally substituted with one or more substituents independently selected from the group consisting of $C_1$-$C_6$ alkyl, $CH_2F$, $CHF_2$, $CF_3$, $(CH_2)_nNH_2$, and $(CH_2)_nOH$;

$R^4$ is:

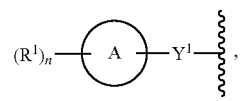

wherein:

$Y^1$ is a direct bond or —S—;

ring A is a monocyclic or polycyclic aryl or heteroaryl; and each $R^1$ is independently H, halogen, CN, $C_1$-$C_6$ alkyl, $NR^5R^6$, or $OR^5$;

each $R^5$ is independently H or $C_1$-$C_6$ alkyl; and each $R^6$ is independently H or $C_1$-$C_6$ alkyl.

35. The method of claim 19, wherein the compound, or stereoisomer thereof, is selected from the group consisting of:

2
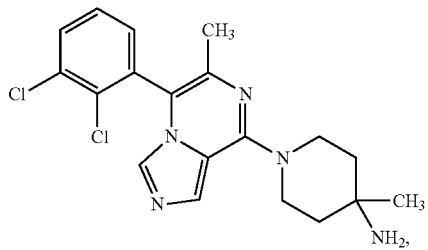
3
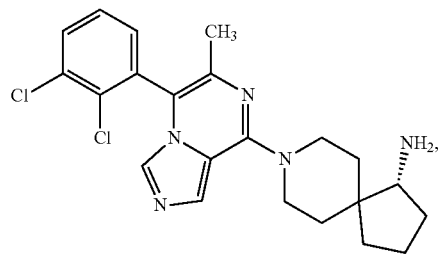
4
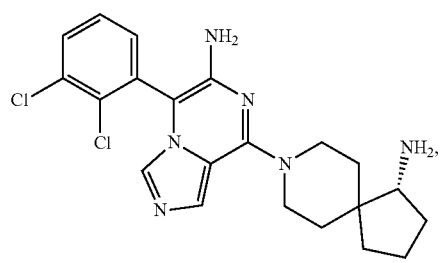
5
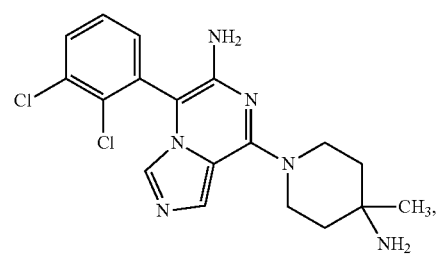
6
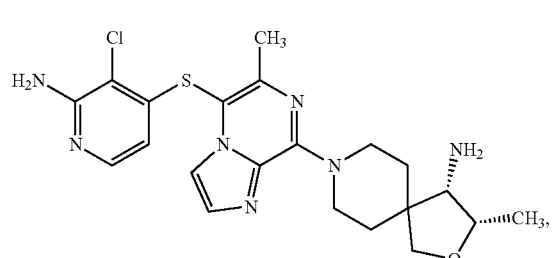
7
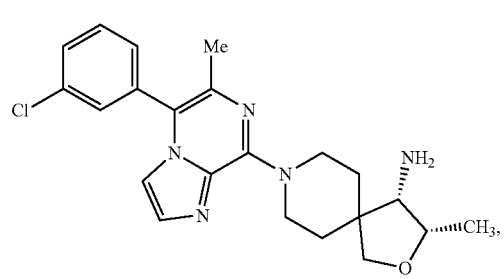
8
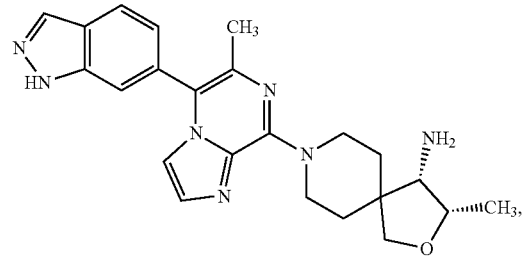
9
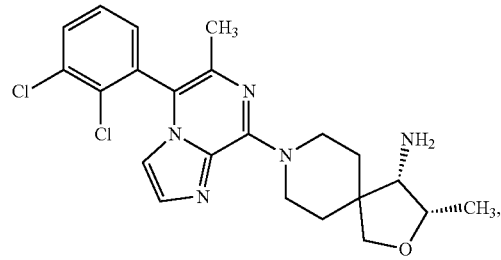
10
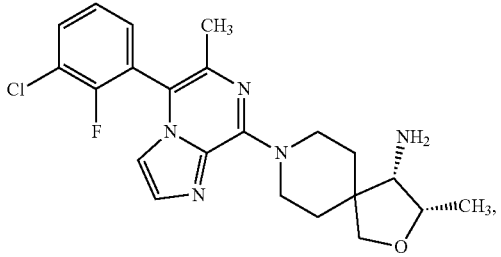
11
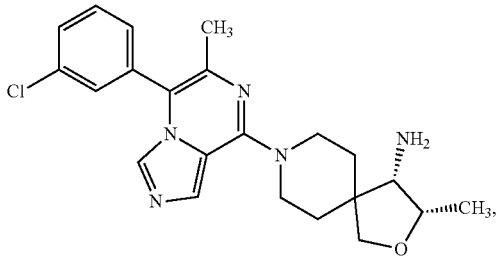
12
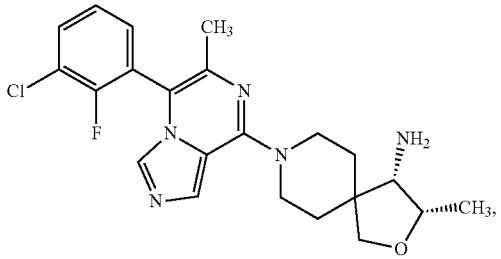
13
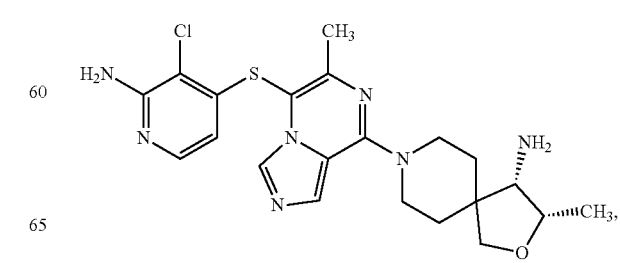

-continued

35
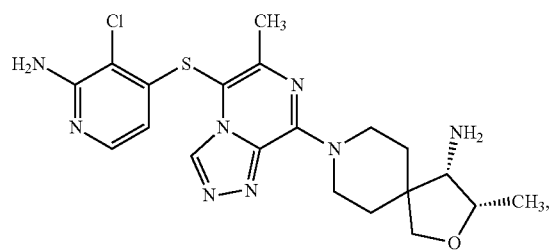
36
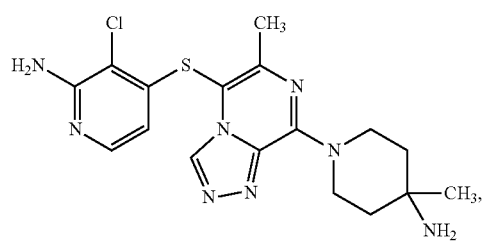
37
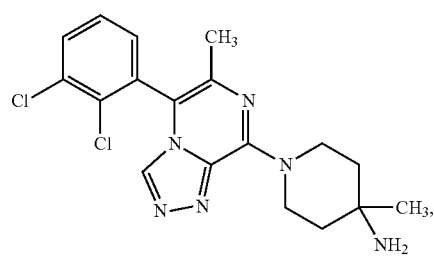
38
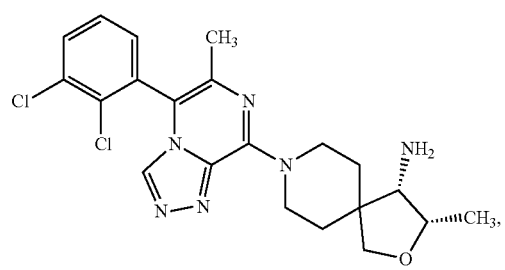
42
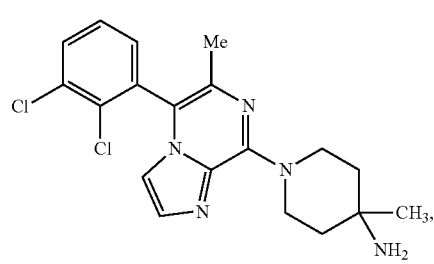
44
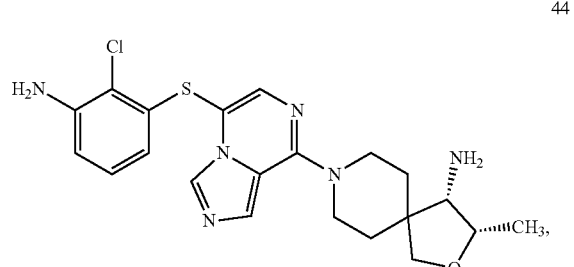
45
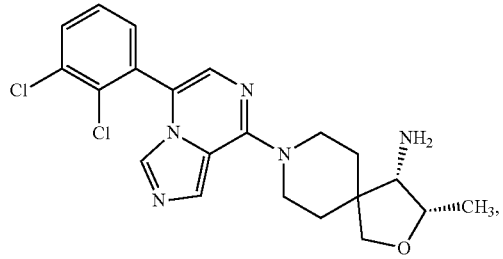
47
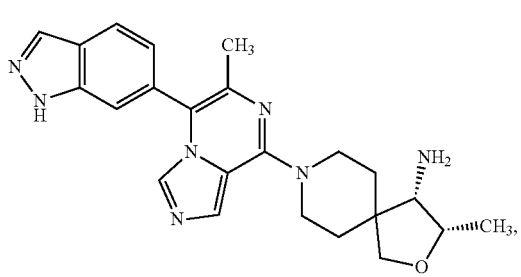
49
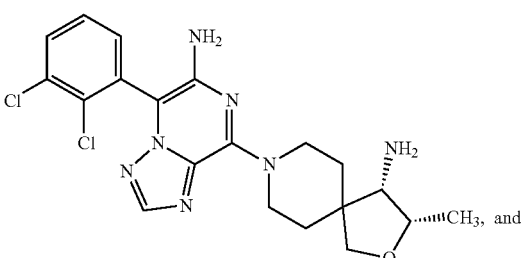
52
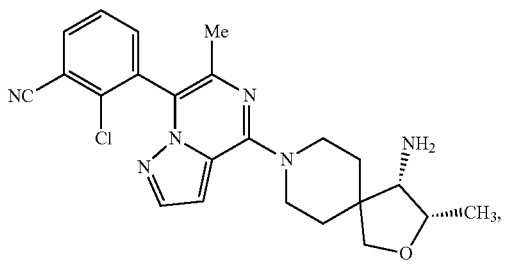
or a pharmaceutically acceptable salt or tautomer thereof.
36. The method of claim 35, wherein the compound, or stereoisomer thereof, is selected from the group consisting of:
2
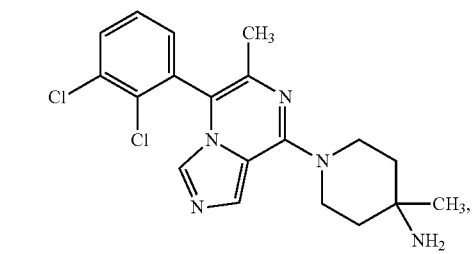

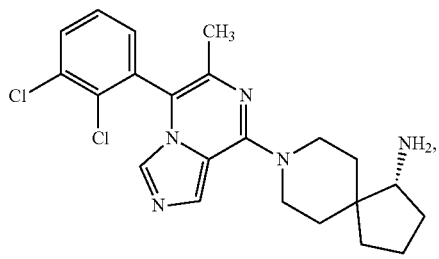
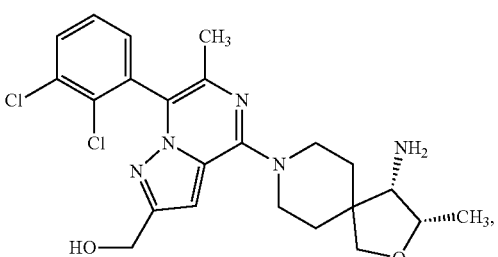
or a pharmaceutically acceptable salt or tautomer thereof.
* * * * *